US012545681B2

(12) United States Patent
Li et al.

(10) Patent No.: US 12,545,681 B2
(45) Date of Patent: Feb. 10, 2026

(54) COMPOUND USED AS RET KINASE INHIBITOR AND APPLICATION THEREOF

(71) Applicant: TYK Medicines, Inc., Huzhou (CN)

(72) Inventors: Jun Li, Huzhou (CN); Maolin Zheng, Huzhou (CN); Chengshan Niu, Huzhou (CN); Apeng Liang, Huzhou (CN); Yusheng Wu, Huzhou (CN)

(73) Assignee: TYK MEDICINES, INC., Zhejiang (CN)

( * ) Notice: Subject to any disclaimer, the term of this patent is extended or adjusted under 35 U.S.C. 154(b) by 590 days.

(21) Appl. No.: 17/926,846

(22) PCT Filed: May 7, 2021

(86) PCT No.: PCT/CN2021/092202

§ 371 (c)(1),
(2) Date: Nov. 21, 2022

(87) PCT Pub. No.: WO2021/233133

PCT Pub. Date: Nov. 25, 2021

(65) Prior Publication Data

US 2023/0234954 A1 Jul. 27, 2023

(30) Foreign Application Priority Data

May 20, 2020 (CN) ......................... 202010432188.2
Nov. 20, 2020 (CN) ......................... 202011315155.6

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .................................................... C07D 487/04
USPC .......................................................... 514/255
See application file for complete search history.

(56) References Cited

U.S. PATENT DOCUMENTS

2009/0281073 A1 11/2009 Bhattacharya et al.

FOREIGN PATENT DOCUMENTS

| | | | | |
|---|---|---|---|---|
| CN | 108473468 A | 8/2018 | | |
| CN | 111285882 A | 6/2020 | | |
| CN | 111961034 A | 11/2020 | | |
| WO | 2006067614 A2 | 6/2006 | | |
| WO | 2014105958 A1 | 7/2014 | | |
| WO | 2017079140 A1 | 5/2017 | | |
| WO | 2018017983 A1 | 1/2018 | | |
| WO | WO-2020175968 A1 * | 9/2020 | .............. | A61P 35/00 |

OTHER PUBLICATIONS

Walther et al, "Prodrugs in Medicinal Chemistry and Enzyme Prodrug Therapies." Advanced Drug Delivery Reviews, vol. 118, Sep. 2017, pp. 65-77 (Year: 2017).*
WO 2020175968 A1, English translation, WIPO Machine Translation (Year: 2020).*
English translation of Abstract of Chinese application No. CN113784963A, 100 pages.
English translation by Google Translate of Chinese application No. CN108473468A, 26 pages.
English translation of Abstract of WO2020175968, 74 pages.
Chinese Application No. 2021104972229 Search Report, 2 pages.

* cited by examiner

*Primary Examiner* — Jeffrey H Murray
*Assistant Examiner* — Rilla Marie Samsell
(74) *Attorney, Agent, or Firm* — NKL Law; Bin Lu; Allen Xue

(57) ABSTRACT

The present invention relates to the technical field of medicines. Specifically disclosed is a compound as represented by formula I', or a pharmaceutically acceptable salt, stereoisomer, solvate, or prodrug thereof, symbols therein being as defined in the claims. The compound of the present invention may be used as a drug for regulating RET kinase activity or treating RET-related diseases, and has good pharmacokinetic properties.

I'

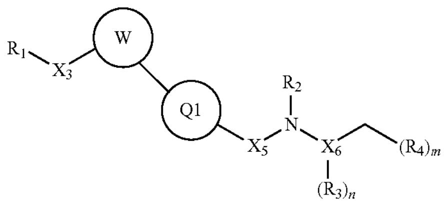

13 Claims, No Drawings

COMPOUND USED AS RET KINASE INHIBITOR AND APPLICATION THEREOF

CROSS REFERENCE TO RELATED APPLICATIONS

The present application is the U.S. National Phase under 35 U.S.C. § 371 of International Application No. PCT/CN2021/092202, filed May 7, 2021, which claims priority of Chinese Patent Application number CN202010432188.2, filed May 20, 2020, titled "Compounds useful as RET kinase inhibitors and uses thereof", and Chinese Patent Application number CN202011315155.6, filed Nov. 20, 2020, titled "Compounds useful as RET kinase inhibitors and uses thereof", the contents of all of which are hereby incorporated by reference in their entirety.

TECHNICAL FIELD

The invention relates to the technical field of medicine, in particular to a compound used as RET kinase inhibitor and application thereof in regulating RET kinase activity or treating RET-related diseases.

BACKGROUND OF THE INVENTION

RET (Rearranged during transfection) gene is located on chromosome 10, RET protein encoded thereby is a receptor tyrosine kinase (RTK) which exists on cell membrane. Its mutation types mainly include fusion mutation with KIF5B, TRIM33, CCDC6 and NCOA4 genes, and point mutation such as M918T. Common RET mutations mainly occur in thyroid cancer, non-small cell lung cancer and other cancer types. The incidence of RET gene fusion is about 1%-2% in NSCLC patients, and is 10%-20% in papillary thyroid carcinoma (accounting for about 85% of all thyroid cancers). RET fusion is more common in young patients, especially in young non-smoking lung adenocarcinoma patients, and the incidence is as high as 7%-17%. At present, the treatment scheme for RET gene change is mainly to use multi-kinase inhibitors, such as carbotinib and vandetanil. Due to the low targeting, serious toxicity related to VEGFR inhibition caused by off-target usually occurs.

Blueprint and Loxo Oncology have disclosed their highly effective and selective oral RET inhibitors BLU-667 and LOXO-292. The results of Blueprint Phase I clinical data show that BLU-667 shows broad anti-tumor activity, and the overall remission rate (ORR) in tumor patients with RET fusion and mutation is 45%, among which the ORR in patients with non-small cell lung cancer and medullary thyroid carcinoma is 50% and 40%, respectively. Recently, FDA granted LOXO-292, a research drug of Loxo Oncology Company, as a breakthrough therapy for treating patients with non-small cell lung cancer (NSCLC) and medullary thyroid cancer (MTC) carrying RET genetic mutations.

Therefore, developing novel compounds with RET kinase inhibitory activity and better pharmacodynamic and pharmacokinetic properties has become an important research project to develop new anti-tumor drugs which can be finally used in the treatment of human tumors and other diseases.

SUMMARY OF THE INVENTION

The invention provides a novel compound with RET kinase inhibitory activity and better pharmacodynamic and pharmacokinetic properties.

In the first aspect of the invention, a compound for use as a RET kinase inhibitor is provided, and the compound is a compound of formula I' or a pharmaceutically acceptable salt, stereoisomer, solvate or prodrug thereof,

I'

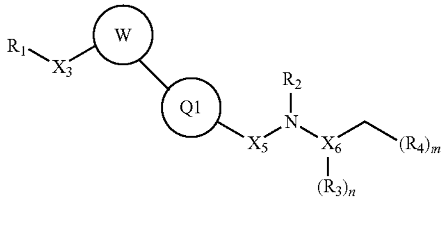

wherein, $R_1$ is substituted or unsubstituted 5-6-membered heterocyclyl or 5-6-membered heteroaryl; the "substituted" means optionally substituted by one or more $R_2$;

$X_3$ is selected from O, $NR_8$, $CR_9R_{10}$

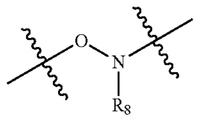

or

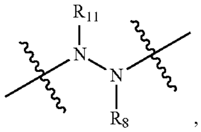

, wherein, $R_8$ and $R_{11}$ are each independently selected from the group consisting of hydrogen, C1-C6 alkyl, C2-C6 alkenyl, C2-C6 alkynyl, C1-C6 haloalkyl, C1-C6 heteroalkyl, C3-C6 cycloalkyl, C3-C6 halocycloalkyl, aryl, heteroaryl, aralkyl and C3-C6 heterocycloalkyl; $R_9$ and $R_{10}$ are each independently selected from the group consisting of hydrogen, halogen, C1-C6 alkyl, C1-C6 haloalkyl, C2-C6 alkenyl, C2-C6 alkynyl, C1-C6 alkoxy, C1-C6 heteroalkyl, C3-C6 cycloalkyl, C3-C6 halocycloalkyl, aryl, heteroaryl, aryloxy, aralkyl, C3-C6 heterocycloalkyl, C1-C6 alkylamino, C3-C6 cycloalkylamino;

ring W is a substituted or unsubstituted heterocyclylene or heteroarylene, the "substituted" means optionally substituted by 0-2 $R_5$;

ring Q1 is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring Q1 can be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl;

$X_5$ is selected from C(O), S(O), $S(O)_2$,

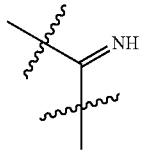

or

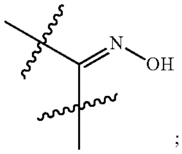

;

$X_6$ is selected from $CR_9$, N or O:

$R_2$ is optionally selected from hydrogen, C1-C6 alkyl, C1-C6 alkoxy, C1-C6 alkylamino, C3-C6 cycloalkyl, or C1-C6 heteroalkyl, wherein alkyl, alkoxy, alkylamino, cycloalkyl and heteroalkyl are each optionally and independently substituted by 0-5 $R^a$, A is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring A can be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl:

$R_3$ is optionally selected from hydrogen, deuterium, C1-C6 alkyl, C1-C6 alkoxy, C1-C6 alkylamino, C3-C6 cycloalkyl, or C1-C6 heteroalkyl, wherein alkyl, alkoxy, alkylamino, cycloalkyl and heteroalkyl are each optionally and independently substituted by 0-5 $R^a$;

$R_4$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, cyano, —$C(O)R_6$, —$OC(O)R_6$, —$C(O)OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)$—$C(O)R_7$, —$N(R_6)$—$C(O)OR_7$, —(C1-C6 alkylene)-$N(R_6)$—$C(O)R_7$, —$N(R_6)S(O)_2R_7$ or —$P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$;

$R_1$ is each independently selected from hydrogen, deuterium, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, oxo, cyano, —$C(O)R_6$, —$OC(O)R_6$, —$C(O)OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)$—$C(O)R_7$, —$N(R_6)$—$C(O)OR_7$, —(C1-C6 alkylene)-$N(R_6)$—$C(O)R_2$, —$N(R_6)S(O)_2R_7$ or —$P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$;

$R_6$ and $R_7$ are each independently selected from the group consisting of H, C1-C6 alkyl, C2-C6 alkenyl, C2-C6 alkynyl, C1-C6 alkoxy, C1-C6 heteroalkyl, C3-C6 cycloalkyl, aryl, heteroaryl, aryloxy, aralkyl, C3-C6 heterocycloalkyl, C1-C6 alkylamino, C3-C6 cycloalkylamino;

$R^a$ is optionally selected from deuterium, C1-C6 alkyl, halogen, hydroxyl, C1-C6 heteroalkyl, C1-C6 alkoxy, C1-C6 alkylamino, cycloalkyl, heterocycloalkyl or cyano:

m is 0, 1, 2, 3, 4, 5 or 6;

n is 0 or 1;

with the proviso that w % ben the ring W is a substituted or unsubstituted 6-membered heteroaryl, the ring W is substituted by $X_4$, wherein $X_4$ is selected from CN,

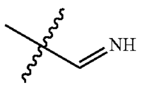
or
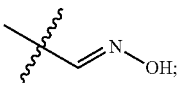

and Q1 is connected to the ring W only by carbon atoms on Q1 ring.

In another preferred embodiment, the W ring is substituted or unsubstituted substitutents selected from the group consisting of 5-6-membered monocyclic heterocyclylene, 8-10-membered bicyclic heterocyclylene or 5-6-membered monocyclic heteroarylene or 8-10-membered bicyclic heteroarylene; the "substituted" means optionally substituted by 0-2 $R_5$; $R_5$ is each independently selected from hydrogen, deuterium, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, oxo, cyano, —$C(O)R_6$, —$OC(O)R_6$, —$C(O)OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)$—$C(O)R_7$, —$N(R_6)$—$C(O)OR_6$, —(C1-C6 alkylene)-$N(R_6)$—$C(O)R_7$, —$N(R_6)S(O)_2R_7$ or —$P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$; $R^a$ is optionally selected from deuterium, C1-C6 alkyl, halogen, hydroxyl, C1-C6 heteroalkyl, C1-C6 alkoxy, C1-C6 alkylamino, cycloalkyl, heterocycloalkyl or cyano.

In another preferred embodiment, the compound represented by formula I', or pharmaceutically acceptable salt, stereoisomer, solvate or prodrug thereof, the W ring is selected from

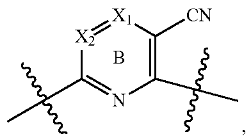
,
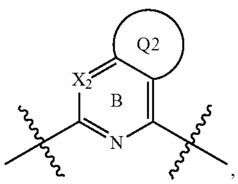
, (or
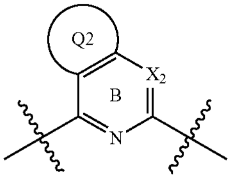
)
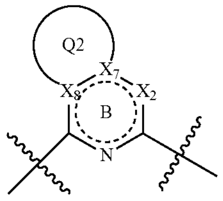

(or
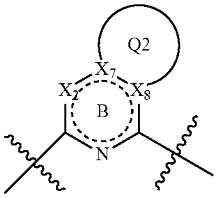
);

wherein $X_1$, $X_2$, $X_7$ and $X_8$ are each independently selected from N or $CR_5$; and at least one of $X_7$ and $X_8$ is N;

$R_5$ is each independently selected from hydrogen, deuterium, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein alkyl, alkenyl, alkynyl, alkoxy, alkylamino, heteroalkyl and cycloalkyl are each independently substituted by 0-5 $R^a$; $R^a$ is optionally selected from C1-C6 alkyl, halogen, hydroxyl, C1-C6 heteroalkyl, C1-C6 alkoxy, C1-C6 alkylamino, cycloalkyl, heterocycloalkyl or cyano; ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N. O or S, and any hydrogen atom on the ring Q2 can be substituted by deuterium, hydroxyl, halogen, cyano, ester, amido, ketocarbonyl, amino, C1-C6 alkyl, C1-C6 deuterated alkyl, C1-C6 alkylhydroxyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, the compound of formula I', or the pharmaceutically acceptable salt, stereoisomer, solvate or prodrug thereof has the structure represented by formula (II), formula (III) or formula (IV), (II)

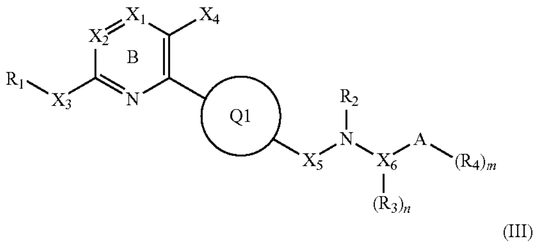

(III)

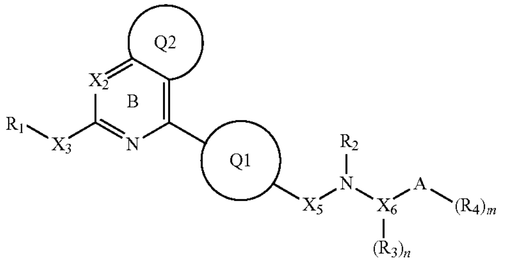

(IV)

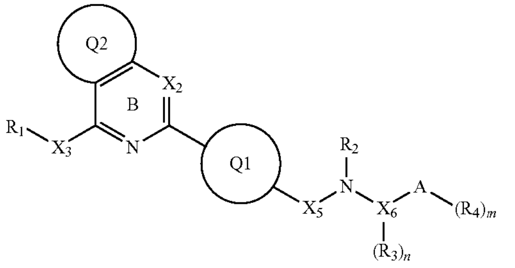

wherein,

A is optionally selected from 3-7 membered saturated ring, unsaturated ring, aromatic ring, heteroaromatic ring, spiro ring or bridge ring, and can contain 0-3 heteroatoms optionally selected from N, O or S;

ring Q1 is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring Q1 can be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl; in formula II, Q1 is connected to the ring B only by carbon atoms on ring Q1;

$R_1$ is optionally selected from one of the following structures:

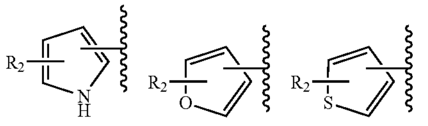

-continued

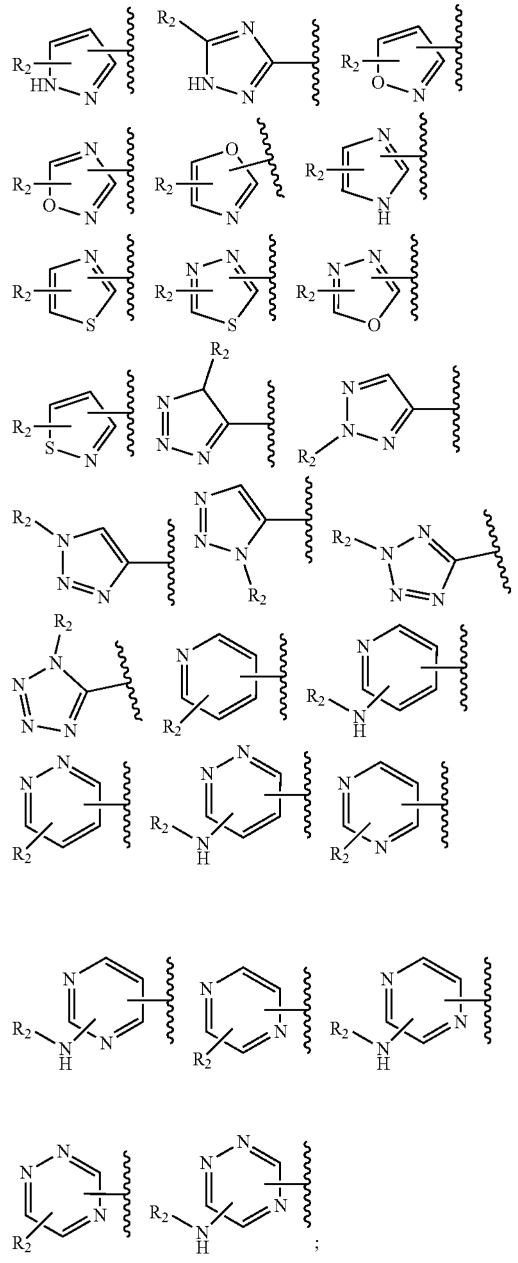

$R_2$ is optionally selected from hydrogen, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$:

$R_3$ is optionally selected from hydrogen, deuterium, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$:

$R^a$ is optionally selected from deuterium, C1-C6 alkyl, halogen, hydroxyl, C1-C6 heteroalkyl, C1-C6 alkoxy, cycloalkyl, heterocycloalkyl or cyano;

$X_1$ and $X_2$ are each independently selected from N or $CR_5$;

$X_3$ is selected from O, $NR_8$, $CR_9R_{10}$,

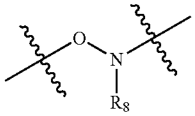 or 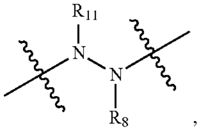 , wherein, $R_8$ and $R_{11}$ are each independently selected from the group consisting of hydrogen, C1-C6 alkyl, C2-C6 alkenyl, C2-C6 alkynyl, C1-C6 haloalkyl, C1-C6 heteroalkyl, C3-C6 cycloalkyl, C3-C6 halocycloalkyl, aryl, heteroaryl, aralkyl and C3-C6 heterocycloalkyl; $R_9$ and $R_{10}$ are each independently selected from the group consisting of hydrogen, halogen, C1-C6 alkyl, C1-C6 haloalkyl, C2-C6 alkenyl, C2-C6 alkynyl, C1-C6 alkoxy, C1-C6 heteroalkyl, C3-C6 cycloalkyl, C3-C6 halocycloalkyl, aryl, heteroaryl, aryloxy, aralkyl, C3-C6 heterocycloalkyl, C1-C6 alkylamino, and C3-C6 cycloalkylamino;

$X_4$ is selected from CN,

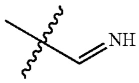 or 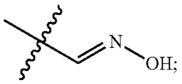

$X_5$ is selected from C(O), S(O), $S(O)_2$,

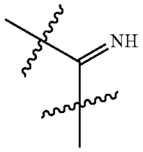 or 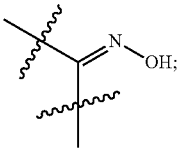

$X_6$ is selected from $CR_9$, N or O;

$R_4$ and $R_5$ are each independently selected from hydrogen, deuterium, C1-C6 alkyl, C2-C6 alkenyl, C2-C6 alkynl, C1-C6 alkoxy, halogen, C1-C6 heteroalkyl, cycloalkyl, aryl, heteroaryl, aryloxy, aralkyl, heterocyclyl, heterocycloalkyl, nitro, cyano, —$C(O)R_6$, —$OC(O)R_6$, —$C(O)OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)$—$C(O)R_7$, —$N(R_6)$—$C(O)OR_7$, —(C1-C6 alkylene)-$N(R_6)$—$C(O)R_7$, —$N(R_6)S(O)_2R_7$ or —$P(O)(R_6)(R_7)$; wherein alkyl, alkenyl, alkynyl, alkoxy, heteroalkyl, cycloalkyl, aryl, heteroaryl, aryloxy, aralkyl, heterocyclyl and heterocycloalkyl are each independently substituted by 0-5 $R^a$; &4, and $R_7$ are each independently selected from C1-C6 alkyl, C2-C6 alkenyl, C2-C6 alkynyl, C1-C6 alkoxy, C1-C6 heteroalkyl, C3-C6 cycloalkyl, aryl, heteroaryl, aryloxy, aralkyl, C3-C6 heterocycloalkyl, C1-C6 alkylamino or C3-C6 cycloalkylamino;

ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S; any hydrogen atom on the ring Q2 can be substituted by deuterium, hydroxyl, halogen, cyano, ester, amido, ketocarbonyl, amino, C1-C6 alkyl, C1-C6 deuterated alkyl, C1-C6 alkylhydroxyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl:

m is 0, 1, 2, 3, 4, 5 or 6;

n is 0 or 1.

In another preferred embodiment, $X_3$ is $NR_8$, wherein, $R_8$ is H.

In another preferred embodiment, the compound of formula I', or the pharmaceutically acceptable salt, stereoisomer, solvate or prodrug thereof has the structure represented by formula (2), formula (3) or formula (4), (2)

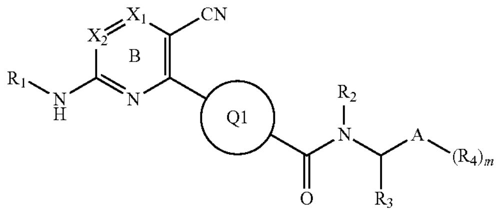

(3)

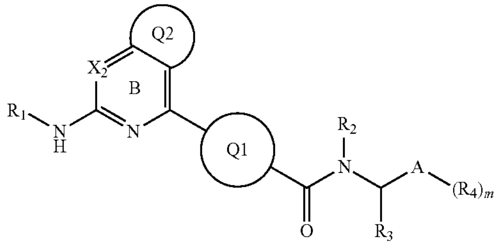

(4)

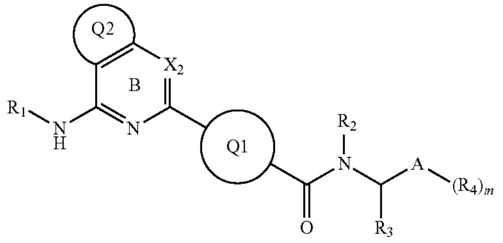

wherein,

A is optionally selected from 3-7 membered saturated ring, unsaturated ring, aromatic ring, heteroaromatic ring, spiro ring or bridge ring, and can contain 0-3 heteroatoms optionally selected from N, O or S;

ring Q1 is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring Q1 can be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl; in formula (2), Q1 is connected to the ring B only by carbon atoms on ring Q1:

$R_1$ is optionally selected from one of the following structures:

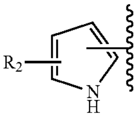 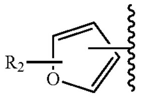 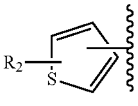

-continued

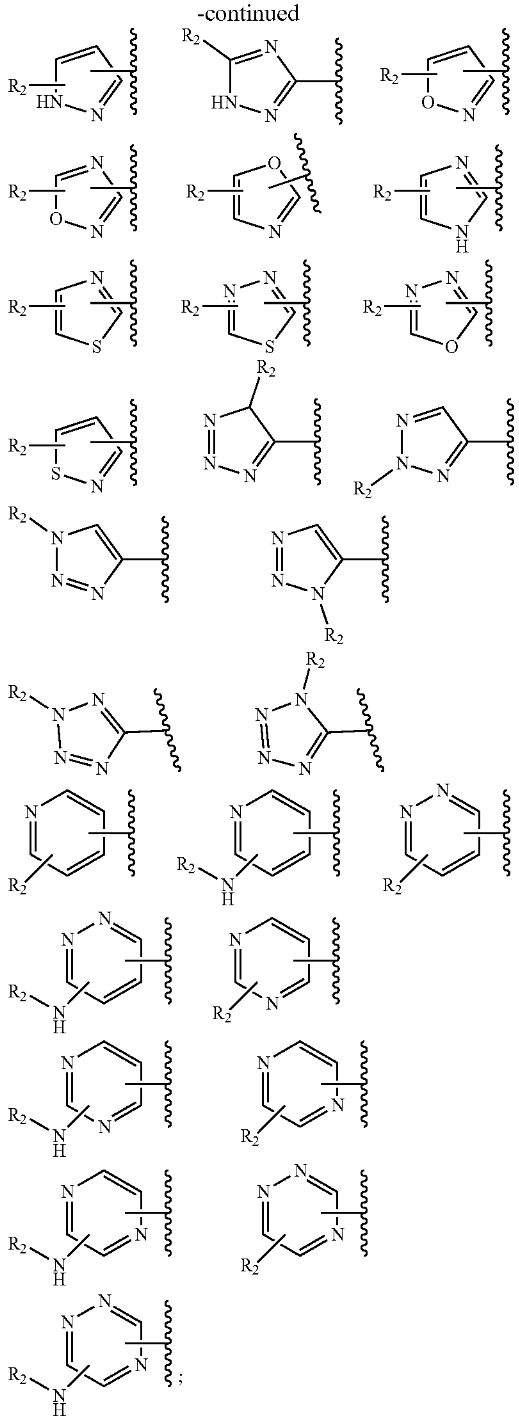

;

$R_2$ is optionally selected from hydrogen, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R_3$ is optionally selected from hydrogen, deuterium, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R^a$ is optionally selected from deuterium, C1-C6 alkyl, halogen, hydroxyl, C1-C6 heteroalkyl, C1-C6 alkoxy, cycloalkyl, heterocycloalkyl or cyano;

$X_1$ and $X_2$ are each independently selected from N or $CR_5$;

$R_4$ and $R_5$ are each independently selected from hydrogen, deuterium, C1-C6 alkyl, C2-C6 alkenyl, C2-C6 alkynyl, C1-C6 alkoxy, halogen, C1-C6 heteroalkyl, cycloalkyl, aryl, heteroaryl, aryloxy, aralkyl, heterocyclyl, heterocycloalkyl, nitro, cyano, —$C(O)R_6$, —$OC(O)R_6$, —$C(O)OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)C(O)R_7$. —$N(R_6)$—$C(O)OR_7$, —(C1-C6 alkylene)-$N(R_6)$—$C(O)R_7$, —$N(R_6)S(O)_2R_7$ or —$P(O)(R_6)(R_7)$, wherein alkyl, alkenyl, alkynyl, alkoxy, heteroalkyl, cycloalkyl, aryl, heteroaryl, aryloxy, aralkyl, heterocyclyl and heterocycloalkyl are each independently substituted by 0-5 $R^a$;

$R_6$ and $R^7$ are each independently selected from C1-C6 alkyl, C2-C6 alkenyl, C2-C6 alkynyl, C1-C6 alkoxy, C1-C6 heteroalkyl, C3-C6 cycloalkyl, aryl, heteroaryl, aryloxy, aralkyl, C3-C6 heterocycloalkyl, C1-C6 alkylamino or C3-C6 cycloalkylamino;

ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S; any hydrogen atom on the ring Q2 can be substituted by deuterium, hydroxyl, halogen, cyano, ester, amido, ketocarbonyl, amino, C1-C6 alkyl, C1-C6 deuterated alkyl, C1-C6 alkylhydroxyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkyl, aryl or heteroaryl;

m is 0, 1, 2, 3, 4, 5 or 6.

In another preferred embodiment, the compound of formula I', or the pharmaceutically acceptable salt, stereoisomer, solvate or prodrug thereof, the W ring is selected from the group consisting of

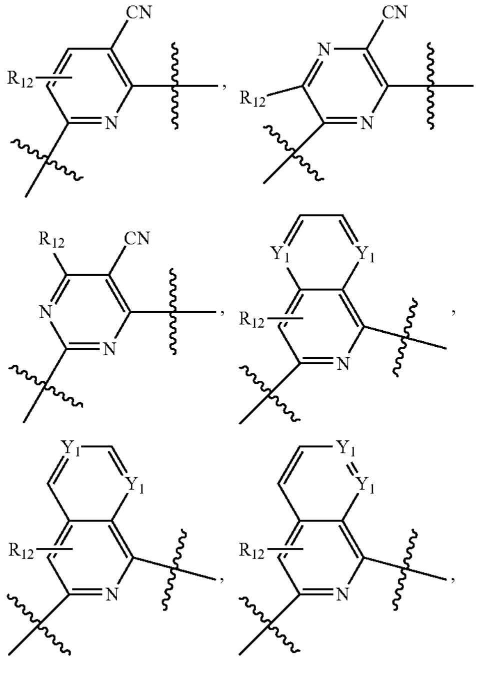

-continued

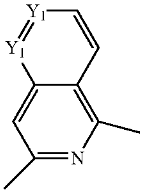,
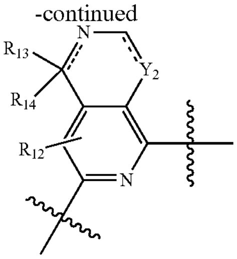,
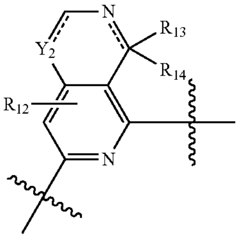,
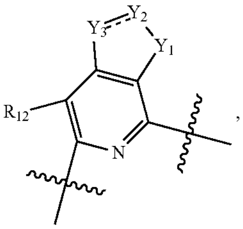,
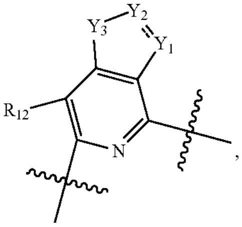,
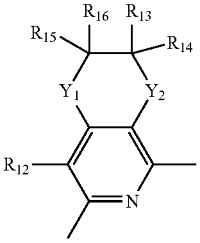,
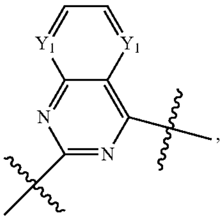,
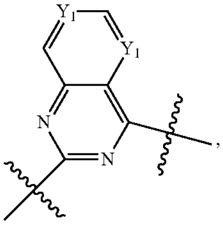,
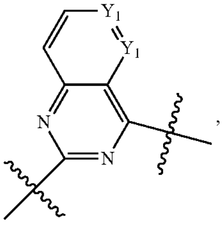,
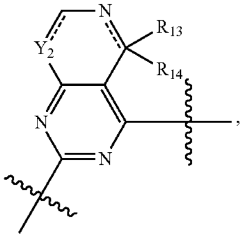,
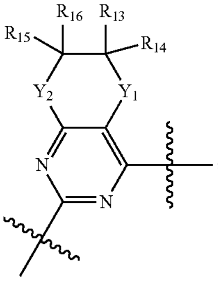,
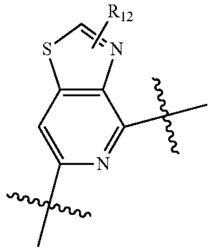,
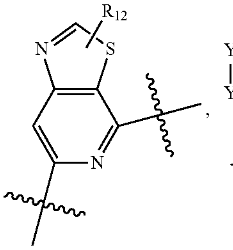,
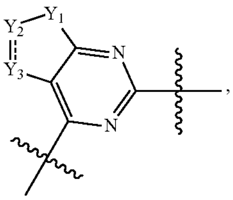, -continued

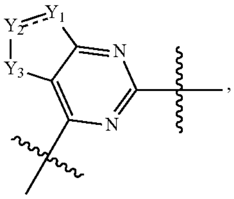,
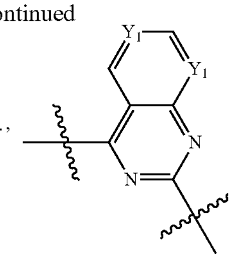,
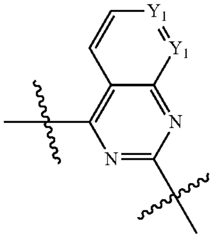,
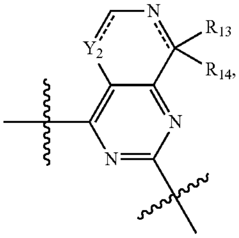,
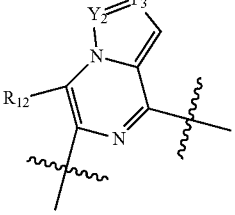,
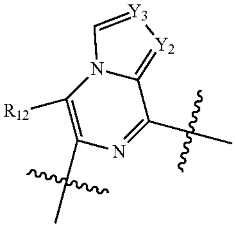,
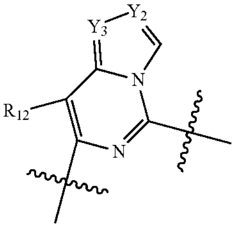,
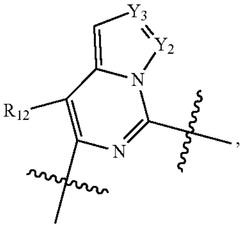,
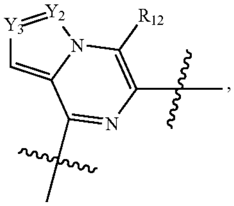,
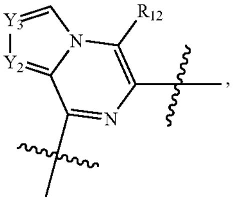,
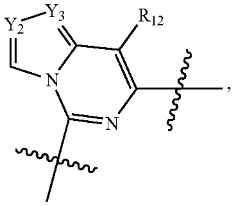, and
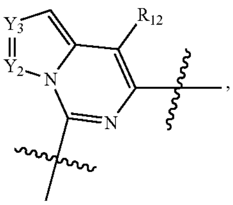, wherein, ⎓ is a single bond or a double bond;

$R_{12}$ is independently selected from H, deuterium, halogen, C1-C6 alkyl, C1-C6 alkoxy, C1-C6 alkylamino, nitro, cyano, or amino;

$Y_1$, $Y_2$, and $Y_3$ are each independently selected from O, N, $NR_{17}$, $CR_{13}$ or $CR_{13}R_{14}$;

$R_{13}$, $R_{14}$, $R_{15}$ and $R_{16}$ are each independently selected from H, halogen, C1-C6 alkyl, deuterated C1-C6 alkyl, C1-C6 alkylhydroxyl, halogenated C1-C6 alkyl, C1-C6 alkoxy, C1-C6 alkylamino, nitro, cyano, or amino; or $R_{13}$ and $R_{14}$ together with the C atom attached to them form a carbonyl (C═O); or $R_{15}$ and $R_{16}$ together with the C atom attached to them form a carbonyl (C═O);

$R_{17}$ is selected from H, C1-C6 alkyl, deuterated C1-C6 alkyl, C1-C6 alkylhydroxyl, or halogenated C1-C6 alkyl.

In another preferred embodiment, the W ring is selected from

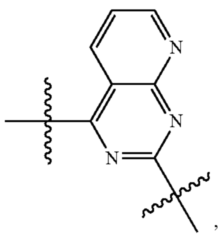
,
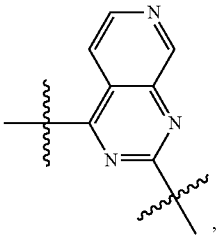
,
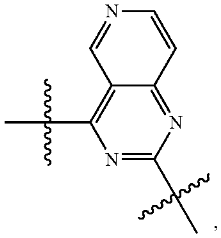
, or
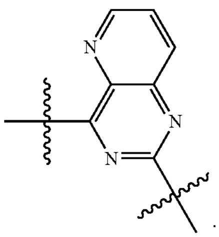
.

In another preferred embodiment, the compound of formula I', or the pharmaceutically acceptable salt, stereoisomer, solvate or prodrug thereof has the structure represented by formula 2'

2'

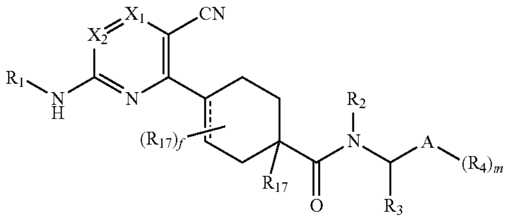

wherein, ═ is a single bond or a double bond;

$R_{17}$ is each independently selected from deuterium, halogen, hydroxyl, amino, C1-C6 alkyl, C1-C6 haloalkyl, C1-C6 thioalkyl, C1-C6 alkoxy, C1-C6 alkylamino or C3-C6 cycloalkyl;

f is 0, 1, 2, 3, 4, 5, 6, 7, 8 or 9;

$X_1$, $X_2$, $R_1$, $R_2$, $R_3$, $R_4$, A and m are as defined above.

In another preferred embodiment, the compound of formula I', or the pharmaceutically acceptable salt, stereoisomer, solvate or prodrug thereof has the structure represented by formula 2"

2"

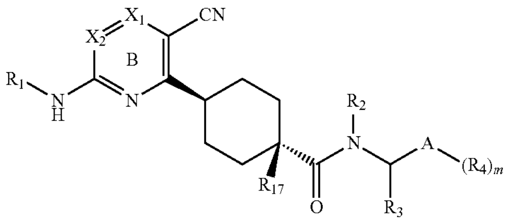

wherein, $R_1$, $R_2$, $R_3$, $R_4$, A, m, $X_1$, $X_2$ and $R_{17}$ are as defined above.

In another referred embodiment,

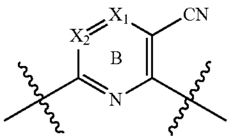

is selected from

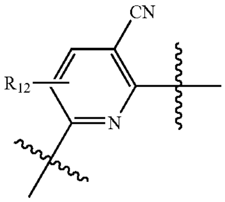
,
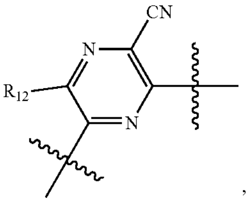
, or
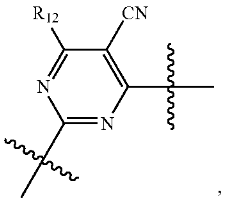
, $R_{12}$ is as defined above.

In another preferred embodiment, the compound of formula I', or the pharmaceutically acceptable salt, stereoisomer, solvate or prodrug thereof has the structure represented by formula 3'

3'

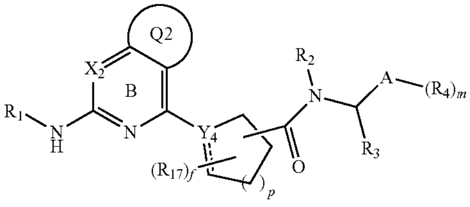

wherein, ═ is a single bond or a double bond;

when ═ is a single bond, $Y_4$ is selected from N or $CR_{17}$, when ═ is a double bond, $Y_4$ is C;

$R_{17}$ is each independently selected from deuterium, halogen, hydroxyl, amino, C1-C6 alkyl, deuterated C1-C6 alkyl, C1-C6 alkylhydroxyl, C1-C6 haloalkyl, C1-C6 thioalkyl, C1-C6 alkoxy, C1-C6 alkylamino or C3-C6 cycloalkyl;

f is 0, 1, 2, 3, 4, 5, 6, 7, 8 or 9;

p is 0, 1, 2 or 3;

$X_2$, Q2, $R_1$, $R_2$, $R_3$, $R_4$, A and m are as defined above.

In another preferred embodiment, the compound of formula I', or the pharmaceutically acceptable salt, stereoisomer, solvate or prodrug thereof has the structure represented by formula 3".

3″
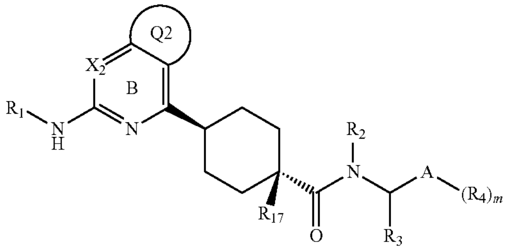
$R_1$, $X_2$, $R_2$, $R_3$, $R_4$, A, Q2, m and $R_{17}$ are as defined above. In another preferred embodiment,
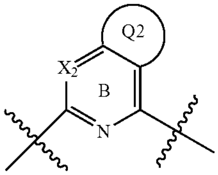
(or
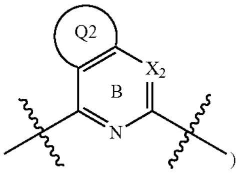
)
moiety is selected from,
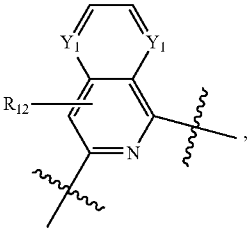
,
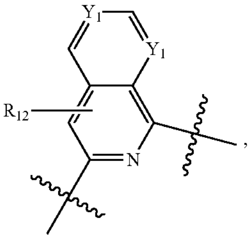
,
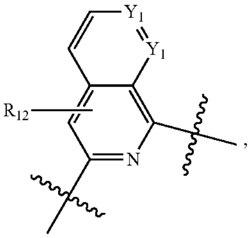
,
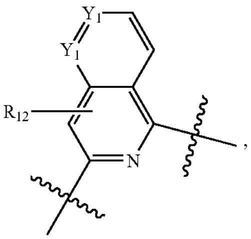
,
-continued
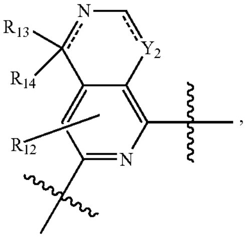
,
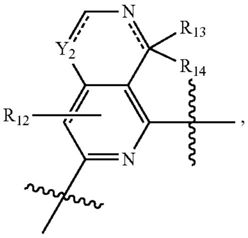
,
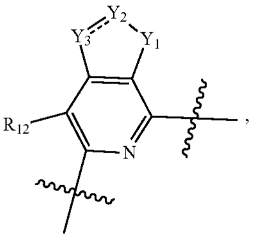
,
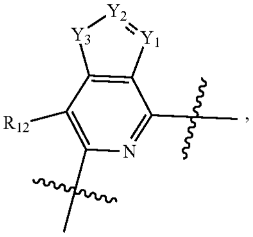
,
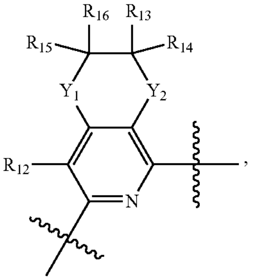
,
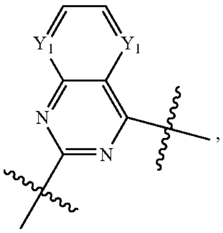
,
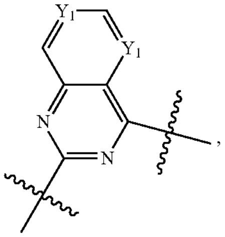
,
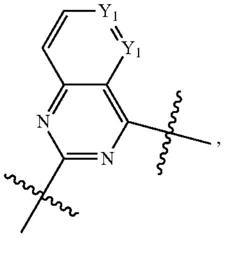
,
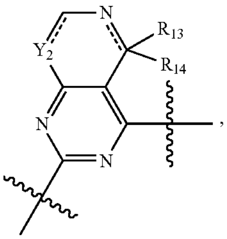
, -continued

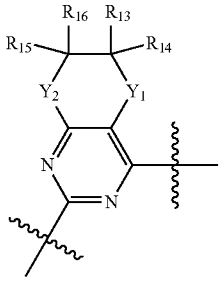,
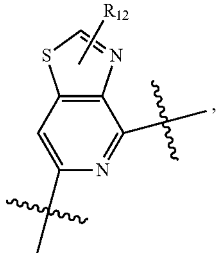,
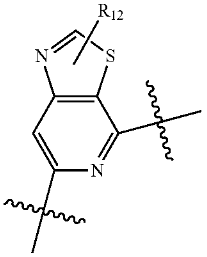,
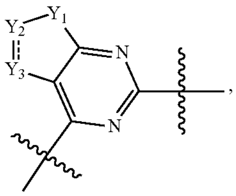,
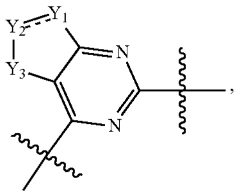,
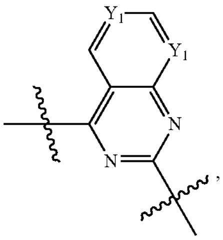,
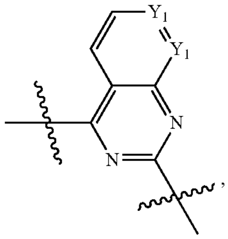, or
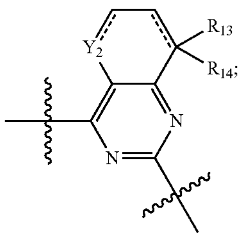;

wherein, ---- is a single bond or a double bond;

$Y_1$, $Y_2$, $Y_3$, $R_{12}$, $R_{13}$, $R_{14}$, $R_{15}$ and $R_{16}$ are as defined above.

In another preferred embodiment, the compound of formula I', or the pharmaceutically acceptable salt, stereoisomer, solvate or prodrug thereof has the structure represented by formula 4'

4'

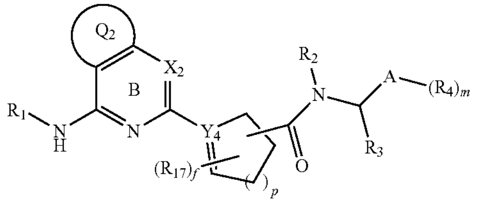

wherein, ---- is a single bond or a double bond;
when ---- is a single bond. $Y_4$ is selected from N or $CR_{17}$,
when ---- is a double bond, $Y_4$ is C;

$R_{17}$ is each independently selected from deuterium, halogen, hydroxyl, amino, C1-C6 alkyl, deuterated C1-C6 alkyl, C1-C6 alkylhydroxyl, C1-C6 haloalkyl, C1-C6 thioalkyl, C1-C6 alkoxy, C1-C6 alkylamino or C3-C6 cycloalkyl;

f is 0, 1, 2, 3, 4, 5, 6, 7, 8 or 9;

p is 0, 1, 2 or 3;

$X_2$, Q2, $R_1$, $R_2$, $R_3$, $R_4$, A and m are as defined above.

In another preferred embodiment, the compound of formula I', or the pharmaceutically acceptable salt, stereoisomer, solvate or prodrug thereof has the structure represented by formula 4"

4"

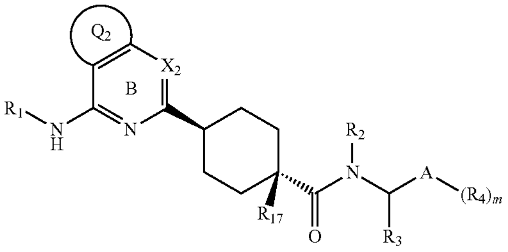

$R_1$, $X_2$, $R_2$, $R_3$, $R_4$, A, Q2, m and $R_{17}$ are as defined above.

In another preferred embodiment,

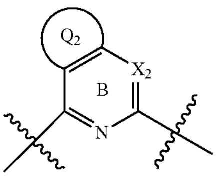

moiety is

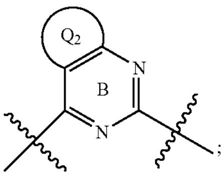;

wherein $Q_2$ is as defined above.

In another preferred embodiment, the compound of formula I', or the pharmaceutically acceptable salt, stereoisomer, solvate or prodrug thereof has the structure represented be formula 5 or formula 6

5

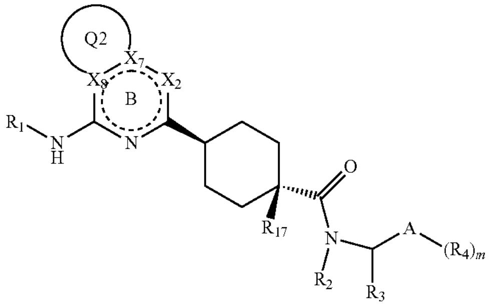

6

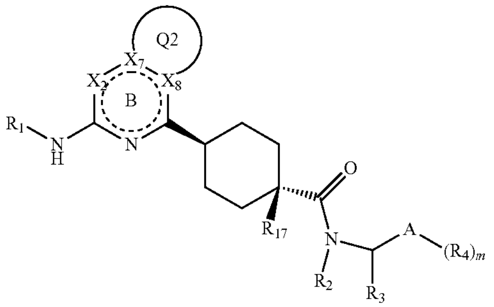

wherein $R_1$, $X_7$, $X_8$, $X_2$, Q2, $R_2$, $R_3$, $R_4$, $R_{17}$, A and m are as defined above, and at least one of $X_7$ and $X_8$ is N.

In another preferred embodiment, the compound of formula I', or the pharmaceutically acceptable salt, stereoisomer, solvate or prodrug thereof, A is aromatic ring or heteroaromatic ring, the heteroaromatic ring contains 0 to 3 heteroatoms selected from N, O or S; any hydrogen atom on the ring A can be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, A is phenyl, pyridyl, pyrazinyl, pyrimidinyl or pyridazinyl, and any hydrogen atom on the ring A can be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, the compound of formula I', or the pharmaceutically acceptable salt, stereoisomer, solvate or prodrug thereof, $R_4$ is each independently selected from aryl, heteroaryl, aryloxy, aralkyl, or heterocyclyl; wherein each aryl, heteroaryl, aryloxy, aralkyl and heterocyclyl is independently substituted by 0 to 5 $R^a$; $R^a$ is optionally selected from C1-C6 alkyl, halogen, hydroxyl, C1-C6 heteroalkyl, C1-C6 alkoxy, C1-C6 alkylamino, cycloalkyl, heterocycloalkyl or cyano.

In another preferred embodiment, $R_4$ is 5-membered heteroaryl, which can be independently substituted by 0 to 5 $R^a$; $R^a$ is optionally selected from C1-C6 alkyl, halogen, hydroxyl, C1-C6 heteroalkyl, C1-C6 alkoxy, C1-C6 alkylamino, cycloalkyl, heterocycloalkyl or cyano;

In another preferred embodiment, $R_4$ is selected from:

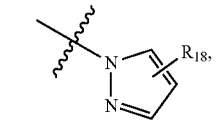

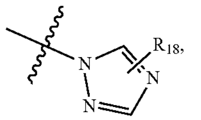

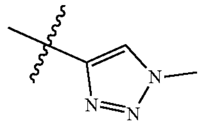

or

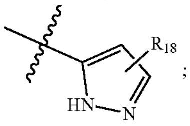

;

wherein $R_{18}$ is selected from halogen (preferably F) or C1-C6 alkyl.

In another preferred embodiment, m is 1.

In another preferred embodiment, $R_3$ is H, C1-C6 alkyl or C1-C6 alkoxy.

In another preferred embodiment, $R_2$ is H.

In another preferred embodiment, $R_1$, $X_3$, W, Q1, $X_5$, $X_6$, $R_2$, $R_3$, $R_4$, A, m and n are the specific group corresponding to each specific compound in the Example.

In another preferred embodiment, $R_1$, $X_1$, $X_2$, $X_3$, Q1, Q2, $X_5$, $X_6$, $R_2$, $R_3$, $R_4$, A, m and m are the specific group corresponding to each specific compound in the Example.

In another preferred embodiment,

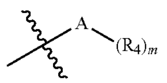

moiety is

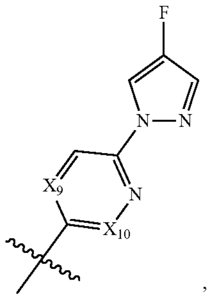

, where $X_9$ and $X_{10}$ are each independently selected from N or $CR_5$, wherein, $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is independently substituted by 0 to 5 $R^a$; $R^a$ is optionally selected from C1-C6 alkyl, halogen, hydroxyl, C1-C6 heteroalkyl, C1-C6 alkoxy, C1-C6 alkylamino, cycloalkyl, heterocycloalkyl or cyano.

In another preferred embodiment, the compound of formula I', or the pharmaceutically acceptable salt, stereoisomer, solvate or prodrug thereof has the structure represented by formula 5' or formula 6'

5'

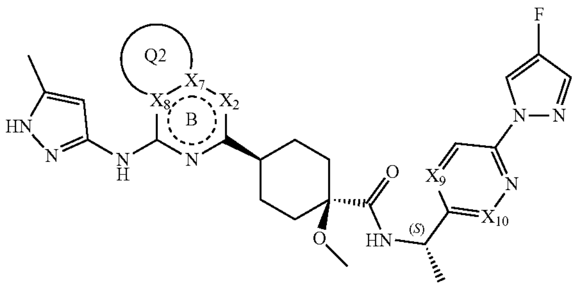

6'

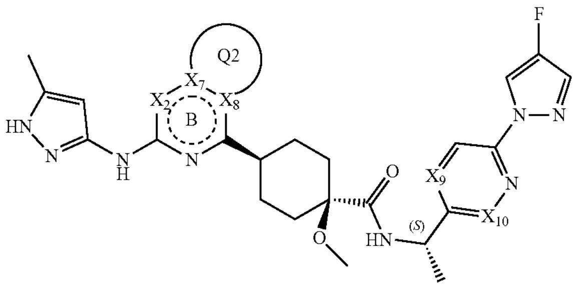

wherein $X_2$, $X_7$, $X_8$, $X_9$ and $X_{10}$ are each independently selected from N or CRS, and at least one of $X_7$ and $X_8$ is N, $R_5$ is each independently selected from hydrogen, deuterium, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is each independently substituted by 0 to 5 $R^a$; $R^a$ is optionally selected from deuterium, C1-C6 alkyl, halogen, hydroxyl. C1-C6 heteroalkyl, C1-C6 alkoxy, C1-C6 alkylamino, cycloalkyl, heterocycloalkyl or cyano;

ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S; any hydrogen atom on the ring Q2 can be substituted by deuterium, hydroxyl, halogen, cyano, ester, amido, ketocarbonyl, amino, C1-C6 alkyl, deuterated C1-C6 alkyl, C1-C6 alkylhydroxyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, the compound of formula I', or the pharmaceutically acceptable salt, stereoisomer, solvate or prodrug thereof has a structure represented by formula 5' wherein,

5'

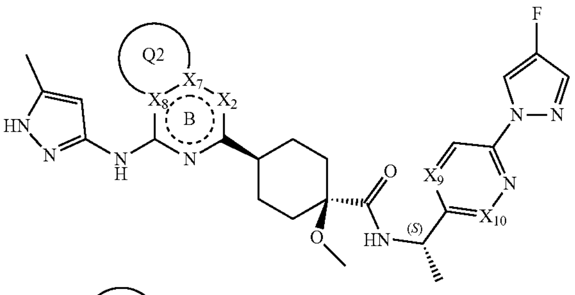

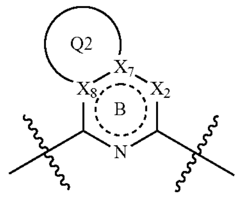

moiety is selected from

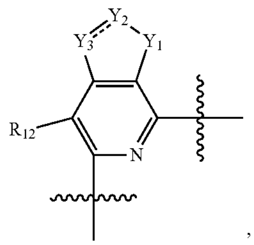

,

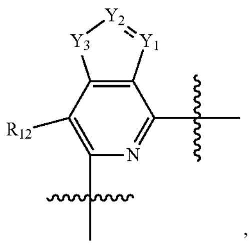

,

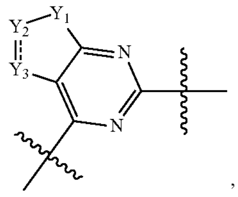

, or

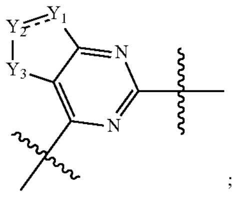

;

wherein, ═ is double bond, each $Y_1$, $Y_2$, and $Y_3$ is independently selected from N, $NR_{17}$, $CR_{13}$;

$R_{12}$ is independently selected from H, deuterium, halogen, C1-C6 alkyl, C1-C6 alkoxy, C1-C6 alkylamino, nitro, cyano, amino;

$R_{17}$ is independently selected from deuterium, C1-C6 alkyl, deuterated C1-C6 alkyl, C1-C6 alkylhydroxyl, C1-C6 haloalkyl;

$R_{13}$ is selected from H, halogen, C1-C6 alkyl, deuterated C1-C6 alkyl, C1-C6 haloalkyl, C1-C6 alkoxy, C1-C6 alkylamino, nitro, cyano, amino;

$X_9$ and $X_{10}$ are each independently $CR_5$;

$R_5$ is selected from hydrogen, deuterium, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is independently substituted by 0 to 5 $R^a$; $R^a$ is optionally selected from deuterium, C1-C6 alkyl, halogen, hydroxyl, C1-C6 heteroalkyl, C1-C6 alkoxy, C1-C6 alkylamino, cycloalkyl, heterocycloalkyl or cyano.

In another preferred embodiment,

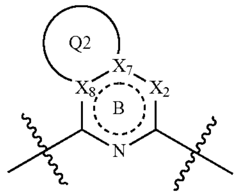

(or

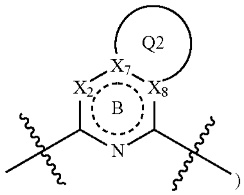

)

moiety is selected from

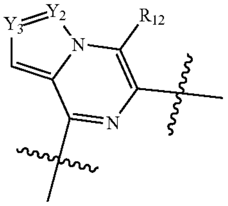

,

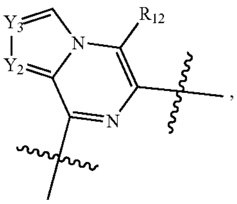

,

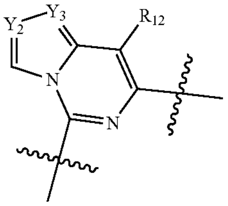

,

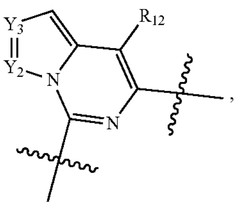

,

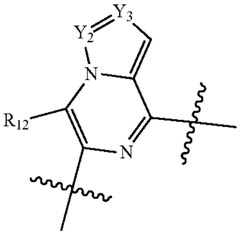

,

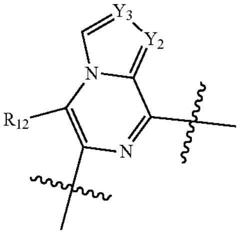

,

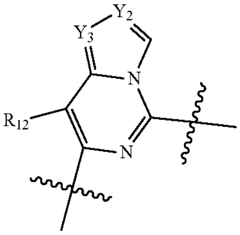

,

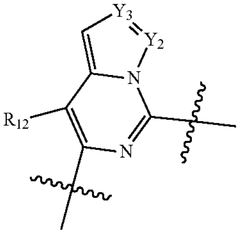

,

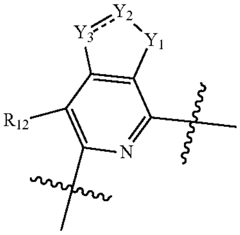

,

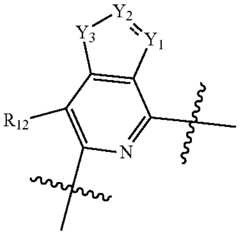

,

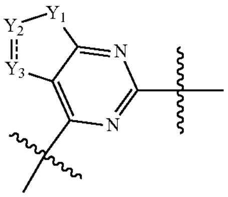

,

-continued

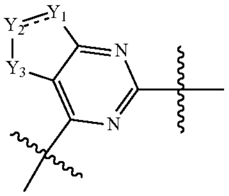

, $Y_1$, $Y_2$, $R_3$ and $R_{12}$ are as defined above.

In another preferred embodiment, in the formula 5, $X_9$ and $X_{10}$ are CH.

In another preferred embodiment, the compound, or the pharmaceutically acceptable salt, stereoisomer, solvate or prodrug thereof can be optionally selected from the following compound:

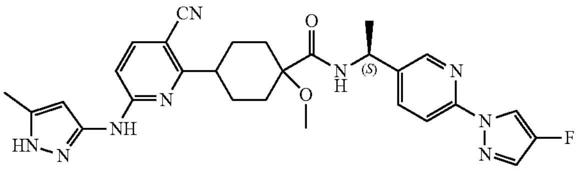

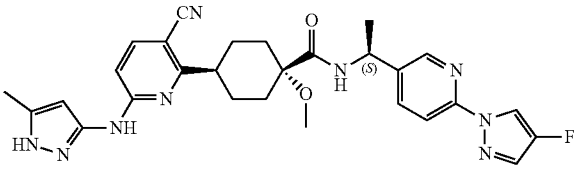

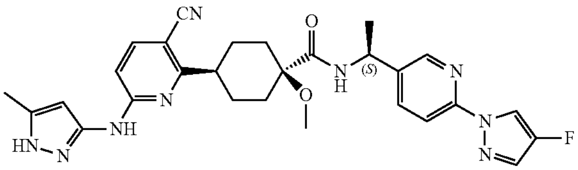

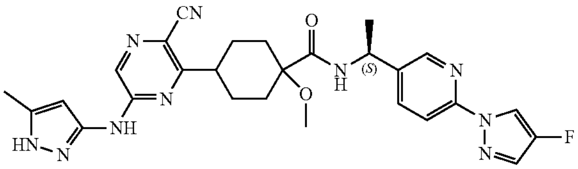

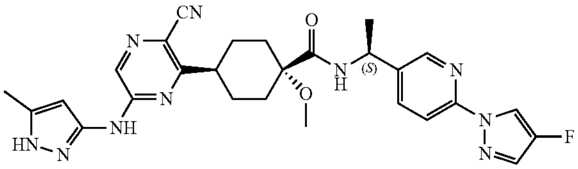

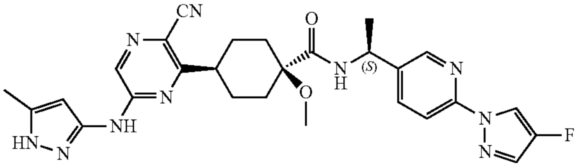

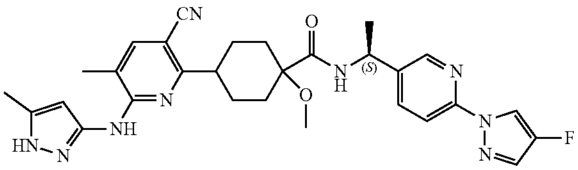

-continued
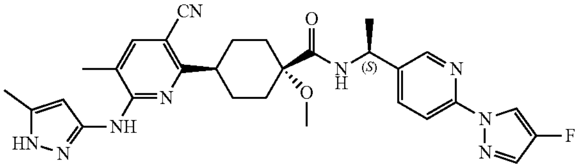
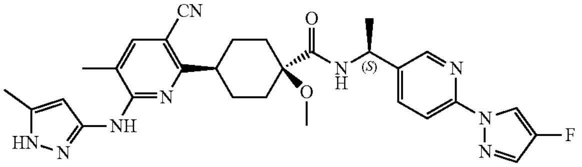
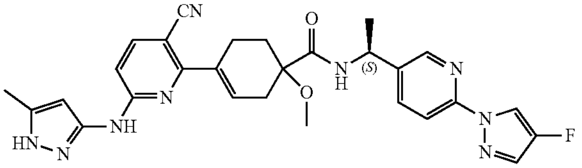
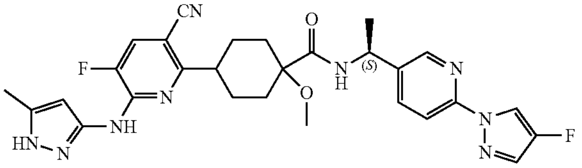
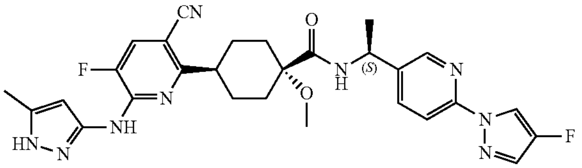
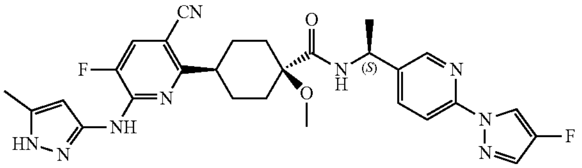
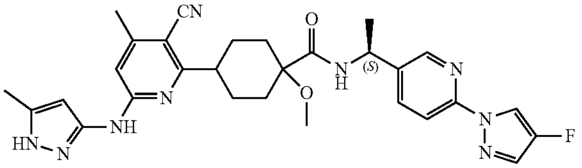
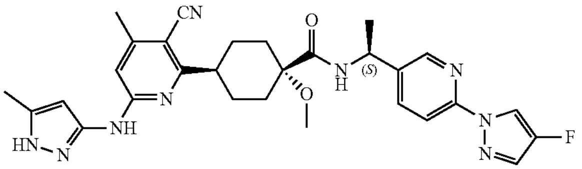
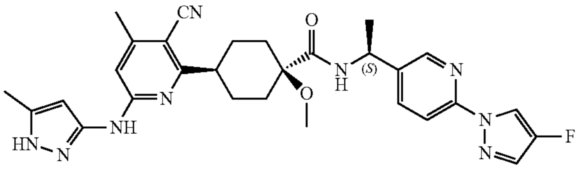
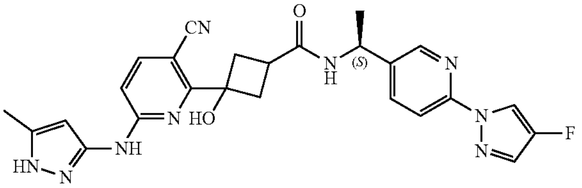
-continued
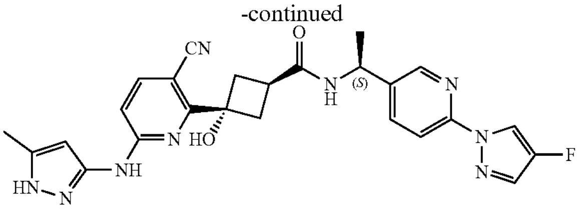
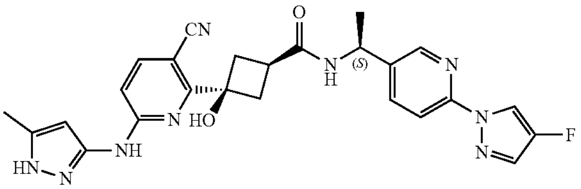
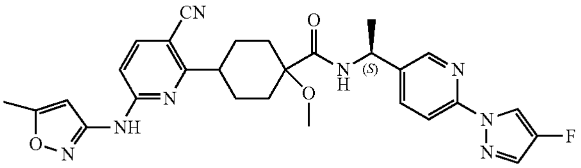
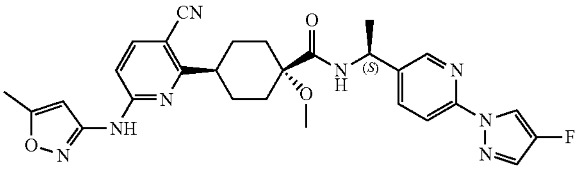
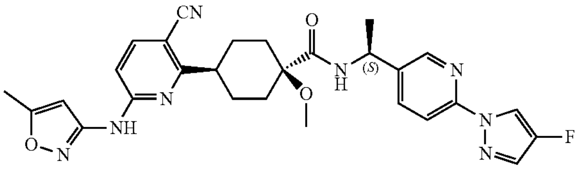
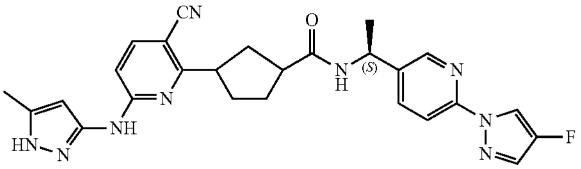
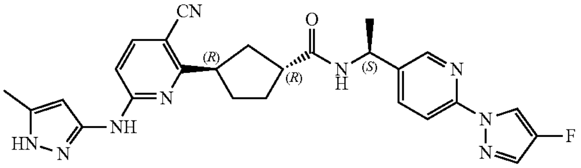
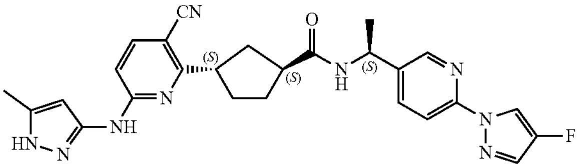
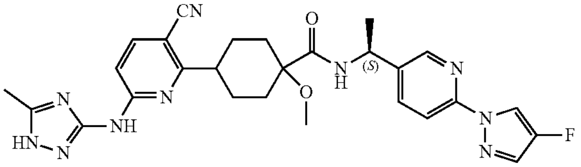
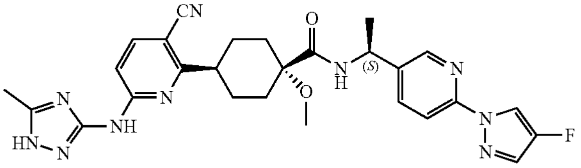

-continued
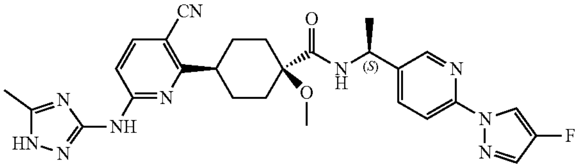
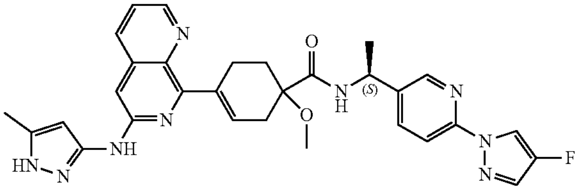
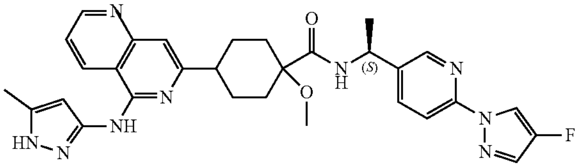
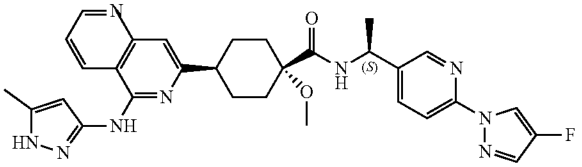
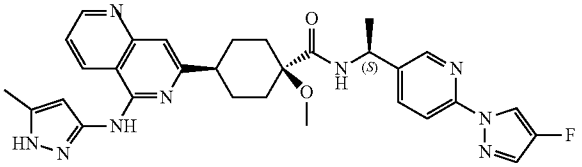
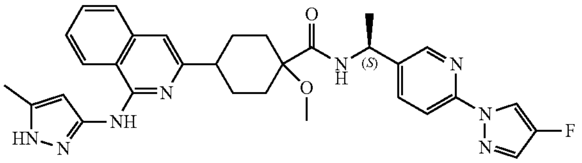
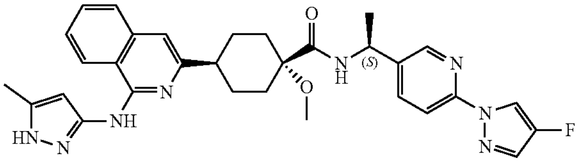
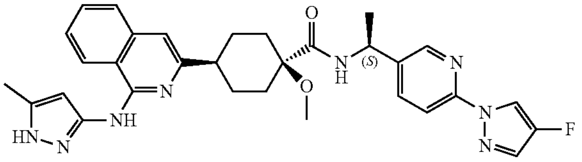
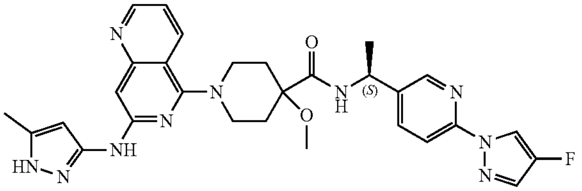
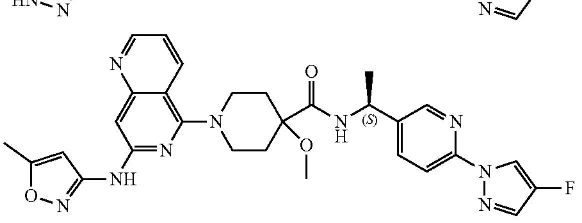
-continued
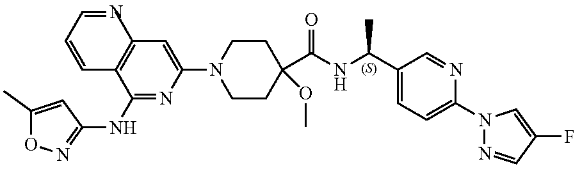
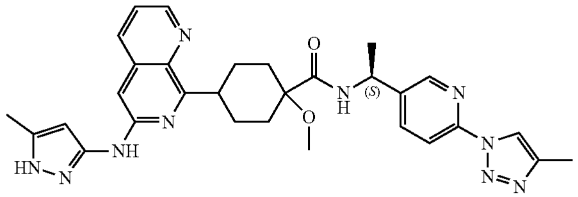
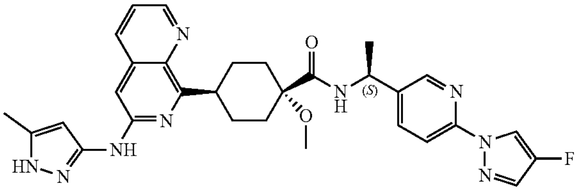
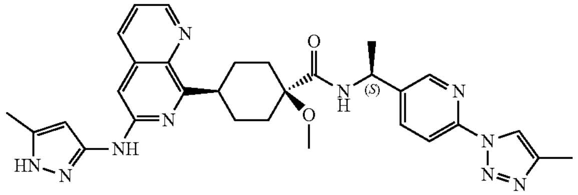
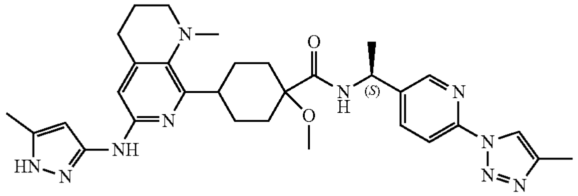
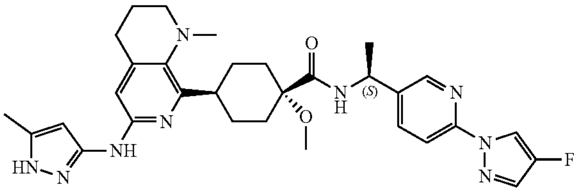
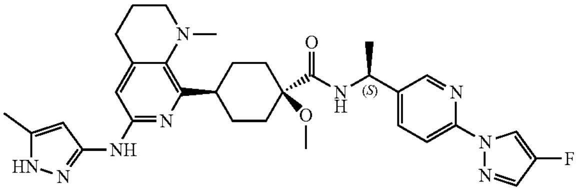
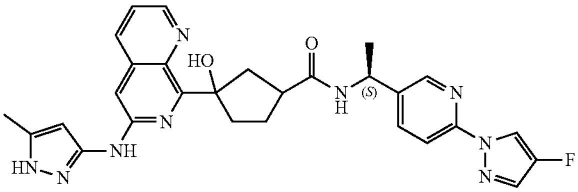
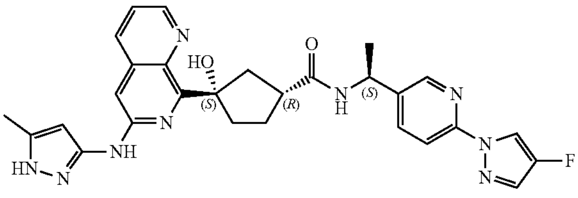

-continued
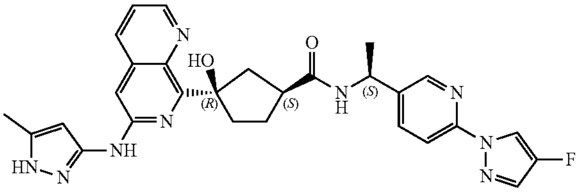
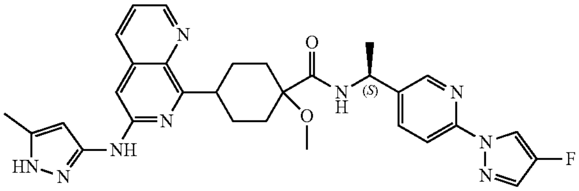
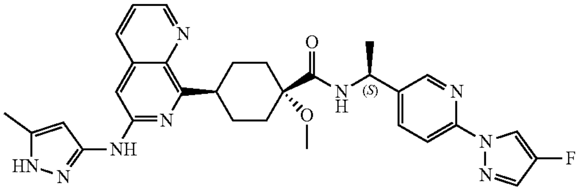
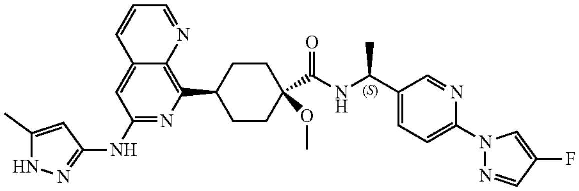
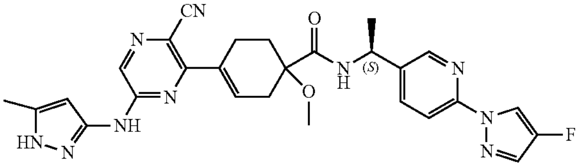
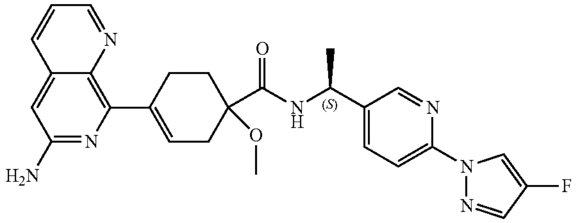
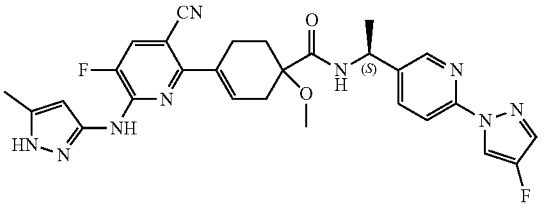
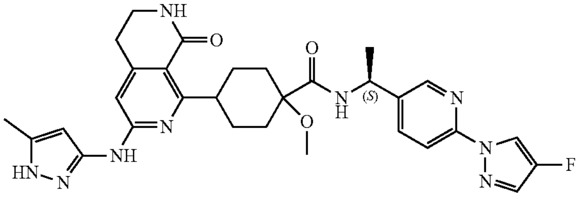
-continued
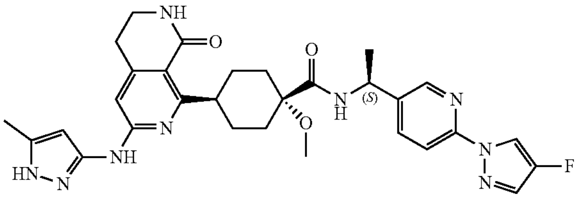
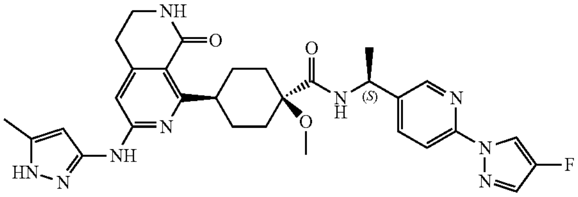
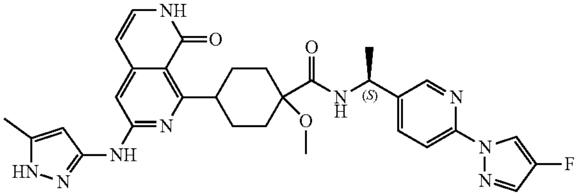
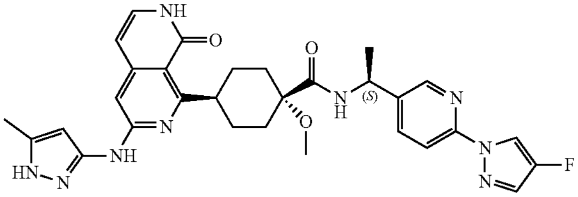
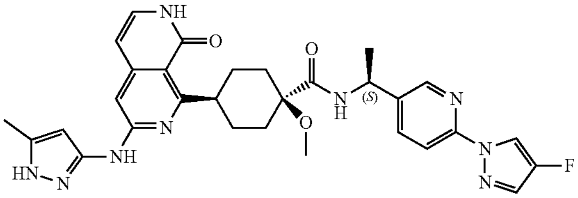
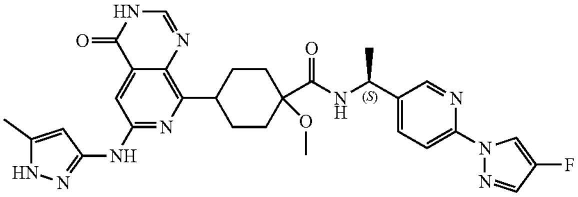
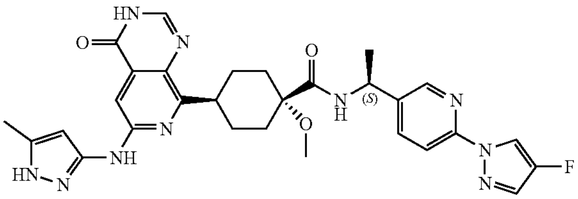
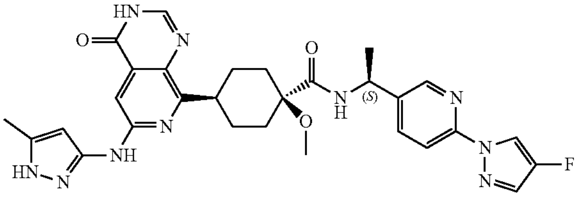

-continued
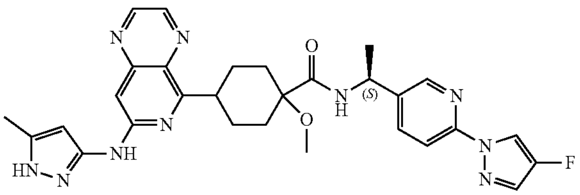
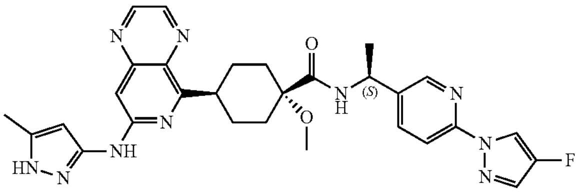
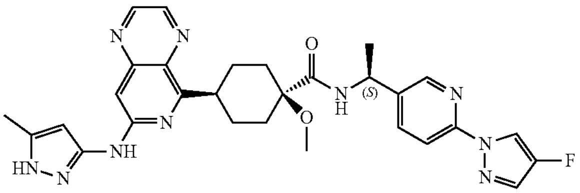
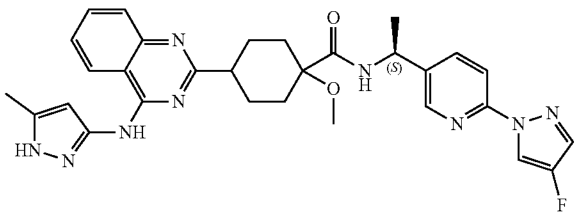
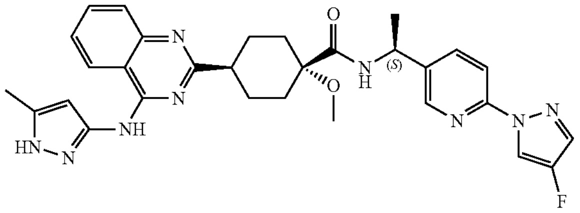
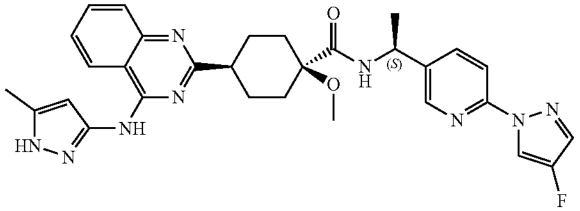
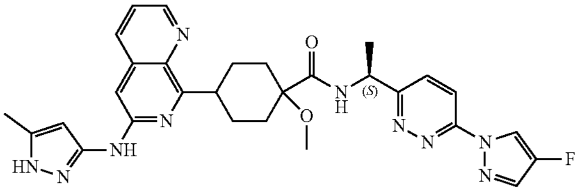
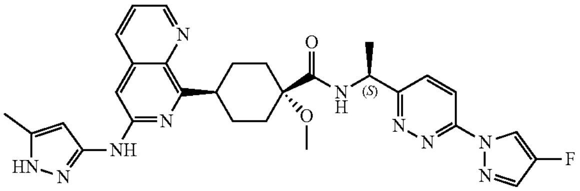
-continued
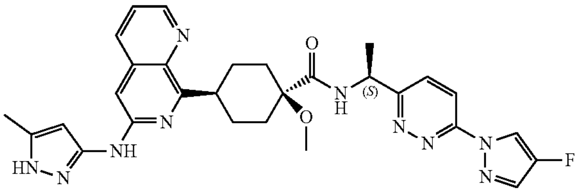
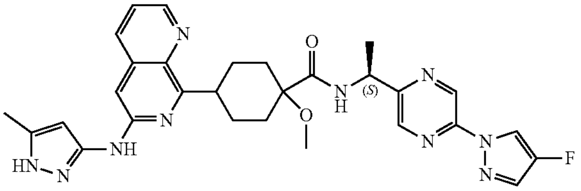
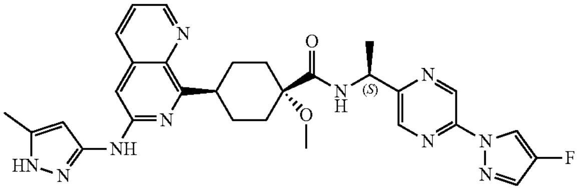
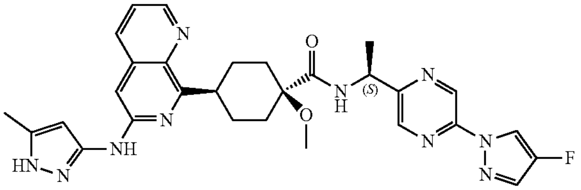
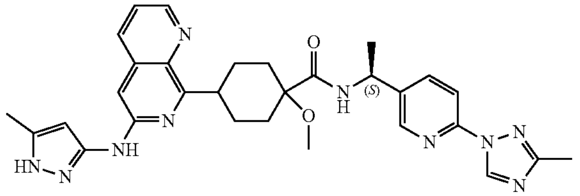
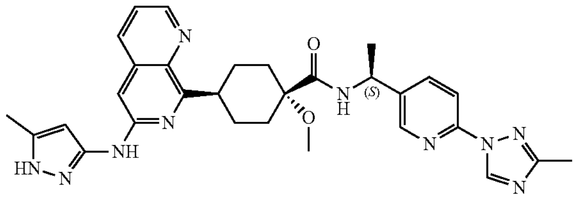
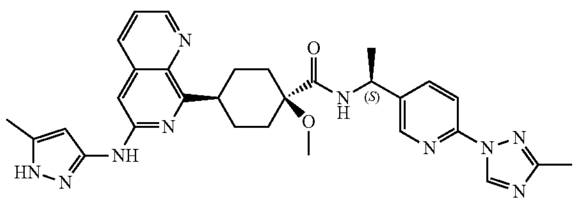
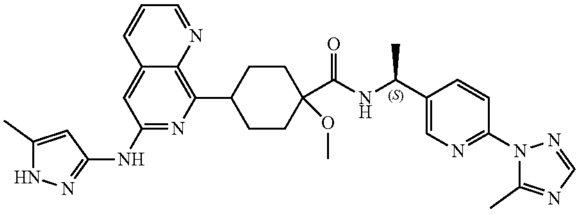

-continued
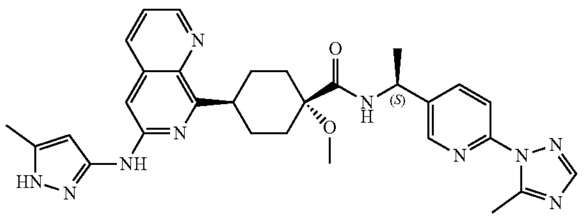
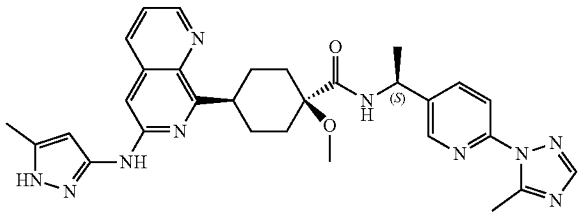
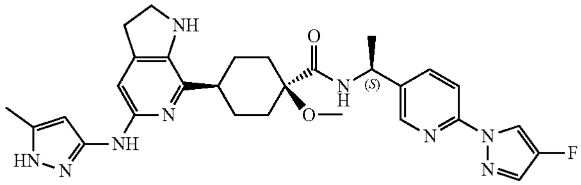
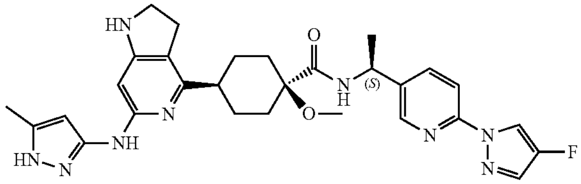
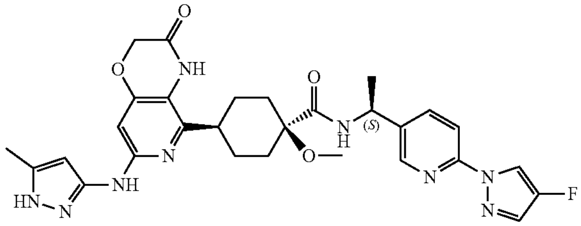
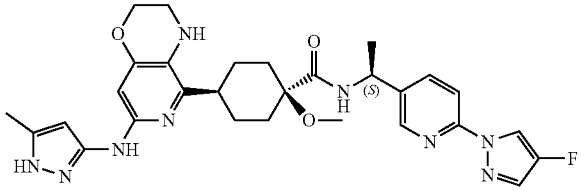
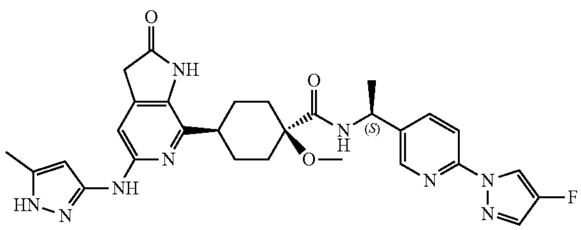
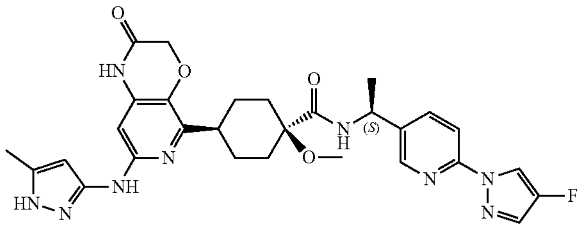
-continued
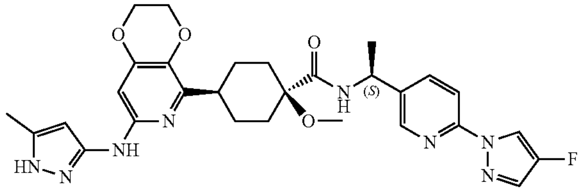
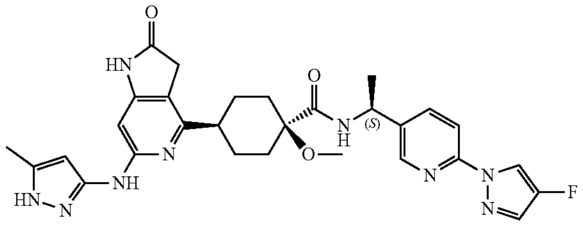
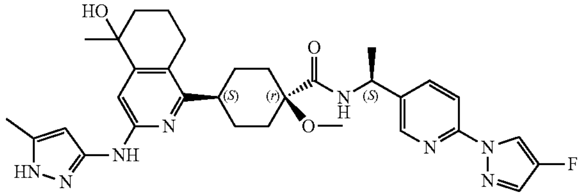
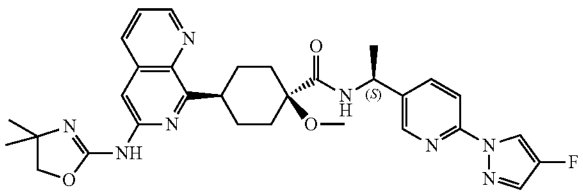
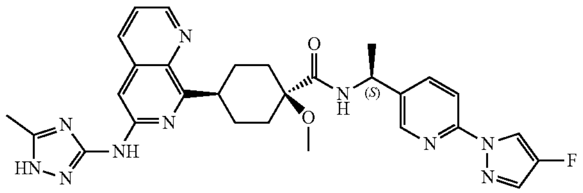
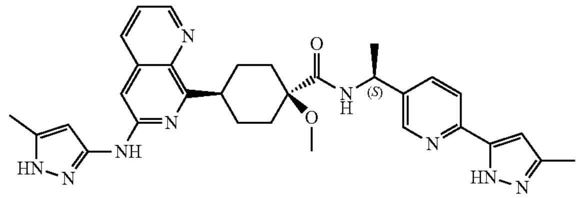
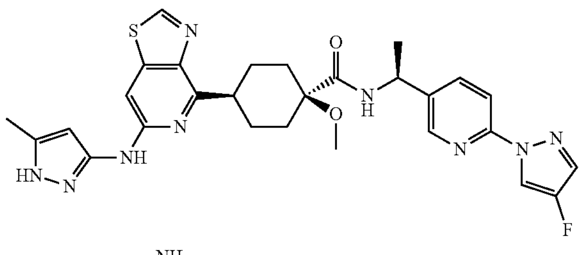
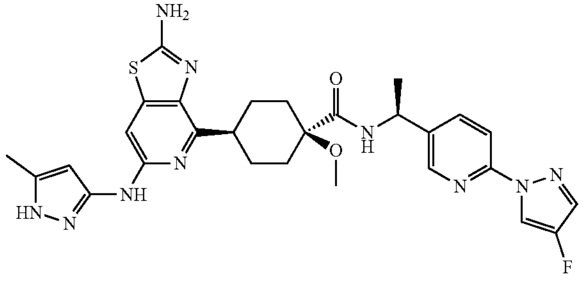

-continued
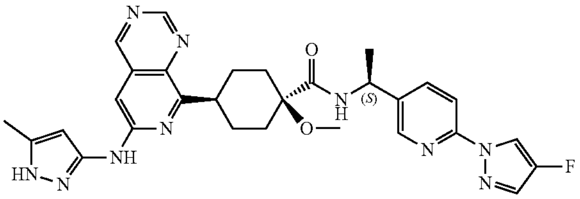
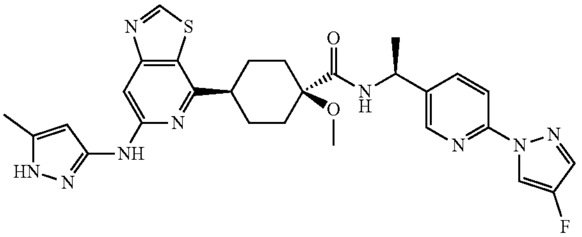
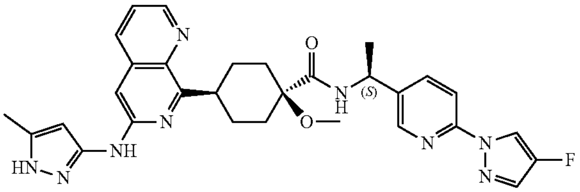
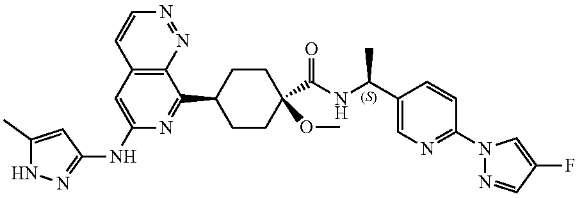
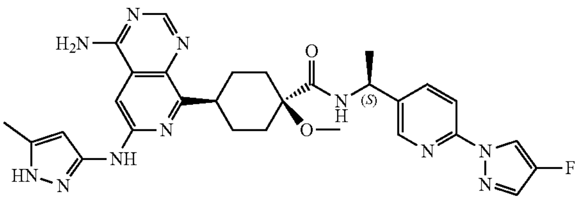
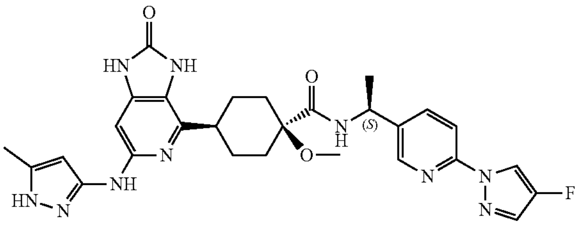
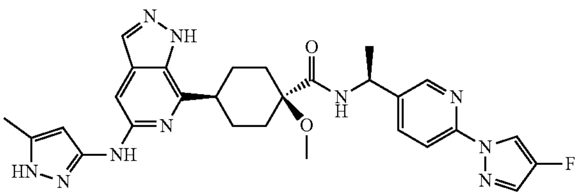
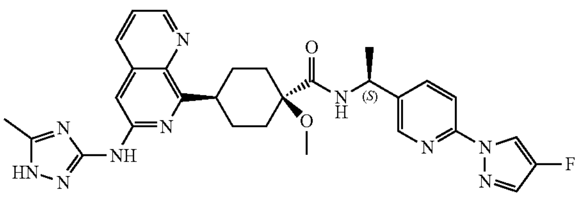
-continued
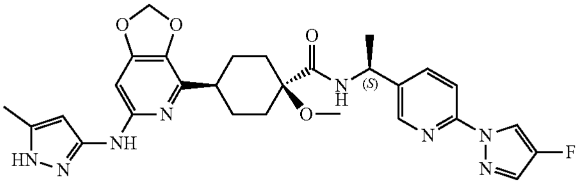
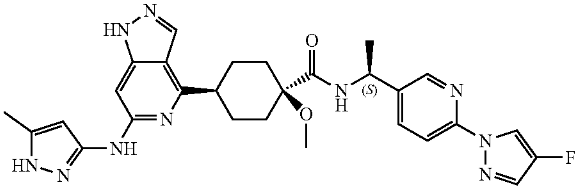
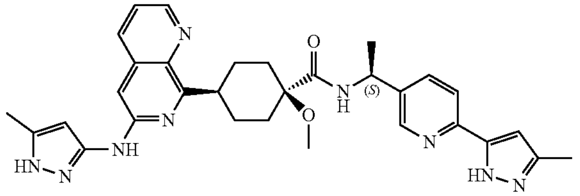
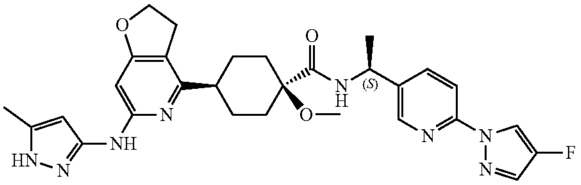
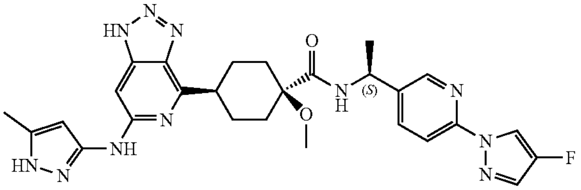
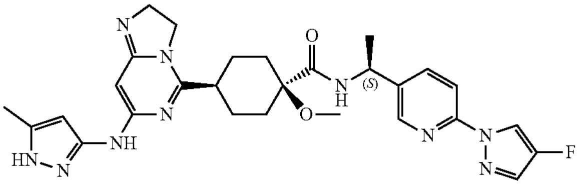
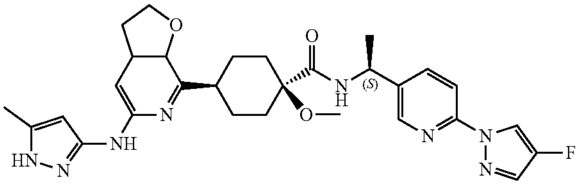
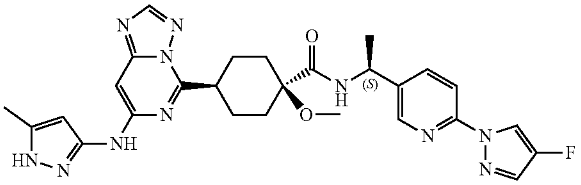
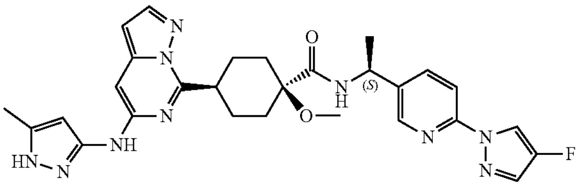

-continued
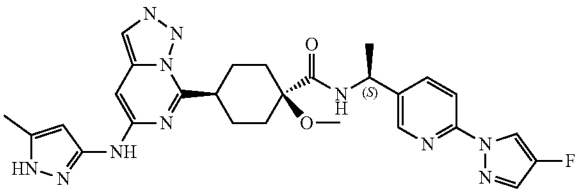
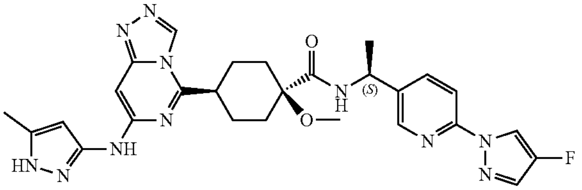
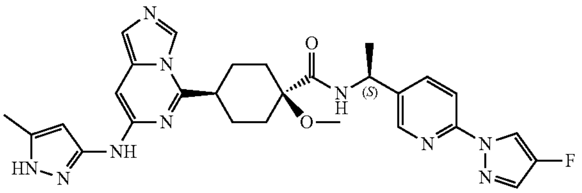
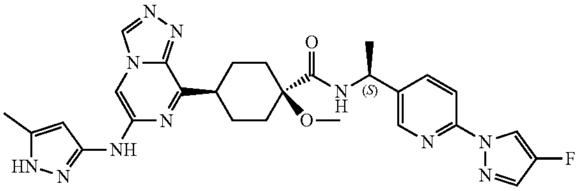
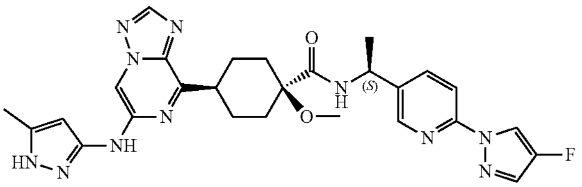
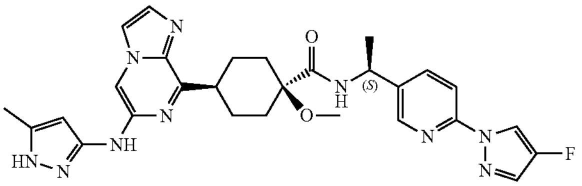
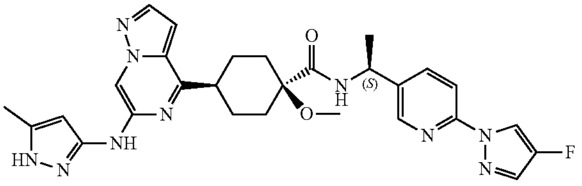
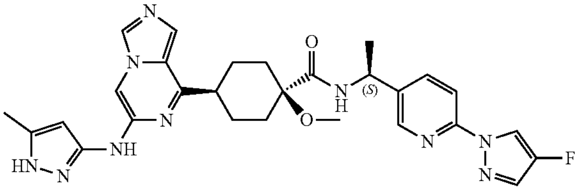
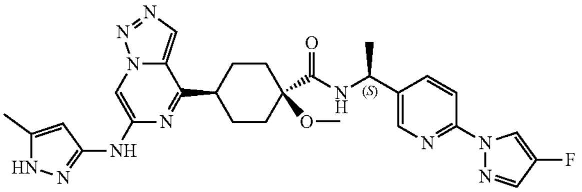
-continued
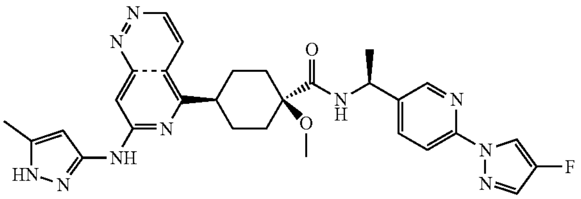
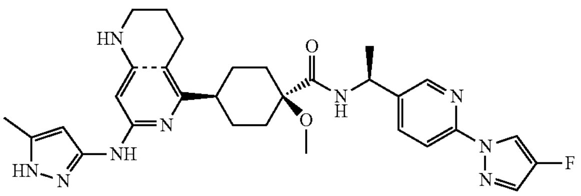
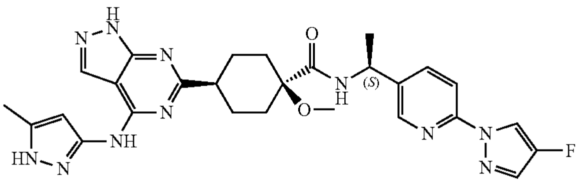
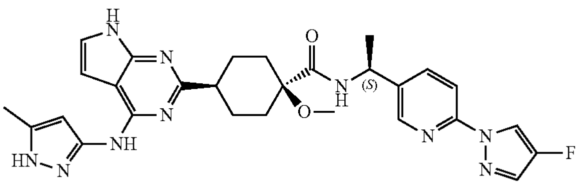
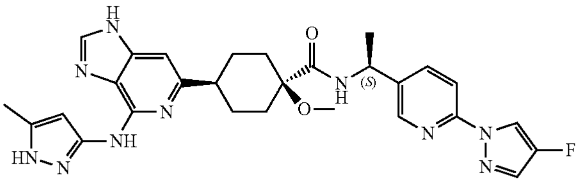
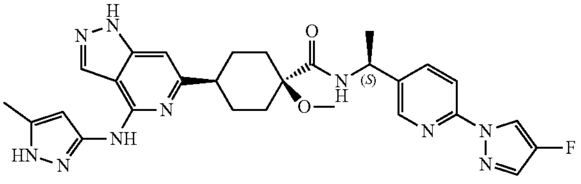
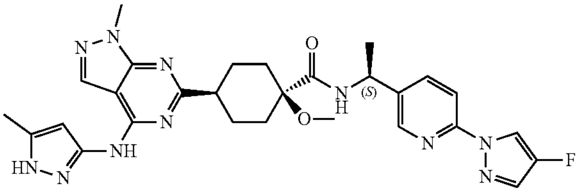
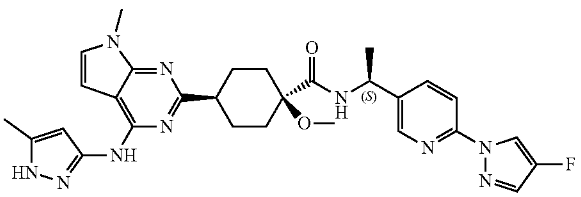
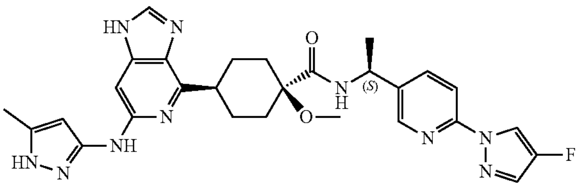

-continued
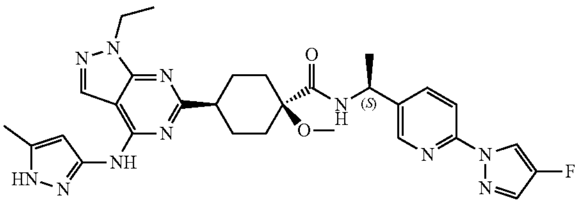
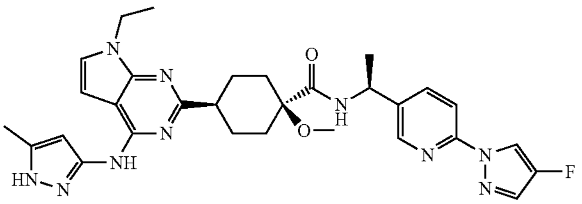
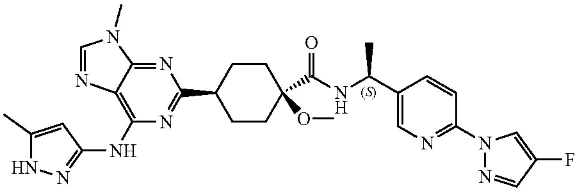
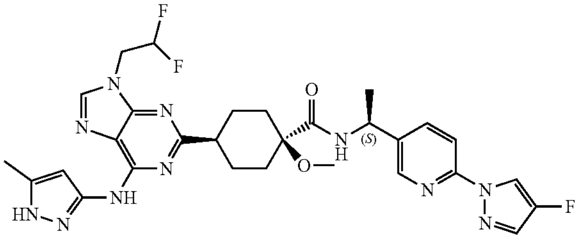
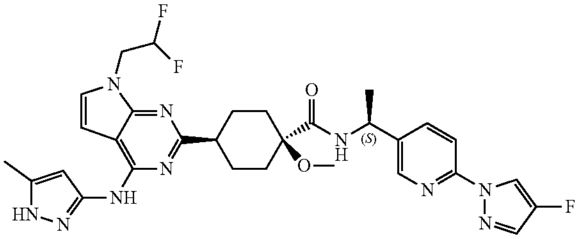
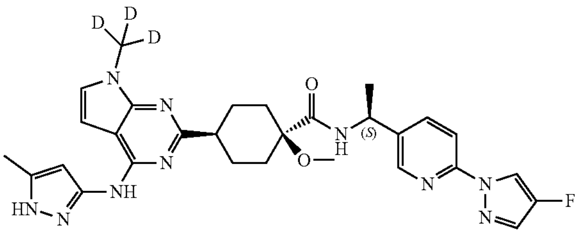
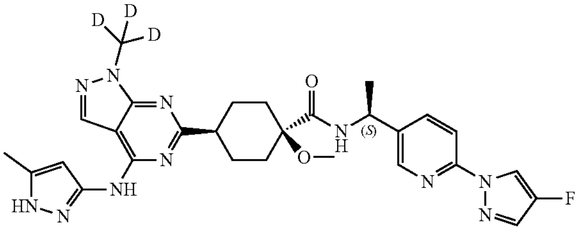
-continued
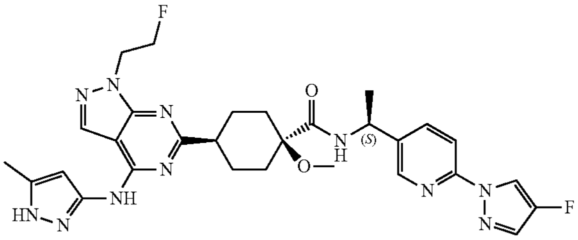
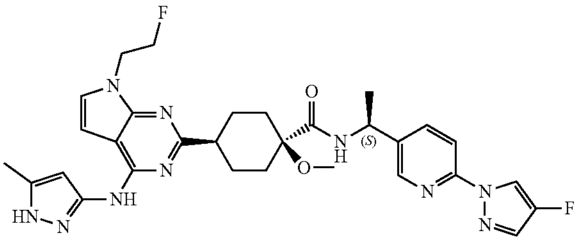
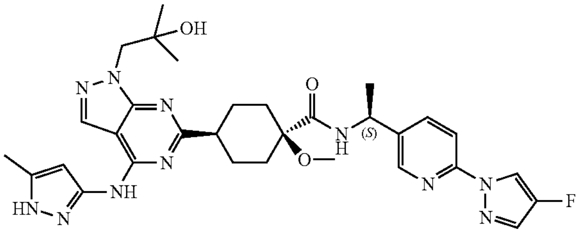
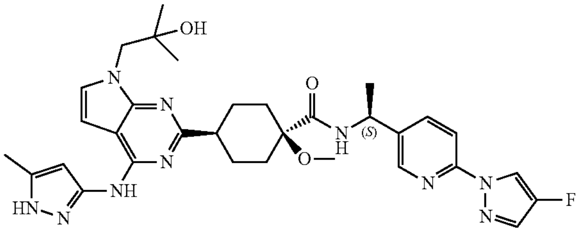
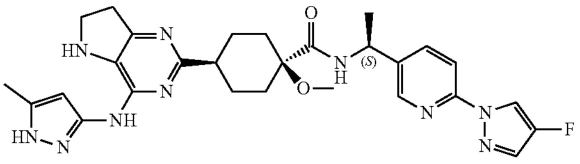
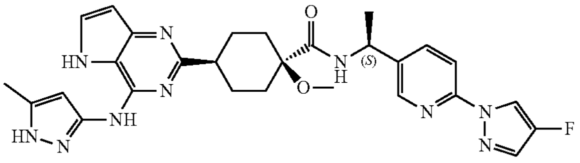
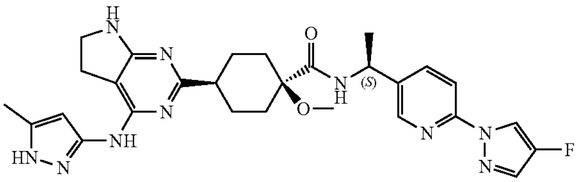
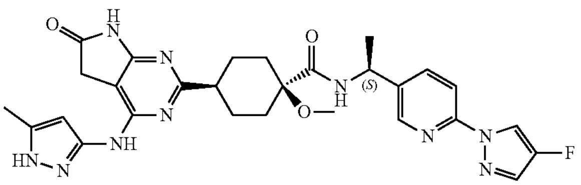

-continued
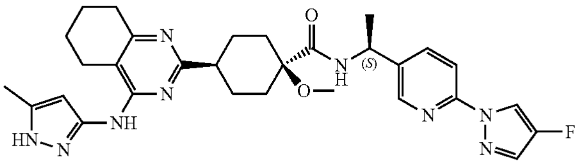
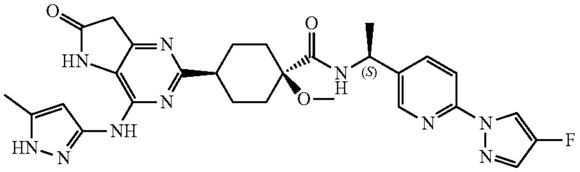
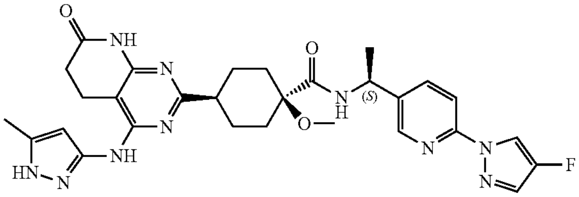
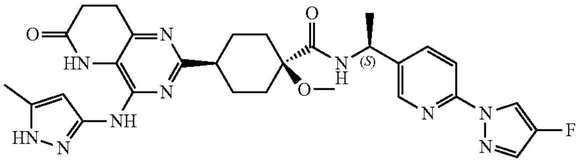
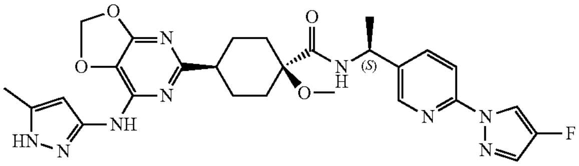
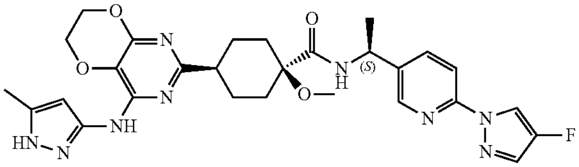
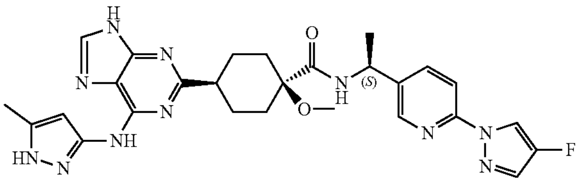
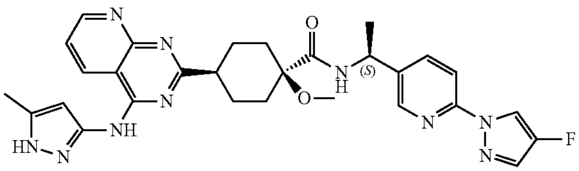
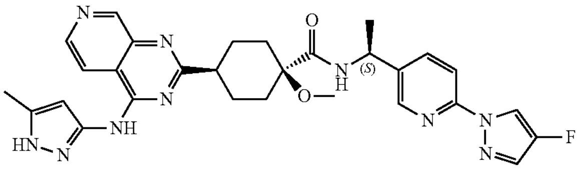
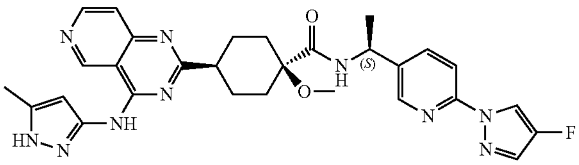
-continued
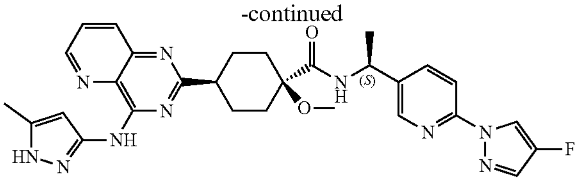
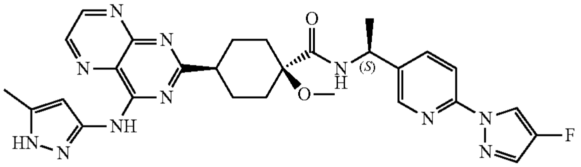
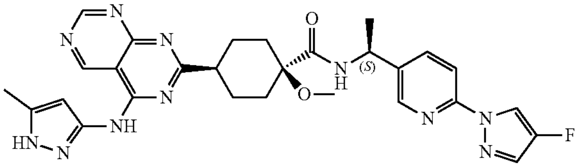
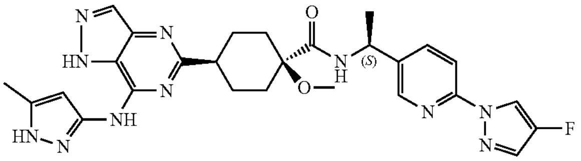
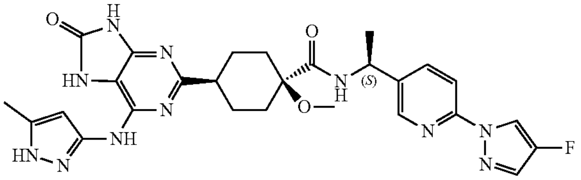
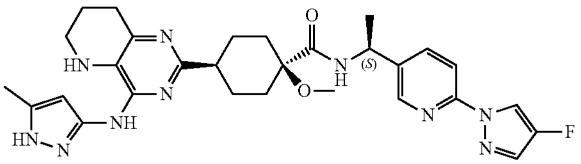
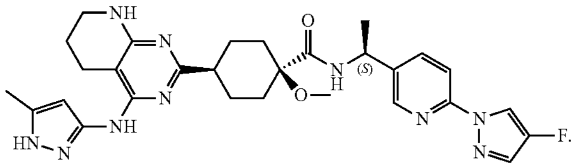
In another preferred embodiment, the compound has a structure shown in formula I
I
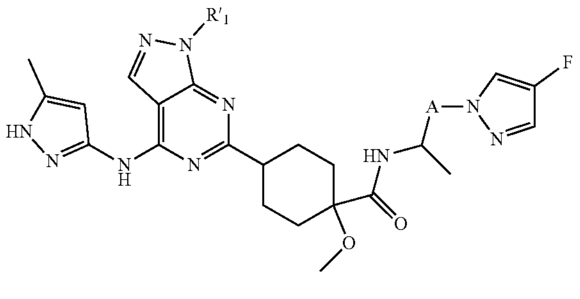
wherein,
R'$_1$ is optionally selected from hydrogen, C1-C6 alkyl, C1-C6 deuterated alkyl, C1-C6 alkoxy, C1-C6 alkylamino, C3-C6 cycloalkyl, C1-C6 heteroalkyl, or 3-6 membered heterocyclyl, wherein the alkyl, deuterated alkyl, alkoxy, alkylamino, cycloalkyl, heteroalkyl and heterocyclyl are optionally and independently substituted with 0 to 5 $R^a$;

A is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on A ring can be is substituted by the following substituents; deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl;

$R^a$ is optionally selected from C1-C6 alkyl, halogen, hydroxyl, amino, C1-C6 heteroalkyl, C1-C6 alkoxy, C1-C6 alkylamino, cycloalkyl, heterocycloalkyl or cyano; In another preferred embodiment, A ring is selected from substituted or unsubstituted 5-6 membered heteroaryl; wherein, any hydrogen atom on the A ring can be substituted by the following substituents: C1-C6 alkyl, halogen, hydroxyl, amino, C1-C6 heteroalkyl, C1-C6 alkoxy, C1-C6 alkylamino, cycloalkyl, heterocycloalkyl or cyano.

In another preferred embodiment, A ring is selected from the substituted or unsubstituted group consisting of imidazolyl, thiazolyl, oxazolyl, pyridyl, pyrazinyl, pyrimidyl or pyridazinyl, wherein any hydrogen atom on the A ring can be independently substituted by the following substituents: C1-C6 alkyl, halogen, hydroxyl, amino, C1-C6 heteroalkyl, C1-C6 alkoxy, C1-C6 alkylamino, cycloalkyl, heterocycloalkyl or cyano.

In another preferred embodiment, the compound has a structure shown in formula II-1 or formula III-1:

II-1

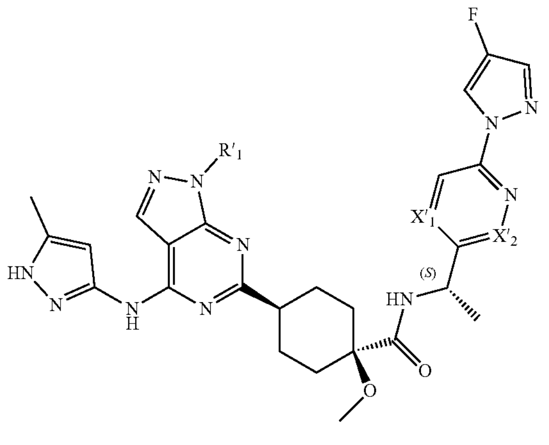

-continued

III-1

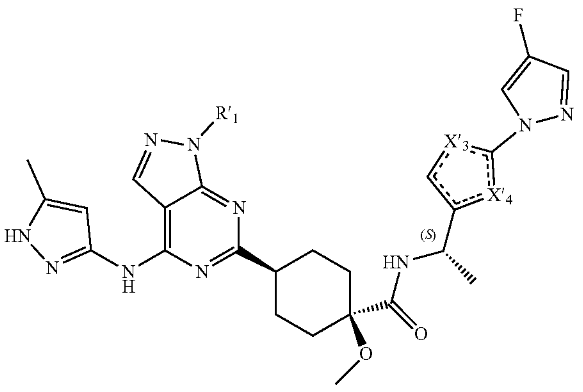

wherein, ⎓ represents single bond or double bond;

$X'_1$ and $X'_2$ are each independently selected from N or $CR_5$;

$X'_1$ and $X'_4$ are each independently selected from N or S;

$R_5$ is each independently optionally selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is each independently substituted by 0 to 5 $R^a$; $R^a$ is optionally selected from C1-C6 alkyl, halogen, hydroxyl, amino, C1-C6 heteroalkyl, C1-C6 alkoxy, C1-C6 alkylamino, cycloalkyl, heterocycloalkyl or cyano;

$R'_1$ is as defined above.

In another preferred embodiment, $X'_1$ is N, $X'_2$ is CH.

In another preferred embodiment, both $X'_1$ and $X'_2$ are CH.

In another preferred embodiment, A ring is substituted or unsubstituted group selected from the group consisting of

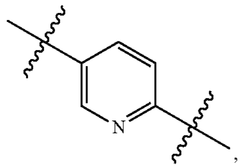,
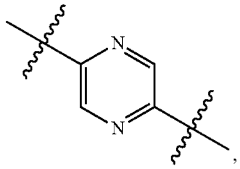,
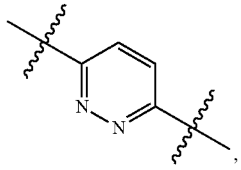,
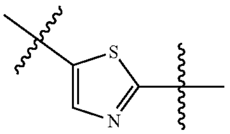 and
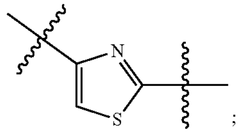;

wherein the "substituted" means being substituted by one or more groups selected from the group consisting of C1-C6 alkyl, halogen, hydroxyl, amino, C1-C6 heteroalkyl, C1-C6 alkoxy, C1-C6 alkylamino, cycloalkyl, heterocycloalkyl and cyano.

In another preferred embodiment. A ring is selected from the substituted or unsubstituted group consisting of

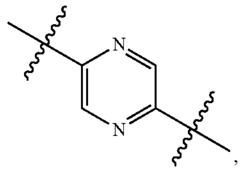,
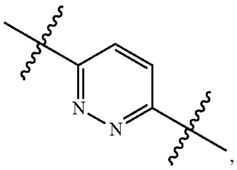,
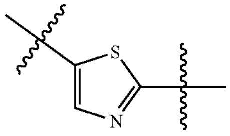 and 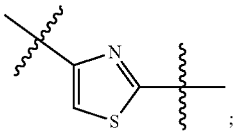;

wherein the "substituted" means being substituted by one or more groups selected from the group consisting of C1-C6 alkyl, halogen, hydroxyl, amino, C1-C6 heteroalkyl, C1-C6 alkoxy, C1-C6 alkylamino, cycloalkyl, heterocycloalkyl and cyano.

In another preferred embodiment,

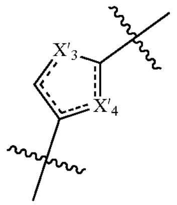 is 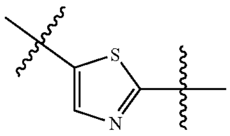 or

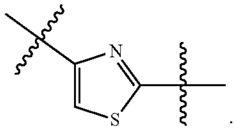.

In another preferred embodiment, R'$_1$ is selected from H, C1-C6 alkyl, C1-C6 deuterated alkyl, C1-C6 haloalkyl, C3-C6 cycloalkyl, 3-6 membered heterocyclyl. C1-C6 heteroalkyl, C1-C6 alkyl hydroxyl, C3-C6 halocycloalkyl, $Me_3SiCH_2CH_2OCH_2$—, C3-C6 cycloalkyl $CH_2$—, or 3-6 membered heterocyclyl $CH_2$—.

In another preferred embodiment, the compound can be selected from the compounds shown in the following structures:

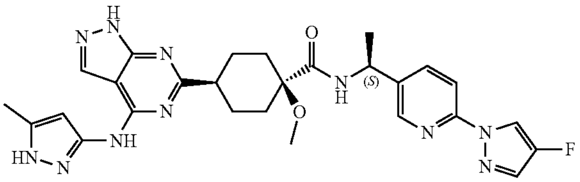

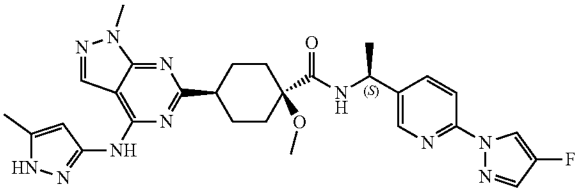

-continued

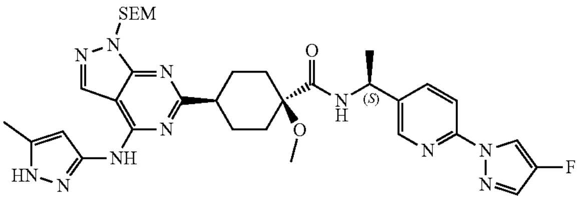

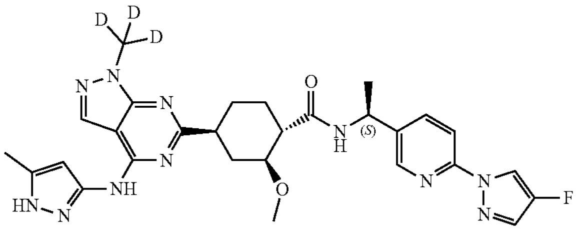

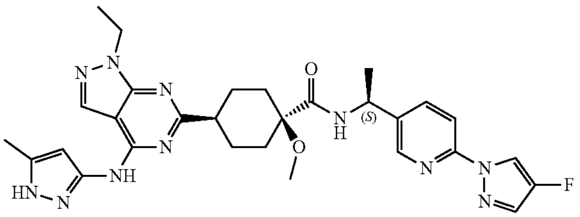

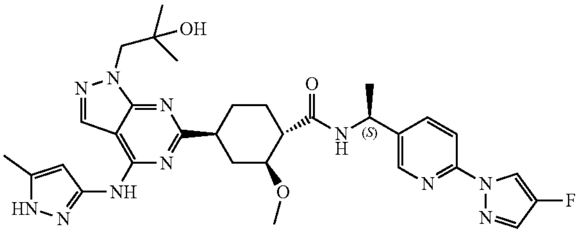

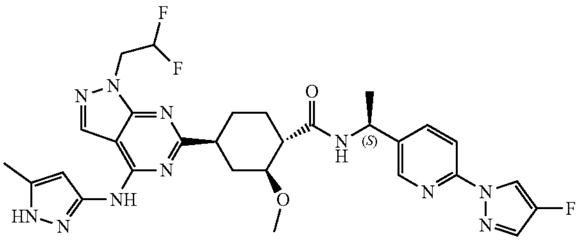

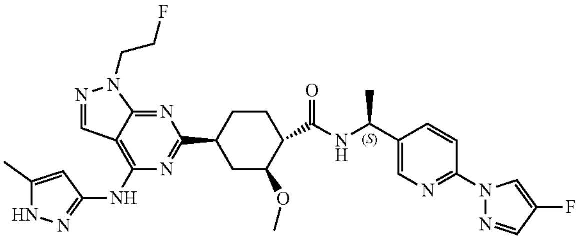

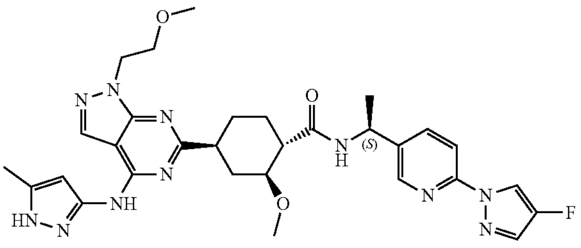

-continued
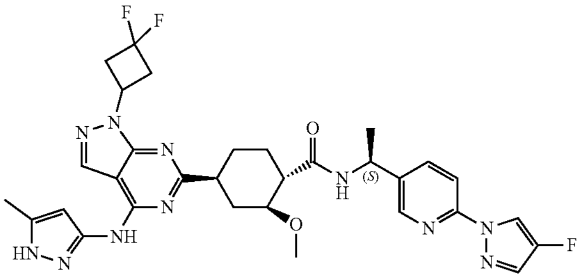
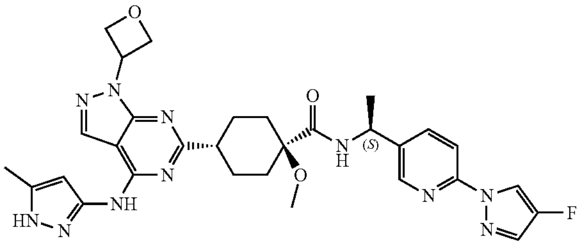
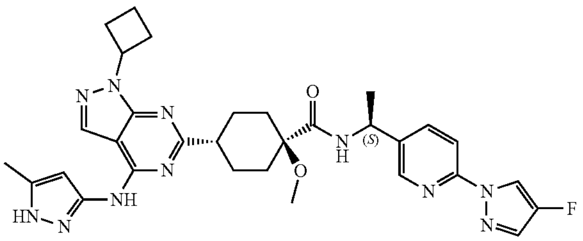
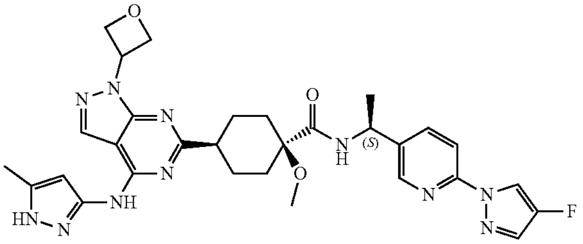
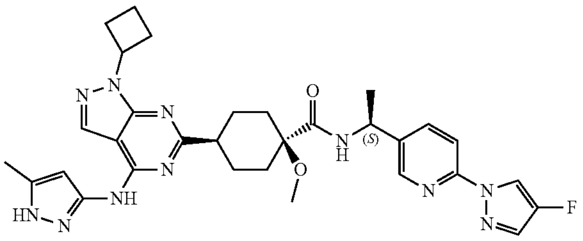
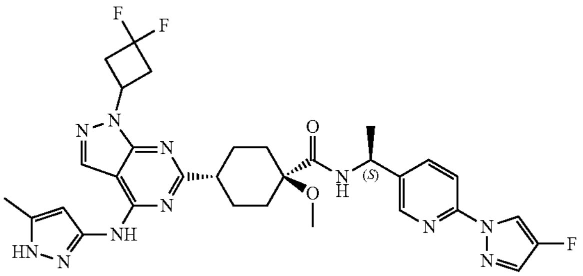
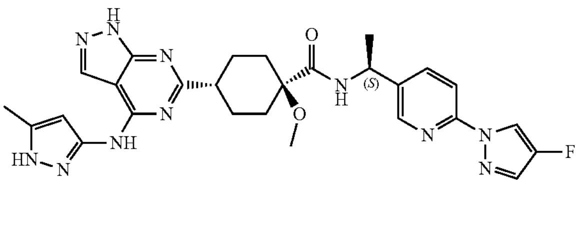
-continued
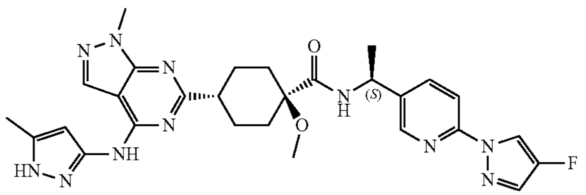
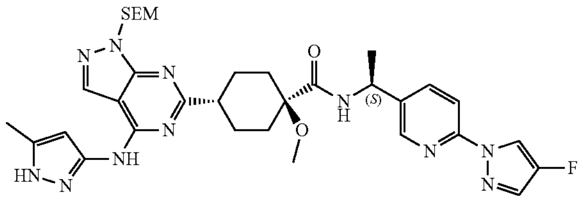
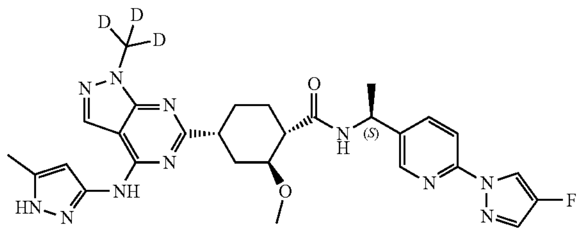
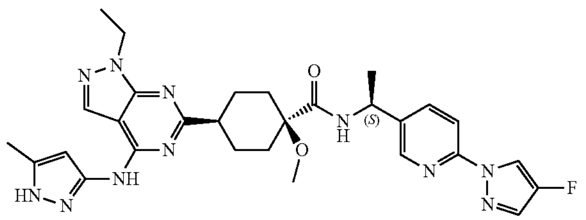
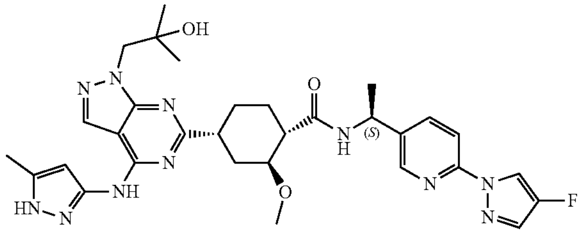
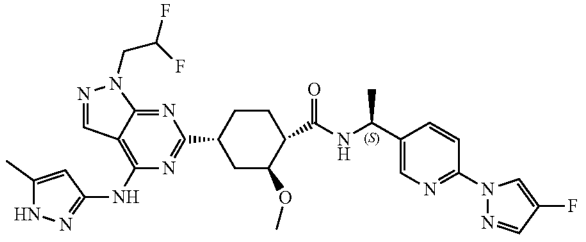
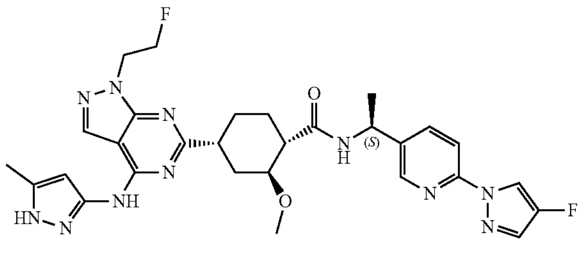

-continued
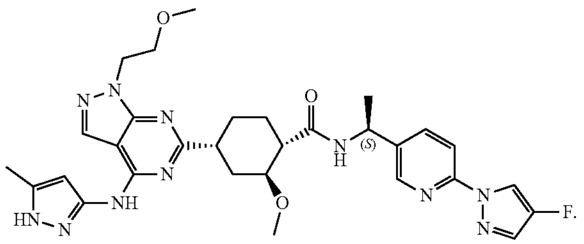
In another preferred embodiment, the compound is selected from the compounds shown in following structures:
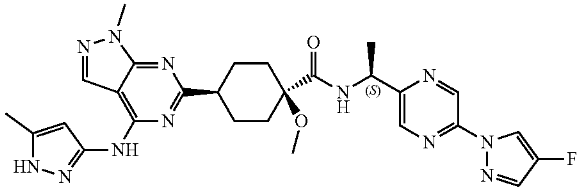
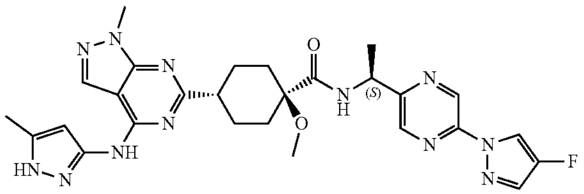
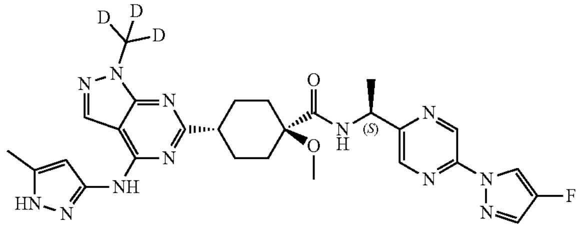
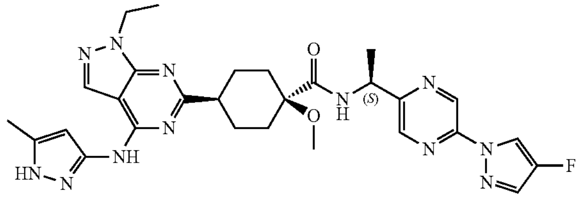
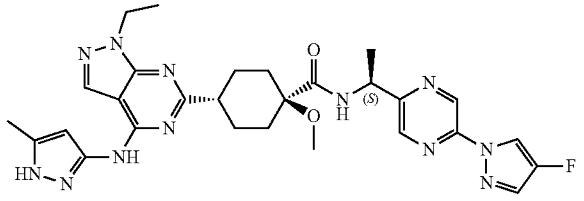
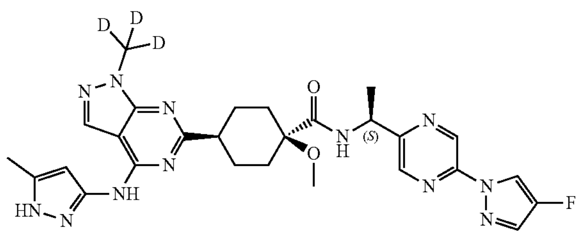
-continued
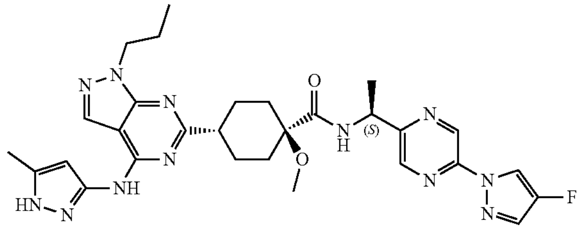
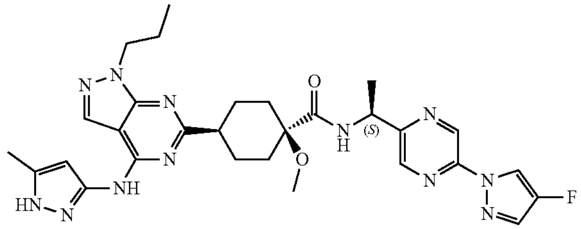
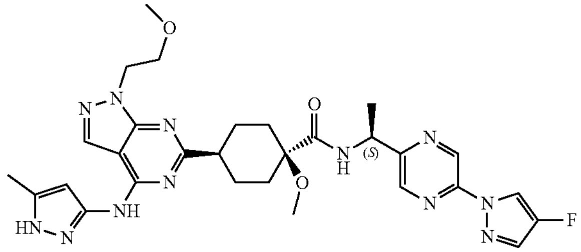
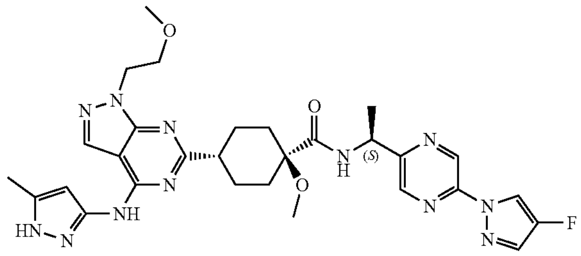
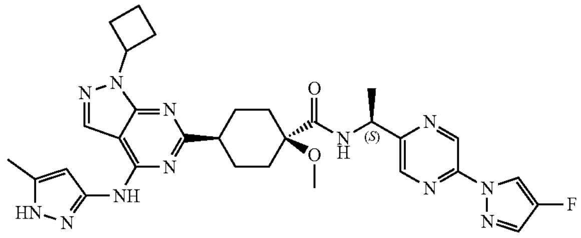
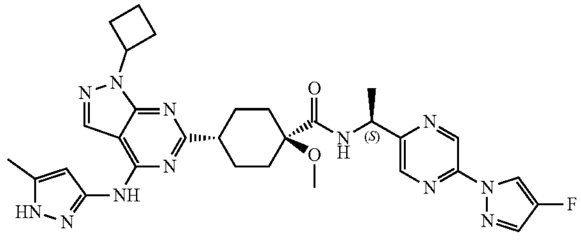
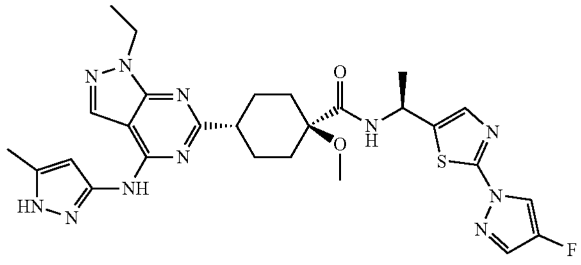

-continued
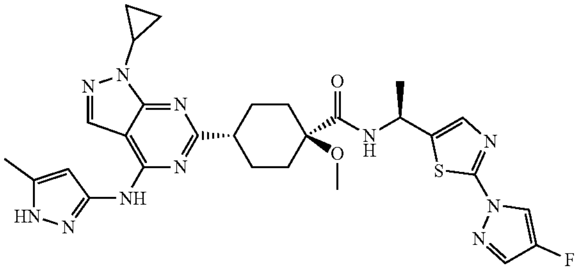
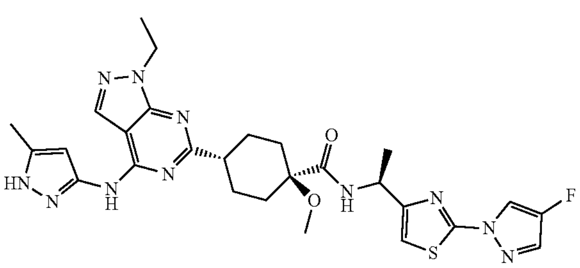
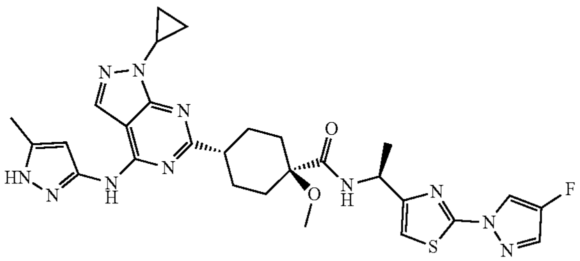
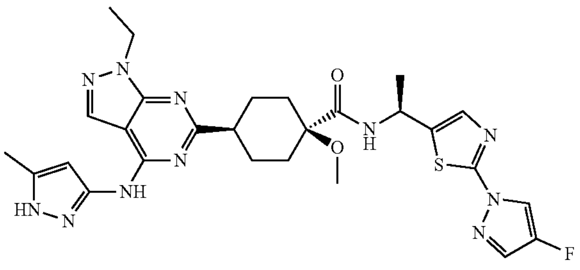
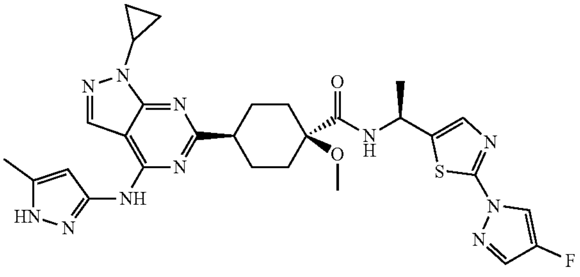
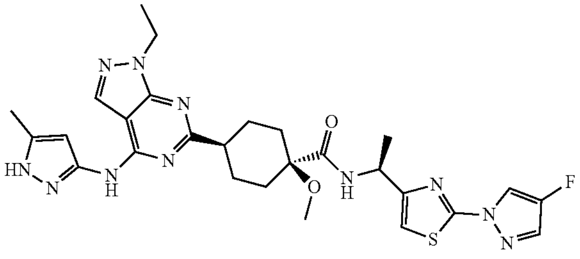
-continued
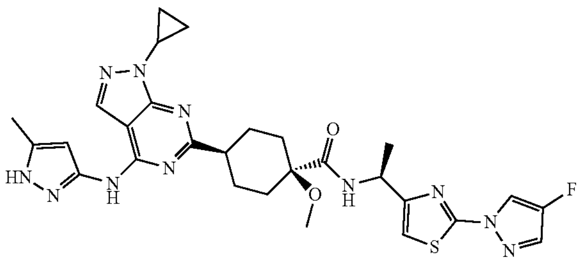
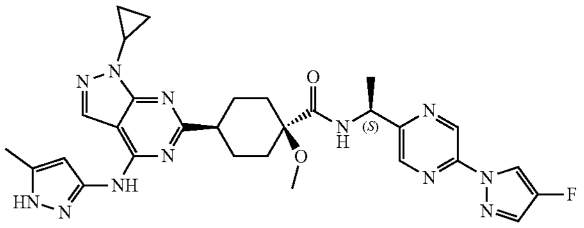
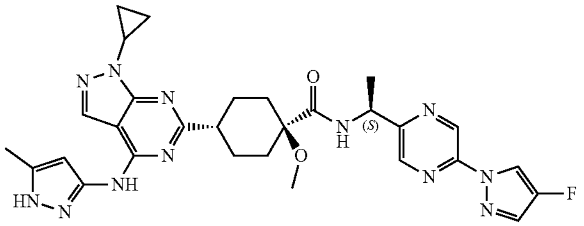
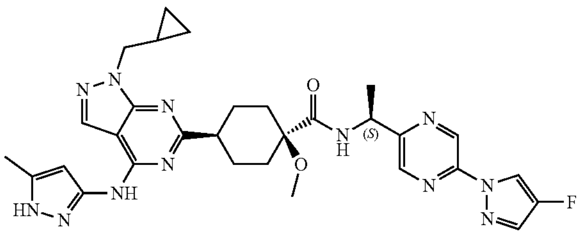
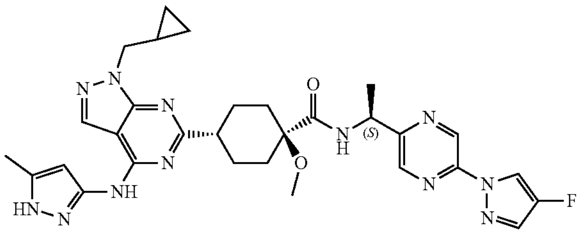
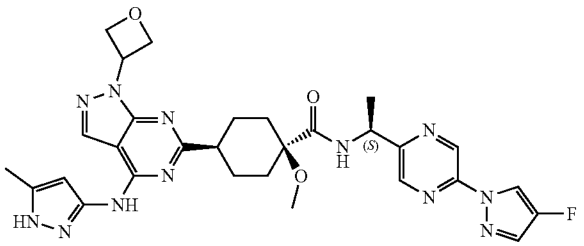
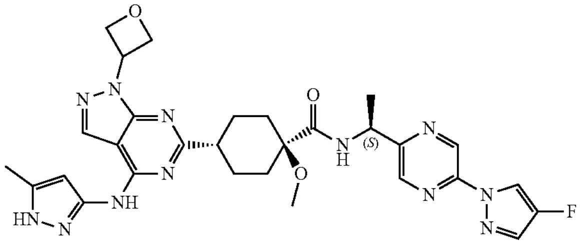

-continued

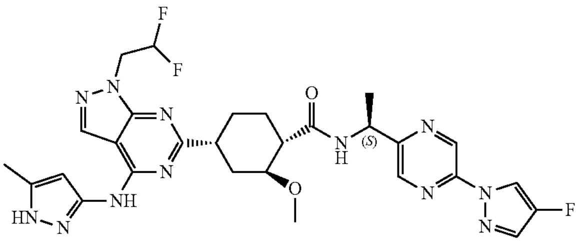

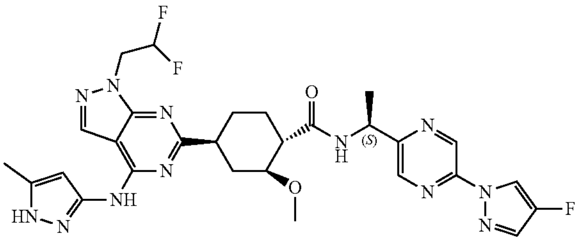

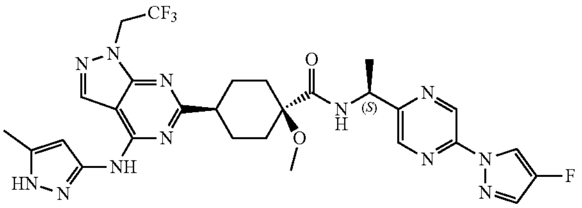

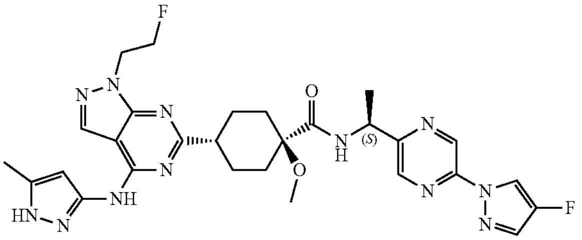

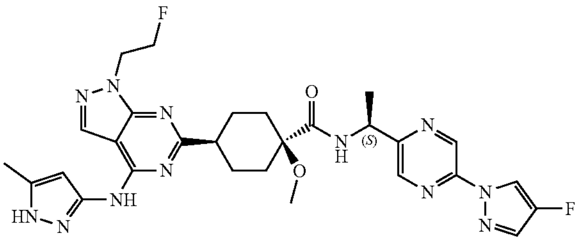

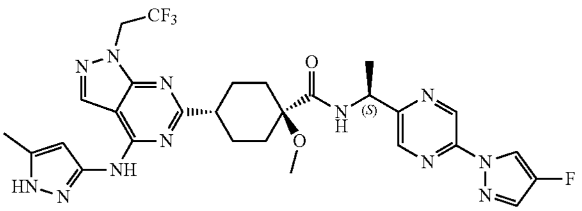

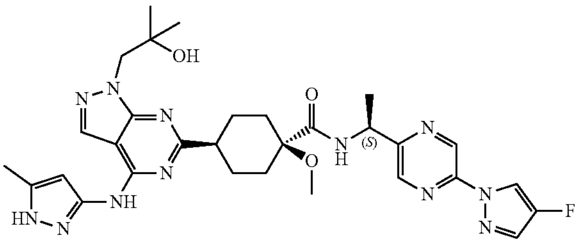

-continued

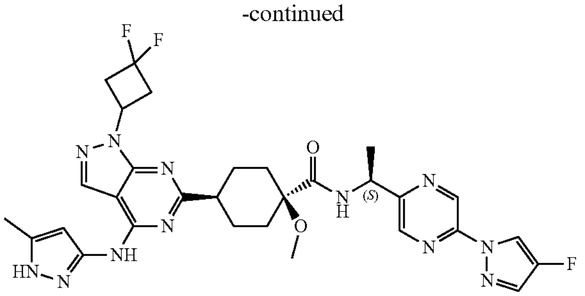

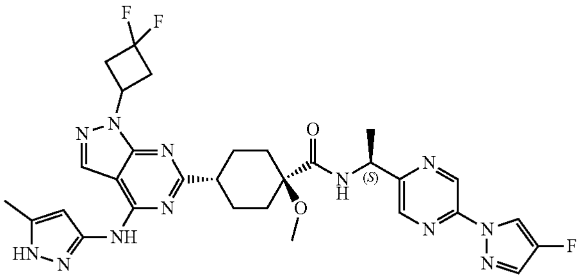

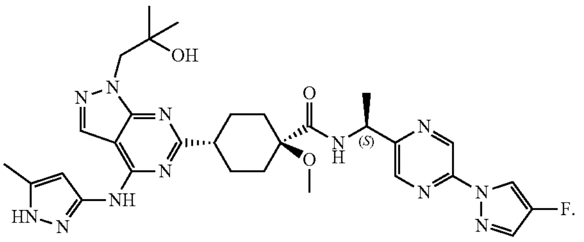

In another preferred embodiment, R'$_1$ and A ring are corresponding group of each specific compound in the Example.

In another preferred embodiment, the compound is selected from the compounds shown in the Example.

In another preferred embodiment, the compound, or the pharmaceutically acceptable salt, stereoisomer, solvate or prodrug thereof, wherein the pharmaceutically acceptable salt is an inorganic acid salt or an organic acid salt, wherein the inorganic acid salt is selected from hydrochloride, hydrobromide, hydroiodide, sulfate, bisulfate, nitrate, phosphate or acid phosphate; the organic acid salt is selected from formate, acetate, trifluoroacetate, propionate, pyruvate, hydroxyacetate, oxalate, malonate, fumarate, maleate, lactate, malate, citrate, tartrate, methanesulfonate, ethanesulfonate, benzenesulfonate, salicylate, picrate, glutamate, ascorbate, camphorate, camphor sulfonate.

In the second aspect of the invention, it provides a pharmaceutical composition comprising a therapeutically effective amount of the compound of the first aspect, or the pharmaceutically acceptable salt, stereoisomer, solvate or prodrug thereof, and a pharmaceutically acceptable carrier.

In another preferred embodiment, the pharmaceutical composition may also comprise one or more other therapeutic agents, and the other therapeutic agents are selected from: PD-1 inhibitor (such as nivolumab, pembrolizumab, JS-001, SHR-120, BGB-A317, IBI-308, GLS-010, GB-226, STW2 (4, HX008, HLX10, BAT 1306, AK105, LZM 009 or the biological analogue thereof, etc.), PD-L1 inhibitor (such as durvalumab, atezolizumab, CS1001, KN035, HLX20, SHR-1316, BGB-A333, JS003, CS1003, KL-A167, F 520, GR1405, MSB2311 or the biological analogue thereof, etc.), CD20 antibody (such as rituximab, obinutuzumab, ofatumumab, tositumomab, ibritumomab, etc.). CD47 antibody (such as Hu5F9-G4, CC-90002, TTI-621, TTI-622, OSE-172, SRF-231, AIX-148, NI-1701, SHR-1603, IBI188, IMM01), ALK inhibitor (such as Ceritinib, Alectinib, Brigatinib, Lorlatinib, Ocatinib), PI3K inhibitor (such as Idelalisib, Dactolisib, Taselisib, Buparlisib, etc.), BTK inhibitor (such as Ibrutinib, Tirabrutinib, Acalabrutinib, etc.), EGFR inhibitor (such as Afatinib. Gefitinib, Erlotinib, Lapatinib. Dacomitinib, Icotinib, Canertinib, etc.), VEGFR inhibitor (such as Sorafenib, Pazopanib, Regorafenib, Cabozantinib, Sunitinib, Donafenib, etc.), HDAC inhibitor (such as Givinostat, Droxinostat, Entinostat, Dacinostat, Tacedinaline, etc.), CDK inhibitor (such as Palbociclib, Ribociclib, Abemaciclib, Lerociclib, etc.), MEK inhibitor (such as Selumetinib (AZD6244), Trametinib (GSK1120212), PD0325901, U0126, AS-703026, PD184352 (CI-1040), etc.), mTOR inhibitor (such as Vistusertib, etc.), SHP2 inhibitor (such as RMC-4630, JAB-3068, TNO 155, etc.), IGF-1R inhibitor (such as Ceritinib, Okatinib, Linsitinib, BMS-754807, GSK1838705A, etc.) or combinations thereof.

In the third aspect of the invention, it provides a use of the compound, or the pharmaceutically acceptable salt, stereoisomer, solvate or prodrug thereof of the first aspect, in the preparation of a medicament used as a RET kinase inhibitor.

In the fourth aspect of the invention, it provides a use of the compound, or the pharmaceutically acceptable salt, stereoisomer, solvate or prodrug thereof of the first aspect, in the preparation of a medicament for modulating RET kinase activity or for the treatment of RET-related disease.

In another preferred embodiment, it provides a use of the compound, or the pharmaceutically acceptable salt, stereoisomer, solvate or prodrug thereof of the first aspect or the pharmaceutical composition of the second aspect in the preparation of i) a medicament used as RET kinase inhibitors; or ii) a medicament for modulating RET kinase activity or for the treatment of RET-related disease. In another preferred embodiment, the RET-related disease includes cancer.

In another preferred embodiment, the cancer is thyroid cancer or lung cancer.

In another preferred embodiment, the cancer is medullary thyroid carcinoma or non-small cell lung cancer.

In the fifth aspect of the invention, it provides a method of treating RET-related diseases comprising administering a therapeutically effective amount of the compound or the pharmaceutically acceptable salt or solvate thereof of the first aspect, or the pharmaceutical composition of the second aspect to a subject identified or diagnosed as having a RET-related disease.

In the sixth aspect of the present invention, it provides a method for inhibiting RET kinase activity in a cell or a subject, the method comprises the step of contacting the cell or administering to the subject the compound or the pharmaceutical composition.

In another preferred embodiment, the cell is mammalian cells.

In another preferred embodiment, the subject is a mammal, preferably a human.

In the seventh aspect of the present invention, it provides a method for the preparation of the compound of formula I, comprising a step of:

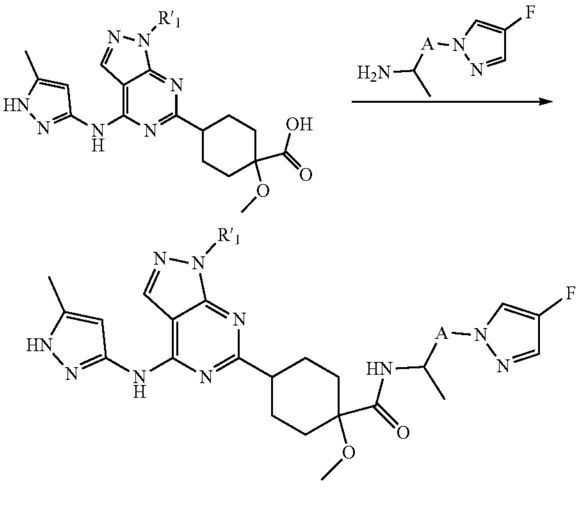

I s3) in an inert solvent,

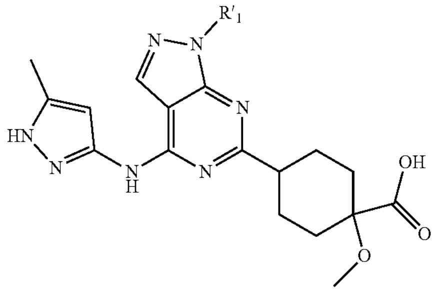

and

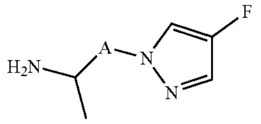

undergo reaction in the presence of a condensing agent to obtain the compound of formula I;

wherein, $R'_1$ and A are as defined above.

In another preferred embodiment, the method further comprises the steps of:

Method 1:

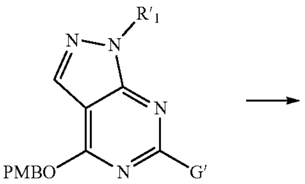

-continued
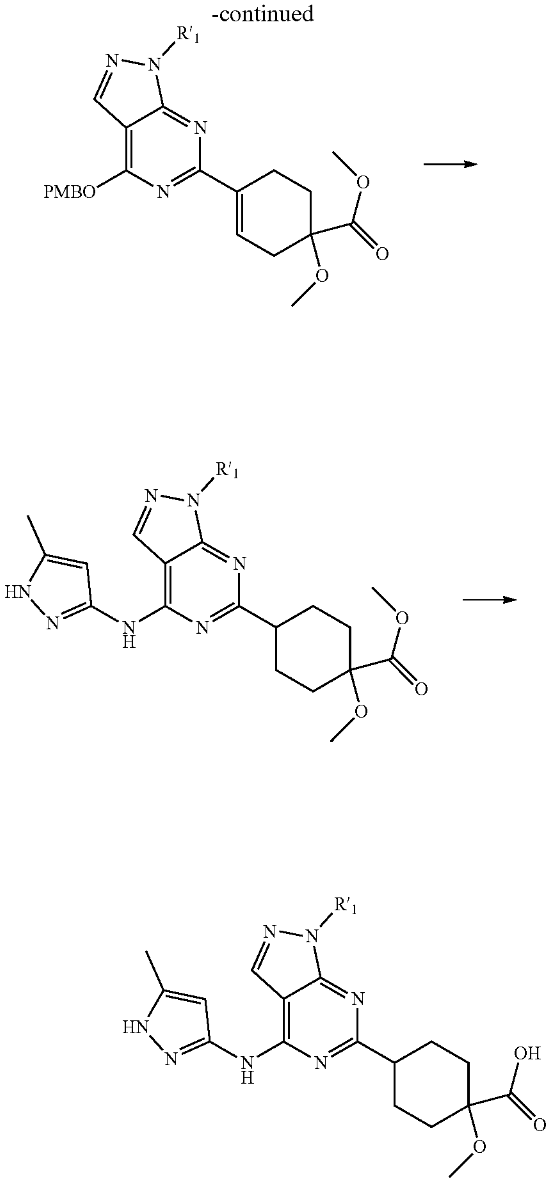
s'1) in an inert solvent,
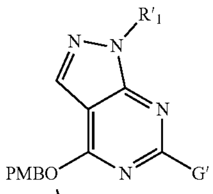
and
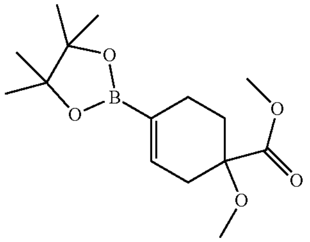
undergo a reaction in the presence of a base, a catalyst and a ligand to obtain
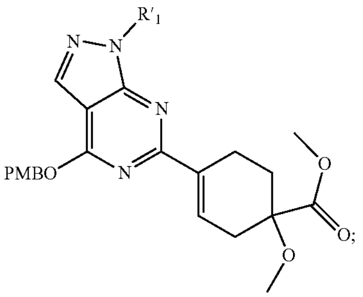
s'2) after reducing
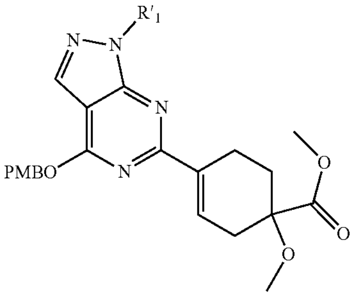
under hydrogen atmosphere, then halogenating or reacting with trifluoromethanesulfonic anhydride to obtain an intermediate which reacts with
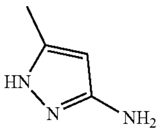
in the presence of a base to obtain
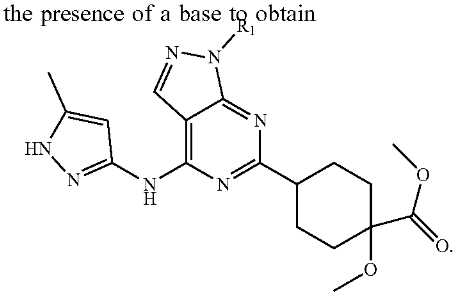
Method Two:
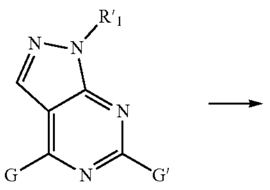

-continued
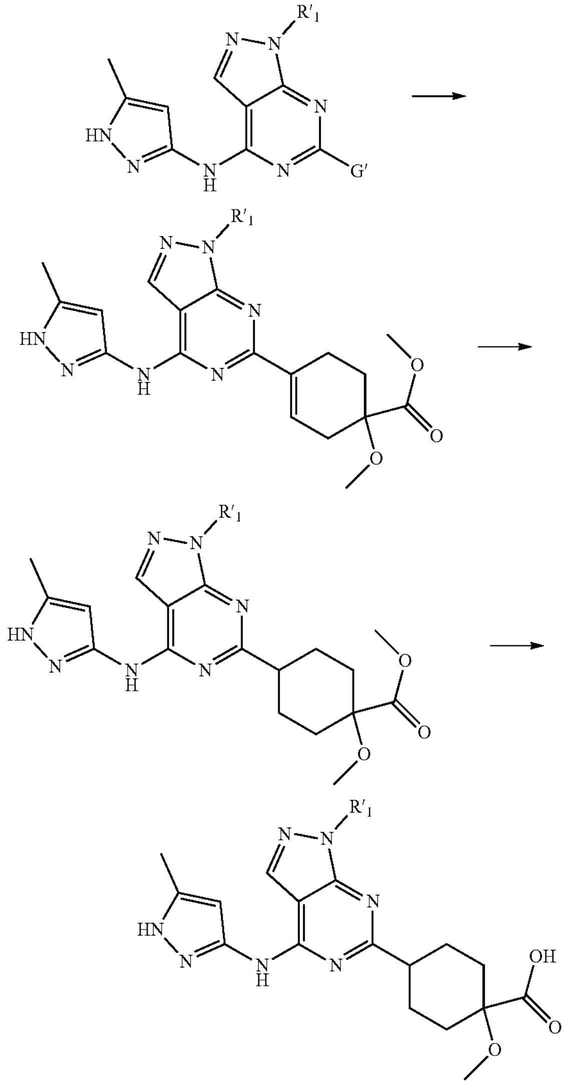
s"1 in an inert solvent, reacted with
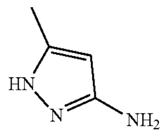
in the presence of a base to obtain
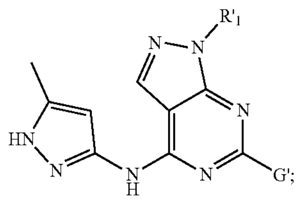
s"2) in an inert solvent,
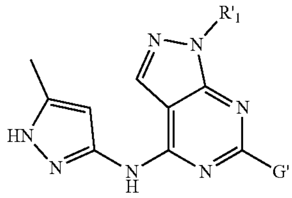
and
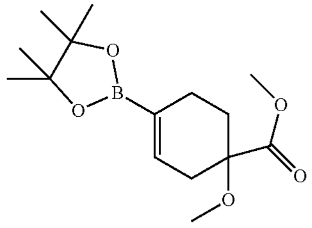
undergo a reaction in the presence of a base, a catalyst and a ligand to obtain
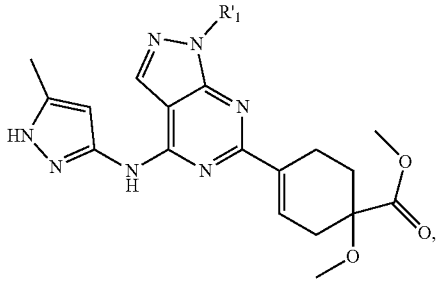
then reducing
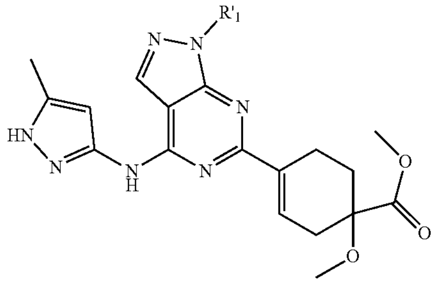
under hydrogen atmosphere to obtain
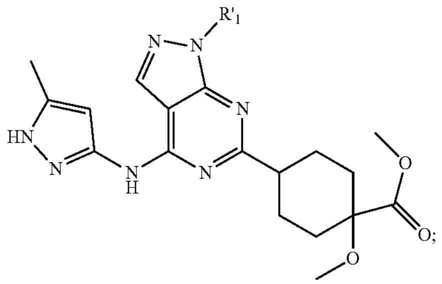

wherein, G and G' are each independently halogen (e.g. Cl or Br);

$R'_1$ is as defined above.

DETAILED DESCRIPTION OF THE INVENTION

After extensive and in-depth research, the inventor unexpectedly discovered a class of compound with excellent RET kinase inhibitory activity. In addition, the compound have excellent inhibitory activity against RET kinase and have better pharmacodynamic/pharmacokinetic properties. On this basis, the present invention was completed.

Term

Unless otherwise stated, the following terms used in this application (including the specification and claims) have the definitions given below.

When a substituent is described by a conventional chemical formula written from left to right, the substituent also includes a chemically equivalent substituent obtained by writing a structural formula from right to left. For example, $—CH_2O—$ is equivalent to $—OCH_2—$.

"Alkyl (alone or as part of other groups)" refers to a monovalent linear or branched saturated hydrocarbon group containing 1 to 12 carbon atoms composed only of carbon and hydrogen atoms. The alkyl is preferably C1-C6 alkyl (i.e. containing 1, 2, 3, 4, 5 or 6 carbon atoms). Examples of alkyl include but are not limited to methyl, ethyl, propyl, isopropyl, isobutyl, sec-butyl, tert-butyl, amyl, n-hexyl, octyl and dodecyl etc. In the present application, alkyl is also intended to comprise a substituted alkyl, i.e. one or more positions in the alkyl are substituted, in particular 1-4 substituents, which may be substituted at any position. "Haloalkyl" refers to an alkyl as defined herein in which one or more hydrogen is replaced by the same or different halogens. Examples of haloalkyl include $—CH_2Cl$, $—CH_2CF_3$, $—CH_2CCl_3$, perfluoroalkyl (e.g. $—CF$), etc.

"Alkylene" refers to divalent group of alkyl, e.g. $—CH_2—$, $—CH_2CH_2—$ and $—CH_2CH_2CH_2—$.

"Alkoxy (alone or as part of other groups)" refers to alkyl to which an oxy is attached with a formula alkyl O—, wherein the alkyl has the definition described above, and preferably the alkoxy is C1-C6 alkoxy. Alkoxy includes but is not limited to methoxy, ethoxy, propoxy, tert-butoxy, etc. "Haloalkoxy" refers to the formula —OR, wherein, R is a halogenated alkyl as defined herein. Examples of haloalkoxy include but are not limited to trifluoromethoxy, difluoromethoxy, and 2, 2, 2-trifluoroethoxy, etc.

"Thioalkyl" refers to that the carbon in the alkyl is substituted by S, S(O) or $S(O)_2$.

"Alkenyl (alone or as part of other groups)" refers to aliphatic group containing at least one double bond, typically having between 2 and 20 carbon atoms. In the present invention, "C2-C6 alkenyl" refers to alkenyl containing 2, 3, 4, 5 or 6 carbon atoms. The alkenyl includes but is not limited to for example, vinyl, propenyl, butenyl, 1-methyl-2-buten-1-yl, etc. In the present invention, the alkenyl includes substituted alkenyl.

"Alkenylene" refers to alkenyl having two connection points. For example, "vinylidene" refers to the group —CH═CH—. The alkenylene may also be in an unsubstituted form or in a substituted form having one or more substituents.

"Alkynyl (alone or as part of other groups)" refers to a straight or branched hydrocarbon chain containing more than 2 carbon atoms and characterized by one or more triple bonds, typically having 2 to 20 carbon atoms. In the present invention, "C2-6 alkynyl" refers to alkynyl having 2, 3, 4, 5 or 6 carbon atoms. Alkynyl includes but is not limited to ethynyl, propargyl and 3-hexynyl. One of the triple-bond carbons can optionally be the connection point of alkynyl substituent. In the invention, the alkynyl also includes substituted alkynyl.

"Alkynylene" refers to alkynyl having two connecting points. For example, "ethynylene" refers to the group: —C≡C—. The alkynylene may also be in an unsubstituted form or in a substituted form having one or more substituents.

"Aliphatic group" refers to straight-chain, branched or cyclic hydrocarbon group including saturated and unsaturated group, such as alkyl, alkenyl and alkynyl.

"Aromatic ring system" refers to monocyclic, bicyclic or polycyclic hydrocarbon ring system in which at least one ring is aromatic.

"Aryl (alone or as part of other groups)" refers to a monovalent group of an aromatic ring system. Representative aryl include all aromatic ring systems, such as phenyl, naphthyl and anthryl; and ring systems in which aromatic carbocyclic rings are fused with one or more non-aromatic carbocyclic rings, such as indanyl, phthalimide, naphthylimide or tetrahydronaphthyl, etc. In the present invention, the aryl is preferably C6-C12 aryl. In the present invention, aryl is also intended to comprise substituted aryl.

"Arylalkyl" or "aralkyl" refers to an alkyl moiety in which the alkyl hydrogen atom is substituted by an aryl. An aralkyl includes a group in which one or more hydrogen atoms are substituted by aryl, wherein aryl and alkyl are defined as above. Examples of "arylalkyl" or "aralkyl" include benzyl, 2-phenylethyl, 3-phenylpropyl, 9-fluorenyl, diphenylmethyl and triethylmethyl, etc.

"Aryloxy" refers to —O-(aryl), wherein the aryl moiety is as defined herein.

"Heteroalkyl" refers to a substituted alkyl having one or more skeleton chain atoms selected from atoms other than carbon, such as oxygen, nitrogen, sulfur, phosphorus, Si or a combination thereof. Numeric ranges may be given for example C1-C6 heteroalkyl refers to the number of carbons in the chain which includes 1 to 6 carbon atoms. For example, $—CH_2OCH_2CH_3$ is called "C3" heteroalkyl. The connection with the rest of the molecule can be through heteroatoms or carbons in heteroalkyl chain. Examples of "heteroalkyl" include but not limited to $CH_2OCH_3$, $CH_2CH_2OCH_3$, $CH_2NHCH_3$, $CH_2CH_2NHCH_3$, $Me_3Si$, $Me_3SiCH_2CH_2O—$, $Me_3SiCH_2CH_2OCH_2$-(SEM). "Heteroalkylene" refers to an optionally substituted divalent alkyl having one or more skeleton chain atoms selected from atoms other than carbon, such as oxygen, nitrogen, sulfur, phosphorus, Si or a combination thereof.

"Carbocyclic system" refers to a monocyclic, dicyclic or polycyclic hydrocarbon ring system in which each ring is fully saturated or contains one or more unsaturated units, but none of the rings are aromatic.

"Carbocyclic group" refers to a monovalent group of a carbocyclic system. These include, for example, cycloalkyl (cyclopentyl, cyclobutyl, cyclopropyl, cyclohexyl, etc.) and cycloalkenyl (e.g. cyclopentenyl, cyclohexenyl, cyclopentadienyl, etc.).

"Cycloalkyl" refers to a monovalent saturated carbocyclic group consisting of monocyclic or dicyclic ring having 3-12, preferably 3-10, more preferably 3-6 ring atoms. The cycloalkyl may optionally be substituted with one or more substituents, wherein each substituent is independently a hydroxyl, alkyl, alkoxy, halogen, haloalkyl, amino, monoalkylamino or dialkylamino. Examples of cycloalkyl include but are not limited to cyclopropyl, cyclobutyl, cyclopentyl, cyclohexyl and cycloheptyl, etc.

"Cycloalkoxy" refers to the formula —OR, wherein R is a cycloalkyl as defined herein. Examples of cycloalkyloxy include cyclopropyloxy, cyclobutyloxy, cyclopentyloxy and cyclohexyloxy, etc. "Cycloalkyl alkyl" means-(cycloalkyl)-alkyl in which cycloalkyl and alkyl are as disclosed herein. "Cycloalkyl alkyl" is bonded to the parent molecular structure by a cycloalkyl.

"Heteroaromatic ring system" refers to a monocyclic (e.g. 5 or 6 membered), dicyclic (6-12 membered), or polycyclic system in which at least one ring is both aromatic and contains at least one heteroatom (e.g. N, O, or S). And none of the other rings are heterocyclyl (as defined below). In some cases, rings that are aromatic and contain heteroatoms contain 1, 2, 3 or 4 ring heteroatoms in the ring. At least one ring is heteroaromatic, and the remaining rings may be saturated, partially unsaturated or completely unsaturated.

"Heteroaryl" refers to a monocyclic (e.g. 5 or 6 membered), dicyclic (e.g. 8-10 membered) or tricyclic group with 5 to 12 ring atoms, and it contains at least one aromatic ring containing 1, 2 or 3 cyclic heteroatoms selected from N, O or S. and the remaining ring atoms are C. It should be clear that the connection point of the heteroaryl should be located on the aromatic ring. Examples of heteroaryl include but are not limited to imidazolyl, aoxazolyl, isoxazolyl, thiazolyl, isothiazolyl, oxadiazolyl, thiadiazolyl, pyrazinyl, thienyl, furanyl, pyranyl, pyridyl, pyrrolyl, pyrazolyl, pyrimidinyl, quinolinyl, isoquinolinyl, benzofuranyl, benzothienyl, benzothiopyranyl, benzimidazolyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinazinyl, naphthyridinyl, pterridinyl, carbazolyl, azepinyl, diazepinyl and acridinyl, etc. Heteroarylene refers to heteroaryl having two connecting points.

"Heterocyclic system" refers to monocyclic, bicyclic and polycyclic systems where at least one ring is saturated or partially unsaturated (but not aromatic) and the ring contains at least one heteroatom. The heterocyclic system can be attached to the side group of any heteroatom or carbon atom to produce a stable structure and any ring atom can be optionally substituted.

"Heterocyclyl" refers to a monovalent group of a heterocyclic system. It usually refers to stable monocyclic (such as 3-8 membered, i.e. 3 membered, 4 membered, 5 membered, 6 membered, 7 membered or 8 membered) or bicyclic (such as 5-12 membered. i.e. 5 membered, 6 membered, 7 membered, 8 membered, 9 membered, 10 membered, 11 membered or 12 membered) or polycyclic (such as 7-14 membered, i.e. 7 membered, 8 membered, 9 membered, 10 membered, 11 membered, 12 membered, 13 membered or 14 membered), including fused ring, spiro ring and/or bridge ring structure, which is saturated and partially unsaturated and contains carbon atoms and 1, 2, 3 or 4 heteroatoms independently selected from N, O or S. Representative heterocyclyl include the following ring systems, where (1) each ring is non-aromatic and at least one ring contains a heteroatom, for example, tetrahydrofuryl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl and quinuclidinyl. (2) At least one ring is non-aromatic and contains heteroatoms and at least one other ring is an aromatic carbocyclic ring, for example, 1, 2, 3, 4-tetrahydroquinolinyl, 1, 2, 3, 4-tetrahydroisoquinolinyl. And (3) at least one ring is non-aromatic and contains a heteroatom and at least one other ring is aromatic and contains a heteroatom, for example, 3, 4-dihydro-1H-pyrano[4, 3-c] pyridine and 1, 2, 3, 4-tetrahydro-2, 6-naphthyridine. Heterocyclylene refers to heterocyclyl having two connecting points. In the present invention, the heterocyclene is preferably bicyclic, wherein one ring is a heteroaryl and connected to the other parts of the general formula through the heteroaryl. In the present invention, the heterocyclylene is preferably a 5-6-membered monocyclic heterocyclylene or an 8-10-membered bicyclic heterocyclene.

"Heterocyclyl alkyl" refers to an alkyl substituted with a heterocyclyl, wherein the heterocyclyl and alkyl are defined as above.

"Alkylamino" refers to a group having a structure of alkyl-NR—, where R is H, or an alkyl, cycloalkyl, aryl, heteroaryl, etc. as described above.

"Cycloalkylamino" refers to the formula —NRaRb, wherein Ra is H, an alkyl as defined herein or a cycloalkyl as defined herein, and Rb is a cycloalkyl as defined herein; or Ra and Rb together with their attached N atoms to form a 3-10-membered N-containing monocyclic or bicyclic heterocyclyl, such as tetrahydropyrrolyl. As used herein, C3-C8 cycloalkylamino refers to an amino containing 3-8 carbon atoms.

As used herein, an "ester" refers to —C(O)—O—R or R—C(O)—O—, wherein R independently represents hydrogen, alkyl, cycloalkyl, aryl, heteroaryl, heterocyclyl as defined above.

As used herein, the term "amido" refers to a group with a structure of —CONRR', wherein R and R' independently represent hydrogen, alkyl or substituted alkyl, cycloalkyl or substituted cycloalkyl, aryl or substituted aryl, heterocyclyl or substituted heterocyclyl with the definitions as described above. R and R' may be the same or different in the dialkylamino segments.

As used herein, the term "sulfonamido" refers to a group with a structure of —$SO_2$NRR', wherein R and R' independently represent hydrogen, alkyl or substituted alkyl, cycloalkyl or substituted cycloalkyl, aryl or substituted aryl, heterocyclyl or substituted heterocyclyl with the definitions as described above. R and R' may be the same or different in the dialkylamino segments.

"Ketocarbonyl" refers to R—C(═O)—, wherein R is alkyl, cycloalkyl, etc. with the definitions as described above.

When the substituent is a non-terminal substituent, it is a subunit of the corresponding substituent, such as alkyl corresponding to alkylene, cycloalkyl corresponding to cycloalkylene, heterocyclyl corresponding to heterocyclene, alkoxy corresponding to alkyleneoxy, etc.

In the present invention, each of the above-mentioned groups of alkyl, alkoxy, cycloalkyl, heteroalkyl, aryl, heteroaryl, cycloheteroalkyl, alkenyl, alkynyl, heterocycle, heterocyclyl, etc. may be substituted or unsubstituted.

As used herein, the term "substituted" refers to the substitution of one or more hydrogen atoms on a specific group by specific substituent. The specific substituents are those described in the preceding paragraph or those present in each Example. Unless otherwise specified, a substituted group may have a substituent selected from a specific group at any substitutable position of the group, and the substituent may be the same or different in each position. Those skilled in the art should understand that the combinations of substituents contemplated by the present invention are those that are stable or chemically achievable. Typical substituents include but are not limited to one or more of the following groups: such as hydrogen, deuterium, halogen (such as monohalogenated substituent or polyhalogenated substituents, and the latter such as trifluoromethyl or alkyl containing $Cl_3$), cyano, nitro, oxo (═O), trifluoromethyl, trifluoromethoxy, cycloalkyl, alkenyl, alkynyl, heterocycle, aromatic ring, $OR_a$, $SR_a$, $S({=}O)R_e$, $S({=}O)_2R_e$, $P({=}O)_2R_e$, $S({=}O)_2OR_e$, $P({=}O)_2OR_e$, $NR_bR_c$, $NR_bS({=}O)_2R_e$, $NR_bP({=}O)_2R_e$, $S({=}O)_2NR_bR_c$, $P({=}O)_2NR_bR_c$, $C({=}O)OR_d$, $C({=}O)R_e$, $C({=}O)NR_bR_c$, $OC({=}O)R_a$, $OC({=}O)NR_bR_c$, $NR_bC({=}O)OR_e$, $NR_dC({=}O)NR_bR_c$, $NRS({=}O)_2NR_bR_c$, $NR_dP({=}O)_2NR_bR_c$, $NR_bC({=}O)R_a$ or $NR_bP({=}O)_2R_e$, wherein $R_a$ can independently represent hydrogen, deuterium, alkyl, cycloalkyl, alkenyl, alkynyl, heterocycle or aromatic ring, $R_b$, $R_c$ and $R_d$ can independently represent hydrogen, deuterium, alkyl, cycloalkyl, heterocycle or aromatic ring, or $R_b$ and $R_c$ together with the N atom form a heterocycle, $R_e$ can independently represent hydrogen, alkyl, cycloalkyl, alkenyl, alkynyl, heterocycle or aromatic ring. The above typical substituents, such as alkyl, cycloalkyl, alkenyl, cycloalkenyl, alkynyl, heterocyclyl or aromatic ring can be optionally substituted. The substituent is such as (but is not limited to): halogen, hydroxyl, cyano, carboxy (—COOH), C1-C6 alkyl, C2-C6 alkenyl, C2-C6 alkynyl, C3-C8 cycloalkyl, 3-to-12 membered heterocyclyl, aryl, heteroaryl, C1-C8 aldehydyl, C2-C10 acyl, C2-C10 ester, amido, C1-C6 alkoxy, C1-C10 sulfonyl, and C1-C6 uramido, etc.

"Cyano" refers to —CN.

"Nitro" refers to —$NO_2$.

"Hydroxyl" refers to —OH.

"Amino" refers to —NH2 or RNH—, wherein R is ketocarbonyl, sulfonyl, sulfonamido, Ra—C(═O)—, RaRbN—C(═O)— and so on, wherein Ra and Rb is alkyl, cycloalkyl, aryl or heteroaryl, etc.

"Halogen (halogenated)" refers to any halogen group, e.g. —F, —Cl, —Br or —I.

"Deuterated compound" refers to the compound obtained by replacing one hydrogen atom (H) or multiple hydrogen atoms (H) with deuterium atoms (D) in a compound.

In the present invention, the term "multiple" independently refers to 2, 3, 4 or 5.

Active Ingredient

As used herein, the terms "compounds of the invention" or "active ingredients of the invention" are used interchangeably and refer to compounds of formula I', or pharmaceutically acceptable salt, hydrate, solvate, isotope compound (e.g. deuterated compound) or prodrug thereof. The term also includes racemate and optical isomer.

The compound of formula I' has the following structure:

I'

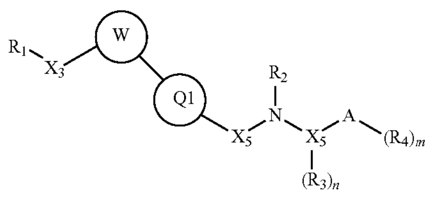

$R_1$, $X_3$, W, Q1, $X_5$, $X_6$, $R_2$, $R_3$, $R_4$, A, m and n are defined as above, Preferably the W ring is substituted or unsubstituted group selected from the group consisting of 5-6-membered monocyclic heterocyclylene, 8-10-membered bicyclic heterocyclylene or 5-6-membered monocyclic heteroarylene or 8-10-membered bicyclic heteroarylene; the "substituted" means optionally substituted by 0-2 $R^5$; $R^5$ is each independently selected from hydrogen, deuterium, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, oxo, cyano, —$C(O)R_6$, —$OC(O)R_6$, —$C(O)OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)$—$C(O)R_6$, —$N(R_6)$—$C(O)OR_7$, —(C1-C6 alkylene)-$N(R_6)$—$C(O)R_7$, —$N(R_6)S(O)_2R_7$ or —P(O)$(R_b)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$; $R^a$ is optionally selected from deuterium, C1-C6 alkyl, halogen, hydroxyl, C1-C6 heteroalkyl, C1-C6 alkoxy, C1-C6 alkylamino, cycloalkyl, heterocycloalkyl or cyano, more preferably. W ring is selected from

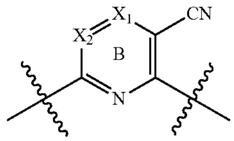
,

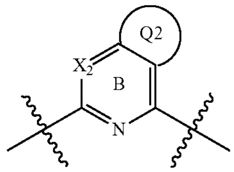
(or

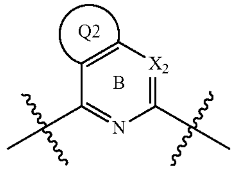
),

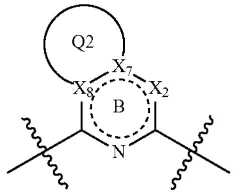
( or

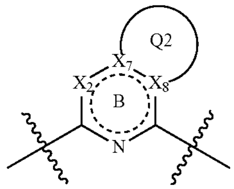
);

Wherein, $X_1$, $X_2$, $X_7$, $X_8$ and Q2 are defined as above, and at least one of $X_7$ and $X_8$ is N.

Preferably, the compound of formula I', or the pharmaceutically acceptable salt, stereoisomer, solvate or prodrug thereof has the structure represented by formula (II), formula (III) or formula (IV)

(II)

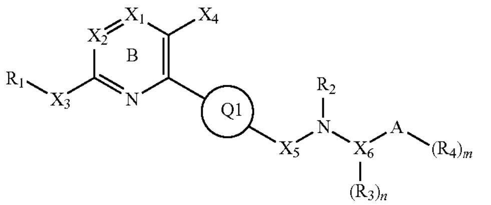

(III)

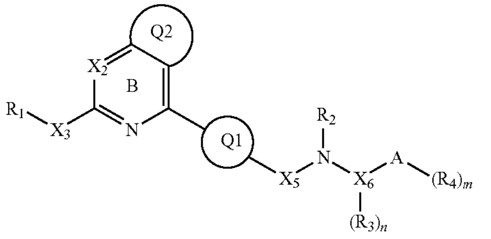

(IV)

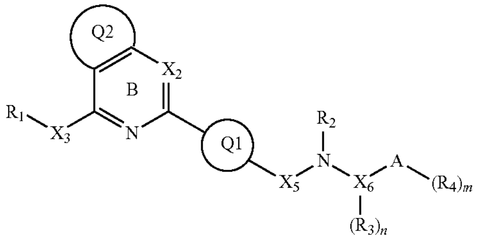

wherein, $R_1$, $X_1$, $X_2$, $X_3$, Q1, Q2, $X_5$, $X_6$, $R_2$, $R_3$, $R_4$, A, m, and n are described as above.

Preferably, the compound of formula I', or the pharmaceutically acceptable salt, stereoisomer, solvate or prodrug thereof has the structure represented by formula (2), formula (3) or formula (4)

(2)

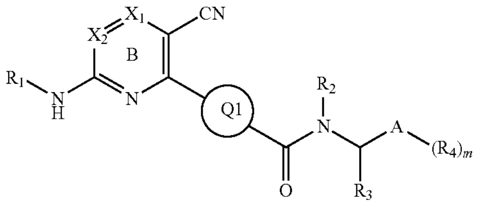

(3)

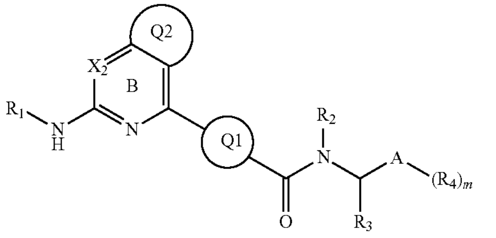

-continued (4)

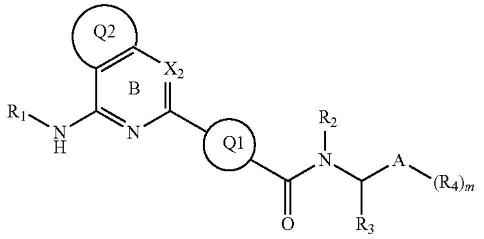

wherein $R_1$, $X_1$, $X_2$, Q1, Q2, $R_2$, $R_3$, $R_4$, A and m are described as above.

Preferably, the compound, or the pharmaceutically acceptable salt, stereoisomer, solvate or prodrug thereof has the structure represented by formula 2'

2′

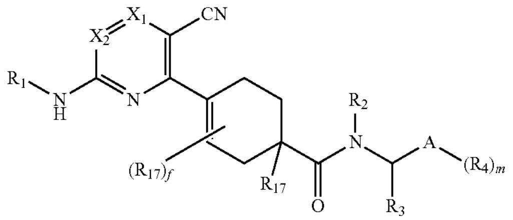

wherein, ⎓ is a single bond or a double bond;

$X_1$, $X_2$, $R_1$, $R_2$, $R_3$, $R_4$, A, $R_{17}$, f and m are defined as above.

Preferably, the compound, or the pharmaceutically acceptable salt, stereoisomer, solvate or prodrug thereof has the structure represented by formula 2"

2″

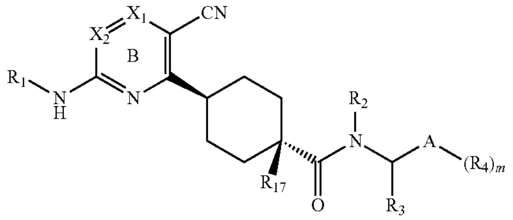

wherein, $X_1$, $X_2$, $R_1$, $R_2$, $R_3$, $R_4$, A, m and $R_{17}$ are defined as above.

Preferably, the compound of formula I', or the pharmaceutically acceptable salt, stereoisomer, solvate or prodrug thereof has the structure represented by formula 3'

3″

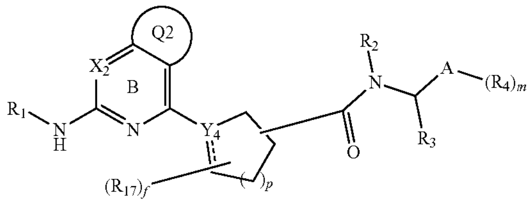

wherein == is a single bond or a double bond:

when == is a single bond, $Y_4$ is selected from N or $CR_{17}$, when == is a double bond, $Y_4$ is C;

$R_1$, $X_2$, $R_2$, $R_3$, $R_4$, $R_{17}$, A, m, f, p and Q2 are defined as above.

In another preferred embodiment, the compound of formula I', or the pharmaceutically acceptable salt, stereoisomer, solvate or prodrug thereof has the structure represented by formula 3"

3"

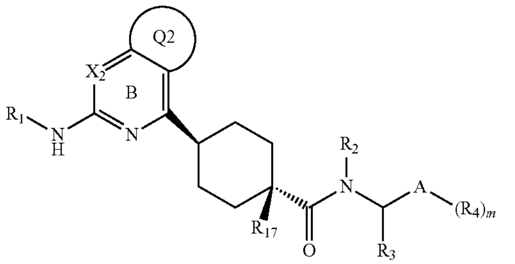

$R_1$, $X_2$, $R_2$, $R_3$, $R_4$, A, Q2, m and $R_{17}$ are defined as above.

Preferably, the compound of formula I', or the pharmaceutically acceptable salt, stereoisomer, solvate or prodrug thereof has the structure represented b formula 4'

4'

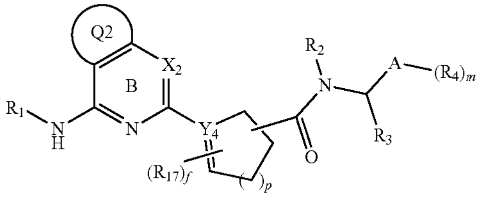

wherein == is a single n or a double bond:

when == is a single bond, $Y_4$ is selected from N or $CR_{17}$, when == is a double bond, $Y_4$ is C;

$R_1$, $X_2$, $R_2$, $R_3$, $R_4$, $R_{17}$, A, m, f, p and Q2 are defined as above.

Preferably, the compound of formula I', or the pharmaceutically acceptable salt, stereoisomer, solvate or prodrug thereof has the structure represented by formula 4"

4"

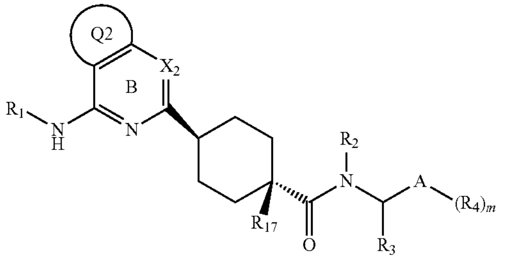

$R_1$, $X_2$, $R_2$, $R_3$, $R_4$, A, Q2, m and $R_{17}$ are defined as above.

Preferably, the compound of formula I', or the pharmaceutically acceptable salt, stereoisomer, solvate or prodrug thereof has the structure represented by formula 5 or formula 6

5

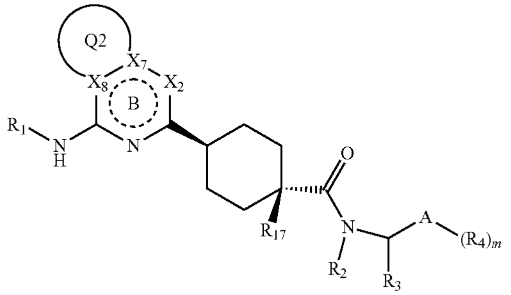

6

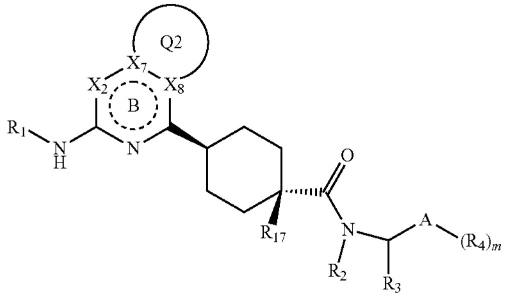

wherein $R_1$, $X_7$, $X_8$, $X_2$, Q2, $R_2$, $R_3$, $R_4$, $R_{17}$, A and m are defined as above, and at least one of $X_7$ and $X_8$ is N.

Preferably, in the above each formula, $R_1$ is optionally selected from one of the following structures:

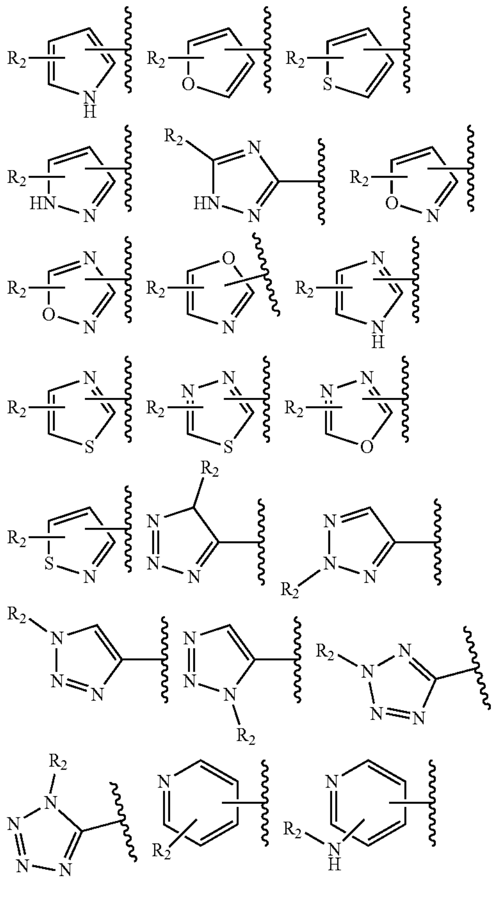

-continued

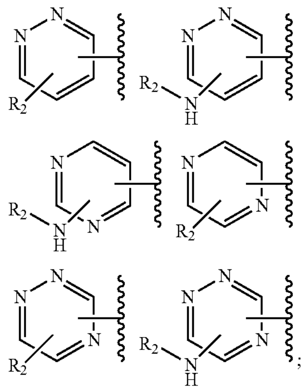

;

more preferably $R_1$ is

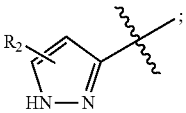

;

$R_2$ is optionally selected from hydrogen, deuterium, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R^a$ is optionally selected from deuterium, C1-C6 alkyl, halogen, hydroxyl, C1-C6 heteroalkyl, C1-C6 alkoxy, cycloalkyl, heterocycloalkyl or cyano.

Preferably, in the above each formula, the W ring is selected from

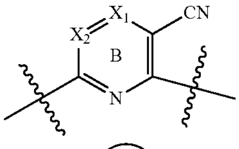

,

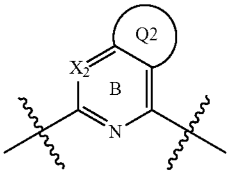

(or

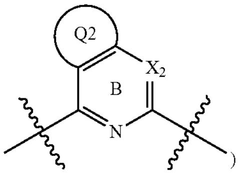

) or

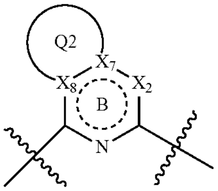

(or

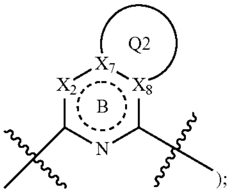

);

wherein,

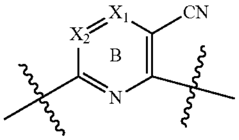

is selected from

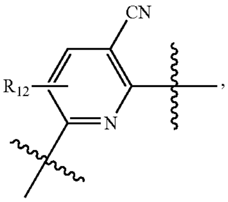

,

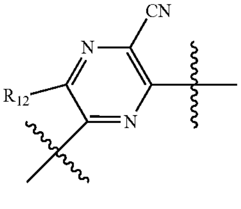

or

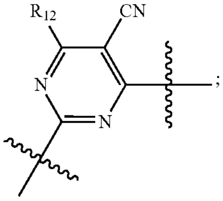

;

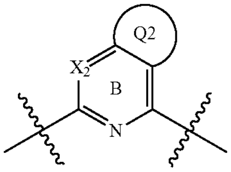

(or

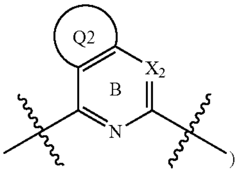

)

is selected from

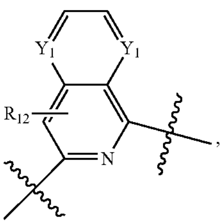

,

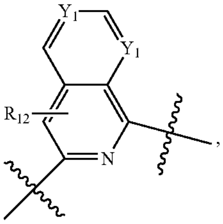

,

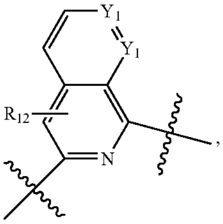

,

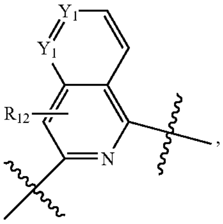

,

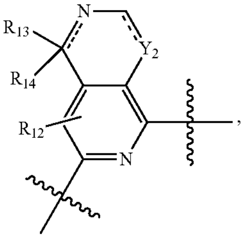

,

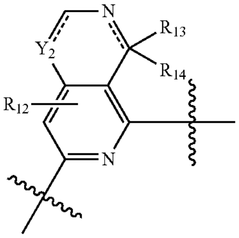

,

-continued
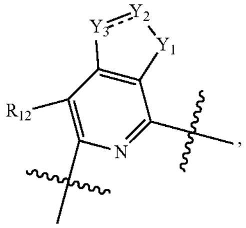
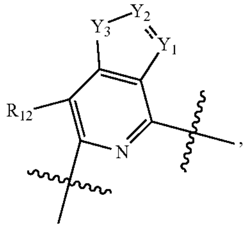
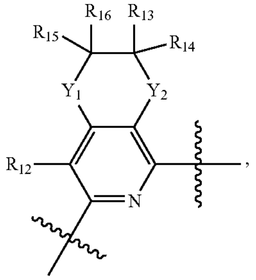
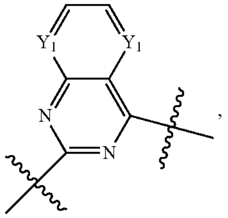
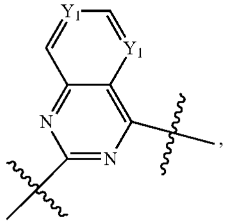
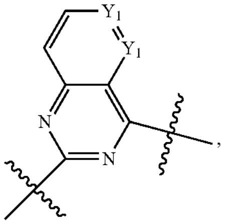
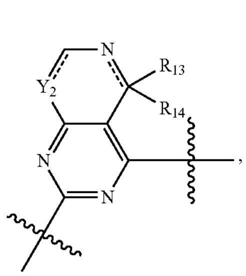
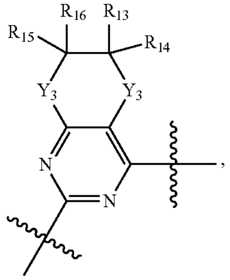
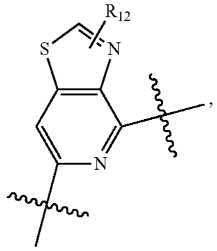
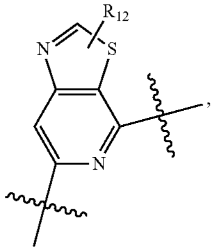
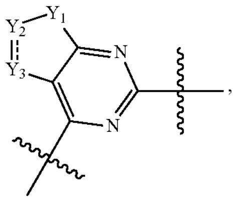
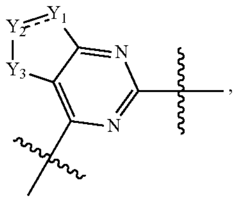
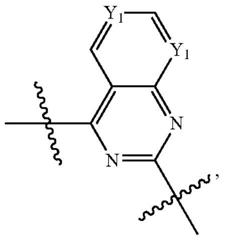
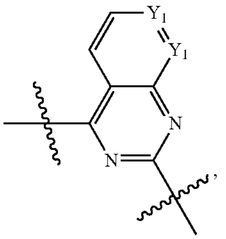
-continued
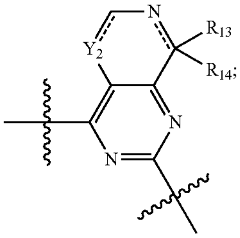
preferably
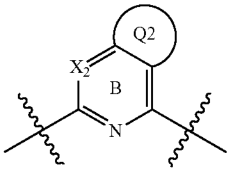
(or
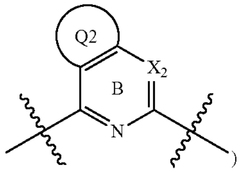
)
is selected from
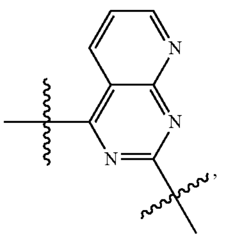
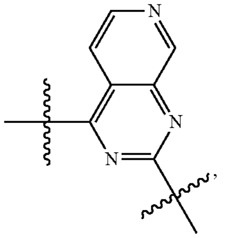
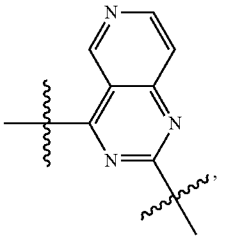
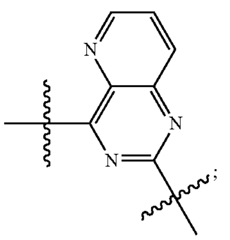
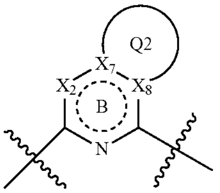
(or
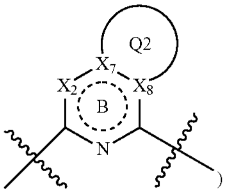
)
is selected from
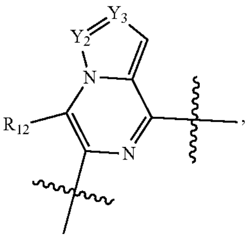
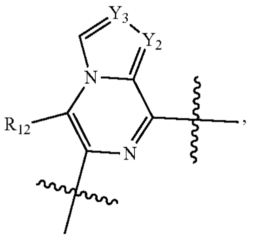

-continued

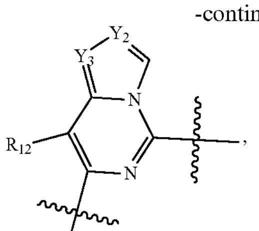

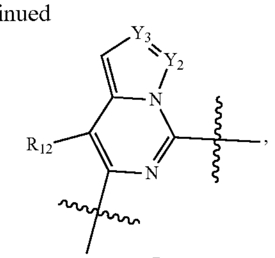

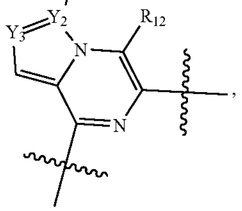

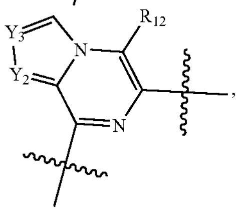

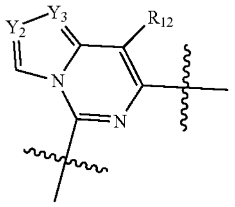

or

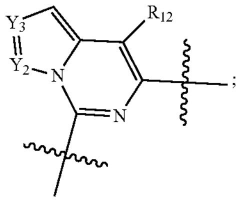

wherein, ⎓ is a single bond or a double bond;

$R_{12}$ is independently selected from H, halogen, C1-C6 alkyl, C1-C6 alkoxy, nitro, cyano or amino:

$Y_1$, $Y_2$ and $Y_3$ are each independently selected from O, N, $NR_{17}$, $CR_{13}$ or $CR_{13}R_{14}$;

$R_{13}$, $R_{14}$, $R_{15}$ and $R_{16}$ are each independently selected from H, halogen, C1-C6 alkyl, deuterated C1-C6 alkyl, C1-C6 alkylhydroxyl, C1-C6 haloalkyl, C1-C6 alkoxy, C1-C6 alkylamino, nitro, cyano, or amino; or $R_{13}$ and $R_{14}$ together with the C atom attached to them form a carbonyl (C═O); or $R_{15}$ and $R_{16}$ together with the C atom attached to them form a carbonyl (C═O);

$R_{17}$, is selected from H, C1-C6 alkyl, deuterated C1-C6 alkyl, C1-C6 alkylhydroxyl, C1-C6 haloalkyl.

Preferably, in the above each formula, A is aromatic ring, or heteroaromatic ring, and more preferably, A is phenyl, pyridyl, pyrazinyl, pyrimidyl or pyridazinyl; the heteroaromatic ring contains 0-3 heteroatoms optionally selected from N, O or S; any hydrogen atom in the A ring may be substituted by deuterium, hydroxyl, halogen, cyano, ester, amido, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

Preferably, in the above each formula, $R_4$ is each independently selected from aryl, heteroaryl, aryloxy, aralkyl, or heterocyclyl, and more preferably $R_4$ is 5-membered heteroaryl; wherein aryl, heteroaryl, aryloxy, aralkyl, heterocyclyl, heterocycloalkyl are each independently substituted by 0 to 5 $R^a$; $R^a$ is optionally selected from C1-C6 alkyl, halogen, hydroxyl, C1-C6 heteroalkyl, C1-C6 alkoxy, C1-C6 alkylamino, cycloalkyl, heterocycloalkyl or cyano; more preferably $R_4$ is selected from:

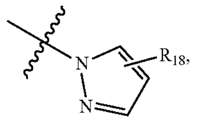

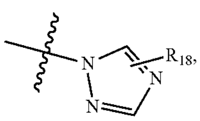

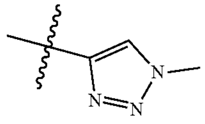

or

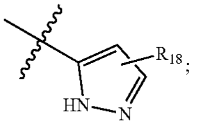

wherein $R_{18}$ is selected from halogen (preferably F) or C1-C6 alkyl.

Preferably, in the above each formula, m is 1.

Preferably, in the above each formula, $R_3$ is H, C1-C6 alkyl or C1-C6 alkoxy.

Preferably, in the above each formula, $R_2$ is H.

Preferably, in the above each formula,

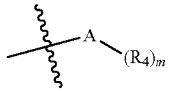

moiety is

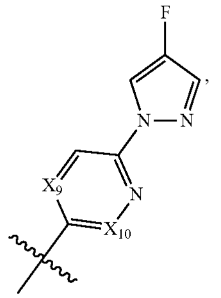

wherein $X_9$ and $X_{10}$ are each independently selected from N or $CR_5$, wherein, $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is independently substituted by 0 to 5 $R^a$; $R^a$ is optionally selected from C1-C6 alkyl, halogen, hydroxyl, C1-C6 heteroalkyl, C1-C6 alkoxy, C1-C6 alkylamino, cycloalkyl, heterocycloalkyl or cyano.

Preferably, the compound of formula I', or the pharmaceutically acceptable salt, stereoisomer, solvate or prodrug thereof has the structure represented by formula 5' or formula 6'

5'

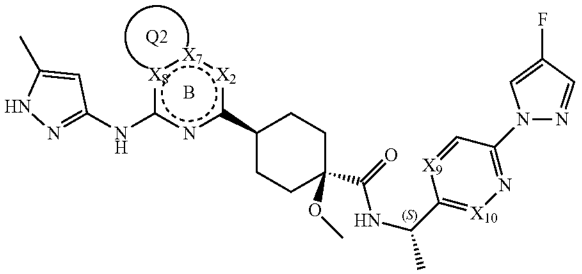

6'

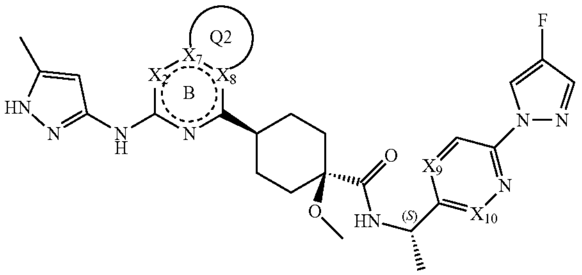

$X_2$, $X_7$, $X_8$, $X_9$, $X_{10}$ and ring Q2 are defined as above, and at least one of $X_7$ and $X_8$ is N.

Preferably, the compound of formula I', or the pharmaceutically acceptable salt, stereoisomer, solvate or prodrug thereof has a structure represented by formula 5' wherein,

5'

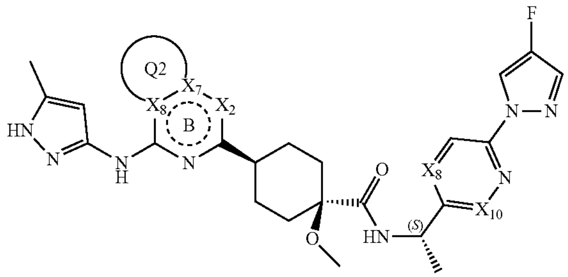

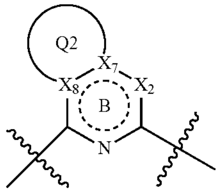

moiety is selected from

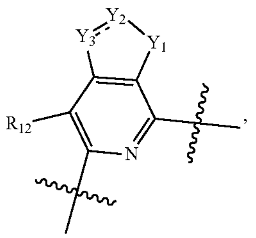

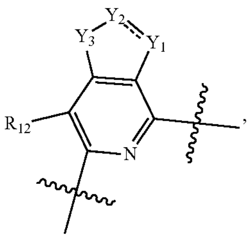

-continued

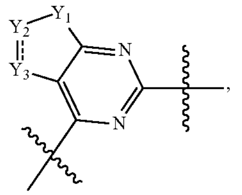

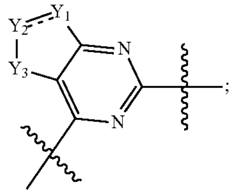

wherein, ═ is double bond, $Y_1$, $Y_2$, and $Y_3$ are each independently selected from N, $NR_{17}$, $CR_{13}$;

$R_{12}$ is independently selected from H, deuterium, halogen, C1-C6 alkyl, C1-C6 alkoxy, C1-C6 alkylamino, nitro, cyano, amino;

$R_{17}$ is independently selected from deuterium, C1-C6 alkyl (such as methyl, ethyl, propyl), deuterated C1-C6 alkyl (deuterated methyl), C1-C6 alkylhydroxyl, C1-C6 haloalkyl (such as fluoro-methyl, fluoro-ethyl);

$R_{13}$ is selected from H, halogen, C1-C6 alkyl, deuterated C1-C6 alkyl, C1-C6 haloalkyl, C1-C6 alkoxy, C1-C6 alkylamino, nitro, cyano, amino;

$X_9$ and $X_{10}$ are each independently CH,

Preferably,

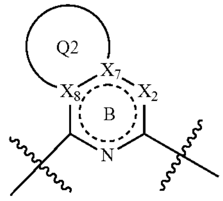

moiety is

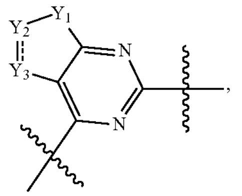

wherein ═ is double bond, and $Y_1$ is $NR_{17}$; $Y_2$ is N; $Y_3$ is CH; $R_{17}$ is defined as above.

Preferably,

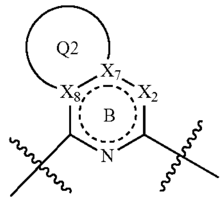

is

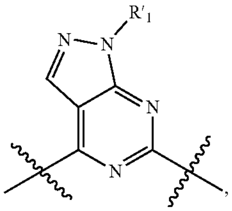

N is R'$_1$ is defined as above.

Preferably, the compound of has a structure shown in formula I:

I

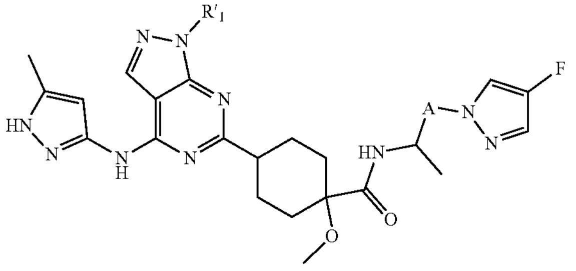

$R'_1$ and A are defined as above.

Preferably. A ring is selected from substituted or unsubstituted 5-6-membered heteroaryl; more preferably, A ring is selected from the substituted or unsubstituted group consisting of imidazolyl, thiazolyl, oxazolyl, pyridyl, pyrazinyl, pyrimidyl or pyridazinyl, more preferably, A ring is substituted or unsubstituted group selected from the group consisting of

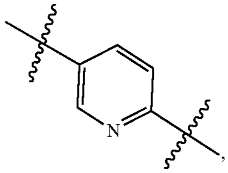

,

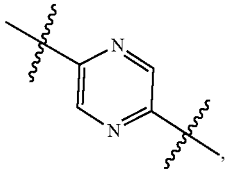

,

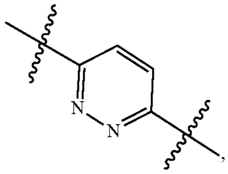

,

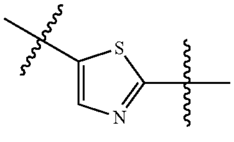

and

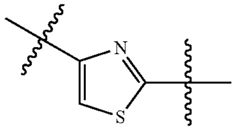

;

wherein, any hydrogen atom on the A ring can be substituted by the following substituents: C1-C6 alkyl, halogen, hydroxyl, amino, C1-C6 heteroalkyl, C1-C6 alkoxy, C1-C6 alkylamino, cycloalkyl, heterocycloalkyl or cyano.

$R'_1$ is selected from H, C1-C6 alkyl, C1-C6 deuterated alkyl, C1-C6 haloalkyl, C3-C6 cycloalkyl, 3-6 membered heterocyclyl, C1-C6 heteroalkyl, C1-C6 alkyl hydroxyl, C3-C6 halocycloalkyl, $Me_3SiCH_2CH_2OCH_2$—, C3-C6 cycloalkyl $CH_2$—, 3-6 membered heterocyclyl $CH_2$—.

The salts that may be formed by the compound in the present invention are also within the scope of the present invention. Unless otherwise stated, the compound in the present invention is understood to include its salt. The term "salt" as used herein refers to a salt formed in the form of acid or base from inorganic or organic acid and base. Further, when the compound in the present invention contains a base fragment which includes, but is not limited to pyridine or imidazole, when it contains an acid segment which includes, but is not limited to carboxylic acid. The zwitter-ion that may form "inner salt" is included within the range of the term "salt". Pharmaceutically acceptable (i.e., non-toxic, physiologically acceptable)salt is preferred, although other salts are also useful and may be used, for example, in the separation or purification steps of the preparation process. The compound of the present invention may form a salt, for example, compound I is reacted with a certain amount (such as an equivalent amount) of an acid or base, and precipitated in a medium, or freeze-dried in aqueous solution.

The base fragment contained in the compounds of the present invention includes but is not limited to amines or pyridine or imidazole rings, and may form salt with organic or inorganic acid. Typical acids that form salts include acetate (such as acetic acid or trihalogenated acetic acid, such as trifluoroacetic acid), adipate, alginate, ascorbate, aspartate, benzoate, benzene sulfonate, disulfate, borate, butyrate, citrate, camphorate, camphor sulfonate, cyclopentane propionate, diethylene glycolate, lauryl sulfate, ethanesulphonate, fumarate, gluceptate, glycerophosphate, hemisulphate, enanthate, caproate, hydrochloride, hydrobromide, hydriodate, isethionate(e.g., 2-hydroxyl-ethesulfonate), lactate, maleate, mesylate, naphthalenesulfonate (e.g., 2-naphthalenesulfonate), nicotinate, nitrate, oxalate, pectate, persulfate, phenylpropionate (e.g., 3-phenylpropionate), phosphate, picrate, pivalate, propionate, salicylate, succinate, sulfate (e.g., formed with sulfuric acid), sulfonate, tartrate, thiocyanate, toluenesulfonate(e.g., tosilate), dodecanoate, etc.

Some compounds of the invention may contain acidic fragments including, but not limited to carboxylic acid which may form salts with various organic or inorganic bases. Salt formed by typical base includes ammonium salt, alkali metal salt (such as sodium, lithium and potassium salts), alkaline earth metal salt (such as calcium and magnesium salts), and salt formed by organic bases (such as organic amines), such as benzathine, dicyclohexylamine, hydrabamine (salt formed with N,N-bis (dehydroabietyl) ethylenediamine), N-methyl-D-glucosamine, N-methyl-D-glucoamide, tert-butyllamine, and the salt formed with amino acids such as arginine, lysine, etc. Basic nitrogen-containing groups can form quaternary ammonium salts with halides, such as small molecular alkyl halides (such as chlorides, bromides and iodides of methyl, ethyl, propyl and butyl), dialkyl sulfate (such as dimethyl, diethyl, dibutyl, and dipentyl sulfates), long chain halides (such as chlorides, bromides and iodides of decyl, dodecyl, tetradecyl, and tetradecyl), aralkyl halides (such as bromides of benzyl and phenyl), etc.

The prodrug and solvate of the compound in the present invention are also included within the scope of the present invention. The term "prodrug" herein refers to a compound, which produces a compound, salt, or solvate in the present invention resulting from the chemical transformation of a metabolic or chemical process when used in the treatment of an associated disease. The compounds of the invention include solvates such as hydrates.

Compound, salt or solvate in the present invention, may be present in tautomeric forms such as amide and imino ether. All of these tautomers are part of the present invention.

Stereoisomers of all compounds (e.g., those asymmetric carbon atoms that may be present due to various substitutions), including their enantiomeric forms and non-enantiomed forms, all belong to the protection scope of the present invention. The independent stereoisomer in the present invention may not coexist with other isomers (e.g., as a pure or substantially pure optical isomer with special activity), or may be a mixture (e.g., racemate), or a mixture formed with all other stereoisomers or a part thereof. The chiral center of the present invention has two configurations of S or R, which is defined by International Union of Pure and Applied Chemistry (IUPAC) in 1974. The racemization form can be solved by physical methods, such as fractional crystallization, or separation crystallization by derivation into diastereomers, or separation by chiral column chromatography. Individual optical isomer can be obtained from racemate by appropriate methods, including but not limited to conventional methods, such as recrystallization after salting with optically active acids.

Weight content of compound in the present invention obtained by preparation, separation and purification in turn is equal to or greater than 90%, such as equal to or greater than 95%, equal to or greater than 99% ("very pure" compound), which is listed in the description of the text. In addition, the "very pure" compound of the present invention is also part of the present invention.

All configuration isomers of the compound of the present invention are within the scope, whether in mixture, pure or very pure form. The definition of the compound of the present invention comprises cis (Z) and trans (E) olefin isomers, and cis and trans isomers of carbocycle and heterocycle.

In the entire specification, the groups and substituents can be selected to provide stable fragments and compounds.

Specific functional groups and chemical term definitions are described in detail below. For the purposes of the present invention, the chemical elements are consistent with Periodic Table of the Elements. CAS version, *Handbook of Chemistry and Physics,* $75^{th}$ Ed. The definition of a particular functional group is also described therein. In addition, the basic principles of Organic Chemistry as well as specific functional groups and reactivity are described in "Organic Chemistry", Thomas Sorrell, University Science Books, Sausalito: 1999, the entire content of which is incorporated herein by reference.

Some compounds of the present invention may exist in specific geometric or stereoisomer forms. The present invention covers all compounds, including their cis and trans isomers, R and S enantiomers, diastereomers, (D) type isomers, (L) type isomers, racemic mixtures and other mixtures. In addition, asymmetric carbon atom can represent substituent, such as alkyl. All isomers and mixtures thereof are included in the present invention.

According to the invention, mixtures of isomers may contain a variety ratios of isomers. For example, mixtures with only two isomers may have the following combinations: 50:50, 60:40, 70:30, 80:20, 90:10, 95:5, 96:4, 97:3, 98:2, 99:1, or 100:0, all ratios of the isomers are within the scope of the present invention. Similar ratios readily understood by those of ordinary skill in the art and ratios for mixtures of more complex isomers are also within the scope of the present invention.

The invention also includes isotope labeled compounds, which are equivalent to the original compounds disclosed herein. However, in practice, it usually occurs when one or more atoms are replaced by atoms with a different atomic weight or mass number. Examples of compound isotopes that may be listed in the present invention include hydrogen, carbon, nitrogen, oxygen, phosphorus, sulfur, fluorine and chlorine isotopes, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$. Compound, or enantiomer, diastereomer, isomer, or pharmaceutically acceptable salt or solvate, the above compound containing isotopes or other isotope atoms are all within the scope of the invention. Some isotope-labeled compounds in the present invention, such as the radioactive isotopes of $^{3}H$ and $^{14}C$, are also included and are useful in experiments on the tissue distribution of drugs and substrates. Tritium ($^{3}H$) and Carbon-14 ($^{14}C$), which are relatively easy to prepare and detect, are the preferred choice. In addition, heavier isotope substitutions such as deuterium, i.e. $^{2}H$, have advantages in certain therapies due to their good metabolic stability, such as increased half-life or reduced dosage in vivo, and thus may be preferred in certain situations. Isotope-labeled compounds can be prepared by conventional methods through replacing non-isotopic reagents with readily available isotope-labeled reagents using the disclosed scheme shown in the Example.

If the synthesis of a specific enantiomer of the compound of the invention is to be designed, it can be prepared by asymmetric synthesis, or derivatized with chiral auxiliary reagent, separating the resulting diastereomeric mixture and removing the chiral auxiliary reagent to obtain a pure enantiomer. In addition, if a molecule contains a basic functional group, such as an amino acid, or an acidic functional group, such as a carboxyl group, a diastereomer salt can be formed with a suitable optically active acids or bases, and it can be separated by conventional means, such as crystallization or chromatography, to obtain a pure enantiomer.

As described herein, the compound in the present invention may be substituted with any number of substituents or functional groups to extend its scope. In general, whether the term "substituted" appears before or after the term "optional", the general formula that includes substituents in the compound of the present invention means the substitution of a specified structural substituent for a hydrogen radical. When multiple locations in a particular structure are replaced by multiple specific substituents, each location of the substituents can be the same or different. The term "substituted" as used herein includes all substitution that allows organic compounds to be substituted. Broadly speaking, the allowable substituents include non-cyclic, cyclic, branched, non-branched, carbocyclic and heterocyclic, aromatic ring and non-aromatic organic compounds. In the present invention, such as heteroatomic nitrogen, its valence state may be supplemented by a hydrogen substituent or by any permitted organic compound described above. Furthermore, the invention does not unintentionally limit the substituted organic compounds in any way. The present invention considers that a combination of substituents and variable groups is good for the treatment of diseases in the form of stable compounds. The term "stable" herein refers to a stable compound which is sufficient for maintaining the integrity of the compound structure within a sufficiently long time, preferably being effective in a sufficiently long time, which is hereby used for the above purposes.

The metabolites of the compounds of the present application and their pharmaceutically acceptable salts, and prodrugs that can be converted into the compounds of the present application and their pharmaceutically acceptable salts thereof in vivo, are also included in the claims.

Preparation Method

Methods for preparing compounds of formula I' are described in the following schemes and examples. Raw materials and intermediates are purchased from commercial sources, prepared by known steps, or otherwise described. In some cases, the sequence of steps to perform the reaction scheme may be changed to facilitate the reaction or avoid unwanted side reaction products.

The preparation method of the compound of formula I' of the present invention is more specifically described below, but these specific methods do not constitute any limitation of the invention. The compound of the invention may also optionally be conveniently prepared by combining the various synthetic methods described in this specification or known in the art, such a combination may be easily performed by a skilled person in the art to which the invention belongs.

Generally, in the preparation process, each reaction is usually carried out under the protection of inert gas and in an appropriate solvent at 0 to 90° C., and the reaction time is usually 2-24 hours.

Preferably, the preparation process is as follows:

Method 1:

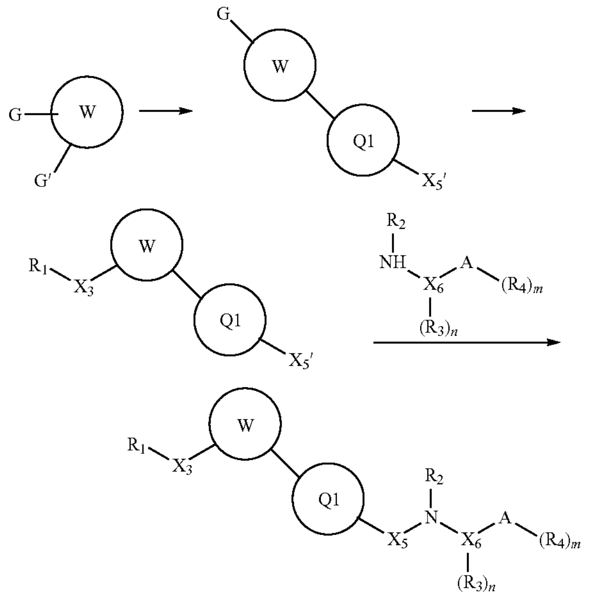

Step 1:

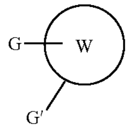

is reacted with

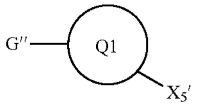

in a solvent (such as DMF/$H_2O$, dioxane, toluene), under basic condition (such as potassium carbonate, sodium carbonate, etc.) and in the presence of catalyst and ligand (such as $Pd(PPh)_3)_4$) to obtain

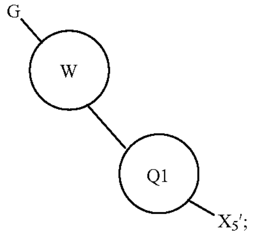

Step 2;

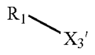

is reacted with

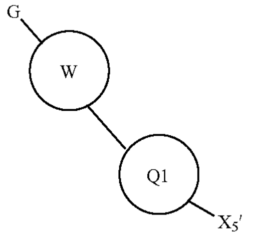

in an inert solvent (such as DMF, dioxane, ethylene glycol dimethyl ether, etc.), under basic condition (such as diisopropylethylamine, potassium acetate, DBU, etc.) or in the presence of catalyst and ligand (such as $Pd(PPh)_3)_4$, $Pd_2(dba)_3$†t-BuXphos, etc.) to obtain

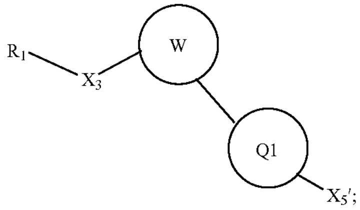

Step 3:

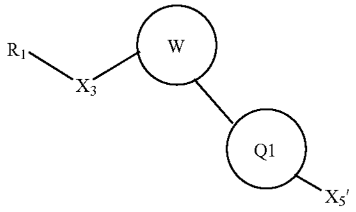

is reacted with

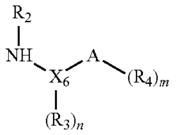

in an inert solvent (such as DMF) and in the presence of condensing agent (such as DMAP, HATU, PyBOP, etc.), to obtain formula I'.

Method 2

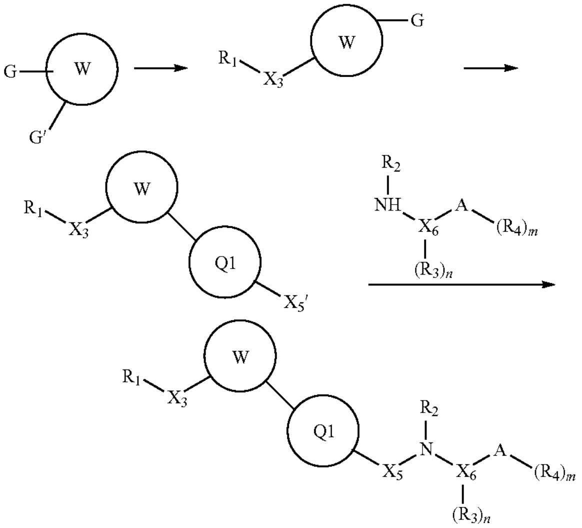

Step 1:

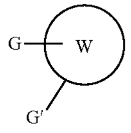

is reacted with

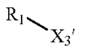

in an inert solvent (such as DMF, dioxane, ethylene glycol dimethyl ether, etc.), under basic condition (such as diisopropylethylamine, potassium acetate, DBU, etc.) or in the presence of catalyst and ligand (such as $Pd(PPh)_3)_4$, $Pd_2(dba)_3$\t-BuXphos, etc.) to obtain

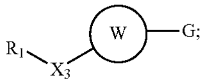

Step 2:

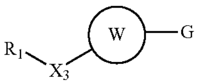

is reacted with

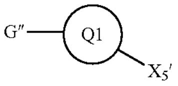

in an inert solvent (such as $DMF/H_2O$), under basic condition (e.g. $K_2CO_3$) and in the presence of catalyst and ligand such as Pd $PPh)_3)_4$) to obtain

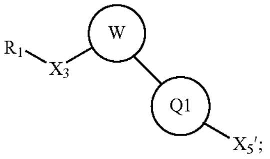

Step 3:

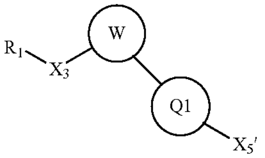

is reacted with

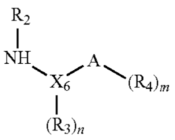

in an inert solvent (such as DMF) an in the presence of condensing agent (such as DMAP, HATU, PyBOP, etc.), to obtain formula I'.

In the above each formula, G and G' are independently halogen (e.g. F, Cl or Br);

G" is borate ester group (e.g.

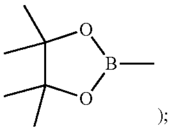

);

X$_3$' is selected from OH, —NHR$_8$, —CHR$_9$R$_{10}$,

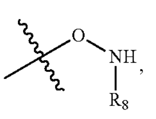, 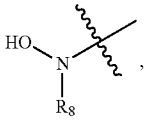, or 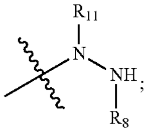;

X$_5$' is selected from —C(O)—OH, —S(O)—OH, —S(O)$_2$—OH,

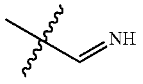 or 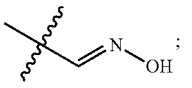;

R$_1$, X$_3$, W, Q1, X$_5$, X$_6$, R$_2$, R$_3$, R$_4$, A, Q2, m and n are defined as above.

Preferably, the compounds are prepared by the following methods:

Method 1:

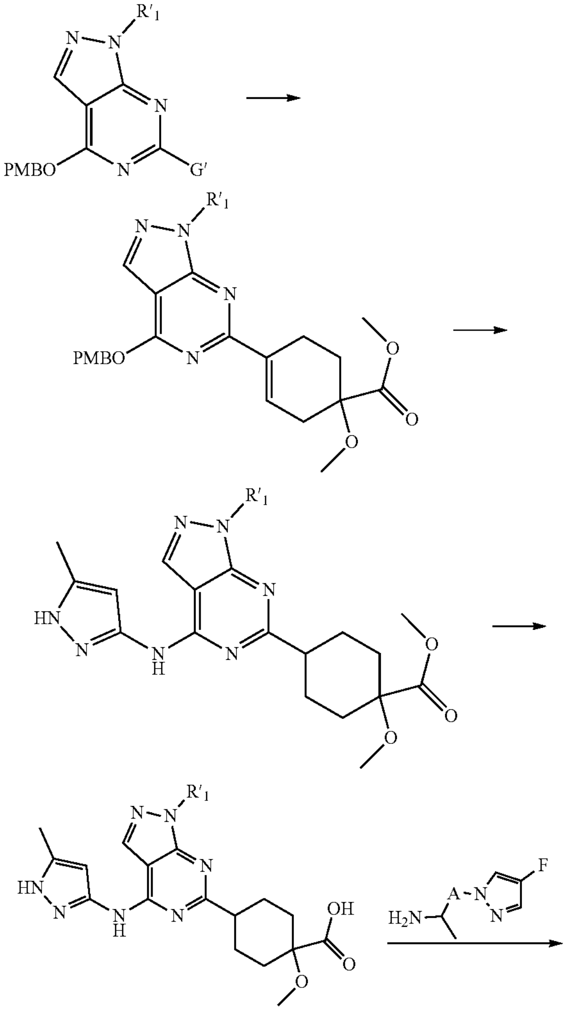

-continued

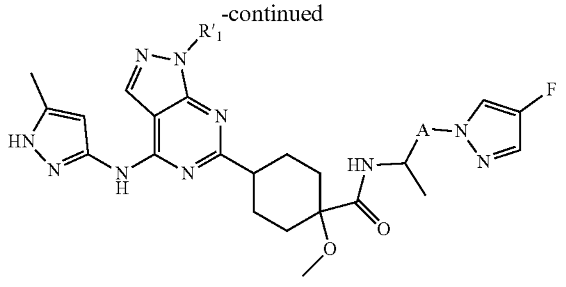

I

Step 1:

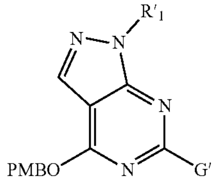

is reacted with

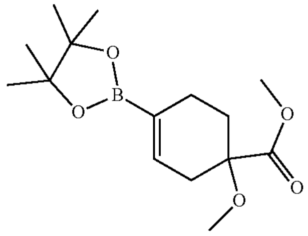 [SMILES: COC(=O)C1(OC)CC=C(B2OC(C)(C)C(C)(C)O2)CC1]

in an inert solvent (such as DMF/$H_2O$, glycol dimethyl ether, dioxane or toluene) in the presence of base (such as potassium carbonate, sodium carbonate, etc.), catalyst and ligand (such as $Pd(PPh_3)_4$) to obtain

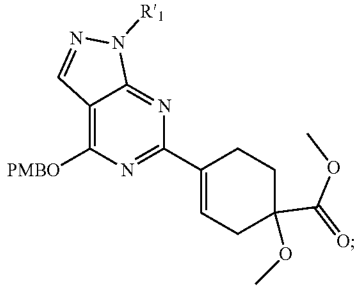

Step 2: in an inert solvent (such as methanol, ethanol, or ethyl acetate, etc.), after reducing

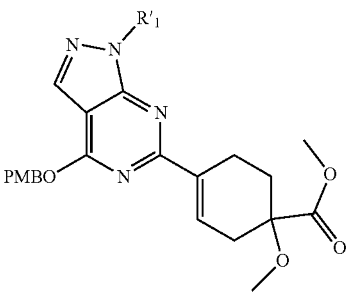

under hydrogen atmosphere, then halogenating or reacting with trifluoromethanesulfonic anhydride to obtain an intermediate which reacts with

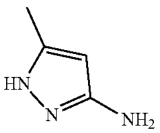

in the presence of a base (such as diisopropylethylamine, potassium carbonate, sodium carbonate or triethylamine, etc.) to obtain

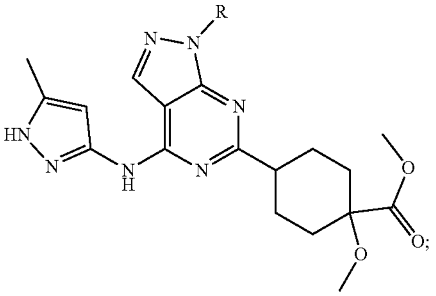

Step 3: in an inert solvent (such as methanol, ethanol, tetrahydrofuran or water),

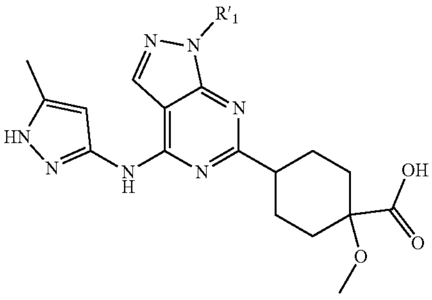

is obtained by reacting under the condition of a base (such as lithium hydroxide, sodium hydroxide or potassium hydroxide etc.

Step 4: in an inert solvent (such as DMF),

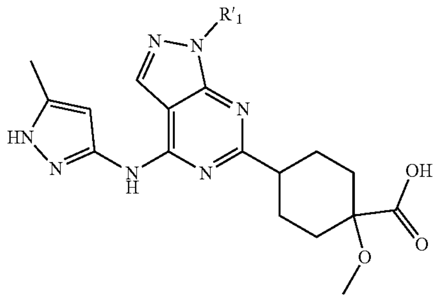

is reacted with

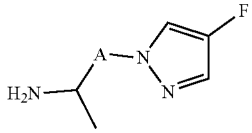

in the presence of a condensing agent (such as DMAP, HATU, PyBOP, etc.) to obtain formula I;

Method Two:

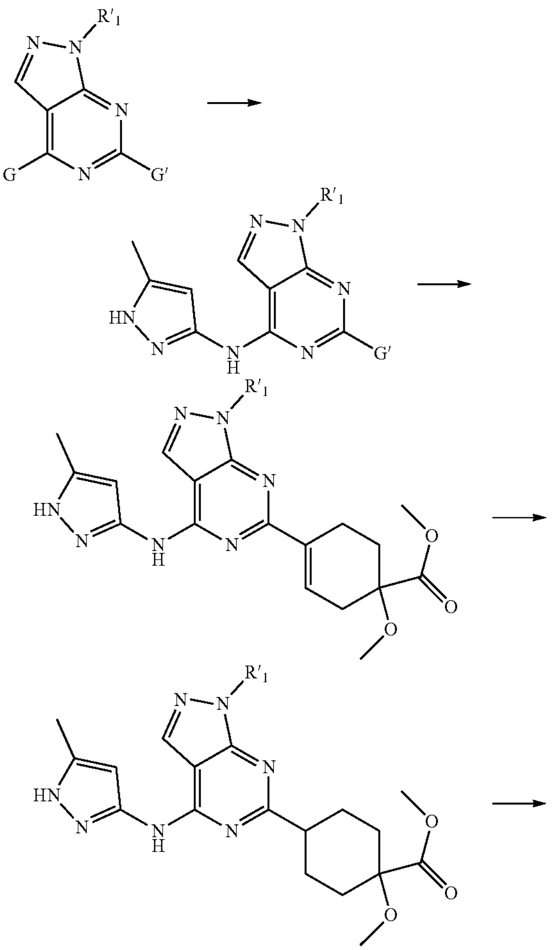

-continued

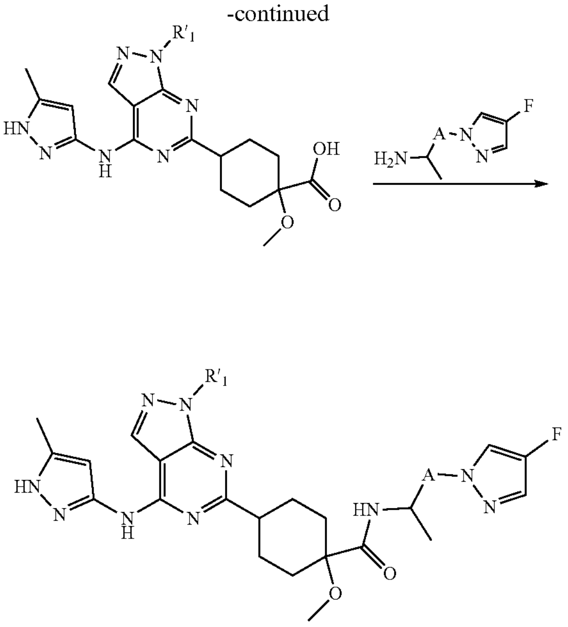

I

Step 1; in an inert solvent (such as DMSO or DMF, etc.), reacted with

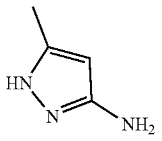

under the condition of a base (such as diisopropylethylamine triethylamine, potassium carbonate or sodium carbonate, etc.) to obtain

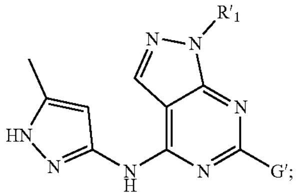

Step 2; in an inert solvent (such as DMF/$H_2O$, glycol dimethyl ether, dioxane or toluene etc. and a base (such as potassium carbonate, sodium carbonate, etc.),

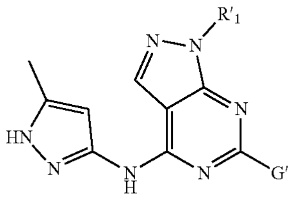

is reacted with

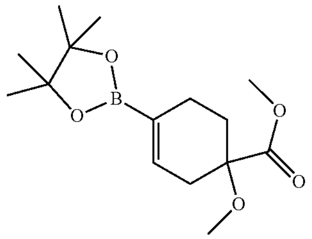 [SMILES: COC(=O)C1(OC)CC=C(B2OC(C)(C)C(C)(C)O2)CC1]

in the presence of base, catalyst and ligand (such as Pd(dppf)$Cl_2$) to obtain

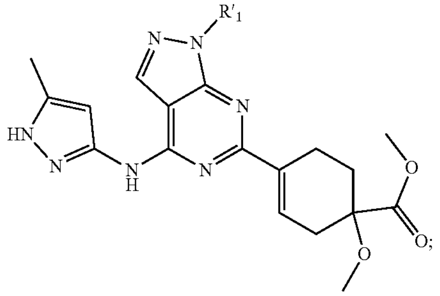

Step 3: in an inert solvent (such as methanol, ethanol, or ethyl acetate, etc.),

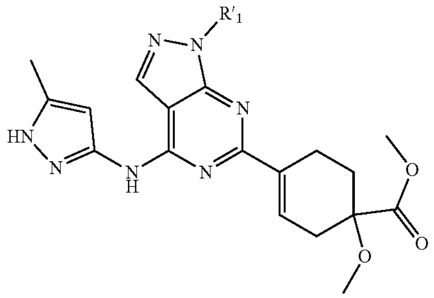

is reduced under hydrogen atmosphere to obtain

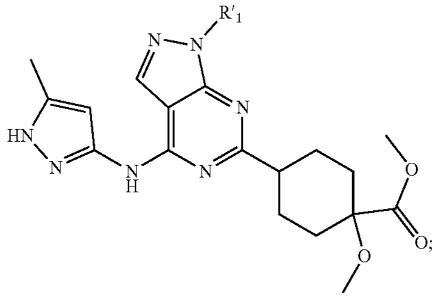

Step 4: in an inert solvent (such as DMF),

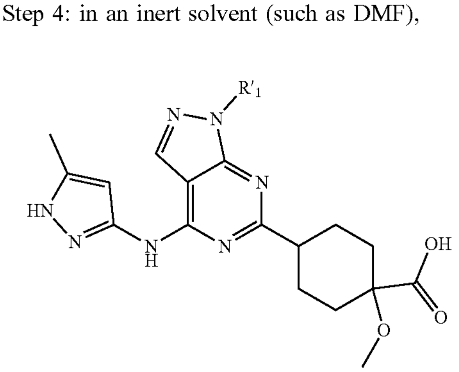

is reacted with

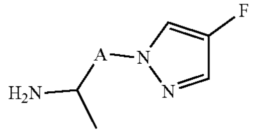

in the presence of a condensing agent (such as DMAP, HATU, PyBOP, etc.) to obtain formula I;

wherein G and G' are each independently halogen (e.g. Cl or Br);

$R'_1$ is defined as above.

Unless otherwise specified, the above starting materials can be purchased commercially or synthesized according to the reported literature.

Pharmaceutical Composition and Method of Administration

The pharmaceutical compositions of the present invention are used to prevent and/or treat the following diseases: inflammation, cancer, cardiovascular disease, infection, immunological disease, metabolic disease.

The compound of the present invention can be used in combination with other drugs known to treat or improve similar conditions. When administered in combination, the original administration method and dosage for the drug can remain unchanged, while the compound of the present invention may be administered simultaneously or subsequently. Pharmaceutical composition simultaneously containing one or more known drugs and the compound of the present invention may be preferred when administered in combination with one or more other drugs. The drug combination also includes administering the compound of the present invention and other one or more known drugs at overlapping time. When the compound of the present invention is combined with other one or more drugs, the dose of the compound of the present invention or known drug may be lower than that of their individual use.

The drug or active ingredients that can be used in pharmaceutical use with the compounds of the present invention include but are not limited to PD-1 inhibitor (such as nivolumab, pembrolizumab, JS-001, SHR-120, BGB-A317, IBI-308. GLS-010, GB-226, STW204, HX008, HLX10, BAT 1306, AK105, LZM 009 or the biological analogue thereof, etc.), PD-L1 inhibitor (such as durvalumab, atezolizumab, CS1001, KN035, HLX20, SHR-1316, BGB-A333, JS003, CS1003, KL-A167, F 520, GR1405, MSB2311 or the biological analogue thereof, etc.), CD20 antibody (such as rituximab, obinutuzumab, ofatumumab, tositumomab, ibritumomab, etc.), CD47 antibody (such as Hu5F9-G4, CC-90002, TTI-621, TTI-622, OSE-172, SRF-231, AIX-148, NI-1701, SHR-1603, IBI188, IMM01), ALK inhibitor (such as Ceritinib, Alectinib, Brigatinib, Lorlatinib, Ocatinib), PI3K inhibitor (such as Idelalisib, Dactolisib, Taselisib, Buparlisib, etc.), BTK inhibitor (such as Ibrutinib, Tirabrutinib, Acalabrutinib, etc.), EGFR inhibitor (such as Afatinib, Gefitinib, Erlotinib, Lapatinib, Dacomitinib, Icotinib, Canertinib, etc.), VEGFR inhibitor (such as Sorafenib, Pazopanib. Regorafenib, Cabozantinib, Sunitinib, Donafenib, etc.), HDAC inhibitor (such as Givinostat, Droxinostat, Entinostat, Dacinostat, Tacedinaline, etc.), CDK inhibitor (such as Palbociclib, Ribociclib, Abemaciclib, Lerociclib, etc.), MEK inhibitor (such as Selumetinib (AZD6244), Trametinib (GSK1120212). PD0325901. U0126, AS-703026, PD184352 (CI-1040), etc.), mTOR inhibitor (such as Vistusertib, etc.), SHP2 inhibitor (such as RMC-4630, JAB-3068, TNO 155, etc.). IGF-1R inhibitor (such as Ceritinib, Okatinib, Linsitinib, BMS-754807, GSK1838705A, etc.) or combinations thereof.

The dosage forms of the pharmaceutical composition of the present invention include (but are not limited to): injection, tablet, capsule, aerosol, suppository, pellicle, pill, liniment for external use, controlled release or sustained-release or nano formulation.

The pharmaceutical composition of the present invention comprises a compound of the present invention or a pharmaceutically acceptable salt and a pharmaceutically acceptable excipient or carrier with safe and effective amount, wherein "safe and effective amount" refers to the amount of compound is sufficient to significantly improve the condition, not to produce severe side effects. Typically, the pharmaceutical composition contains 1-2000 mg of the compound of the present invention/dosage, and preferrably contains 10-1000 mg of the compound of the present invention/dosage. Preferably, "one dosage" is a capsule or a pill.

"Pharmaceutically acceptable carrier" refers to one or more compatible solid or liquid filler or gel substances, which are suitable for human use, and must be sufficiently pure and of sufficiently low toxicity. "Compatible" herein refers to ability of each component of a composition can be mixed with the compound of the present invention and can be mixed with each other without appreciably reducing the efficacy of the compound. Examples of pharmaceutically acceptable carrier include cellulose and derivatives thereof (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc.), emulsifier (such as Tween®), wetting agent (such as lauryl sodium sulfate), colorant, flavoring, stabilizer, antioxidant, preservative, pyrogen-free water, etc.

There is no special limitation of administration mode for the compound or pharmaceutical compositions of the present invention, and the representative administration mode includes (but is not limited to): oral, intratumorally, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid: (b) binders, such as hydroxylmethyl cellulose, alginate, gelatin, polyvinylpyrrolidone, sucrose and arabic gum; (c)

humectant, such as, glycerol; (d) disintegrating agent, such as agar, calcium carbonate, potato starch or tapioca starch, alginic acid, certain composite silicates, and sodium carbonate; (e) dissolution-retarding agents, such as paraffin; (f) absorption accelerators, such as quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, lauryl sodium sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, such as ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

The treatment method of the present invention can be administered alone or in combination with other treatment means or therapeutic drugs.

When the pharmaceutical compositions are used, a safe and effective amount of compound of the present invention is administrated to a mammal (such as human) in need thereof, wherein the dose of administration is a pharmaceutically effective dose. For a person weighed 60 kg, the daily dose is usually 1-2000 mg, preferably 50-1000 mg. Of course, the particular dose should also depend on various factors, such as the route of administration, patient healthy status, which are well within the skills of an experienced physician.

The present invention also provides a preparation method of pharmaceutical composition comprising the step of mixing a pharmaceutically acceptable carrier with the compound of formula I' or crystal form, pharmaceutically acceptable salt, hydrate or solvate thereof of the present invention, thus forming the pharmaceutical composition.

The invention also provides a treatment method comprising the step of administering the compound of formula I', or its crystalline form, pharmaceutically acceptable salt, hydrate or solvate thereof, or the pharmaceutical composition of the invention to a subject in need thereof to inhibit RET.

The Invention has the Following Main Advantages:

(1) The compound of the present invention has excellent inhibitory ability to RET kinase, especially WT-RET, RET-V804L and RET-V804M:

(2) The compound of the invention has lower toxic and side effects;

(3) The compound of the invention has better pharmacodynamic and pharmacokinetic properties;

(4) The compound of the present invention can effectively inhibit tumor growth.

EXAMPLE

The technical solution of the present invention will be further described below, but the protection scope of the present invention is not limited thereto.

Example 1

The compound synthesized in the present invention:

C1

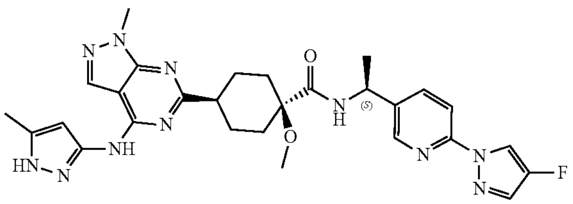

The experimental process was as follows:

1. Synthesis of Intermediate C1-7

The synthetic route was as follows:

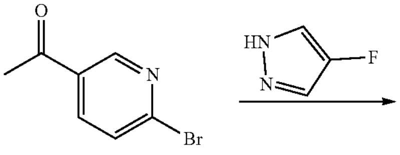

C1-8

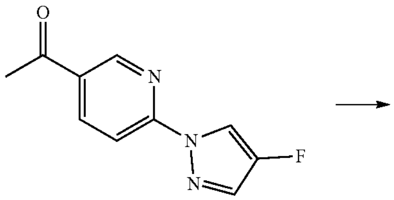

C1-9

-continued

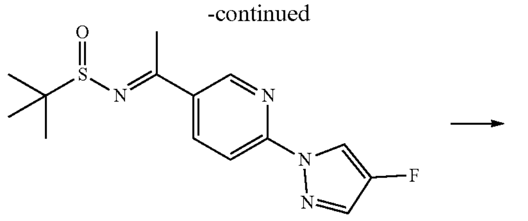

C1-10

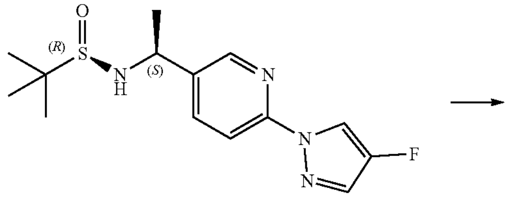

C1-11

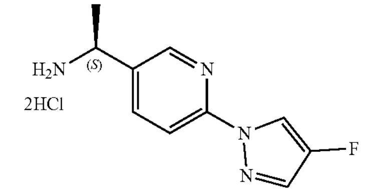

C1-7

1. Synthesis of C1-9

C1-8 (6.98 g, 34.9 mmol), 4-fluoro-1H-pyrazole(3.3 g, 35 mmol), potassium carbonate (11.1 g, 73.6 mmol) and DMF (30 mL) were added into a 100 mL single-neck flask to react at 100° C. for 15 h. Then it was cooled to room temperature, poured into water, filtered and dried to obtain 5.93 g of compound C1-9. Nuclear magnetic analysis data of compound C1-9: $^1$H NMR (400 MHz, $CDCl_3$): δ 8.96-8.95 (d, J=1.8 Hz, 1H), 8.47-8.45 (dd, 1H), 8.37-8.34 (dd, 1H), 8.05-8.03 (dd, 1H), 7.66-7.65 (d, J=3.96, 1H), 2.65 (s, 3H).

2. Synthesis of C1-10

C1-9 (4.2 g, 0.02 mol), R-tert-butyl sulfinamide (2.48 g, 0.02 mol), tetraethyl titanate (9.34 g, 0.041 mol) and THF (50 mL) were added into a 100 mL three-neck flask to react at 75° C. for 15 h. Then it was cooled to room temperature, poured into water, filtered. The filter cake was washed with ethyl acetate, and the organic phases were combined, dried, concentrated, and purified by column chromatography to obtain 5.35 g of compound C1-10.

Nuclear magnetic analysis data of compound C1-10: $^1$H NMR (400 MHz, $CDCl_3$): δ8.96-8.95 (d, J=1.8 Hz, 1H), 8.47-8.45 (dd, 1H), 8.37-8.34 (dd, 1H), 8.05-8.03 (dd, 1H), 7.66-7.65 (d, J=3.96, 1H), 2.65 (s, 3H).

3. Synthesis of C1-11

C1-10 (3.5 g) and THF (50 mL) were added into a 100 mL three-neck flask, cooled to −70° C., lithium tri-sec-butylborohydride in THF (1M, 34.1 mL) was added dropwise, and stirred at this temperature for half an hour, then naturally raised to room temperature. TLC showed the reaction was completed. Methanol (5 mL) was added to quench the reaction, then water was added, filtered, and the filter cake was washed with ethyl acetate. Organic phases were combined, dried, concentrated, and purified by column chromatography to obtain 3.1 g of compound C1-11. Nuclear magnetic analysis data of compound C1-11: $^1$H NMR (400 MHz, $CDCl_3$): δ 8.40-8.39 (d, J=4.6 Hz, 1H), 8.36-8.35 (d, J=2.08 Hz, 1H), 7.94-7.91 (d, J=8.48 Hz, 1H), 7.79-7.76 (m, 1H), 7.59-7.58 (d, J=4.28, 1H), 4.68-4.63 (m, 1H), 3.37-3.36 (m, 1H), 1.59-1.57 (d, J=6.72, 3H), 1.21 (s, 9H).

4. Synthesis of C1-7

C1-11 (3.1 g) was added into a 100 mL three-neck flask, then methanol (10 mL) and 1, 4-dioxane (10 mL) were added to dissolve under stirring. Then HCl/1, 4-dioxane (4M, 25 mL) was added, stirred at room temperature for 2 h. The reaction solution was concentrated to obtain a crude product, and the crude product was slurried in ether to obtain 2.27 g of compound C1-7.

Nuclear magnetic analysis data of compound C1-7: $^1$H NMR (400 MHz, DMSO-$D_6$): δ 8.79 (br, 3H), 8.74-8.72 (m, 1H), 8.64-8.63 (d, J=2.08 Hz, 1H), 8.23-8.20 (m, 1H), 7.97-7.95 (m, 2H), 4.52-4.52 (m, 1H), 1.60-1.58 (d, J=6.84 Hz, 3H).

II. Synthesis of Intermediate C1-3

The synthetic route was as follows:

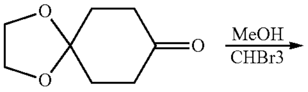

C1-12

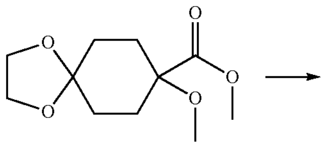

C1-13

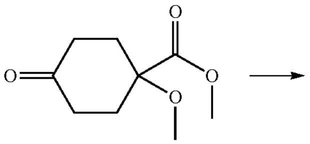

C1-14

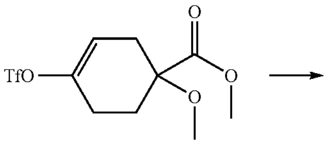

C1-15

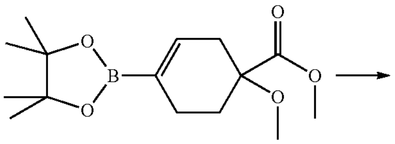

C1-3

1. Synthesis of Compound C1-13

Bromoform (125 mL) and C1-12 (128 mmol, 20 g) were added into a 250 mL three-neck flask, and stirred to dissolve, then cooled to 0° C., and KOH (1 mol, 57.4 g) in methanol (300 ml) was added dropwise slowly. After addition, the temperature was raised to room temperature and stirred for 16 h. TLC showed the reaction was completed. The reaction solution was concentrated, diluted with water (50 mL), extracted with ethyl acetate three times. Organic phase was washed with saturated brine, dried, and concentrated under reduced pressure to obtain 25 g of C1-13, which was directly used in the next step.

2. Synthesis of Compound C1-14

C1-13 (86 mmol, 20 g) and methanol (200 mL) were added into a 500 mL single-neck flask, then concentrated hydrochloric acid (100 mL) was added under stirring at room temperature, and stirred at room temperature for 16 h. TLC showed that the reaction was completed. The reaction solution was concentrated, and saturated $NaHCO_3$ aqueous solution was added for adjusting pH to 6-7, extracted with ethyl acetate for three times. Organic phase was washed with saturated brine, dried, concentrated under reduced pressure to obtain crude product, and purified by column chromatography (developing agent:ethyl acetate/petroleum ether=1: 30-1:5) to obtain 10 g of C1-14.

3. Synthesis of Compound C1-15

Anhydrous toluene (50 mL) and anhydrous pyridine (4.5 mL, 53 mmol) were added into a 250 mL three-neck flask and cooled to −10° C. Trifluoromethylsulfonic anhydride (10.8 mL, 60 mmol) in anhydrous toluene (60 mL) was slowly added dropwise under the protection of nitrogen. After addition, the temperature was raised to room temperature slowly, and C1-14 (9 g, 48 mmol) in anhydrous toluene (30 mL) was added. The reaction solution was raised to 40° C. and stirred for 16 h. TLC showed that the reaction was completed, diluted with 10 ml water, extracted with ethyl acetate for three times. Organic phase was washed with saturated brine, dried, concentrated under reduced pressure to obtain crude product, and it was purified by column chromatography (developing agent:ethyl acetate/petroleum ether=1: 40-1:20) to obtain 9 g of C1-15.

4. Synthesis of Compound C1-3

C1-15 (9 g, 28 mmol), bis(pinacolato)diboron (8.7 g, 34 mmol), dppf (1.5 g, 3 mmol), palladium acetate (350 mg, 1.5 mmol), potassium acetate (8.25 g, 88 mmol) and dioxane (120 mL) were added sequentially into a 250 mL three-neck flask under the protection of nitrogen, replaced with nitrogen for three times, then the reaction solution was stirred at 95° C. for 16 hours. TLC showed the reaction was completed, filtered and concentrated under reduced pressure, then diluted with 20 mL water, extracted with ethyl acetate for three times. Organic phase was washed with saturated brine, dried, concentrated under reduced pressure to obtain crude product, and it was purified by column chromatography (developing agent:ethyl acetate/petroleum ether=1:20-1:10) to obtain product C1-3 (yellowish solid, 8 g).

III. Synthesis of Compound C1

The synthetic route was as follows:

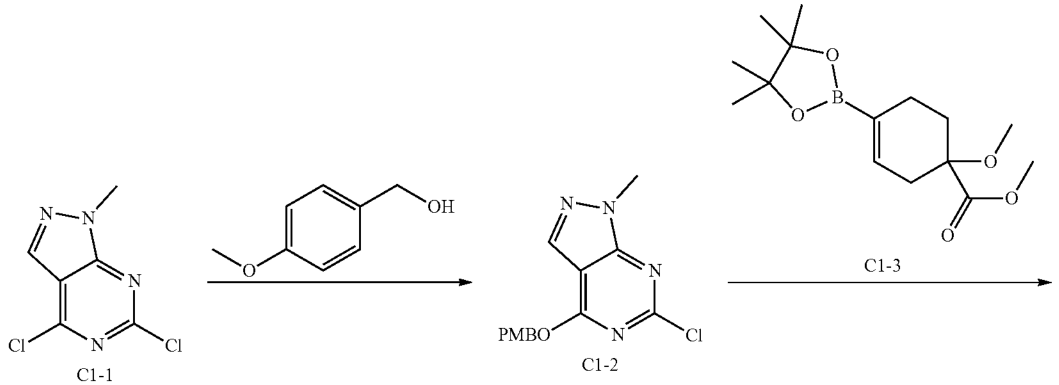

C1-1 C1-2 C1-3

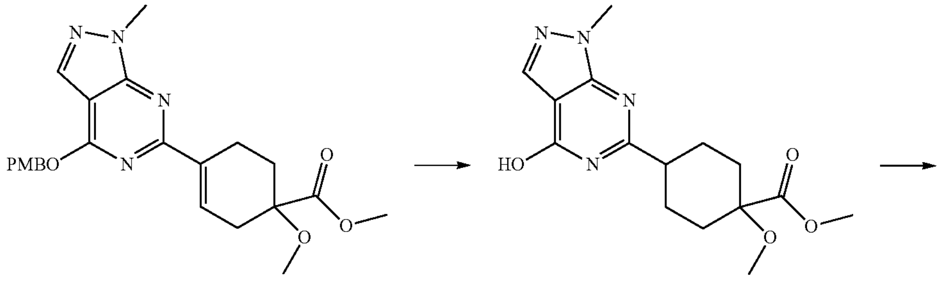

C1-4 C1-5

-continued

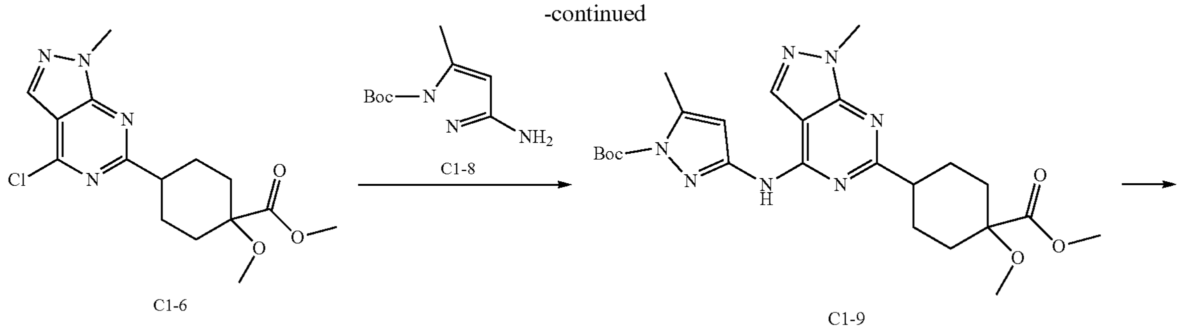

C1-6 C1-9

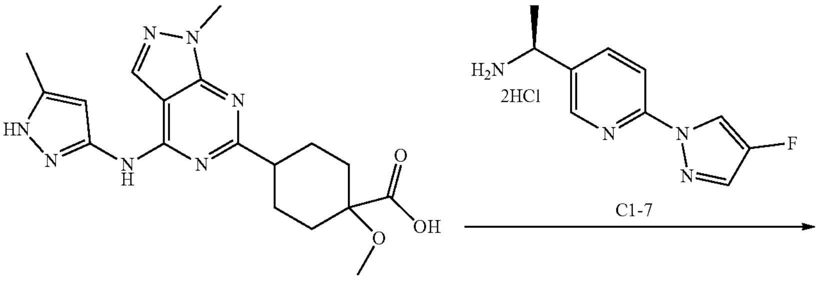

C1-10

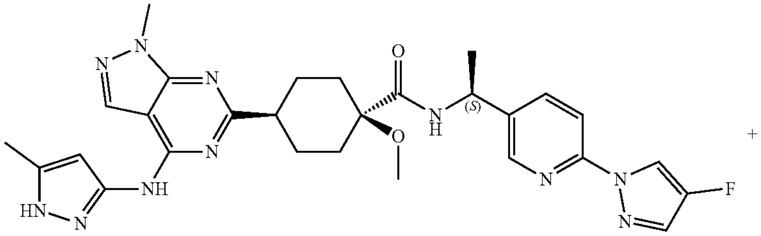

C1

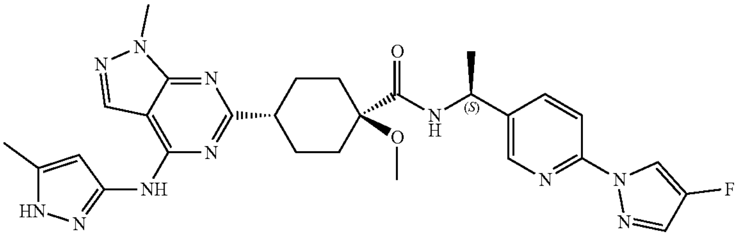

C1A

1. Synthesis of Compound C1-2

Compound C1-1 (1.0 g, 4.93 mmol) was dissolved in anhydrous THF (20 mL), then a solution of potassium tert-butoxide (1.1 g, 9.86 mmol) and p-methoxybenzyl alcohol (0.68 g, 4.93 mmol) in anhydrous THF (20 mL) was added dropwise under cooling in an ice-salt bath. After the addition was completed, the mixture was raised to room temperature naturally and stirred overnight. The reaction was quenched by adding saturated salt water, then extracted with ethyl acetate, the organic phase was separated and washed with saturated salt water, dried over anhydrous sodium sulfate, concentrated under reduced pressure to obtain the crude product, and purified by column chromatography to obtain 0.7 g of compound C1-2.

$^{1}$H NMR (400 MHz, DMSO-d6) δ 8.26 (s, 1H), 7.50-7.47 (d, 2H, J=9.03 Hz), 6.99-6.97 (d, 2H, J=9.03 Hz), 5.54 (s, 2H), 3.97 (s, 3H), 3.78 (s, 3H).

2. Synthesis of Compound C1-4

Compound C1-2 (680 mg, 2.24 mmol) and compound C1-3 (795 mg, 2.68 mmol) were dissolved in a mixture solvent of 20 mL 1,4-dioxane and 4 mL water, and palladium acetate (50 mg, 0.224 mmol), dppf (248 mg, 0.447 mmol) and potassium carbonate (463 mg, 3.36 mmol) were added sequentially. The reaction solution was stirred at 102° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 515 mg of compound C1-4. MS [M+H] 439.1.

3. Synthesis of Compound C1-5

Compound C1-4 (515 mg, 1.17 mmol) was dissolved in a mixed solvent of ethyl acetate (5 mL) and methanol (5 mL), then Pd/C (103 mg) was added, stirred overnight at room temperature under hydrogen atmosphere. After the reaction was completed, the reaction solution was filtered through diatomite, washed with methanol, and the filtrate was concentrated under reduced pressure to obtain 255 mg Compound C1-5. $^1$H NMR (400 MHz, MeOD-d4) δ 7.89 (s, 1H), 3.86-3.84 (d, 3H, J=6.46 Hz), 3.69-3.65 (d, 3H, J=13.25 Hz), 3.18-3.14 (d, 3H, J=13.62 Hz), 2.66-2.57 (m, 1H), 2.39-2.50 (m, 1H), 2.07-2.04 (m, 1H), 1.95-1.82 (m, 2H), 1.76-1.69 (m, 3H), 1.55-1.51 (m, 1H).

4. Synthesis of Compound C1-6

Compound C1-5 (255 mg) was dissolved in phosphorus oxychloride (5 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, and concentrated under reduced pressure to obtain 254 mg of the crude compound C1-6, which was used directly in the next step without purification.

$^1$H NMR (400 MHz, MeOD-d4) δ 8.08 (s, 1H), 3.99-3.98 (d, 3H, J=3.86 Hz), 3.67-3.66 (d, 3H, J=3.19 Hz), 3.19-3.16 (d, 3H, J=13.74 Hz), 2.96-2.87 (m, 1H), 2.29-2.24 (m, 1H), 2.09-1.74 (m, 6H), 1.59-1.52 (m, 1H).

5. Synthesis of Compound C1-9

Compound C1-6 (300 mg, 0.89 mmol) and Compound C1-8 (210 mg, 1.07 mmol) were dissolved in 10 ml of superdried 1,4-dioxane, and then $Pd_2(dba)_3$ (91 mg, 0.09 mmol), t-Buxphos (75 mg, 0.18 mmol) and KOAc (171 mg, 1.78 mmol) were successively added. Then the reaction solution was stirred overnight at 60° C. under nitrogen protection. After the reaction was completed, the reaction was cooled to room temperature, concentrated under reduced pressure to remove solvent, and diluted with ethyl acetate. The organic phase was washed with saturated salt water, dried over anhydrous sodium sulfate, concentrated under reduced pressure and purified by column chromatography to obtain 279 mg of compound C1-9. MS [M+H] 500.4. $^1$H NMR (400 MHz, MeOD-d4) δ 8.15-8.12 (d, 1H, J=7.36 Hz), 7.02 (s, 1H), 3.90-3.89 (d, 3H, J=3.40 Hz), 3.69-3.67 (d, 3H, J=8.58 Hz), 3.25 (s, 3H), 2.80-2.77 (m, 1H), 2.51 (s, 3H), 2.34-2.24 (m, 1H), 2.09-1.92 (m, 4H), 1.81-1.77 (m, 3H), 1.56 (s, 9H).

6. Synthesis of Compound C1-10

Compound C1-9 (279 mg, 0.56 mmol) was dissolved in a mixed solvent of methanol (10 mL) and water (2 mL), then lithium hydroxide monohydrate (70 mg, 1.68 mmol) was added, stirred overnight at 60° C. After the reaction was completed, the reaction solution was cooled to room temperature and 300 mg of crude C1-10 was obtained by evaporation of methanol under reduced pressure.

7. Synthesis of Compound C1

Compound C1-10 (285 mg, 0.73 mmol) and compound C1-7 (177 mg, 0.73 mmol) were dissolved in DMF (5 mL), then DIPEA (752 mg, 5.83 mmol) was added, stirred at room temperature for 15 min, then HATU (416 mg, 1.09 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C1 with Ms [M+H] 574, and compound C1A with [M+H] 574.

Nuclear magnetic of compound C1: $^1$H NMR (400 MHz, DMSO+$D_2O$) δ 8.70-8.69 (d, 1H, 4.05 Hz), 8.57-8.55 (d, 1H, 8.31 Hz), 8.45-8.44 (d, 1H, 2.15 Hz), 8.33 (br, 1H), 8.02-7.99 (dd, 1H, 8.58 Hz, 2.41 Hz), 7.93-7.88 (m, 2H), 6.77 (br, 1H), 5.10-5.03 (m, 1H), 3.90 (s, 3H), 3.18 (s, 3H), 2.78-2.68 (m, 1H), 2.28 (s, 3H), 2.03-1.64 (m, 8H), 1.48-1.46 (d, 3H, 6.97 Hz).

C1 and C1A were separated by high performance liquid chromatography from Agilent under the following conditions:

Instrument: Agilent 1290 infinity II

Chromatographic column: Agilent Prep-C18 (250×21.2 mm, 10 μm)

Mobile phase: Phase A: water (containing 0.1% trifluoroacetic acid)

Phase B: methanol

Flow rate: 15.0 mL/min, Detection wavelength: 254 nm

Solvent: DMSO

Injection concentration: about 50 mg/ml

Injection volume: 500 μL

Peak time of C1: 24.5 min

Peak time of C1A: 20.5 min

Gradient Program:

| t/min | Phase B | Phase A |
|---|---|---|
| 0 | 57 | 43 |
| 30 | 57 | 43 |

Example 2

The compound synthesized in the present invention

C2

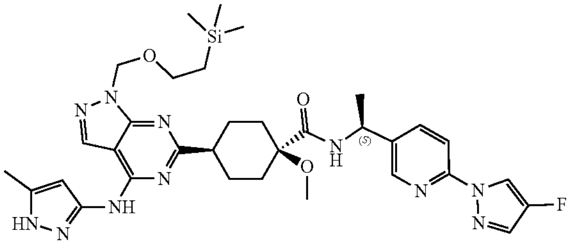

The synthetic route and experimental process were as follows:
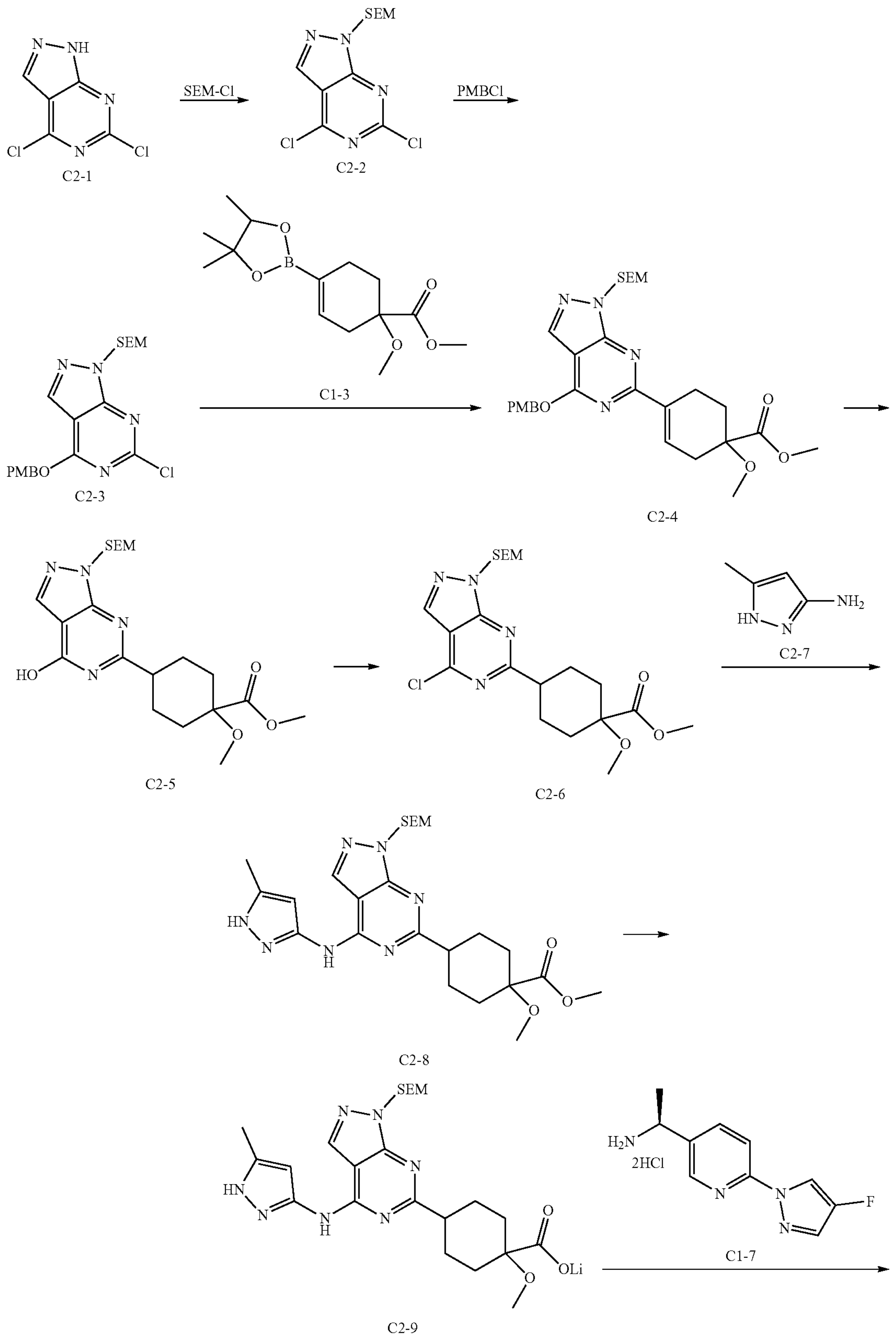

-continued

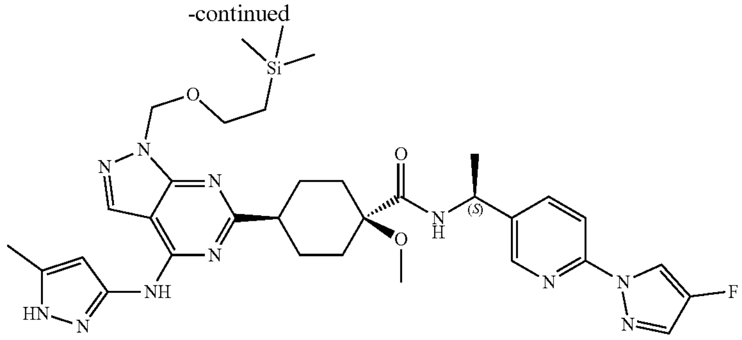

+

C2

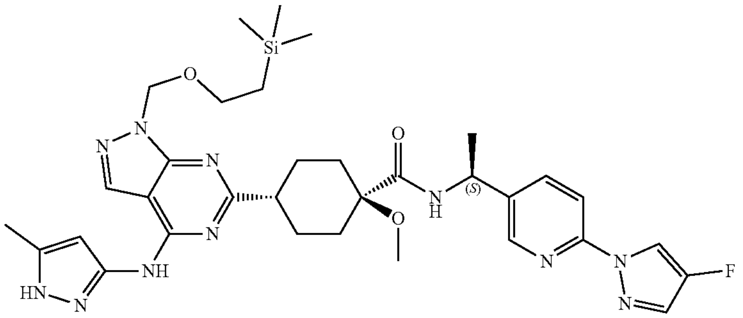

C2A

1. Synthesis of C2-2

Compound C2-1 (1.0 g, 5.32 mmol) was dissolved in dichloromethane (30 mL), then DIPEA (2.06 g, 15.96 mmol) was added, cooled to 0° C. in an ice water bath, SEM-Cl (2.22 g, 13.30 mmol) was added dropwise, maintained the temperature and stirred for 1.5 h, diluted with water, and extracted with dichloromethane. The combined organic phases were washed with saturated salt water, dried over anhydrous sodium sulfate, concentrated and purified by column chromatography to obtain 1.19 g of compound C2-2. $^1$H NMR (4 (0) MHz, $CDCl_3$) δ 8.23 (s, 1H), 5.82 (s, 2H), 3.72-3.68 (t, 2H), 0.99-0.95 (t, 2H), 0.00 (s, 9H).

2. Synthesis of C2-3

Compound C2-2 (1.09 g, 3.43 mmol) was dissolved in anhydrous THF (50 mL), then a solution of potassium tert-butoxide (0.38 g, 3.43 mmol) and p-methoxybenzyl alcohol (0.45 g, 3.26 mmol) in anhydrous THF (20 mL) was added dropwise under cooling in an ice-salt bath. After the addition was completed, the mixture was raised to room temperature naturally and stirred overnight. The reaction was quenched by adding saturated salt water, then extracted with ethyl acetate, the organic phase was separated and washed with saturated salt water, dried over anhydrous sodium sulfate, concentrated under reduced pressure to obtain the crude product, and purified by column chromatography to obtain 0.7 g of compound C2-3.

$^1$H NMR (400 MHz, $CDCl_3$) δ 8.04 (s, 1H), 7.46-7.44 (d, 2H, J=7.31 Hz), 6.95-6.93 (d, 2H, J=9.02 Hz), 5.72 (s, 2H), 5.55 (s, 2H), 3.82 (s, 3H), 3.65-3.62 (t, 2H), 0.95-0.90 (t, 2H), −0.04 (s, 9H).

3. Synthesis of C2-4

Compound C2-3 (633 mg, 1.51 mmol) and compound C1-3 (535 mg, 1.81 mmol) were dissolved in a mixture solvent of 30 mL 1,4-dioxane and 6 mL water, and palladium acetate (34 mg, 0.16 mmol), tricyclohexylphosphine (85 mg, 0.30 mmol) and potassium carbonate (312 mg, 2.26 mmol) were added sequentially. The reaction solution was stirred at 90° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 574 mg of compound C2-4. $^1$H NMR (400 MHz, $CDCl_3$) δ8.06 (s, 1H), 7.51-7.49 (d, 2H, J=9.59 Hz), 7.42 (s, 1H), 6.99-6.97 (d, 2H, J=8.39 Hz), 5.82 (s, 2H), 5.62 (s, 2H), 3.88 (s, 3H), 3.87 (s, 3H), 3.73-3.68 (t, 2H), 3.39 (s, 3H), 2.93-2.67 (m, 4H), 2.35-2.30 (m, 2H), 2.21-2.17 (m, 1H), 0.00 (s, 9H).

4. Synthesis of C2-5

Compound C2-4 (762 mg, 1.38 mmol) was dissolved in a mixed solvent of 30 mL ethyl acetate and 30 mL methanol, then $Pd(OH)_2/C$ (76 mg) was added and the reaction solution was stirred overnight at room temperature under hydrogen atmosphere. After the reaction was completed, the reaction solution was filtered through diatomite, washed with methanol, the filtrate was concentrated under reduced pressure to obtain 600 mg crude Compound C2-5 which was directly used in the next step without purification. MS [M+H] 437.1.

5. Synthesis of C2-6

Compound C2-5 (120 mg, crude) was dissolved in phosphorus oxychloride (5 mL), and then DIPEA (177 mg, 1.376 mmol) was added and stirred at 100° C. for 3 h under nitrogen protection. After the reaction was completed, the solvent was evaporated under reduced pressure and 70 mg of compound C2-6 was obtained by column chromatography.

$^1H$ NMR (400 MHz, $CDCl_3$) δ 8.18 (s, 1H), 5.86-5.84 (d, 2H, J=8.23 Hz), 3.84-3.83 (d, 2H, J=2.10 Hz), 3.74-3.70 (m, 2H), 3.34-3.33 (d, 3H, J=5.26 Hz), 3.17-3.03 (m, 1H), 2.46-2.40 (m, 1H), 2.26-2.18 (m, 2H), 2.08-1.86 (m, 5H), 1.76-1.68 (m, 1H), 1.10-0.96 (m, 2H), 0.00 (s, 9H).

6. Synthesis of C2-8

Compound C2-6 (98 mg, 0.22 mmol) and compound C2-7 (23 mg, 0.24 mmol) were dissolved in dimethyl sulfoxide (1 mL), and then DIPEA (56 mg, 0.43 mmol) was added, and the reaction solution was stirred overnight at 100° C. under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 90 mg of compound C2-8. MS [M+H] 516.4.

7. Synthesis of C2-9

Compound C2-8 (90 mg, 0.18 mmol) was dissolved in a mixed solvent of methanol (2 mL) and water (0.4 mL), then lithium hydroxide monohydrate (23 mg, 0.53 mmol) was added, stirred overnight at 60° C. After the reaction was completed, the reaction solution was cooled to room temperature and 68 mg of crude compound C2-9 was obtained by evaporation of methanol under reduced pressure, which was used directly in the next step without purification.

8. Synthesis of C2

Compound C2-9 (68 mg, 0.14 mmol) and compound C1-7 (37 mg, 0.15 mmol) were dissolved in 2 ml DMF, then DIPEA (145 mg, 1.12 mmol) was added, stirred at room temperature for 15 min, then HATU (80 mg, 0.21 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C2. Ms [M+H] 691, compound C2A, MS [M+H] 691.

Example 3

The compound synthesized in the present invention:

C3

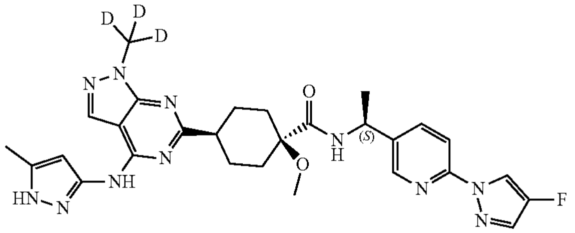

The synthetic route and experimental process were as follows:

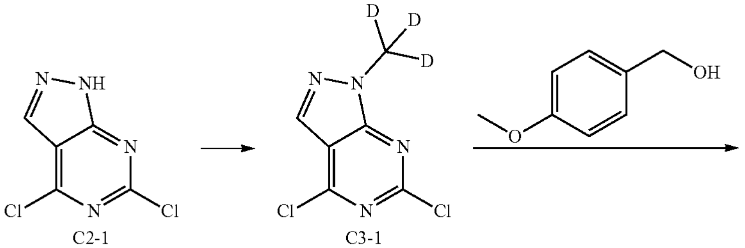

C2-1

C3-1

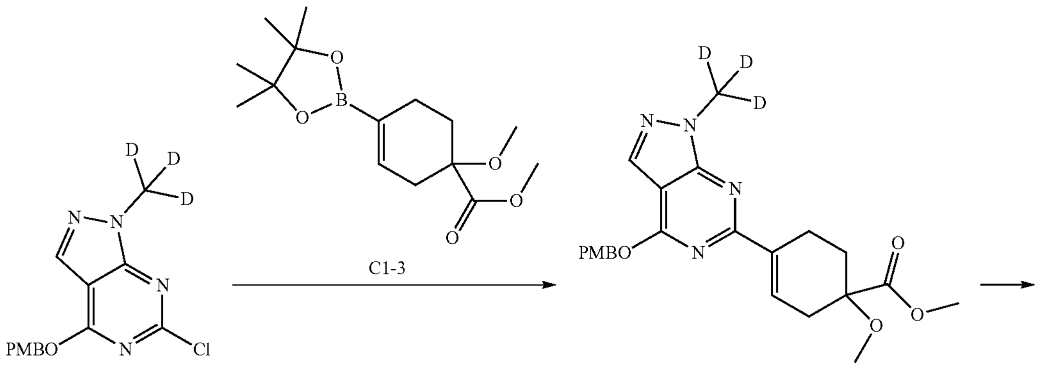

C3-2

C1-3

C3-3

-continued
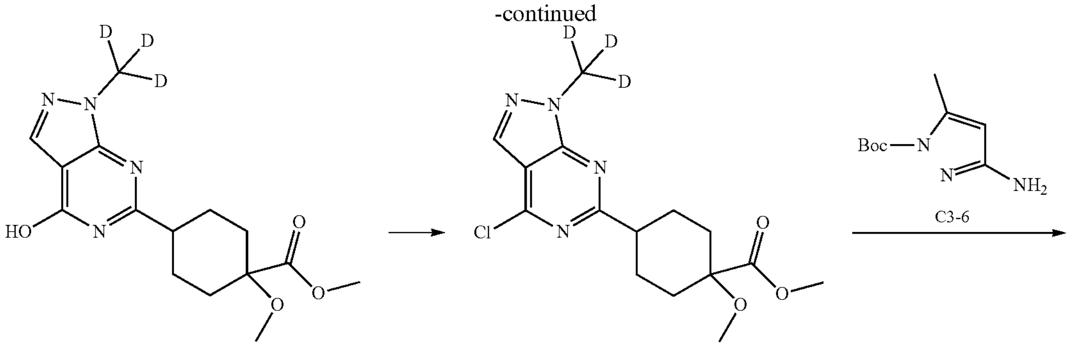
C3-4 C3-5
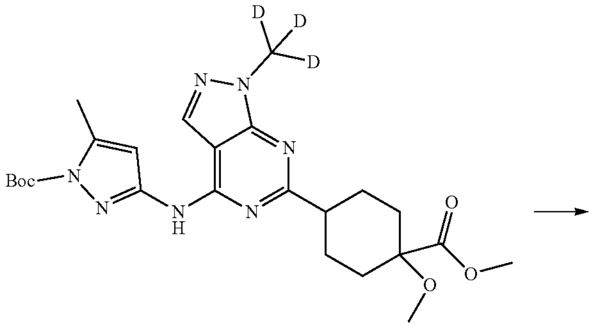
C3-7
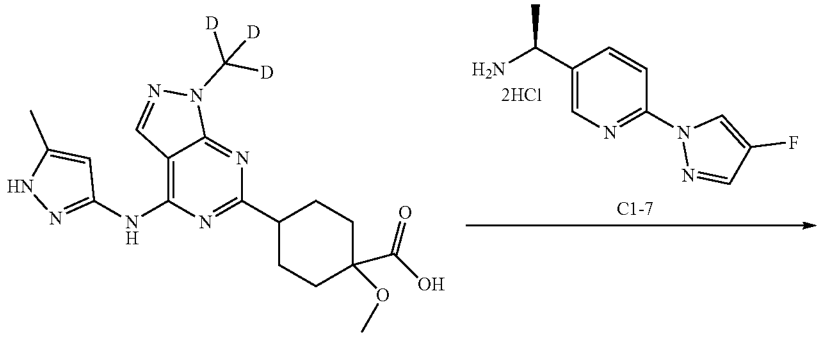
C3-8
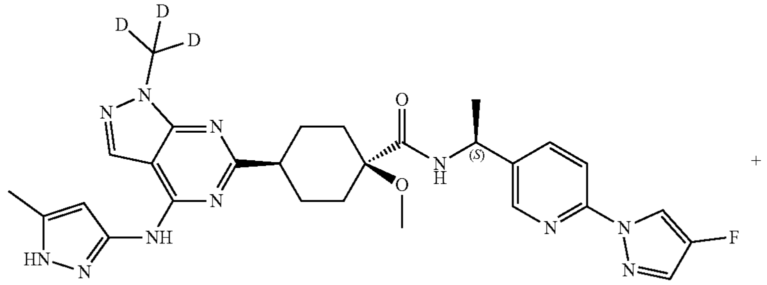
C3
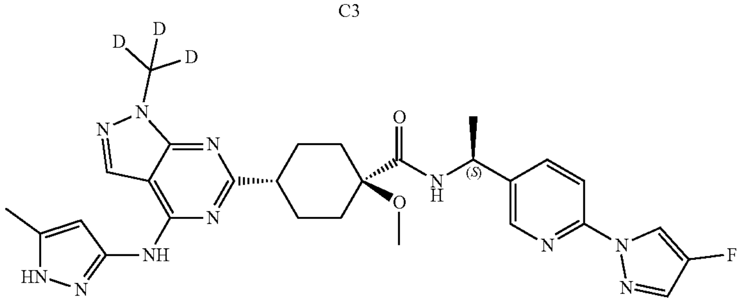
C3A 1. Synthesis of C3-1

Compound C2-1 (1.0 g, 5.29 mmol) and triphenylphosphine (2.22 g, 8.46 mmol) were dissolved in anhydrous tetrahydrofuran (30 mL), then deuterated methanol (5 (0) mg, 14.28 mmol) was added, and the reaction was cooled to 0° C. DIAD (2.14 g, 10.58 mmol) was added dropwise, and after the addition, the reaction mixture was raised to room temperature naturally, and stirred overnight. After the reaction was completed, the reaction solution was concentrated and purified by column chromatography to obtain 0.7 g of compound C3-1. MS [M+H] 206.0. $^1$H NMR (400 MHz, $CDCl_3$) δ 8.13 (s, 1H).

2. Synthesis of C3

Synthesis of compound C3 with reference to the synthesis of compound C1. $^1$H NMR (400 MHz, DMSO+$D_2O$) δ 8.69-8.67 (d, 1H, 4.21 Hz), 8.54-8.52 (d, 1H, 8.42 Hz), 8.44-8.43 (d, 1H, 1.92 Hz), 8.34 (br, 1H), 8.01-7.98 (dd, 1H, 8.56 Hz, 2.18 Hz), 7.92-7.87 (m, 2H), 6.67 (br, 1H), 5.08-5.04 (m, 1H), 3.17 (s, 3H), 2.79-2.16 (m, 1H), 2.28 (s, 3H), 2.03-1.64 (m, 8H), 1.48-1.46 (d, 3H, 7.35 Hz).

Example 4

The compound synthesized in the present invention:

C4

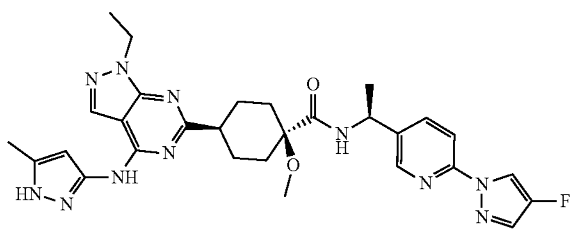

The synthetic route and experimental process were as follows:

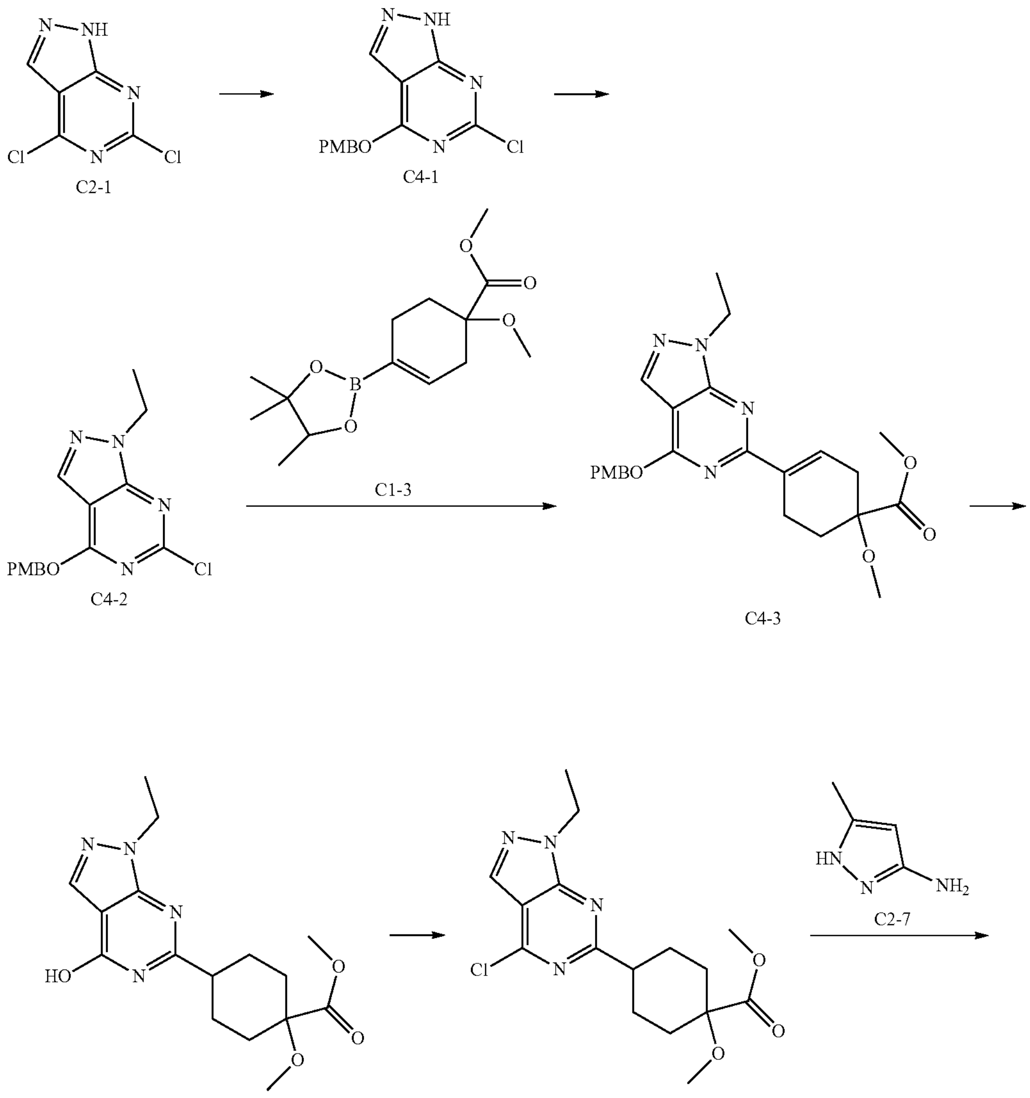

C2-1
C4-1
C4-2
C4-3
C4-4
C4-5
C2-7

-continued

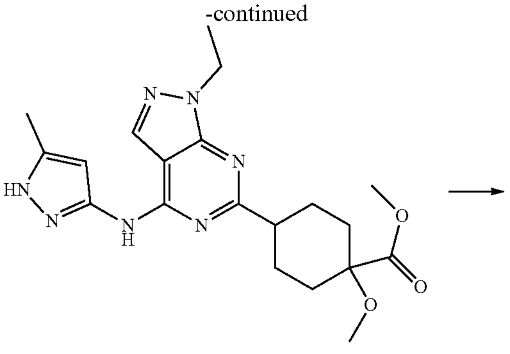

C4-6

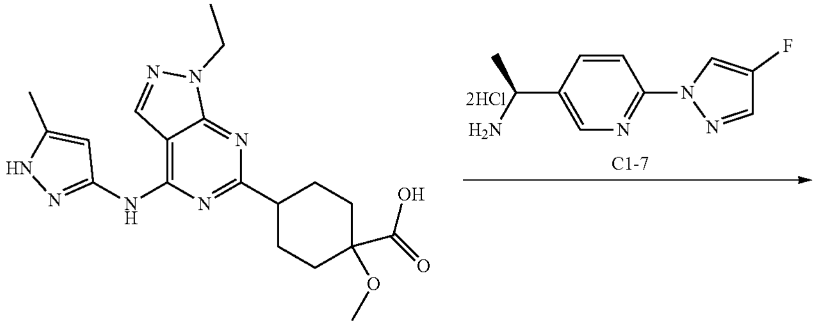

C1-7

C4-7

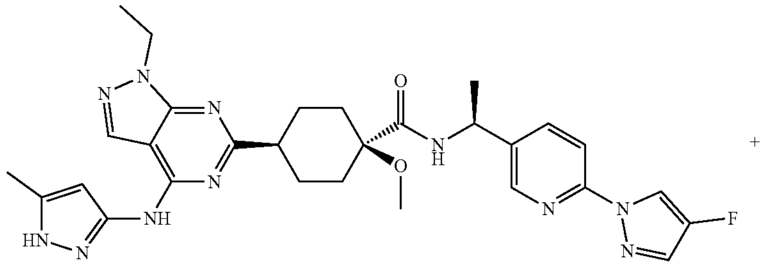

C4

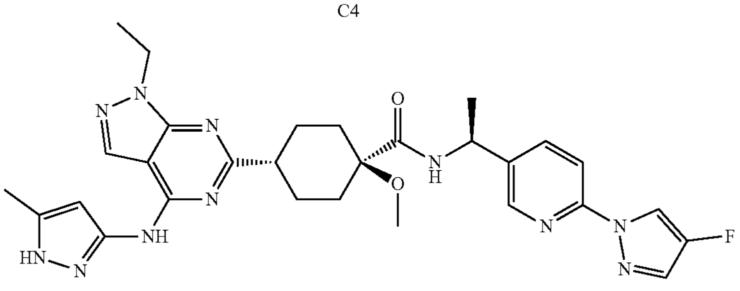

C4A

1. Synthesis of C4-1 p-Methoxybenzyl alcohol (16.0 g, 116.4 mmol) and t-BuOK (24.9 g, 222.2 mmol) were dissolved in anhydrous dioxane (400 mL), and compound C2-1 (20.0 g, 105.8 mmol) dissolved in dioxane (300 mL) was added dropwise to the reaction flask under ice bath. The solution was gradually turned into colloidal form under magnetic stirring for 2 h. After the reaction was completed, the reaction was quenched with water, the aqueous phase was extracted with ethyl acetate, and the separated organic phase was washed with saturated salt water, dried over anhydrous sodium sulfate, spin-dried under reduced pressure to obtain the crude product, then slurried with petroleum ether for two hours, filtered, and dried under vacuum to obtain 28.8 g of compound C4-1, MS [M+H] 291. $^1H$ NMR (400 MHz, Chloroform-d) δ 8.07 (s, 1H), 7.47 (d, J=8.7 Hz, 2H), 6.95 (d, J=8.7 Hz, 2H), 5.56 (s, 2H), 3.84 (s, 3H).

2. Synthesis of C4-2

Compound C4-1 (2.0 g, 6.80 mmol) was dissolved in anhydrous THF (60 mL), EtOH (1.1 mL, 17.2 mmol) and $PPh_3$ (2.9 g, 11.0 mmol) were added sequentially, the reaction solution was protected by nitrogen, DIAD (2.8 g, 13.6 mmol) was added under ice bath, warmed up to room temperature naturally and stirred for 3 h. The reaction was quenched by adding saturated salt water, then extracted with ethyl acetate, the organic phase was separated and washed with saturated salt water, dried over anhydrous sodium sulfate, and concentrated under reduced pressure to obtain the crude product, which was purified by column chromatography to obtain 1.78 g of compound C4-2, MS [M+H] 319.

$^1$H NMR (400 MHz, Chloroform-d) δ 7.99 (s, 1H), 7.45 (d, J=8.8 Hz, 2H), 6.94 (d, J=8.7 Hz, 2H), 5.54 (s, 2H), 4.45 (q, J=7.2 Hz, 2H), 3.83 (s, 3H), 1.50 (t, J=7.3 Hz, 3H).

3. Synthesis of C4-3

Compound C4-2 (1.78 g, 5.60 mmol) and compound C1-3 (1.82 g, 6.16 mmol) were dissolved in a mixed solvent of 1,4-dioxane (20 mL) and water (12 mL), and palladium acetate (126 mg, 0.56 mmol), dppf (621 mg, 1.12 mmol) and potassium carbonate (1.16 g, 8.40 mmol) were added sequentially. The reaction solution was stirred at 90° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 1.52 g of compound C4-3. MS [M+H] 453. $^1$H NMR (400 MHz, Chloroform-d) δ 7.93 (s, 1H), 7.42 (s, 2H), 7.35-7.29 (m, 1H), 6.91 (d, J=8.7 Hz, 2H), 5.55 (s, 2H), 4.46 (q, J=7.3 Hz, 2H), 3.81 (d, J=2.9 Hz, 6H), 3.33 (s, 3H), 2.97-2.49 (m, 4H), 2.41-2.20 (m, 1H), 2.20-2.08 (m, 1H), 1.50 (t, J=7.2 Hz, 3H).

4. Synthesis of C4-4

Compound C4-3 (1.52 g, 3.36 mmol) was dissolved in a mixed solvent of ethyl acetate (15 mL) and methanol (15 mL), then wet palladium carbon (152 mg) was added, stirred overnight at room temperature under hydrogen atmosphere. After the reaction was completed, the reaction solution was filtered through diatomite, washed with methanol, and the filtrate was concentrated under reduced pressure to obtain 1.33 g Compound C4-4, MS [M+H] 335. $^1$H NMR (400 MHz, Chloroform-d) δ 10.64 (s, 1H), 8.00 (s, 1H), 4.33 (q, J=7.1 Hz, 2H), 3.73 (s, 3H), 3.24 (s, 3H), 2.71-2.60 (m, 1H), 2.14 (d, J=12.4 Hz, 2H), 1.97-1.72 (m, 6H), 1.44 (t, J=7.2 Hz, 3H).

5. Synthesis of C4-5

Compound C4-4 (1.33 g, crude) was dissolved in phosphorus oxychloride (30 mL) and stirred at 100° C. for 3 h under nitrogen protection. After the reaction was 50 completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure, and purified by column chromatography to obtain 936 mg of compound C4-5, MS [M+H] 353. H NMR (400 MHz, Chloroform-d) δ 8.00 (s, 1H), 4.46 (q, J=7.3 Hz, 2H), 3.73 (s, 3H), 3.24 (s, 3H), 3.09-2.84 (m, 1H), 2.13 (d, J=11.8 Hz, 2H), 2.00-1.72 (m, 6H), 1.47 (t, J=7.3 Hz, 3H).

6. Synthesis of C4-6

Compound C4-5 (936 mg, 2.66 mmol) and compound C2-7 (284 mg, 2.92 mmol) were dissolved in DMSO (15 mL), then DIPEA (686 mg, 5.32 mmol) was added, stirred overnight at 100° C. under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 728 mg of compound C4-6. MS [M+H] 414. $^1$H NMR (400 MHz, Chloroform-d) δ 7.78 (s, 1H), 6.54 (s, 1H), 4.44 (q, J=6.3, 5.3 Hz, 2H), 3.80 (s, 3H), 3.33 (s, 3H), 2.93-2.82 (m, 1H), 2.36 (s, J=6.5 Hz, 3H), 2.23-1.62 (m, 8H), 1.49 (t, J=7.2 Hz, 3H).

7. Synthesis of C4-7

Compound C4-6 (728 mg, 1.76 mmol) was dissolved in a mixed solvent of methanol (16 mL) and water (2 mL), lithium hydroxide monohydrate (222 mg, 5.29 mmol) was added, stirred at 60° C. overnight. After the reaction was completed, the reaction solution was cooled to room temperature, methanol was evaporated under reduced pressure, slurried with DCM, filtered by suction filtration to obtain 797 mg of crude product C4-7 (MS [M+H] 400), which was used directly in the next step without purification.

8. Synthesis of C4

Compound C4-7 (114 mg, crude) and compound C1-7 (69 mg, 0.28 mmol) were dissolved in DMF(5 mL), then DIPEA (290 mg, 2.25 mmol) was added, stirred at room temperature for 15 min, then HATU (160 mg, 0.42 mmol) was added, and continued to stir at room temperature for 1 h. The reaction solution was diluted with ethyl acetate, the organic phase was washed with saturated salt water, dried over anhydrous sodium sulfate, concentrated, and purified by Prep-HPLC to obtain compound C4 with Ms [M+H] 588, and compound C4A with MS [M+H] 588.

Nuclear magnetic of compound C4: $^1$H NMR (400 MHz, Chloroform-d) δ 8.41-8.22 (m, 2H), 7.97-7.79 (M, 1H), 7.71 (dd, J=8.6, 2.4 Hz, 1H), 7.51 (dd, J=4.3, 0.9 Hz, 1H), 6.81 (d, J=7.9 Hz, 1H), 6.15 (s, 1H), 5.10 (p, J=7.1 Hz, 1H), 4.35 (q, J=7.3 Hz, 2H), 3.21 (s, 3H), 2.92-2.78 (m, 1H), 2.24 (s, 3H), 2.01-1.75 (m, 8H), 1.51 (d, J=7.0 Hz, 3H), 1.42 (t, J=7.3 Hz, 3H).

Example 5

The compound synthesized in the present invention:

C5

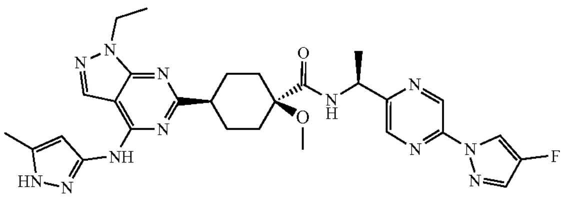

The synthetic route and experimental process were as follows
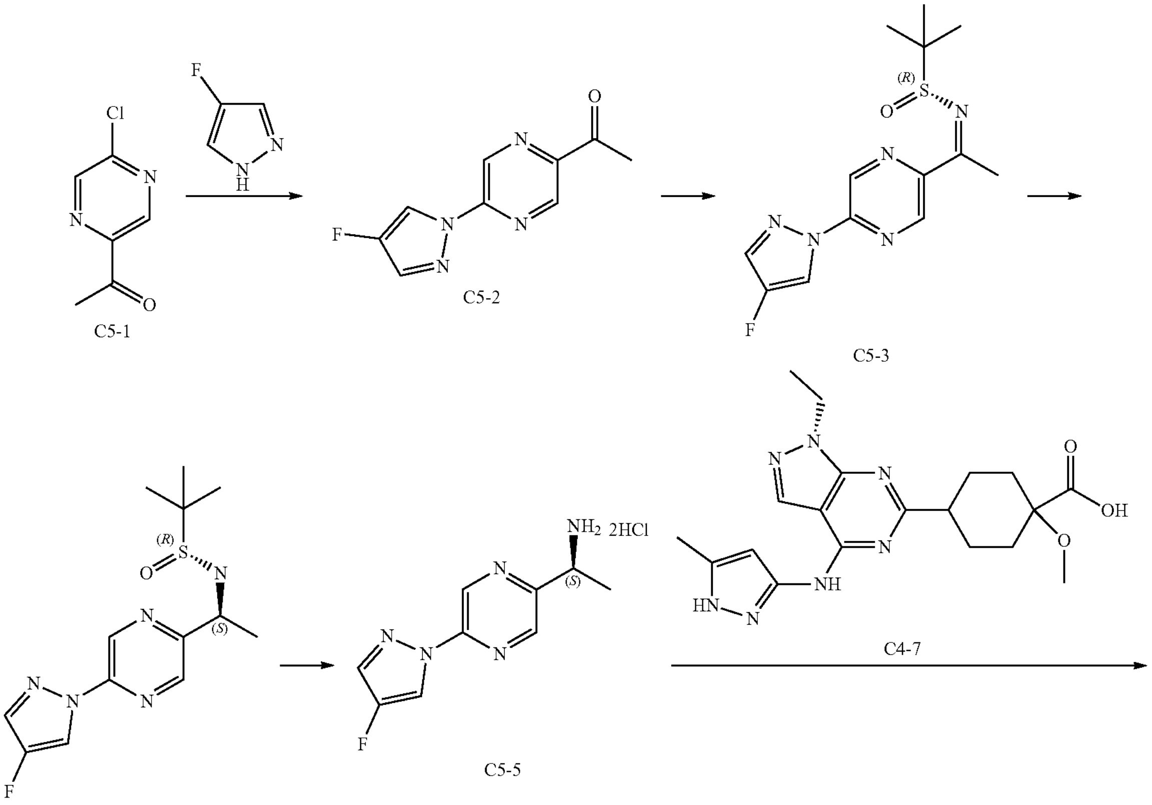
C5-1 C5-2 C5-3
C5-4 C5-5
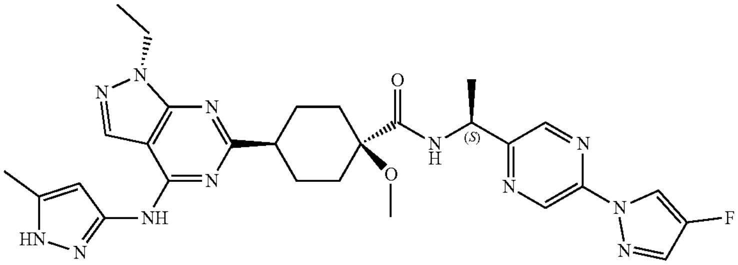
C5
+
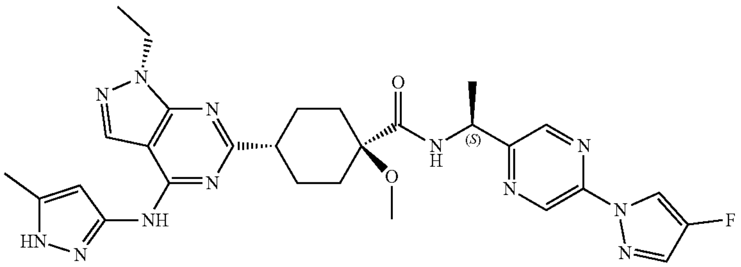
C5A 1. Synthesis of C5-2

C5-1 (1.57 g, 10 mmol), 4-fluoro-1H pyrazole (860 mg, 10 mmol), N, N-dimethylformamide (10 mL) and potassium carbonate (2.76 g, 20 mmol) were added into a 50 mL single-neck flask to react at 100° C. for 8 h. LC-MS showed that the reaction was completed, the reaction solution was poured into water (200 mL) under stirring, and solid was precipitated, then filtered. The filter cake was washed with water, and dried to obtain 1.08 g solid. [M+1]: 207.03.

2. Synthesis of C5-3

C5-3 (870 mg, 4.2 mmol), R-tert-butyl sulfinamide (560 mg, 4.63 mmol), tetraethyl titanate (1.92 g, 8.4 mmol), and dry tetrahydrofuran (10 ml) were successively added into a 100 mL single-neck flask to react at 75° C. overnight. The reaction solution was cooled, diluted with water (30 mL), suction-filtered. Filtrate was extracted with ethyl acetate (20 mL) for three times. Organic phase was dried over anhydrous sodium sulfate, evaporated under reduced pressure, and purified by column chromatography to obtain 500 mg of product.

3. Synthesis of C5-4

C5-3 (100 mg, 0.32 mmol) and dry tetrahydrofuran (2 mL) were successively added into a 50 mL single-neck flask, cooled to −78° C., then tri-sec-butyl lithium borohydride (0.7 mL, 0.7 mmol, 1.0M) was added dropwise and reacted at −78° C. for 1 h. The reaction was quenched with methanol (I mL) at −60° C., diluted with water (5 mL), extracted with ethyl acetate (5 mL) for three times. Organic phase was dried, evaporated under reduced pressure and purified by column chromatography to obtain 93 mg of product.

1H NMR (400 MHz, CDCl3) δ 9.23 (d, J=1.4 Hz, 1H), 8.36 (d, J=1.5 Hz, 1H), 8.33 (d, J=4.6 Hz, 1H), 7.66 (d, J=4.3 Hz, 1H), 4.77 (p. J=6.6 Hz, 1H), 3.74 (d, J=5.9 Hz, 1H), 1.67 (d, J=6.8 Hz, 3H), 1.22 (s, 9H).

4. Synthesis of C5-5

C5-4 (100 mg, 0.32 mmol), dichloromethane (3 mL), methanol (0.5 mL), and HCl/dioxane (4M, 1.5 mL) were successively added into a 50 mL single-neck flask to react at room temperature for 3 h. LC-MS detected the reaction was completed, diluted with dichloromethane, filtered, the filter cake was washed with ethyl acetate. The filter cake was dried to obtain 67 mg of product. [M+1]: 208.06.

5. Synthesis of C5

Compound C4-7 (270 mg, 0.68 mmol) and compound C5-5 (165 mg, 0.68 mmol) were dissolved in DMF(9 mL), then DIPEA (699 mg, 5.41 mmol) was added, stirred at room temperature for 15 min, then HATU (386 mg, 1.02 mmol) was added, and continued to stir at room temperature for 1 h. The reaction solution was diluted with ethyl acetate, the organic phase was washed with saturated salt water, dried over anhydrous sodium sulfate, concentrated, and purified by Prep-HPLC to obtain compound C5 with Ms [M+H] 589, and compound C5A with MS [M+H] 589.

Nuclear magnetic of compound C5: $^1$H NMR (400 MHz, Chloroform-d) δ 9.23 (d, J=1.4 Hz, 1H), 8.37 (d, J=1.4 Hz, 1H), 8.34 (d, J=4.6 Hz, 1H), 7.78 (s, 1H), 7.66 (d, J=4.3 Hz, 2H), 5.32 (p, J=6.8 Hz, 1H), 4.44 (q, J=7.2 Hz, 2H), 3.32 (s, 3H), 2.93-2.77 (m, 1H), 2.38 (s, 3H), 2.13-1.90 (m, 8H), 1.56 (d, J=6.9 Hz, 3H), 1.48 (t, J=7.2 Hz, 3H).

Example 6

The compound synthesized in the present invention:

C6

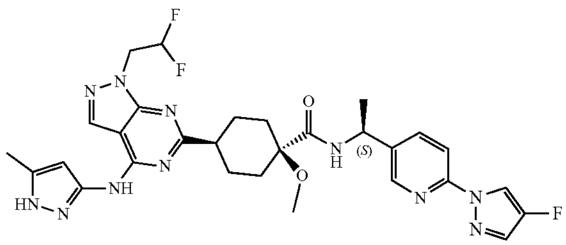

The synthetic route and experiments process were as follows

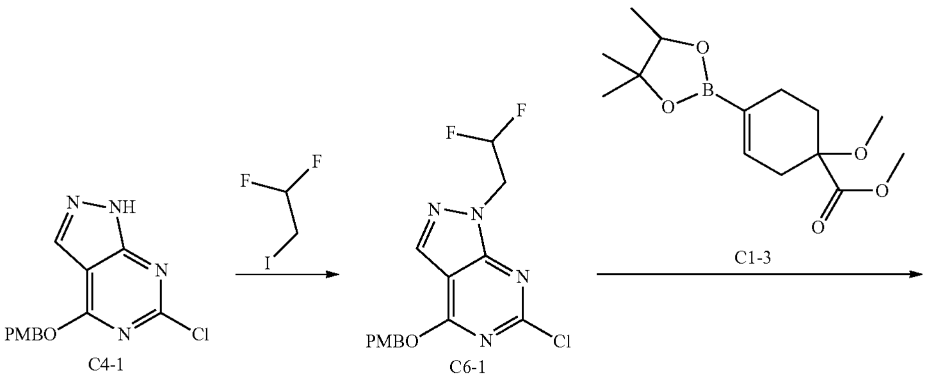

C4-1

C6-1

C1-3

-continued
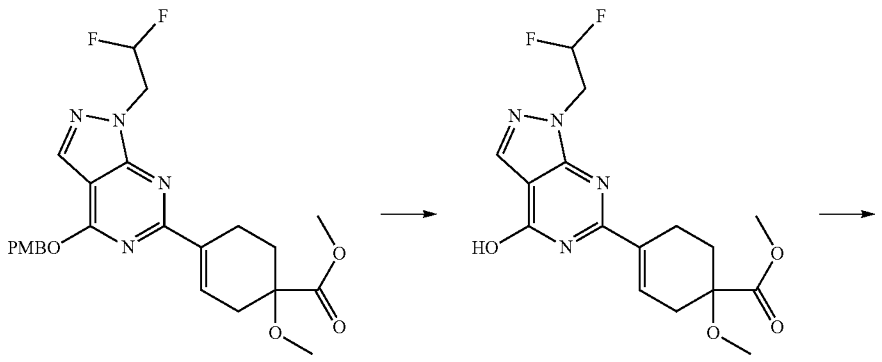
C6-2 C6-3
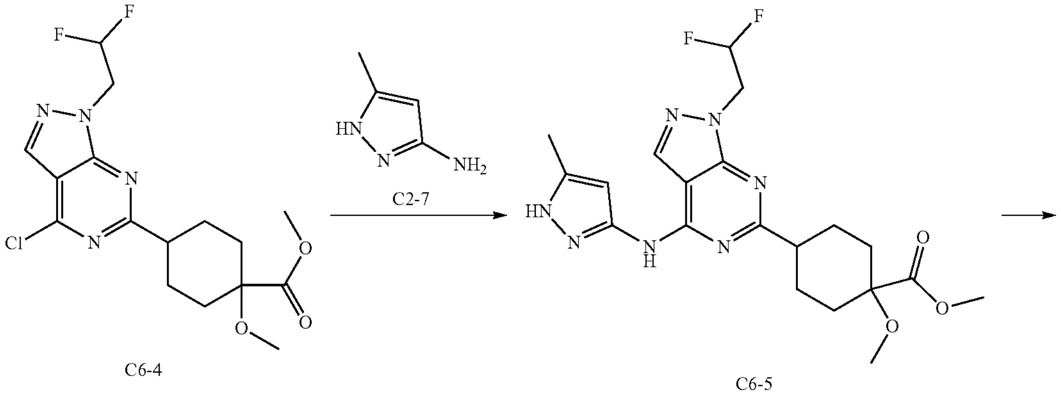
C6-4 C6-5
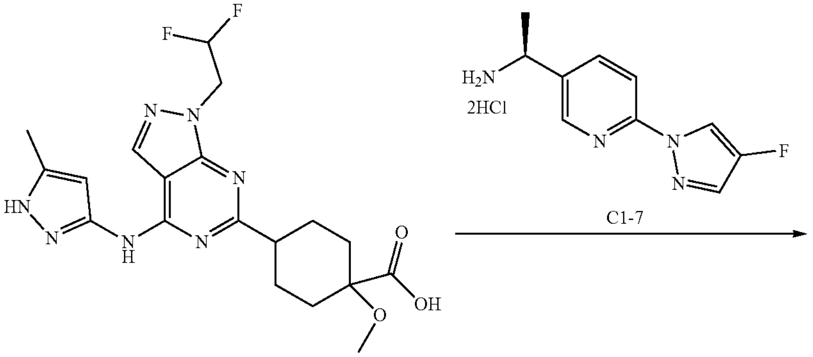
C6-6
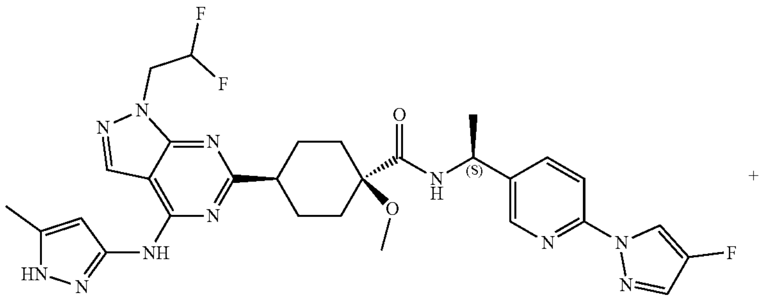
C6

-continued

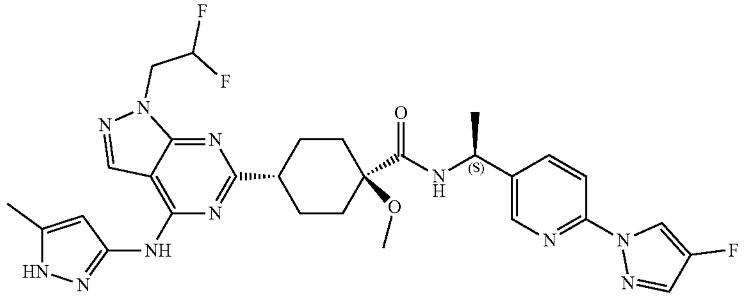

C6A

1. Synthesis of C6-1

Compound C4-1 (2.0 g, 6.90 mmol) was dissolved in anhydrous DMF (20 mL), and cesium carbonate (2.25 g, 6.90 mmol) and 1,1-difluoro-2-iodoethane (2.65 g, 13.79 mmol) were added sequentially, stirred at room temperature overnight, DMF was evaporated under reduced pressure. The reaction was quenched by adding saturated salt water, then extracted with ethyl acetate, the organic phase was separated and washed with saturated salt water, dried over anhydrous sodium sulfate, concentrated under reduced pressure to obtain the crude product, and purified to obtain 440 mg of compound C6-1. $^{1}$H NMR (400 MHz, $CDCl_3$) δ 7.98 (s, 1H), 7.40-7.37 (d, 2H, 8.34 Hz), 6.88-6.86 (d, 2H, 8.65 Hz), 6.29-5.99 (m, 1H), 5.48 (s, 2H), 4.72-4.64 (m, 2H), 3.76 (s, 3H).

2. Synthesis of C6-2

Compound C6-2 (440 mg, 1.24 mmol) and compound C1-3 (441 mg, 1.49 mmol) were dissolved in a mixture solvent of 10 mL 1,4-dioxane and 2 mL water, and palladium acetate (28 mg, 0.13 mmol), dppf (138 mg, 0.25 mmol) and potassium carbonate (257 mg, 1.86 mmol) were added sequentially. The reaction solution was stirred at 90° C. overnight under nitrogen protection. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 297 mg of compound C6-2. $^{1}$H NMR (400 MHz, $CDCl_3$) δ 8.00 (s, 1H), 7.44-7.42 (d, 2H, 8.34 Hz), 7.37 (br, 1H), 6.94-6.89 (d, 2H, 9.10 Hz), 6.38-6.10 (m, 1H), 5.57 (s, 2H), 4.80-4.72 (m, 2H), 3.82 (s, 3H), 3.81 (s, 3H), 3.40 (s, 3H), 2.88-2.61 (m, 5H), 2.34-2.11 (m, 3H).

3. Synthesis of C6-3

Compound C6-2 (297 mg, 0.84 mmol) was dissolved in a mixed solvent of ethyl acetate (10 mL) and methanol (10 mL), then wet palladium carbon (30 mg) was added, stirred overnight at room temperature under hydrogen atmosphere. After the reaction was completed, the reaction solution was filtered through diatomite, washed with methanol, and the filtrate was concentrated under reduced pressure to obtain 196 mg Compound C6-3. $^{1}$H NMR (400 MHz, MeOD-d4) δ 10.27-10.19 (d, 1H, 57.39 Hz), 8.05 (s, 1H), 6.30-6.02 (m, 1H), 3.74-3.73 (d, 3H, 6.02 Hz), 3.24-3.22 (d, 3H, 9.02 Hz), 2.75-2.61 (m, 1H), 2.56-2.35 (m, 1H), 2.27-2.02 (m, 3H), 1.87-1.78 (m, 5H).

4. Synthesis of C6-4

Compound C6-3 (168 mg) was dissolved in phosphorus oxychloride (5 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure, and purified by column chromatography to obtain 118 mg of compound C6-4. MS [M+H] 389.2.

5. Synthesis of C6-5

Compound C6-4 (118 mg, 0.31 mmol) and compound C2-7 (33 mg, 0.34 mmol) were dissolved in 1 mL DMSO, then DIPEA (78 mg, 0.61 mmol) was added, stirred overnight at 100° C. under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 134 mg of compound C6-5. MS [M+H] 450.3. $^{1}$H NMR (400 MHz, $CDCl_3$) δ 9.57 (br, 0.4H), 8.24 (br, 0.6H), 7.79 (s, 1H), 6.57 (br, 1H), 6.39-6.08 (m, 1H), 4.78-4.70 (m, 2H), 3.80-3.79 (d, 3H, 2.83 Hz), 3.34-3.30 (d, 3H, 14.91 Hz), 2.89-2.82 (m, 1H), 2.44-2.40 (m, 1H), 2.38-2.37 (d, 3H, 5.91 Hz), 2.21-2.17 (m, 1H), 2.10-1.95 (m, 5H), 1.90-1.82 (m, 1H), 1.71-1.63 (m, 2H).

6. Synthesis of C6-6

Compound C6-5 (134 mg, 0.30 mmol) was dissolved in a mixed solvent of methanol (5 mL) and water (1 mL), then lithium hydroxide monohydrate (38 mg, 0.90 mmol) was added, stirred overnight at 60° C. After the reaction was completed, the reaction solution was cooled to room temperature and 151 mg of crude compound C6-6 was obtained by evaporation of methanol under reduced pressure, which was used directly in the next step without purification.

7. Synthesis of C6

Compound C6-6 (54 mg, 0.12 mmol) and compound C1-7 (34 mg, 0.12 mmol) were dissolved in 1 ml DMF, then DIPEA (126 mg, 0.98 mmol) was added, stirred at room temperature for 15 min, then HATU (70 mg, 0.18 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C6 with Ms [M+H] 624, and compound C6A with [M+H] 624.

Nuclear magnetic of compound C6: $^1$H NMR (400 MHz, $CDCl_3$) δ 8.32-8.30 (m, 2H), 7.85-7.83 (d, 1H, 8.38 Hz), 7.71-7.68 (dd, 1H, 8.72 Hz, 2.35 Hz), 7.67 (br, 1H), 7.52-7.51 (d, 1H, 4.36 Hz), 6.83-6.81 (d, 1H, 8.05 Hz), 6.38 (br, 1H), 6.33-6.01 (m, 1H), 5.12-5.09 (q, 1H), 4.70-4.62 (m, 2H), 3.23 (s, 3H), 2.75 (br, 1H), 2.28 (s, 3H), 1.95-1.86 (m, 8H), 1.52-1.50 (d, 3H, 7.38 Hz).

Example 7

The compound synthesized in the present invention:

C7

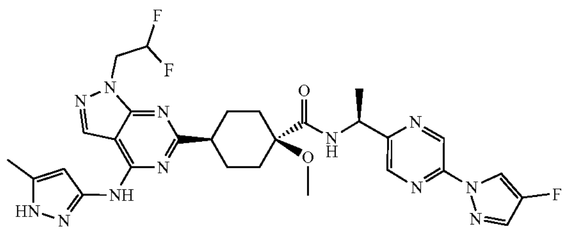

The synthetic route and experimental process were as follows:

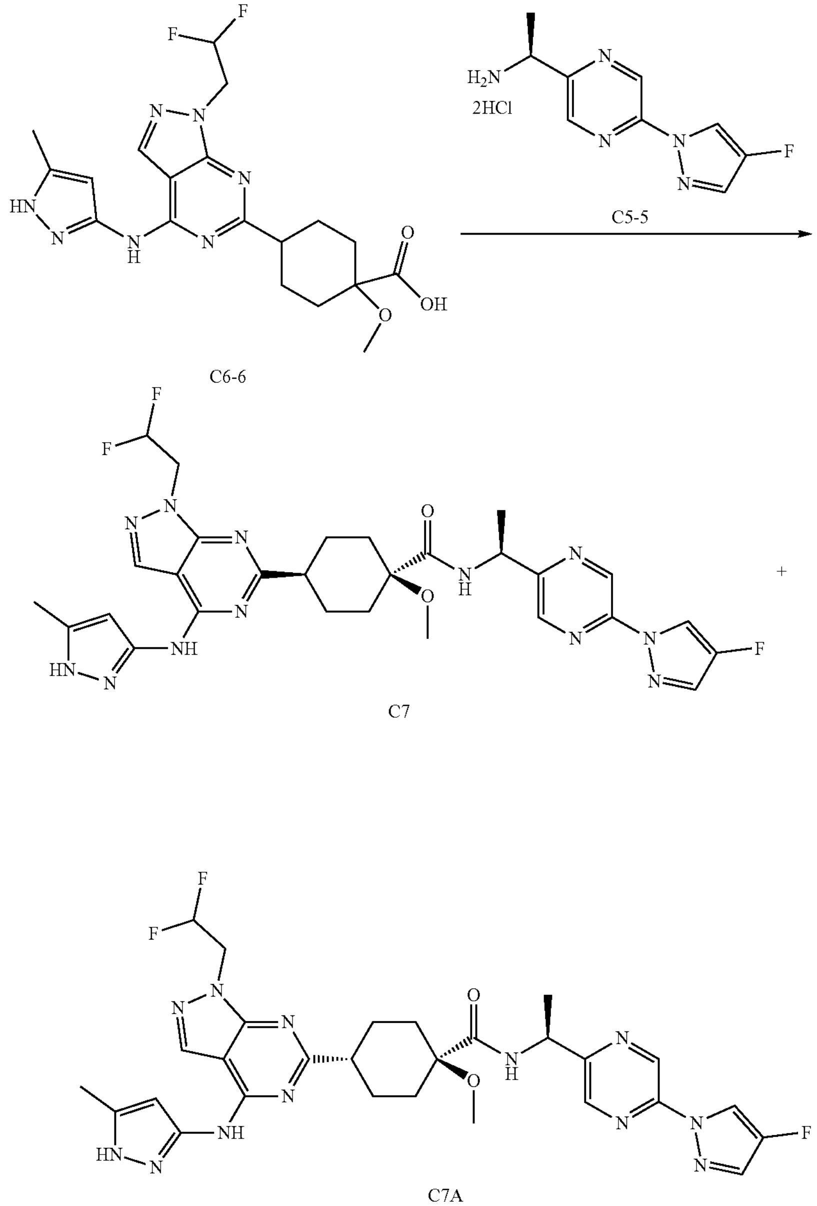

C5-5

C6-6

C7

+

C7A

1. Synthesis of C7

Compound C6-6 (96 mg, crude) and compound C5-5 (61 mg, 0.218 mmol) were dissolved in DMF(2 mL), then DIPEA (225 mg, 1.744 mmol) was added, stirred at room temperature for 15 min, then HATU (124 mg, 0.327 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C7. Ms [M+H] 625.4. $^1H$ NMR (400 MHz, $CDCl_3$) δ 9.16-9.15 (d, 1H, 1.24 Hz), 8.29-8.26 (m, 2H), 7.94 (br, 1H), 7.59-7.58 (m, 1H), 7.45-7.43 (m, 1H), 6.30-6.01 (m, 2H), 5.24-5.19 (m, 1H), 4.71-4.63 (m, 2H), 3.22 (s, 3H), 2.85 (br, 1H), 2.26 (s, 3H), 1.99-1.88 (m, 9H), 1.50-1.48 (d, 3H, 7.11 Hz).

Example 8

The compound synthesized in the present invention:

C8

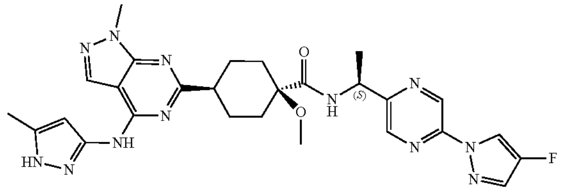

The synthetic route and experimental process were as follows:

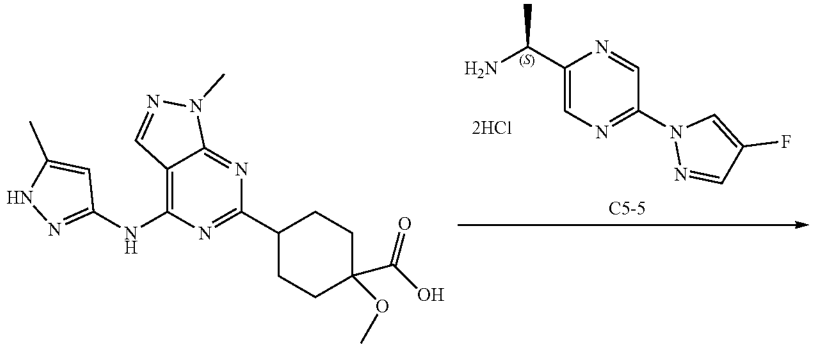

C5-5

C1-10

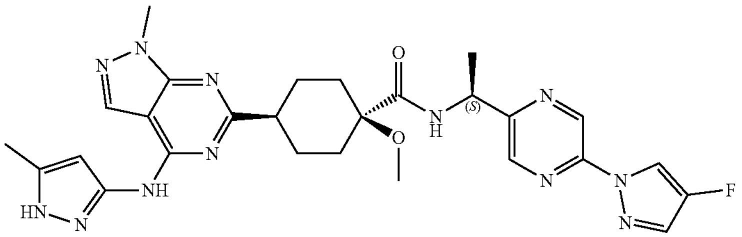

+

C8

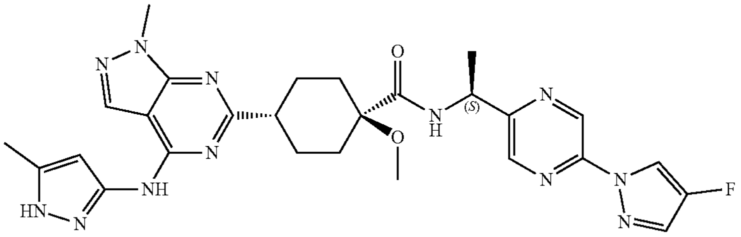

C8A

1. Synthesis of C8

Compound C1-10 (100 mg, crude) and compound C5-5 (72 mg, 0.256 mmol) were dissolved in DMF(2 mL), then DIPEA (264 mg, 2.048 mmol) was added, stirred at room temperature for 15 min, then HATU (146 mg, 0.384 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C8. Ms [M+H] 575.5. $^{1}$H NMR (400 MHz, DMSO+$D_2O$) δ 9.13-9.12 (d, 1H, 1.32 Hz), 8.74-8.72 (dd, 1H, 4.48 Hz, 0.66 Hz), 8.53-8.52 (d, 1H, 1.32 Hz), 8.33 (br, 1H), 8.03-8.02 (dd, 1H, 4.21 Hz, 0.73 Hz), 6.77 (br, 1H), 5.16-5.10 (m, 1H), 3.91 (s, 3H), 3.22 (s, 3H), 2.82-2.76 (m, 1H), 2.28 (s, 3H), 2.03-1.73 (m, 9H), 1.51-1.49 (d, 3H, 7.77 Hz).

Example 9

The compound synthesized in the present invention:

C9

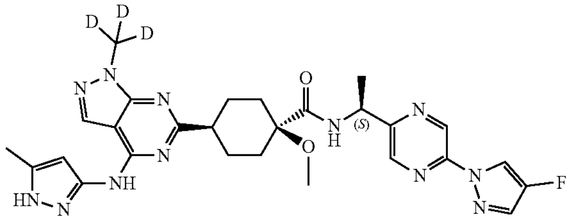

The synthetic route and experimental process were as follows:

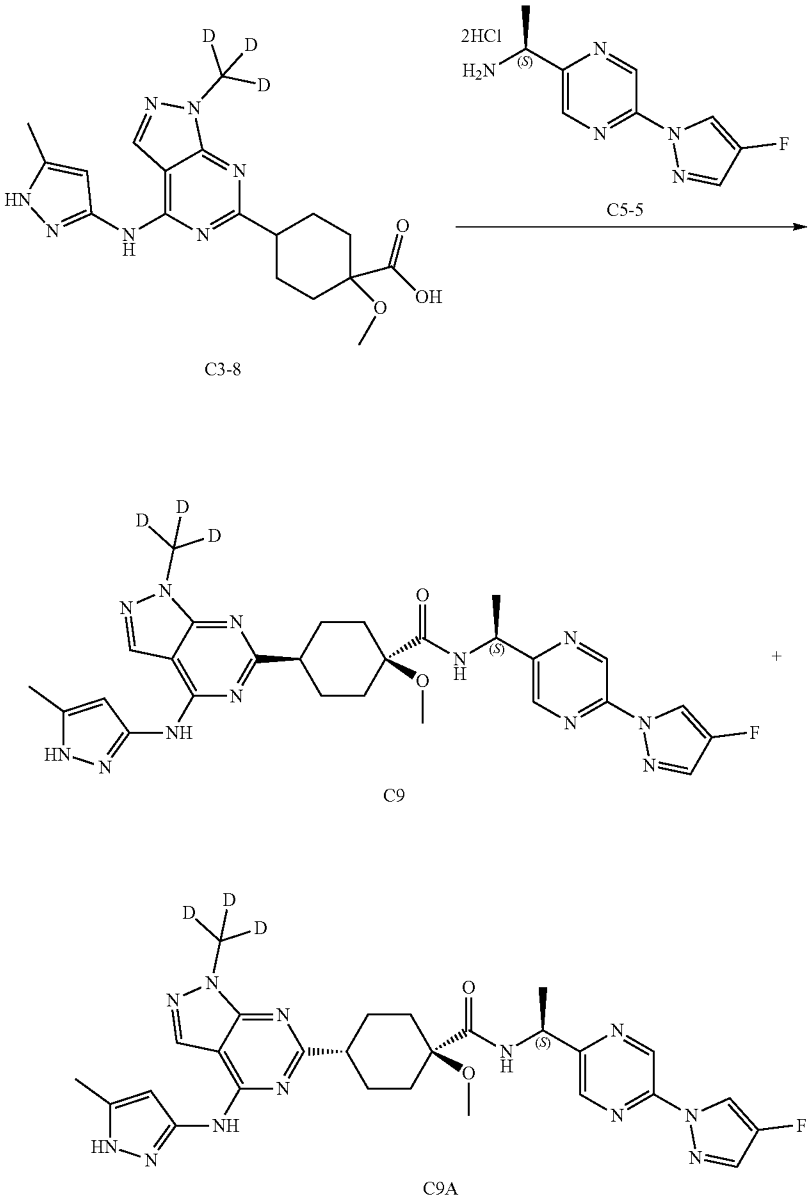

C3-8

C5-5

C9

+

C9A

1. Synthesis of C9

Compound C3-8 (100 mg, crude) and compound C5-5 (71 mg, 0.254 mmol) were dissolved in DMF(2 mL), then DIPEA (262 mg, 2.032 mmol) was added, stirred at room temperature for 15 min, then HATU (14.5 mg, 0.381 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C9 with Ms [M+H] 578, and compound C9A with MS [M+H] 578. Nuclear magnetic of compound C9: $^1$H NMR (400 MHz, DMSO+$D_2O$) δ 9.13-9.12 (d, 1H, 1.35 Hz), 8.74-8.73 (dd, 1H, 4.56 Hz, 0.67 Hz), 8.52-8.51 (d, 1H, 1.30 Hz), 8.29 (br, 1H), 8.03-8.02 (dd, 1H, 4.15 Hz, 0.60 Hz), 6.83 (br, 1H), 5.17-5.11 (m, 1H), 3.23 (s, 3H), 2.76-2.68 (m, 1H), 2.27 (s, 3H), 2.03-1.71 (m, 9H), 1.51-1.49 (d, H, 6.77 Hz).

Example 10

The compound synthesized in the present invention:

C10

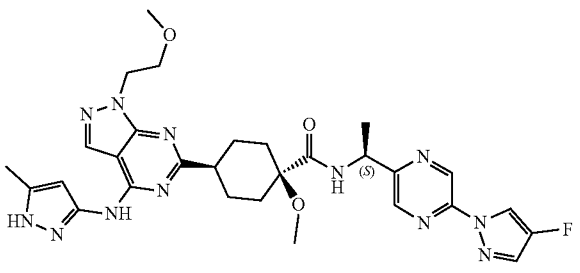

The synthetic route and experimental process were as follows:

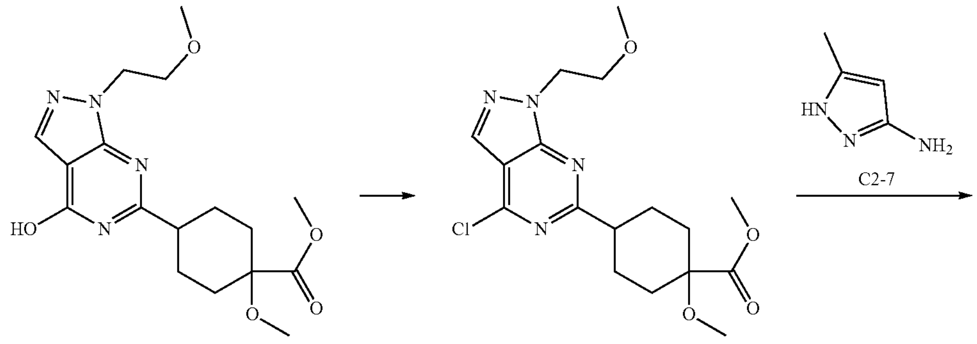

C10-1 C10-2

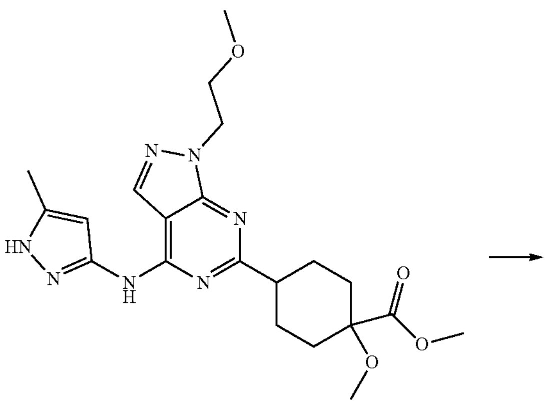

C10-3

-continued

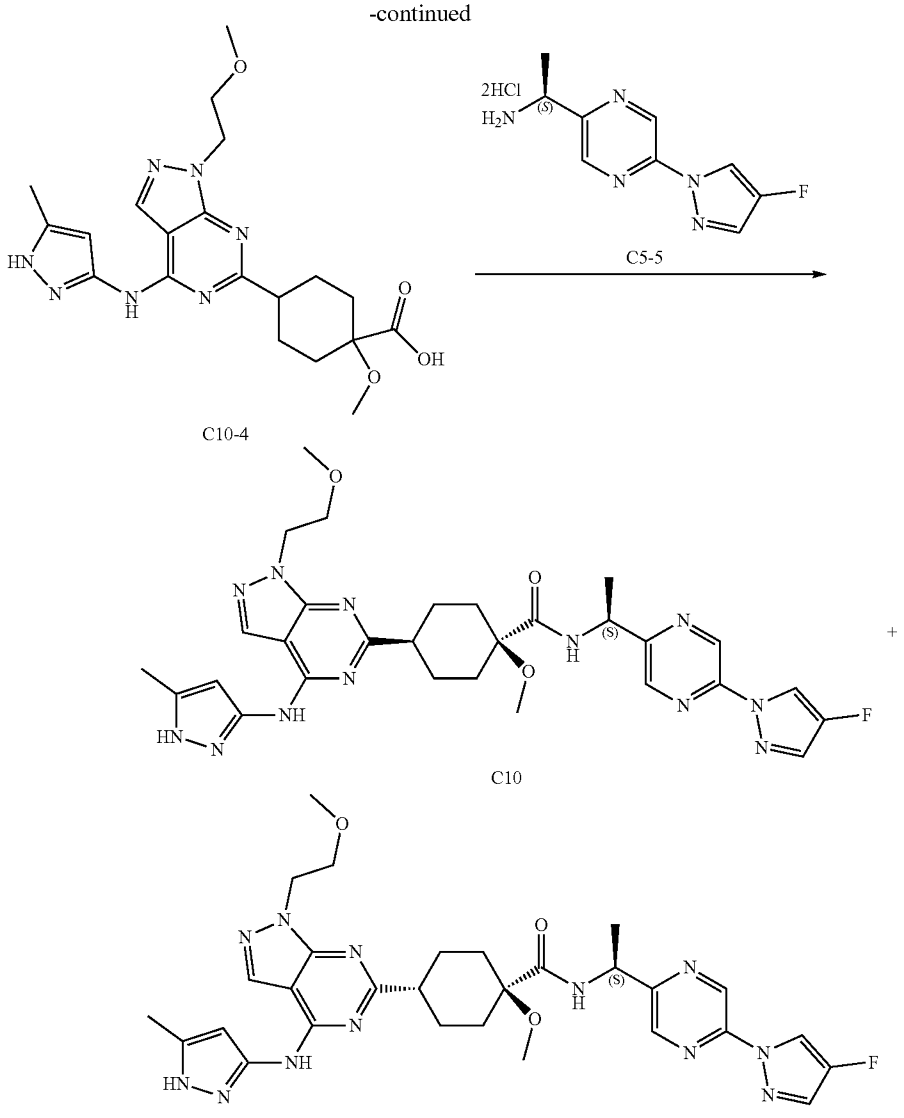

C10-4 C5-5 C10 C10A

1. Synthesis of C10-2

Compound C10-1 (273 mg) was dissolved in phosphorus oxychloride (5 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified by column chromatography to obtain 187 mg of compound C10-2. MS [M+H] 383.2. $^1$H NMR (400 MHz, $CDCl_3$) δ 8.08-8.07 (d, 1H, 1.21 Hz), 4.67-4.61 (m, 2H), 3.90-3.86 (q, 2H), 3.77-3.76 (d, 3H, 1.57 Hz), 3.33-3.26 (d, 3H, 5.10 Hz), 3.28-3.27 (d, 3H, 7.25 Hz), 3.08-2.95 (m, 1H), 2.38-2.11 (m, 3H), 2.03-1.79 (m, 5H), 1.70-1.64 (m, 1H).

2. Synthesis of C10-3

Compound C10-2 (187 mg, 0.488 mmol) and compound C2-7 (52 mg, 0.537 mmol) were dissolved in DMSO(2 mL), then DIPEA (126 mg, 0.976 mmol) was added, and stirred at 100° C. overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 181 mg of compound C10-3. MS [M+H] 444.3.

3. Synthesis of C10-4

Compound C10-3 (181 mg, 0.409 mmol) was dissolved in a mixed solvent of methanol (10 mL) and water (2 mL), then lithium hydroxide monohydrate (51.48 mg, 1.226 mmol) was added, stirred overnight at 60° C. After the reaction was completed, the reaction solution was cooled to room temperature and 193 mg of crude compound C10-4 was obtained by evaporation of methanol under reduced pressure, which was used directly in the next step without purification.

4. Synthesis of C10

Compound C10-4 (72 mg, crude) and compound C5-5 (46.5 mg, 0.165 mmol) were dissolved in DMF(2 mL), then DIPEA (170 mg, 1.32 mmol) was added, stirred at room temperature for 15 min, then HATU (94 mg, 0.248 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C10. Ms [M+H] 619.5. $^1H$ NMR (400 MHz, DMSO-$d_6$) δ 12.10 (br, 1H), 10.61 (br, 1H), 9.14 (s, 1H), 8.74 (s, 1H), 8.53-8.32 (m, 3H), 8.04 (s, 1H), 6.80 (br, 1H), 6.38 (br, 1H), 5.15 (br, 1H), 4.43 (s, 2H), 3.77 (s, 2H), 3.23 (s, 3H), 3.21 (s, 3H), 2.72 (br, 1H), 2.27 (s, 3H), 2.04-1.73 (m, 9H), 1.52-1.50 (d, 3H, 5.51 Hz).

Example 11

The compound synthesized in the present invention:

C11

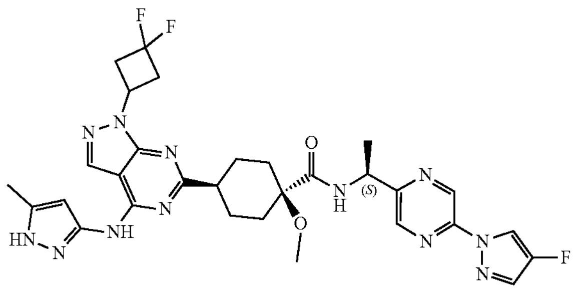

The synthetic route and experimental process were as follows:

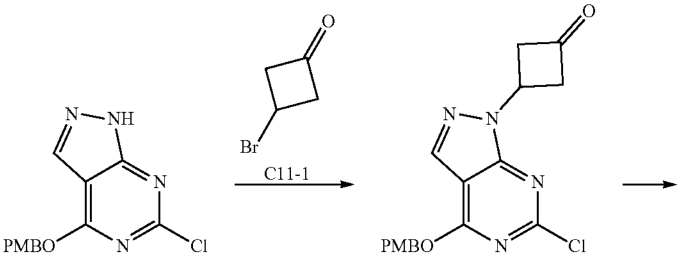

C4-1 C11-2

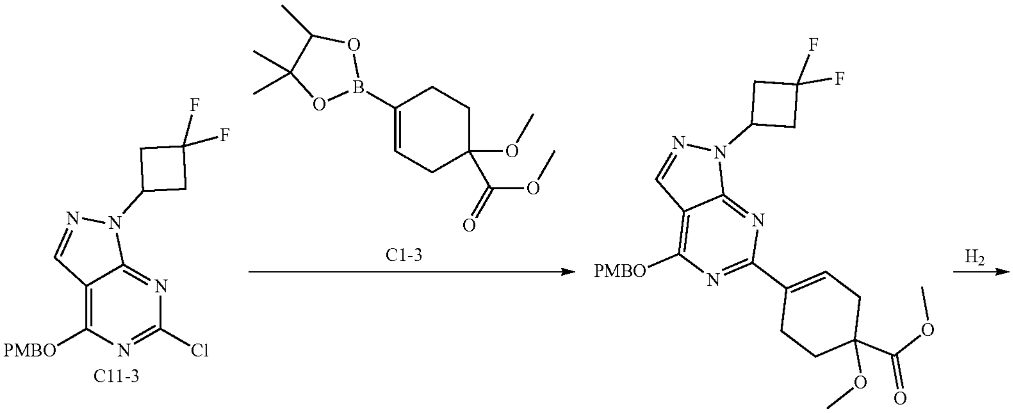

C11-3 C11-4

-continued
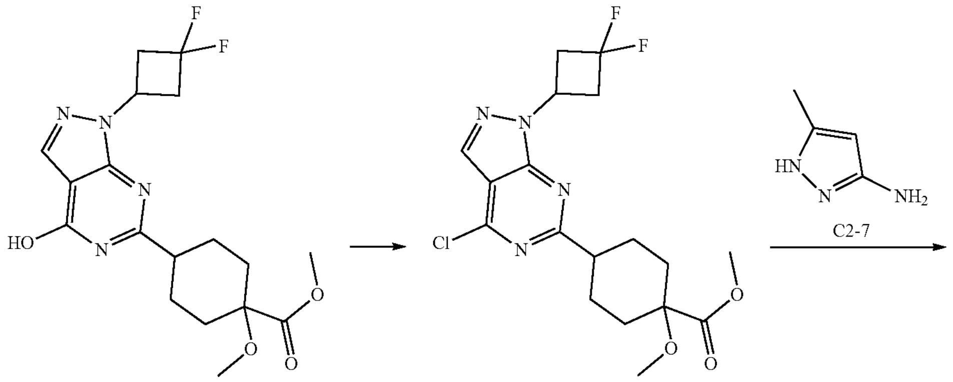
C11-5 C11-6
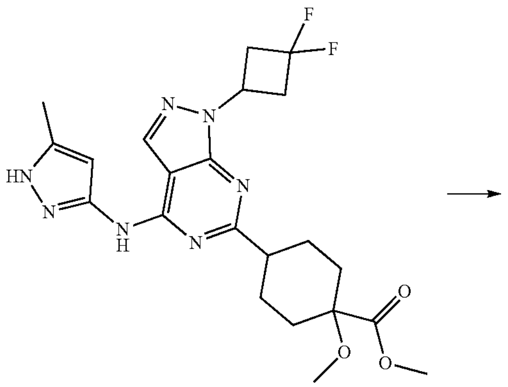
C11-7
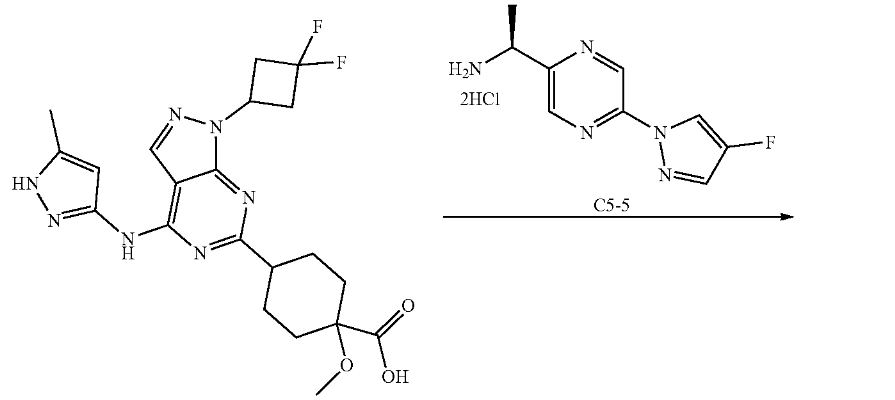
C11-8
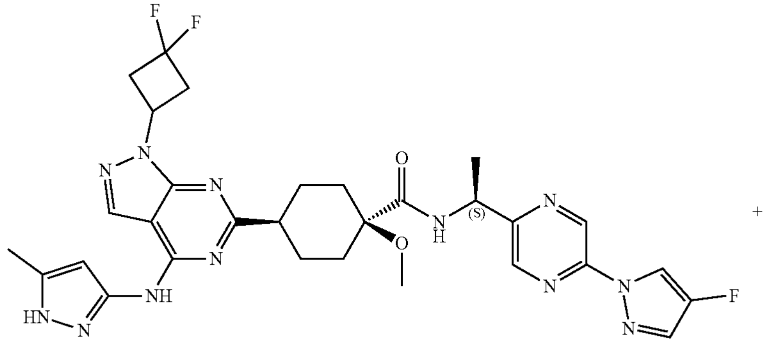
C11

-continued

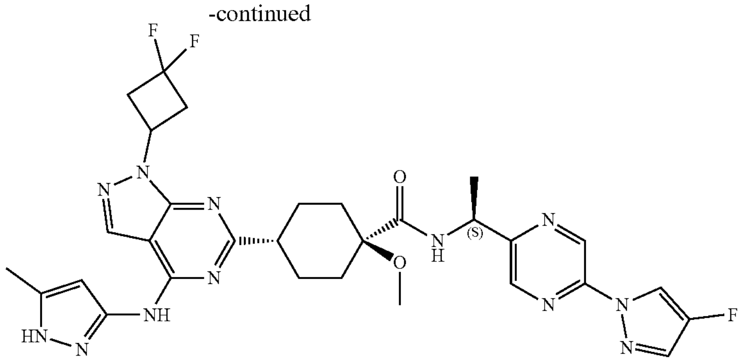

C11A

1. Synthesis of C11-2

Compound C4-1 (1.0 g, 3.448 mmol) was dissolved in DMF (15 mL), then cesium carbonate (1.124 g, 3.448 mmol) was added, and a solution of compound C11-1 (0.617 g, 4.138 mmol) in DMF (1 mL) was added dropwise under cooling in an ice-water bath, stirred for 15 min at that temperature, and then stirred for 0.5 h at room temperature. TLC detection showed that the reaction was completed. The reaction solution was diluted with ethyl acetate, washed with saturated brine, dried over anhydrous sodium sulfate, concentrated, and purified by column chromatography to obtain 333 mg of compound C11-2. $^1$H NMR (400 MHz, $CDCl_3$) δ 7.98 (s, 1H), 7.40-7.38 (dd, 2H, 6.92 Hz, 2.01 Hz), 6.88-6.86 (dd, 2H, 6.69 Hz, 2.01 Hz), 5.59-5.54 (m, 1H), 5.52 (s, 2H), 3.81-3.75 (m, 5H), 3.58-3.51 (m, 2H).

2. Synthesis of C11-3

Compound C11-2 (723 mg, 2.02 mmol) was dissolved in dichloromethane (20 mL), then a solution of DAST (845 mg, 5.25 mmol) in dichloromethane (10 mL) was added dropwise at −10° C., warmed up to room temperature naturally, stirred overnight, concentrated under reduced pressure to obtain the crude product, and purified by column chromatography to obtain 255 mg of compound C11-3.

$^1$H NMR (400 MHz, $CDCl_3$) δ 7.92 (s, 1H), 7.39-7.37 (d, 2H, 9.06 Hz), 6.88-6.86 (dd, 2H, 6.69 Hz, 2.14 Hz), 5.47 (s, 2H), 5.28-5.23 (m, 1H), 3.76 (s, 3H), 3.30-3.20 (m, 2H), 3.12-3.03 (m, 2H).

3. Synthesis of C11-4

Compound C11-3 (255 mg, 0.671 mmol) and compound C1-3 (239 mg, 0.805 mmol) were dissolved in a mixed solvent of 1,4-dioxane (10 mL) and water(2 mL), and palladium acetate (15 mg, 0.067 mmol), dppf (75 mg, 0.134 mmol) and potassium carbonate (139 mg, 1.007 mmol) were added sequentially. The reaction solution was stirred at 95° C. for 4 h under nitrogen protection. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 347 mg of compound C11-4. MS [M+H] 515.3. $^1$H NMR (400 MHz, $CDCl_3$) δ 7.91 (s, 1H), 7.37-7.35 (m, 2H), 7.29-7.27 (m, 1H), 6.87-6.84 (m, 2H), 5.49 (s, 2H), 5.31-5.26 (m, 1H), 3.76 (s, 3H), 3.75 (s, 3H), 3.43-3.31 (m, 2H), 3.27 (s, 3H), 3.20-3.199 (d, 1H, 2.53 Hz), 3.12-3.02 (m, 2H), 2.82-2.54 (m, 5H), 2.27-2.18 (m, 2H), 2.10-2.03 (m, 1H).

4. Synthesis of C11-5

Compound C11-4 (347 mg, 0.675 mmol) was dissolved in a mixed solvent of ethyl acetate (10 mL) and methanol (10 mL), then wet palladium carbon (35 mg) was added, stirred overnight at room temperature under hydrogen atmosphere. After the reaction was completed, the reaction solution was filtered through diatomite, washed with methanol, and the filtrate was concentrated under reduced pressure to obtain 237 mg of compound C11-5. MS [M+H] 397.3.

5. Synthesis of C11-6

Compound C11-5 (207 mg, 0.523 mmol) was dissolved in phosphorus oxychloride (5 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified to obtain 153 mg of compound C11-6. MS [M+H] 415.2.

6. Synthesis of C11-7

Compound C11-6 (153 mg, 0.370 mmol) and compound C2-7 (39 mg, 0.407 mmol) were dissolved in 3 mL DMSO, then DIPEA (96 mg, 0.740 mmol) was added, and the temperature was raised to 100° C. and stirred overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 151 mg of compound C11-7. MS [M+H] 476.3.

7. Synthesis of C11-8

Compound C11-7 (151 mg, 0.318 mmol) was dissolved in a mixed solvent of methanol (5 mL) and water (1 mL), then lithium hydroxide monohydrate (40 mg, 0.953 mmol) was added, stirred overnight at 60° C. After the reaction was completed, the reaction solution was cooled to room temperature and 186 mg of crude compound C11-8 was obtained by evaporation of methanol under reduced pressure, which was used directly in the next step without purification.

8. Synthesis of C11

Compound C11-8 (176 mg, crude) and compound C5-5 (106 mg, 0.377 mmol) were dissolved in DMF(3 mL), then DIPEA (389 mg, 3.016 mmol) was added, stirred at room temperature for 15 min, then HATU (215 mg, 0.566 mmol) was added, and stirred at room temperature for 1 h. The reaction solution was diluted with ethyl acetate, and the organic phase was washed with saturated salt water, dried over anhydrous sodium sulfate, concentrated, and purified to obtain compound C11. Ms [M+H] 651.4. $^{1}$H NMR (400 MHz, $CDCl_3$) δ 9.54 (br, 1H), 9.17-9.16 (d, 1H, 1.40 Hz), 8.30-8.26 (m, 2H), 7.70 (br, 2H), 7.59-7.58 (m, 1H), 7.50-7.49 (m, 1H), 6.47 (br, 1H), 5.28-5.22 (m, 2H), 3.37-3.27 (m, 2H), 3.24 (s, 3H), 3.11-3.01 (m, 2H), 2.77 (br, 1H), 2.32 (s, 3H), 2.01-1.88 (m, 8H), 1.50-1.48 (d, 3H, 6.77 Hz).

Example 12

The compound synthesized in the present invention

C12

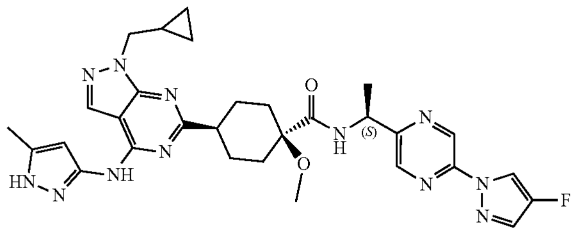

The synthetic route and experimental process were as follows:

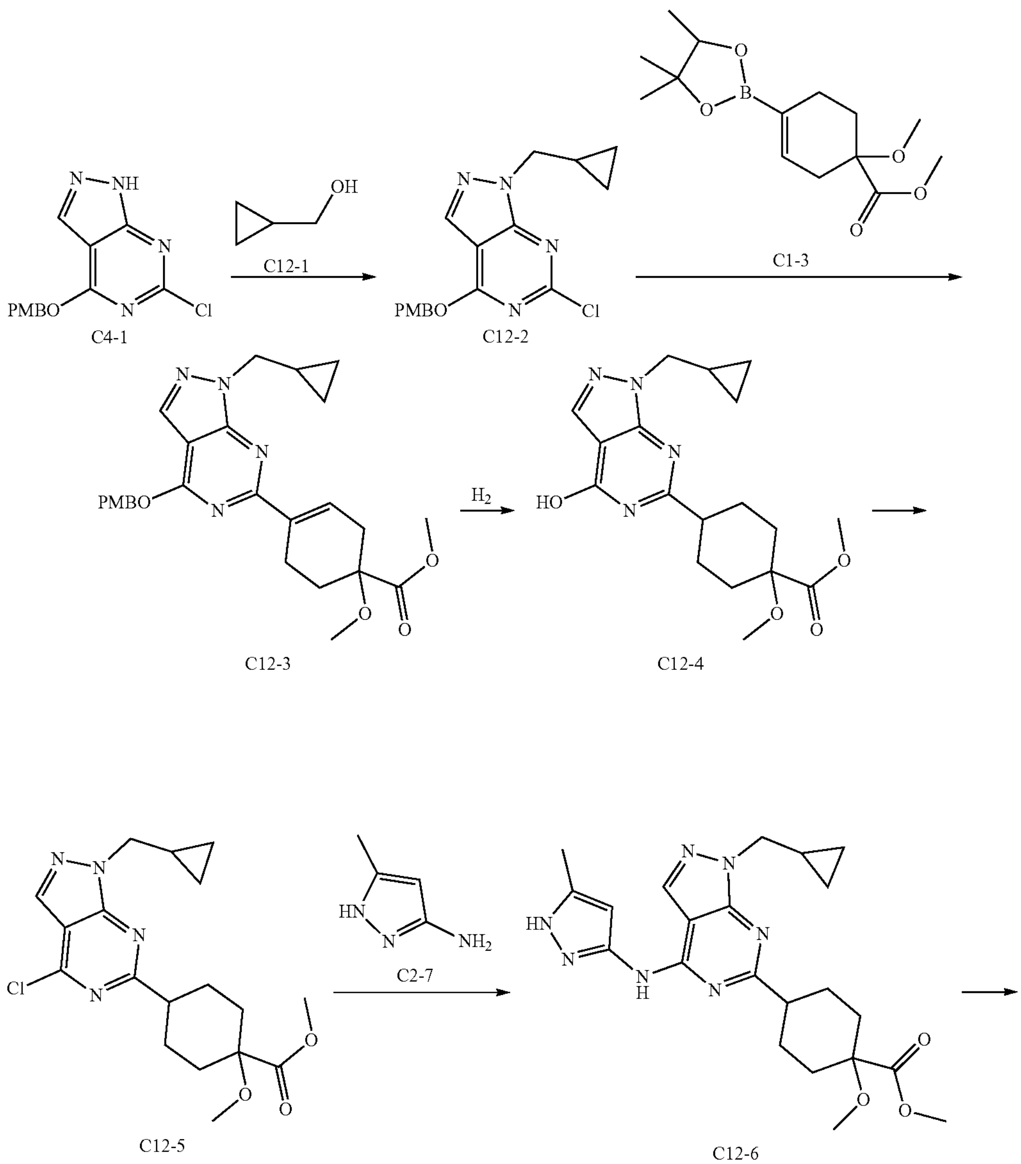

-continued

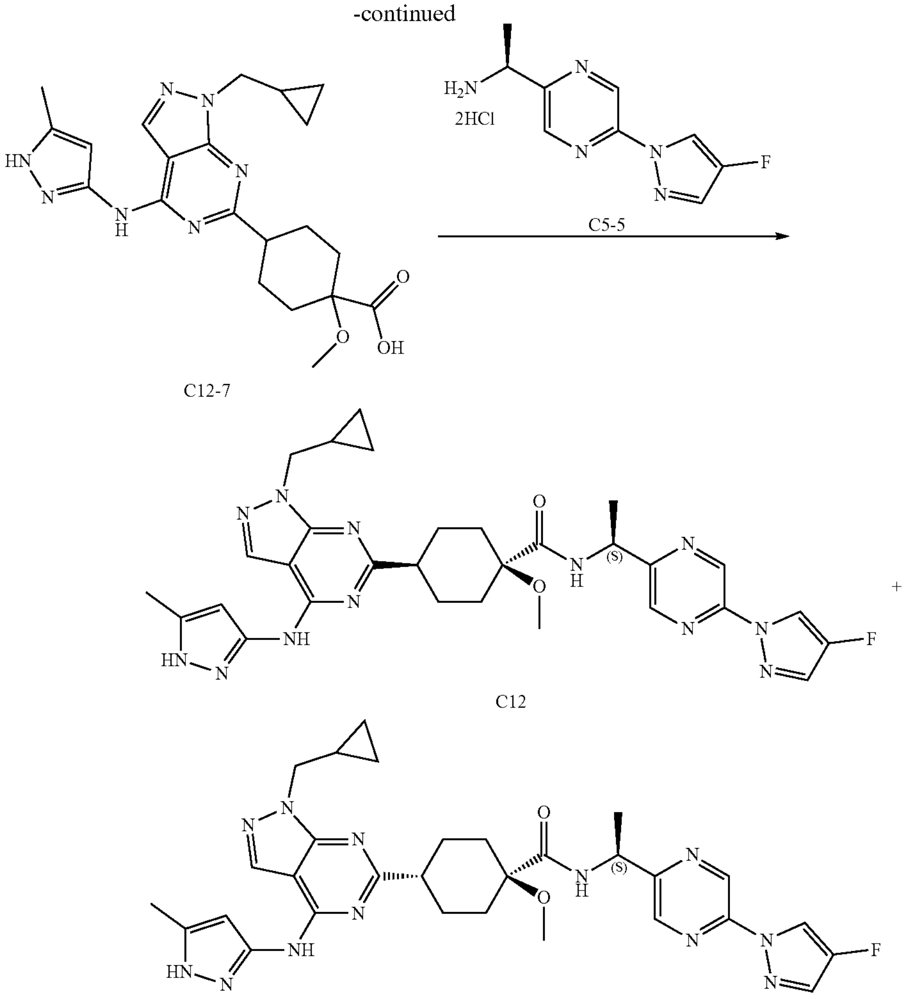

C12-7

C12

+

C12A

1. Synthesis of C2-2

Compound C4-1 (200 mg, 0.688 mmol) and triphenylphosphine (356 mg, 1.36 mmol) were dissolved in 6 ml of anhydrous tetrahydrofuran, and then compound C12-1 (148 mg, 2.06 mmol) was added, and the reaction was cooled to 0° C. DIAD (274 mg, 1.36 mmol) was added dropwise, and after the addition, the reaction was warmed up to room temperature naturally and stirred overnight. After the reaction was completed, the reaction solution was concentrated and purified by column chromatography to obtain 164 mg of compound C12-2.

2. Synthesis of C12-3

Compound C12-2 (164 mg, 0.476 mmol) and compound C1-3 (169 mg, 0.571 mmol) were dissolved in a mixed solvent of 1,4-dioxane (3 mL) and water(0.6 mL), and palladium acetate (11 mg, 0.0476 mmol), dppf (53 mg, 0.095 mmol) and potassium carbonate (99 mg, 0.714 mmol) were added sequentially. The reaction solution was stirred at 90° C. overnight under nitrogen protection. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 200 mg of compound C12-3. MS [M+H] 479.4.

3. Synthesis of C12-4

Compound C12-3 (200 mg, 0.418 mmol) was dissolved in a mixed solvent of ethyl acetate (5 mL) and methanol (5 mL), then wet palladium carbon (20 mg) was added, stirred at room temperature overnight under hydrogen atmosphere. After the reaction was completed, the reaction solution was filtered through diatomite, washed with methanol, and the filtrate was concentrated under reduced pressure to obtain 131 mg of compound C12-4, MS [M+H] 361.3.

4. Synthesis of C12-5

Compound C12-4 (131 mg, 0.3 (4 mmol) was dissolved in phosphorus oxychloride (3 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified to obtain 90 mg of compound C12-5. MS [M+H] 379.3.

5. Synthesis of C12-6

Compound C12-5 (90 mg, 0.238 mmol) and compound C2-7 (25.4 mg, 0.261 mmol) were dissolved in DMSO (1 mL), then DIPEA (61.4 mg, 0.476 mmol) was added, and stirred at 100° C. overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 56 mg of compound C12-6. MS [M+H] 440.4.

6. Synthesis of C12-7

Compound C12-6 (56 mg, 0.128 mmol) was dissolved in a mixed solvent of methanol (3 mL) and water (0.6 mL), then lithium hydroxide monohydrate (16 mg, 0.383 mmol) was added, stirred overnight at 60° C. After the reaction was completed, the reaction solution was cooled to room temperature and 73 mg of crude compound C12-7 was obtained by evaporation of methanol under reduced pressure, which was used directly in the next step without purification.

7. Synthesis of C12

Compound C12-7 (73 mg, crude) and compound C5-5 (47 mg, 0.169 mmol) were dissolved in DMF(2 mL), then DIPEA (175 mg, 1.352 mmol) was added, stirred at room temperature for 15 min, then HATU (96.3 mg, 0.254 mmol) was added, and stirred at room temperature for 1 h. The reaction solution was diluted with ethyl acetate, the organic phase was washed with saturated brine, dried over anhydrous sodium sulfate, concentrated, and purified by HPLC to obtain compound C12. Ms [M+H] 615.5. $^1$H NMR (400 MHz, DMSO-$d_6$+$D_2O$) δ 9.14-9.13 (d, 1H, 1.30 Hz), 8.75-8.74 (d, 1H, 4.43 Hz), 8.53-8.49 (m, 2H), 8.33 (br, 1H), 8.05-8.04 (d, 1H, 4.32 Hz), 6.83 (br, 1H), 5.16-5.12 (t, 1H), 4.16-4.15 (d, 1H, 7.18 Hz), 3.23 (s, 3H), 2.74-2.68 (m, 1H), 2.27 (s, 3H), 2.04-1.73 (m, 9H), 1.52-1.50 (d, 3H, 6.70 Hz).

Example 13

The compound synthesized in the present invention:

C13

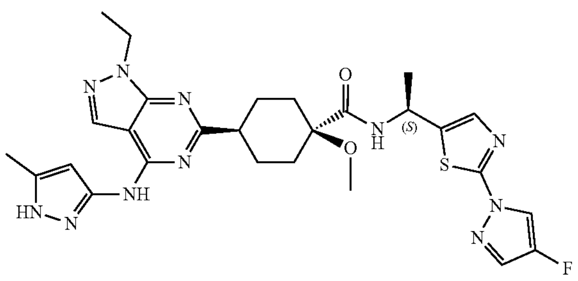

The synthetic route and experimental process were as follows:

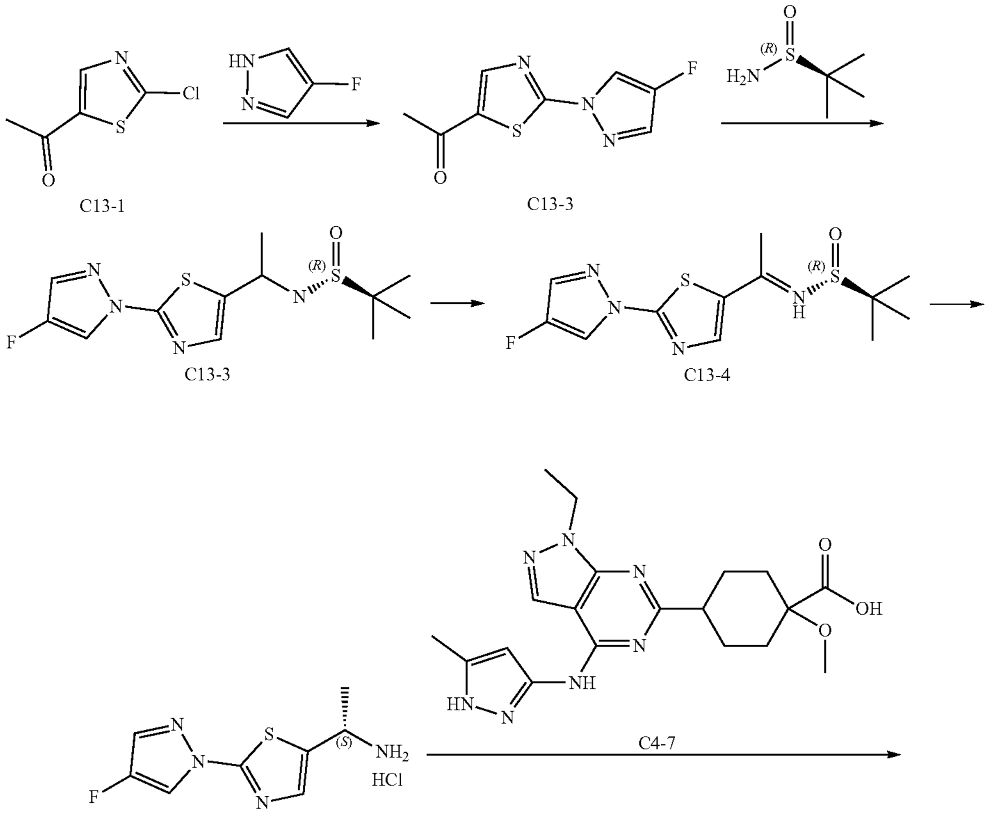

C13-1 C13-3 C13-3 C13-4 C13-5

-continued

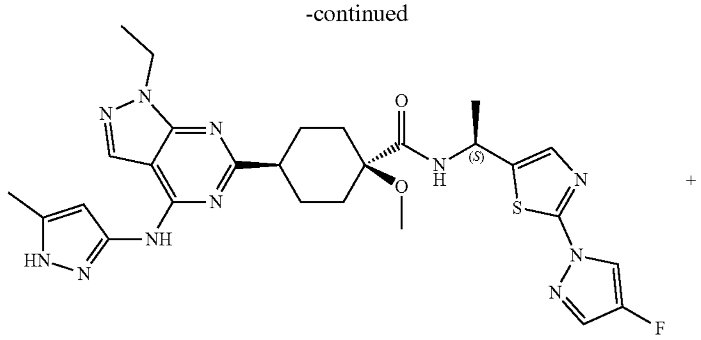

C13

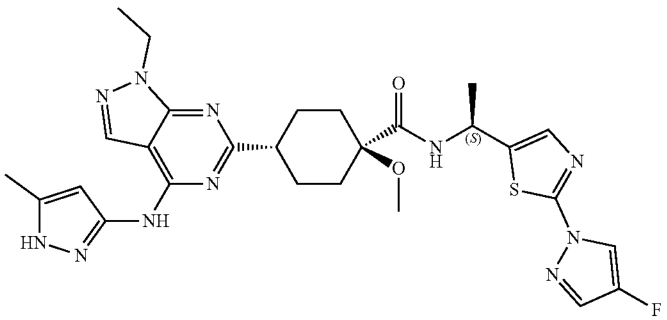

C13A

1. Synthesis of C13-2

Compound C13-1 (1.33 g, 8.23 mmol) was dissolved in DMF (20 mL), and then 4-fluoro-1H-pyrazole (0.78 g, 9.05 mmol) and cesium carbonate (2.68 g, 8.23 mmol) were added sequentially, and the reaction solution was stirred at room temperature for 1 h. The reaction solution was diluted by adding ethyl acetate, and the organic phase was washed with saturated saline, dried over anhydrous sodium sulfate, and purified by column chromatography to obtain 1.43 g of compound C13-2. $^1$H NMR (400 MHz, $CDCl_3$) δ 8.22-8.20 (d, 1H, 4.98 Hz), 8.03 (s, 1H), 7.66-7.65 (d, 1H, 4.28 Hz), 2.57 (s, 3H).

2. Synthesis of C13-3

Compound C13-2 (1.43 g, 6.79 mmol) and R-tert-butyl sulfinamide (1.48 g, 12.23 mmol) were dissolved in super-dry tetrahydrofuran (30 mL), then tetraethyl titanate (4.65 g, 20.37 mmol) was added, and the reaction solution was stirred at 70° C. overnight under nitrogen protection. After the reaction was completed, it was cooled to room temperature, quenched with water, a large amount of solid appeared and filtered through diatomite and washed with ethyl acetate, the filtrate was washed with saturated salt water, dried over anhydrous sodium sulfate and purified by column chromatography to obtain 1.88 g of compound C13-3. $^1$H NMR (400 MHz, $CDCl_3$) δ 8.15-8.13 (dd, 1H, 4.74 Hz, 0.62 Hz), 7.79 (s, 1H), 7.59-7.58 (dd, 1H, 4.23 Hz, 0.59 Hz), 2.67 (s, 3H), 1.23 (s, 9H).

3. Synthesis of C13-4

Compound C13-3 (1.78 g, 5.65 mmol) was dissolved in 30 mL of super-dry tetrahydrofuran, and a solution of 1 M L-selectride in tetrahydrofuran(17 mL, 16.96 mmol) was added dropwise at −70° C. under nitrogen protection. The temperature was maintained and stirred for 30 min, the reaction was quenched by dropwise addition of methanol and warmed up to room temperature and stirred for 15 min. The reaction solution was diluted with ethyl acetate, and the organic phase was washed with saturated salt water, dried over anhydrous sodium sulfate and purified to obtain 2.43 g of crude compound C13-4. $^1$H NMR (400 MHz, $CDCl_3$) δ 8.18-8.17 (d, 1H, 4.98 Hz), 7.38 (s, 1H), 7.59-7.58 (d, 1H, 4.42 Hz), 4.85-4.79 (m, 1H), 3.44-3.43 (d, 1H, 5.03 Hz), 1.69-1.67 (d, 3H, 6.58 Hz), 1.24 (s, 9H).

4. Synthesis of C13-5

The crude compound C13-4 (2.33 g, 7.37 mmol) was dissolved in dichloromethane (10 mL) and anhydrous methanol (3 mL), and a solution of 4 M hydrochloride in 1,4-dioxane (18.4 mL, 73.73 mmol) was added with stirring under nitrogen protection and stirred at room temperature for 2 h. The mixture was diluted by adding dichloromethane, and the solid was filtered, washed with dichloromethane, and dried under vacuum to obtain 1.1 g of compound C13-5. $^{1}$H NMR (400 MHz, DMSO-$d_6$) δ 8.74-8.73 (d, 1H, 4.48 Hz), 8.62 (br, 3H), 8.07-8.06 (d, 1H, 3.95 Hz), 7.74 (s, 1H), 4.83-4.77 (m, 1H), 1.62-1.61 (d, 3H, 6.22 Hz).

5. Synthesis of C13

Compound C4-7 (60 mg, 0.148 mmol) and compound C13-5 (37 mg, 0.148 mmol) were dissolved in DMF(2 mL), then DIPEA (153 mg, 1.184 mmol) was added, stirred at room temperature for 15 min, then HATU (84 mg, 0.222 mmol) was added, and stirred at room temperature for 1 h. The reaction solution was diluted with ethyl acetate, the organic phase was washed with saturated salt water, dried over anhydrous sodium sulfate, concentrated and separated by preparative HPLC to obtain compound C13. Ms [M+H] 594.3. $^{1}$H NMR (400 MHz, DMSO-$d_6$+$D_2O$) δ 8.67-8.63 (m, 2H), 8.32 (br, 1H), 7.47-7.46 (d, 1H, 1.06 Hz), 6.82 (br, 1H), 5.26-5.20 (q, 1H), 4.33-4.28 (q, 2H), 3.17 (s, 3H), 2.72-2.67 (m, 1H), 2.25 (s, 3H), 2.00-1.93 (m, 4H), 1.80-1.73 (m, 4H), 1.56-1.54 (d, 3H, 6.88 Hz), 1.38-1.34 (t, 3H).

Example 14

The compound synthesized in the present invention:

C14

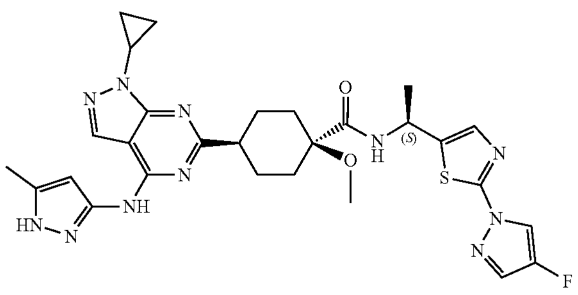

The synthetic route and experimental process were as follows:

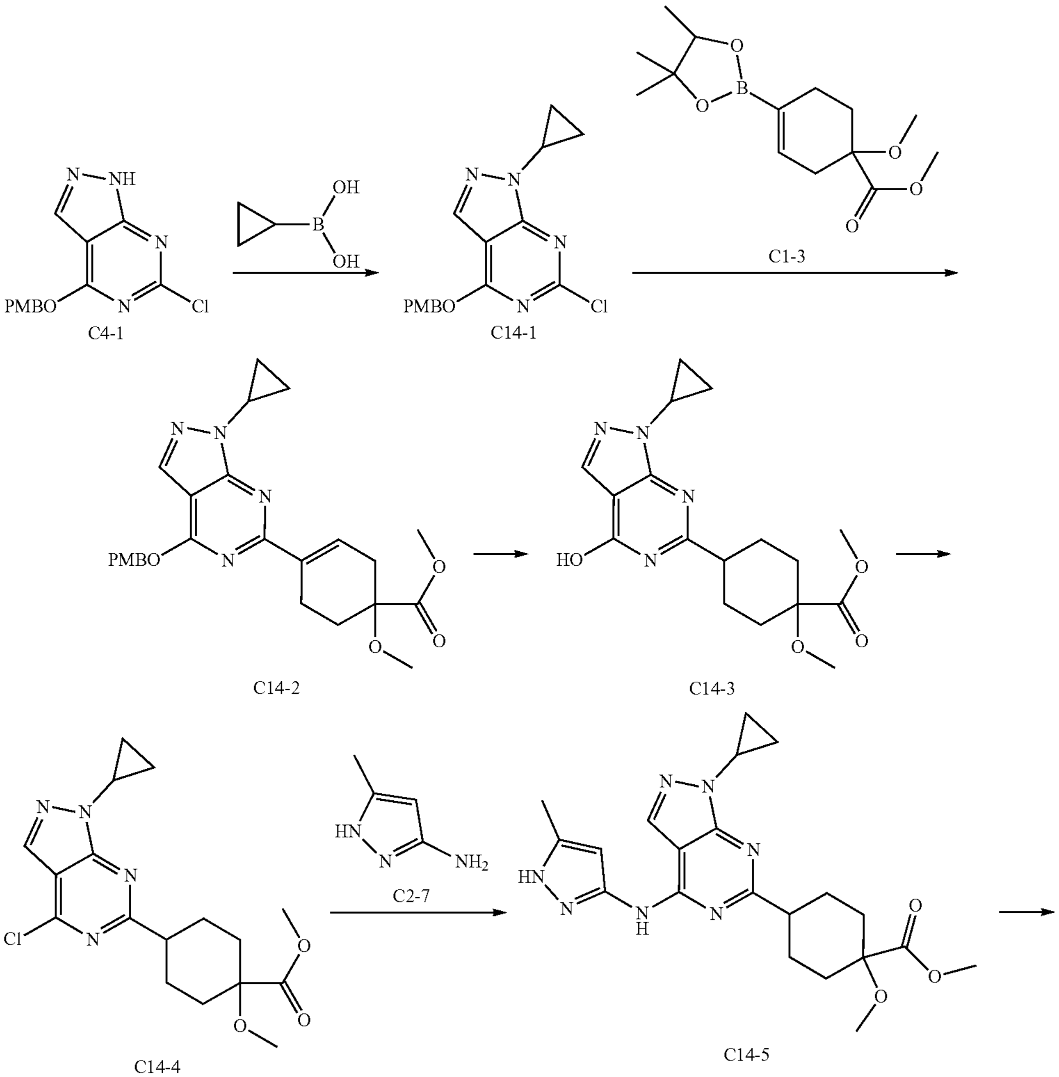

C4-1
C14-1
C14-2
C14-3
C14-4
C14-5

-continued

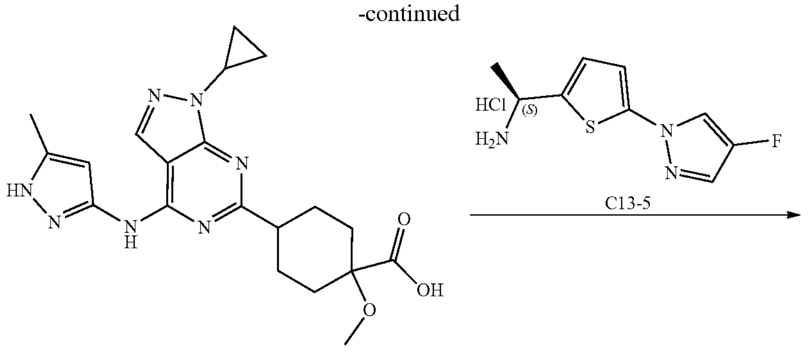

C14-6

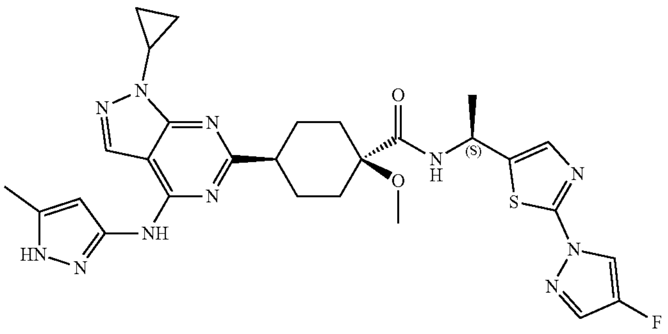

+

C14

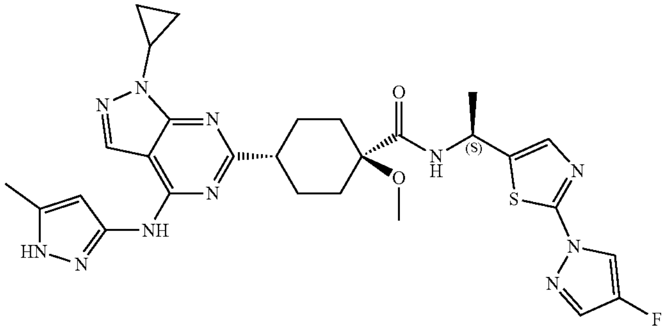

C14A

1. Synthesis of C14-1

Compound C4-1 (2.00 g, 6.90 mmol) was dissolved in DCE (150 mL), and 2,2-bipyridine (1.10 g, 6.90 mmol), $Na_2CO_3$ (1.50, 13.79 mmol), $Cu(OAc)_2$ (0.85 g, 6.90 mmol) and cyclopropylboronic acid (1.20 g, 13.79 mmol) were added sequentially, and stirred overnight at 60° C. in an oil bath under nitrogen protection. After the reaction was completed, the reaction solution was filtered by suction filtration, concentrated and diluted with EA, then washed with 1% dilute hydrochloric acid in water, the organic phase was separated and washed with saturated salt water, dried over anhydrous sodium sulfate, and concentrated under reduced pressure to obtain the crude product, which was purified by column chromatography to obtain 1.05 g of compound C14-1, MS [M+H] 331. $^1H$ NMR (400 MHz, Chloroform-d) δ 7.91 (s, 1H), 7.52-7.40 (m, 2H), 6.98-6.89 (m, 2H), 5.53 (s, 2H), 3.86-3.75 (m, 4H), 1.34-1.23 (m, 2H), 1.22-1.07 (m, 2H).

2. Synthesis of C14-2

Compound C14-1 (1.50 g, 4.55 mmol) and compound C1-3 (1.60 g, 5.45 mmol) were dissolved in a mixture solvent of 50 mL 1,4-dioxane and 10 mL water, and palladium acetate (102 mg, 0.45 mmol), dppf (504 mg, 0.91 mmol) and potassium carbonate (941 mg, 6.82 mmol) were added sequentially. The reaction solution was stirred at 90° C. overnight under nitrogen protection. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 1.40 g of compound C14-2. MS [M+H] 465. $^1H$ NMR (400 MHz, Chloroform-d) δ 7.88 (s, 1H), 7.43 (d, J=8.7 Hz, 2H), 7.36-7.32 (m, 1H), 6.92 (d, J=8.7 Hz, 2H), 5.55 (s, 2H), 3.90-3.84 (m, 1H), 3.82 (s, 6H), 3.34 (s, 3H), 2.91-2.72 (m, 3H), 2.71-2.50 (m, 1H), 2.42-2.09 (m, 3H), 1.36-1.31 (m, 2H), 1.17-1.07 (m, 2H).

3. Synthesis of C14-3

Compound C14-2 (1.36 g, 2.93 mmol) was dissolved in a mixed solvent of ethyl acetate (20 mL) and methanol (20 mL), then wet palladium carbon (150 mg) was added, stirred overnight at room temperature under hydrogen atmosphere.

After the reaction was completed, the reaction solution was filtered through diatomite, washed with methanol, and the filtrate was concentrated under reduced pressure to obtain 985 mg of Compound C14-3, MS [M+H] 347. $^1$H NMR (400 MHz, Chloroform-d) δ 11.67 (s, 1H), 8.01 (s, 1H), 3.93-3.83 (m, 1H), 3.80 (s, 3H), 3.32 (s, 3H), 2.25-2.06 (m, 2H), 2.05-1.84 (m, 5H), 1.80-1.66 (m, 1H), 1.36-1.28 (m, 2H), 1.15-1.06 (m, 2H).

4. Synthesis of C14-4

Compound C14-3 (985 mg, 2.85 mmol) was dissolved in phosphorus oxychloride (20 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified by column chromatography to obtain 931 mg of compound C14-4, MS [M+H] 365. $^1$H NMR (400 MHz, Chloroform-d) δ 8.00 (s, 1H), 3.97-3.87 (m, 1H), 3.79 (s, 3H), 3.30 (s, 3H), 2.51-1.77 (m, 8H), 1.45-1.27 (m, 2H), 1.22-1.09 (n, 2H).

5. Synthesis of C14-5

Compound C14-4 (931 mg, 2.56 mmol) and compound C2-7 (273 mg, 2.81 mmol) were dissolved in 7 mL DMSO, then DIPEA (660 mg, 5.12 mmol) was added, and the temperature was raised to 100° C. and stirred overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 700 mg of compound C14-5. MS [M+H] 426.

$^1$H NMR (400 MHz, Chloroform-d) δ 7.70 (s, 1H), 6.56 (s, 1H), 3.94-3.83 (m, 1H), 3.80 (d, J=6.7 Hz, 3H), 3.32 (d, J=16.5 Hz, 3H), 2.97-2.83 (m, 1H), 2.37 (d, J=7.1 Hz, 3H), 2.24-1.80 (m, 6H), 1.77-1.60 (m, 2H), 1.35-1.22 (m, 2H), 1.17-1.08 (m, 2H).

6. Synthesis of C14-6

Compound C14-5 (700 mg, 1.65 mmol) was dissolved in a mixed solvent of methanol (12 mL) and water (2 mL), then lithium hydroxide monohydrate (208 mg, 4.94 mmol) was added, stirred overnight at 60° C. After the reaction was completed, the reaction solution was cooled to room temperature, the solvent was evaporated under reduced pressure, and crude solid was slurried with DCM, filtered by suction filtration to obtain 885 mg of crude product C14-6 (MS [M+H] 412), which was used directly in the next step without purification.

7. Synthesis of C14

Compound C14-6 (70 mg, crude) and compound C13-5 (42 mg, 0.168 mmol) were dissolved in DMF(2 mL), then DIPEA (173 mg, 1.344 mmol) was added, stirred at room temperature for 15 min, then HATU (96 mg, 0.252 mmol) was added, and stirred at room temperature for 1 h. The reaction solution was diluted with ethyl acetate, and the organic phase was washed with saturated brine, dried over anhydrous sodium sulfate, concentrated, and purified to obtain compound C14. Ms [M+H] 606.4. $^1$H NMR (400 MHz, DMSO-$d_6$+$D_2O$) δ 8.67-8.63 (m, 2H), 8.26 (br, 1H), 7.99-7.98 (m, 1H), 7.47-7.46 (d, 1H, 1.07 Hz), 6.82 (br, 1H), 5.24-5.20 (q, 1H), 3.86-3.82 (m, 1H), 3.18 (s, 3H), 2.25 (s, 3H), 2.00-1.93 (m, 4H), 1.81-1.74 (m, 4H), 1.56-1.54 (d, 3H. 7.30 Hz), 1.16-1.09 (m, 2H), 1.08-1.02 (m, 2H).

Example 15

The compound synthesized in the present invention:

C14

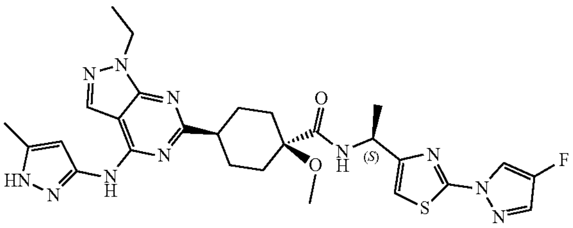

The synthetic route and experimental process were as follows:

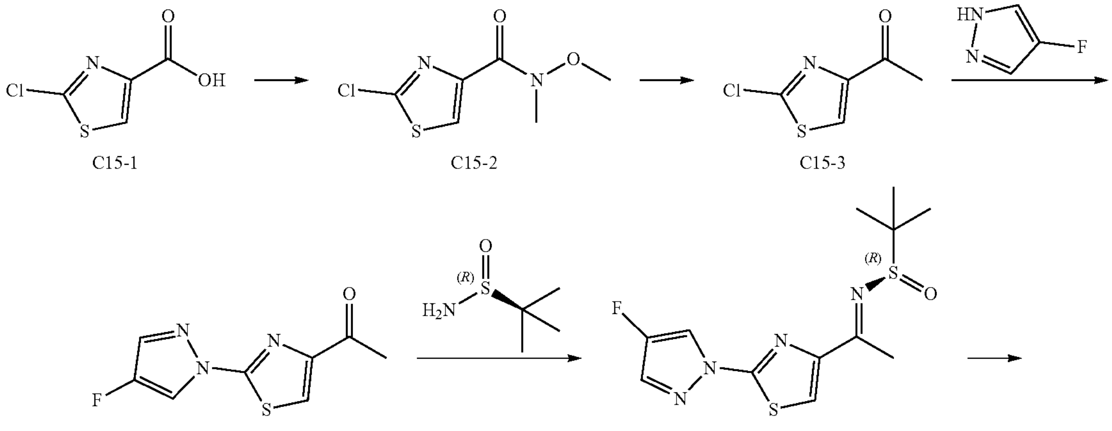

C15-1 C15-2 C15-3

C15-4 C15-5

-continued

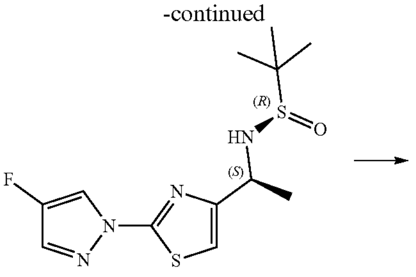

C15-6

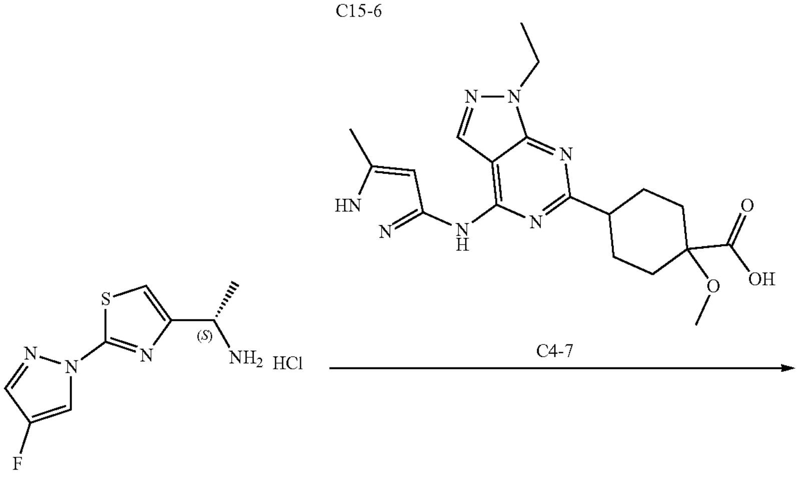

C15-7

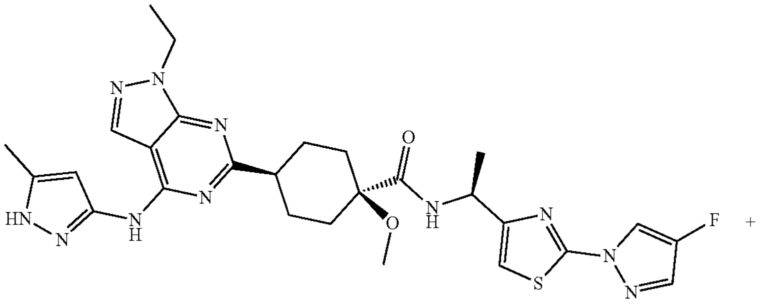

C15

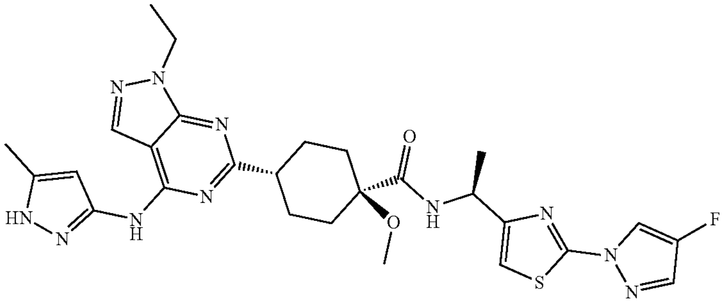

C15A

1. Synthesis of C15-2

Compound C15-1 (5 g, 0.03 mol) was suspended in dichloromethane (50 ml), and then oxalyl chloride (7.75 mL, 0.09 mol) was added at once, followed by 3 drops of DMF, and the reaction solution was stirred at room temperature for 2 h. After the reaction was completed, the reaction solution was evaporated under reduced pressure, and the crude product was dissolved in dichloromethane (30 mL) and used directly in the next step.

N,O-dimethylhydroxylamine hydrochloride (4.45 g, 0.045 mol) was suspended in dichloromethane (100 mL), triethylamine (29.5 mL, 0.18 mol) was added, stirred at room temperature for 5 min, and then a solution of the acyl chloride obtained in the previous step in dichloromethane was added dropwise and stirred at room temperature for 2 h. After the reaction was completed, saturated salt water was added, extracted with dichloromethane, and the combined organic phases were dried over anhydrous sodium sulfate and concentrated to obtain the crude product, which was purified to obtain 5.14 g of compound C15-2. $^1$H NMR (400 MHz, $CDCl_3$) δ 7.94 (s, 1H), 3.80 (s, 3H), 3.42 (s, 3H).

2. Synthesis of C15-3

Compound C15-2 (4.03 g, 0.019 mol) was dissolved in anhydrous tetrahydrofuran (100 mL), then a solution of 1 M methylmagnesium bromide in tetrahydrofuran (32 mL, 0.032 mol) was added dropwise at 0° C. under nitrogen protection, stirred for 1 h under cooling in an ice-water bath. The reaction was quenched with water, extracted with ethyl acetate, and the combined organic phases were washed with saturated saline, dried over anhydrous sodium sulfate, concentrated under reduced pressure to obtain crude product which was purified to obtain 1.98 g of compound C15-3. $^1$H NMR (400 MHz, $CDCl_3$) δ 7.97 (s, 1H), 2.58 (s, 3H).

3. Synthesis of C15-4

Compound C15-3 (1.83 g, 0.011 mmol) was dissolved in DMF (20 mL), then 4-fluoro-1H-pyrazole (1.17 g, 0.014 mol) and potassium carbonate (3.13 g, 0.022 mol) were added sequentially and stirred at 110° C. for 16 h. After the reaction was completed, the solvent was evaporated under reduced pressure, diluted by adding ethyl acetate, and the organic phase was washed with saturated saline, dried over anhydrous sodium sulfate, and purified by column chromatography to obtain 0.86 g of compound C15-4. $^1$H NMR (400 MHz, $CDCl_3$) δ 8.21-8.20 (t, 1H), 7.84 (s, 1H), 7.57-7.56 (d, 1H, 4.02 Hz), 2.57 (s, 3H).

4. Synthesis of C15-5

Compound C15-4 (856 mg, 4.057 mmol) was dissolved in anhydrous tetrahydrofuran (30 mL), and then R-tert-butyl sulfinamide (884 mg, 7.302 mmol) and tetraethyl titanate (2.77 g, 12.171 mmol) were added sequentially, and the reaction solution was stirred for 16 h at 70° C. under nitrogen protection. After the reaction was completed, the reaction solution was cooled to room temperature, quenched with water, a large amount of solid appeared and filtered through diatomite and washed with ethyl acetate, the filtrate was washed with saturated salt water, dried over anhydrous sodium sulfate and purified to obtain 1.05 g of compound C15-5. $^1$H NMR (400 MHz, $CDCl_3$) δ 8.24-8.23 (dd, 1H, 4.74 Hz, 0.73 Hz), 7.80 (s, 1H), 7.63-7.62 (dd, 1H, 4.21 Hz, 0.68 Hz), 2.81 (s, 3H), 1.32 (s, 9H).

5. Synthesis of C15-6

Compound C15-5 (1.05 g, 3.34 mmol) was dissolved in super-dry tetrahydrofuran (30 mL), and a solution of 1 M L-selectride in tetrahydrofuran(10 mL, 10.03 mmol) was added dropwise at −70° C. under nitrogen protection. The temperature was maintained and stirred for 30 min, the reaction was quenched by dropwise addition of methanol and warmed up to room temperature and stirred for 15 min. The reaction solution was diluted with ethyl acetate, and the organic phase was washed with saturated salt water, dried over anhydrous sodium sulfate and purified to obtain 810 g of compound C15-6. $^1$H NMR (400 MHz, $CDCl_3$) δ 8.11-8.10 (dd, 1H, 4.68 Hz, 0.60 Hz), 7.52-7.51 (d, 1H, 4.28 Hz), 6.83-6.82 (d, 1H, 0.62 Hz), 4.59-4.52 (q, 1H), 3.39-3.37 (d, 1H, 5.99 Hz), 1.58-1.57 (d, 3H, 6.99 Hz), 1.16 (s, 9H).

6. Synthesis of C15-7

The crude compound C15-6 (810 mg, 2.56 mmol) was dissolved in dichloromethane (10 mL) and a solution of 4 M hydrochloride in 1,4-dioxane (6.4 mL, 25.6 mmol) was added with stirring, stirred at room temperature for 2 h under nitrogen protection. The mixture was diluted by adding dichloromethane, the solid was filtered and washed with dichloromethane, and dried under vacuum to obtain 550 mg of compound C15-7. $^1$H NMR (400 MHz, DMSO-$d_6$) δ 9.61-9.58 (t, 4H), 9.08-8.07 (d, 1H, 4.10 Hz), 8.58 (s, 1H), 5.52-5.49 (m, 1H), 4.44 (br, 3H).

7. Synthesis of C15

Compound C4-7 (60 mg, 0.148 mmol) and compound C15-7 (37 mg, 0.148 mmol) were dissolved in DMF(2 mL), then DIPEA (153 mg, 1.184 mmol) was added, stirred at room temperature for 15 min, then HATU (84 mg, 0.222 mmol) was added, and stirred at room temperature for 1 h. The reaction solution was diluted with ethyl acetate, and the organic phase was washed with saturated brine, dried over anhydrous sodium sulfate, concentrated, and purified by preparative HPLC to obtain compound C15. Ms [M+H] 594.4. $^1$H NMR (400 MHz, DMSO-$d_6$+$D_2O$) δ 8.72-8.71 (d, 1H, 4.86 Hz), 8.39 (br, 1H), 8.08-8.07 (d, 1H, 3.89 Hz), 7.25 (br, 1H), 6.90 (br, 1H), 5.17-5.12 (q, 1H), 4.42-4.36 (q, 2H), 3.32 (s, 3H), 2.84-2.76 (m, 1H), 2.35 (s, 3H), 2.10-2.01 (m, 4H), 1.89-1.83 (m, 4H), 1.55-1.53 (d, 3H, 6.89 Hz), 1.47-1.43 (t, 3H).

Example 16

The compound synthesized in the present invention:

C16

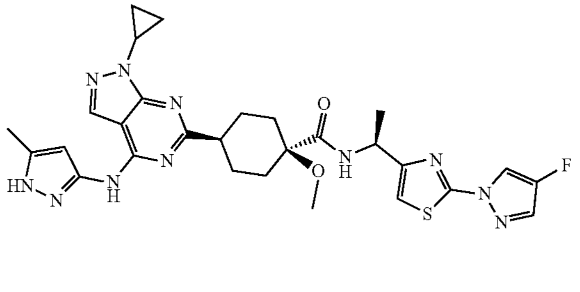

The synthetic route and experimental process were as follows:

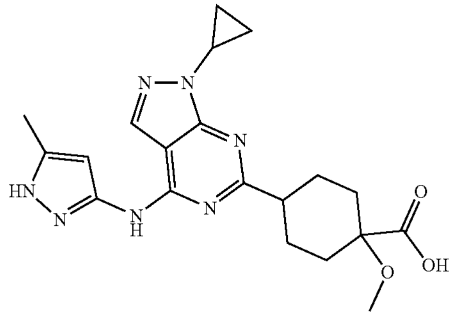

C14-6

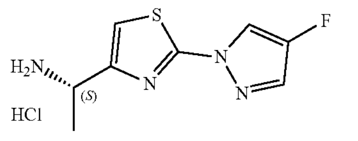

C15-7

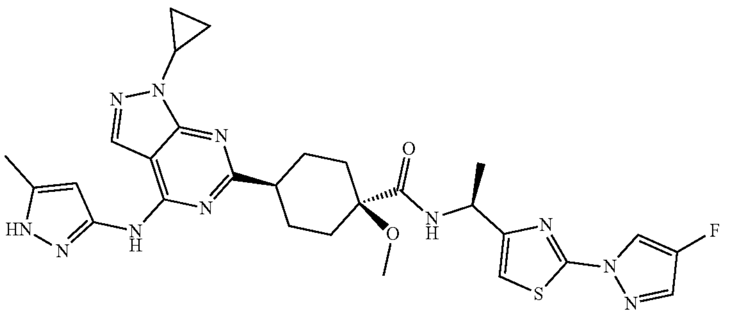

C16

+

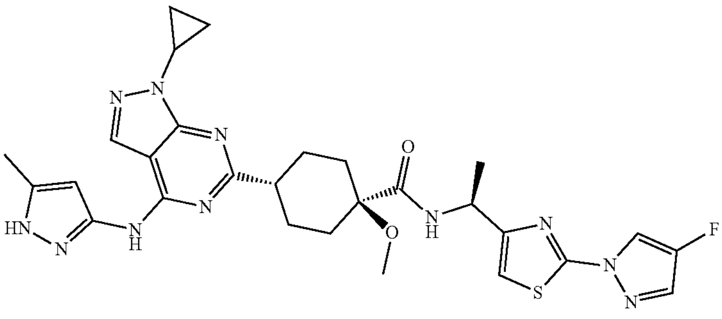

C16A

1. Synthesis of C16

Compound C14-6 (70 mg, 0.168 mmol) and compound C15-7 (42 mg, 0.168 mmol) were dissolved in DMF(2 mL), then DIPEA (173 mg, 1.344 mmol) was added, stirred at room temperature for 15 min, then HATU (96 mg, 0.252 mmol) was added, and stirred at room temperature for 1 h. The reaction solution was diluted with ethyl acetate, and the organic phase was washed with saturated brine, dried over anhydrous sodium sulfate, concentrated, and purified to obtain compound C16. Ms [M+H] 606.4. $^1$H NMR (400 MHz, DMSO-$d_6$+$D_2O$) δ 8.64-8.63 (d, 1H, 4.43 Hz), 8.30-8.22 (m, 1H), 8.00-7.99 (d, 1H, 4.11 Hz), 7.17 (br, 1H), 6.81 (br, 1H), 5.09-5.04 (q, 1H), 3.86-3.83 (m, 1H), 3.24 (s, 3H), 2.75-2.68 (m, 2H), 2.26 (s, 3H), 2.01-1.75 (m, 9H), 1.47-1.45 (d, 3H, 6.82 Hz), 1.16-1.11 (m, 2H), 1.09-1.02 (m, 2H).

Example 17
The compound synthesized in the present invention:
C17
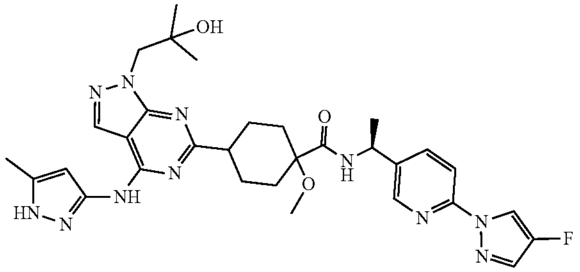
The synthetic route and experimental process were as follows:
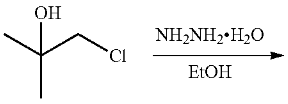
C17-1
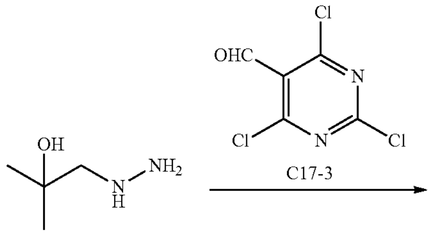
C17-3
C17-2
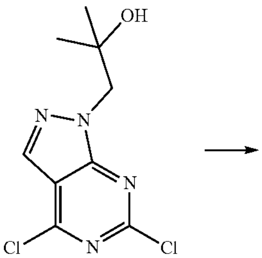
C17-4
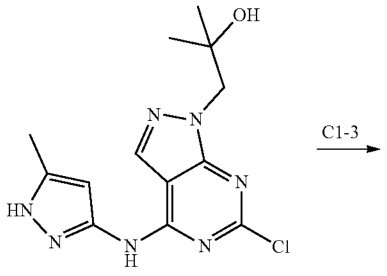
C17-5
-continued
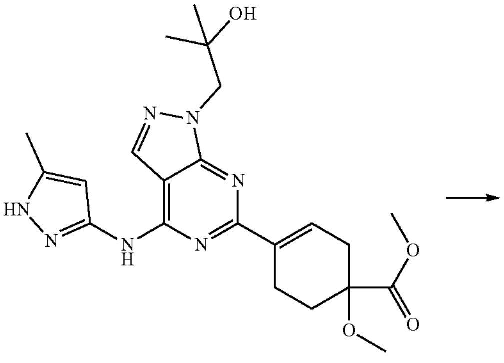
C17-6
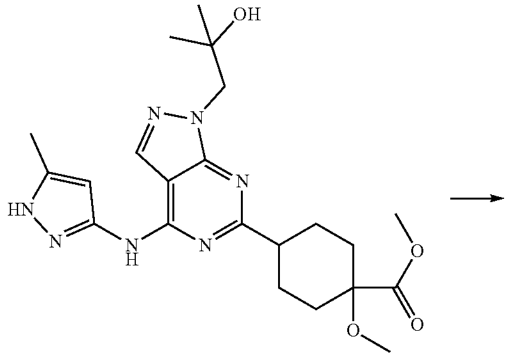
C17-7
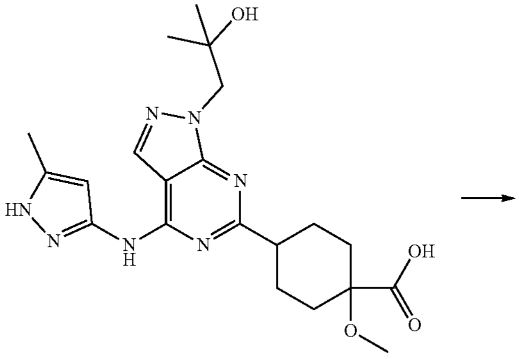
C17-8
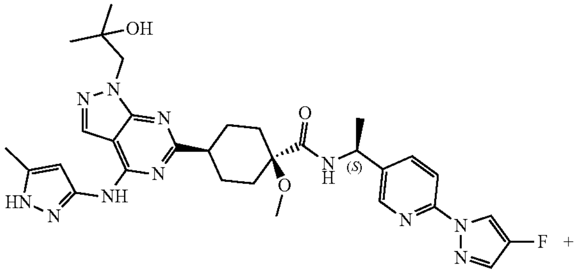
C17

-continued

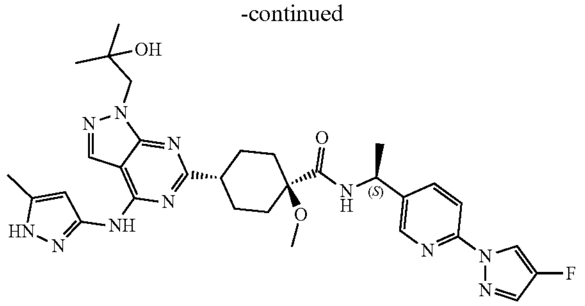

C17A

1. Synthesis of C17-2

Compound C17-1 (4.36 g, 40 mmol) and hydrazine hydrate (40 g, 800 mmol) were dissolved in ethanol (100 mL) and stirred at reflux overnight. The reaction solution was cooled to room temperature, a solid was precipitated, a small amount of ethanol was added, stirred for 30 min, filtered, and the filtrate was concentrated to obtain the crude product of C17-2.

2. Synthesis of C17-4

Compound C17-2 (1.04 g, 10 mmol) was dissolved in ethanol (8 mL), and the solution was added dropwise to a solution of C17-3 (2.1 g, 10 mmol) in ethanol (125 mL) at −78° C. After addition, triethylamine (4.17 mL, 30 mmol) was added, stirred at that temperature for 30 min, naturally warmed to room temperature and stirred for 30 min, 3M hydrochloric acid was added until pH=5-6, concentrated, ethyl acetate and water were added, liquid was separated, dried over anhydrous sodium sulfate, and concentrated by column chromatography to obtain the product C17-4.

3. Synthesis of C17-5

C17-4 (700 mg, 2.69 mmol), C2-7 (395 mg, 3.5 mmol) and diisopropylethylamine (694 mg, 5.38 mmol) were dissolved in DMSO (14 mL) and stirred at 25° C. for 3 hours. After the reaction was completed, water was added and extracted with ethyl acetate, dried, concentrated and purified by column chromatography to obtain 845 mg of product C17-5.

$^1$H NMR (400 MHz, DMSO) δ 12.26 (s, 1H), 11.14 (s, 1H), 8.43 (s, 1H), 6.58 (s, 1H), 4.71 (s, 1H), 4.18 (s, 2H), 2.27 (s, 3H), 1.11 (s, 6H).

4. Synthesis of C17-6

C17-5 (353 mg, 1.09 mmol), C1-3 (446 mg, 1.5 mmol), $Pd(dppf)Cl_2$ (124 mg, 0.169 mmol) and sodium carbonate (175 mg, 1.65 mmol) were added to a mixed solution of dioxane (10 mL) and water (2 mL), reacted under nitrogen protection at 90° C. for 24 h, concentrated, water (20 mL) was added, extracted with ethyl acetate, dried, concentrated, and purified by column chromatography to obtain 333 mg of compound C17-6.

5. Synthesis of C17-7

C17-6 (284 mg, 0.62 mmol) and palladium hydroxide/carbon (70 mg, 50% water) were added to a mixed solvent of methanol (20 mL) and ethyl acetate (20 mL), and reacted at 45° C. for 7 days. HPLC showed the reaction was completed, filtered and concentrated to obtain 243 mg of crude compound C17-7. Ms [M+H] 458.40

6. Synthesis of C17-8

Compound C17-7 (56 mg, 0.122 mmol) was dissolved in a mixed solvent of methanol (3 mL) and water (0.6 mL), then lithium hydroxide monohydrate (20.5 mg, 0.49 mmol) was added, stirred overnight at 60° C. After the reaction was completed, the reaction solution was cooled to room temperature and 73 mg of crude compound C17-8 was obtained by evaporation of methanol under reduced pressure, which was used directly in the next step without purification.

7. Synthesis of C17

Compound C17-8 (50 mg, crude) and compound C1-7 (32 mg, 0.11 mmol) were dissolved in DMF(2 mL), then DIPEA (117 mg, 0.91 mmol) was added, stirred at room temperature for 15 min, then HATU (64 mg, 0.168 mmol) was added, and stirred at room temperature for 1 h. The reaction solution was diluted with ethyl acetate, and the organic phase was washed with saturated brine, dried over anhydrous sodium sulfate, concentrated, and purified by HPLC to obtain compound C17. Ms [M+H] 632.50

Example 18

The compound synthesized in the present invention:

C18

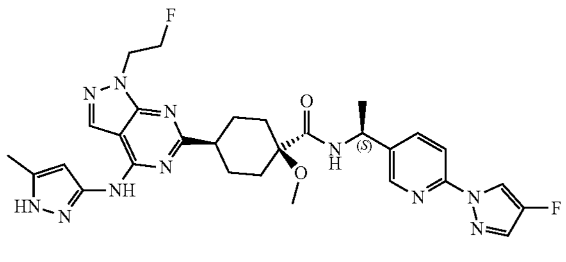

The synthetic route and experimental process were as follows:
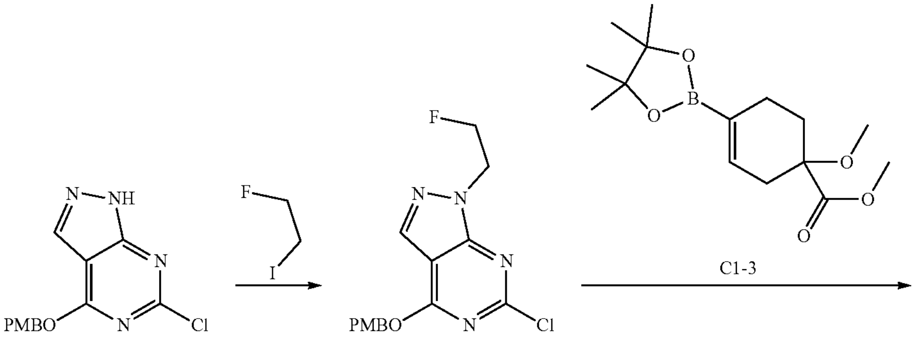
C4-1 C18-1
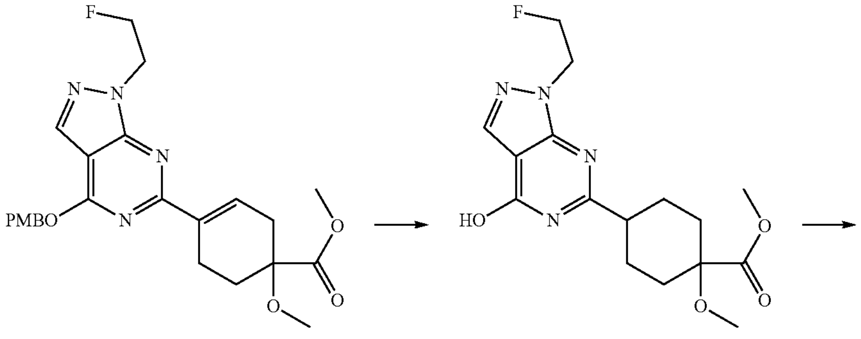
C18-2 C18-3
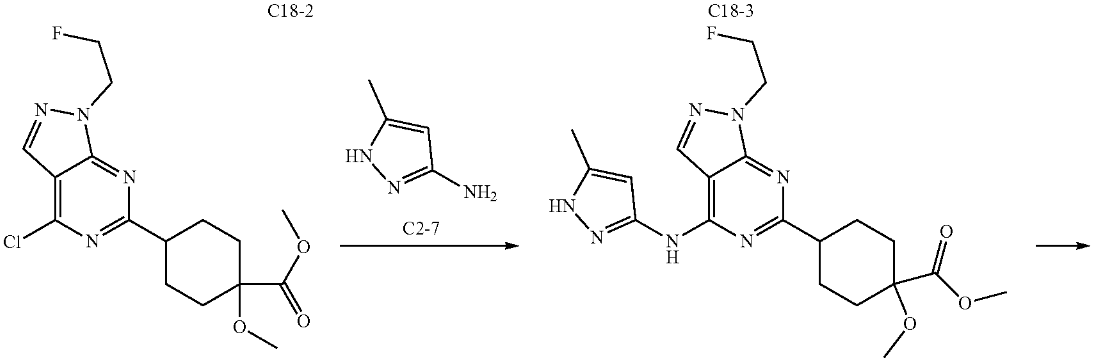
C18-4 C18-5
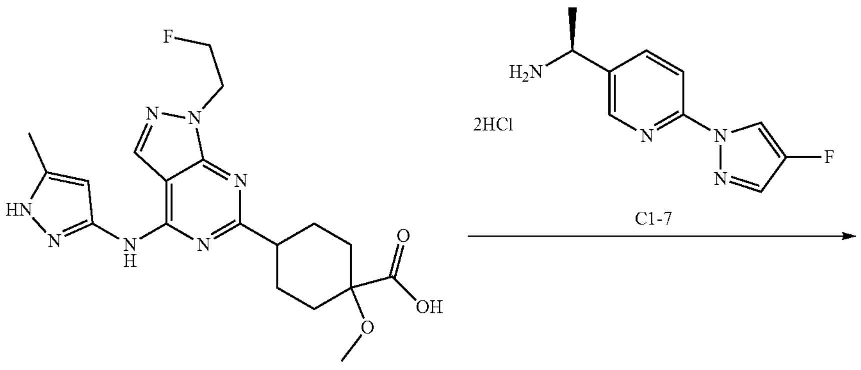
C18-6

-continued

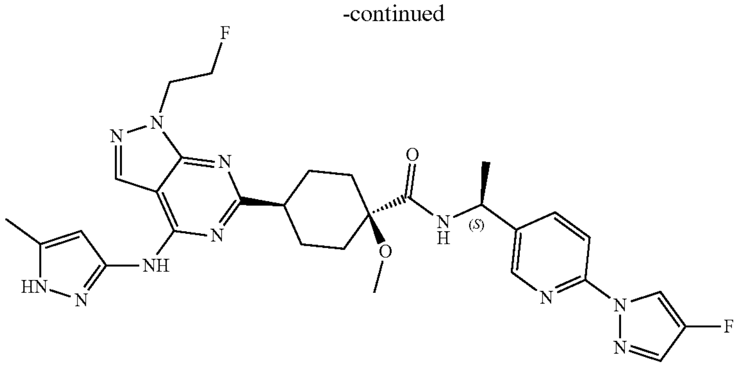

+

C18

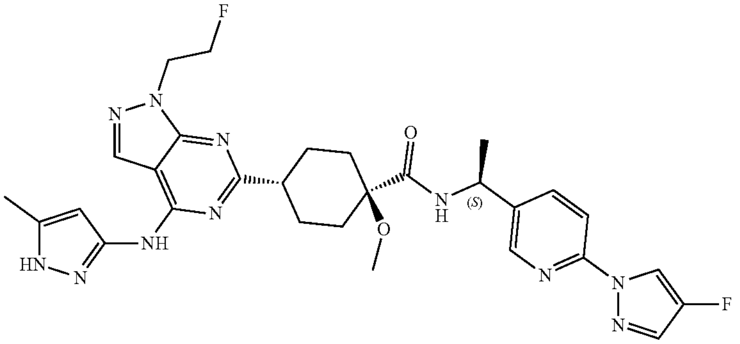

C18A

1. Synthesis of C18-1

Compound C4-1 (3.0 g, 10.34 mmol) was dissolved in anhydrous DMF (60 mL), and cesium carbonate (5.1 g, 15.52 mmol) and compound 1-fluoro-2-iodoethane (3.60 g, 20.68 mmol) were added sequentially, stirred in an oil bath at 50° C. for 3 h. DMF was evaporated under reduced pressure. The reaction was quenched by adding saturated salt water, then extracted with ethyl acetate, the organic phase was separated and washed with saturated salt water, dried over anhydrous sodium sulfate, and concentrated under reduced pressure to obtain the crude product which was purified by column chromatography to obtain 2.13 g of compound C18-1. MS [M+Na] 359. $^1$H NMR (400 MHz, $CDCl_3$) δ 7.96 (s, 1H), 7.38 (d, J=8.7 Hz, 2H), 6.87 (d, J=8.7 Hz, 2H), 5.47 (s, 2H), 4.84 (dd, J=5.3, 4.6 Hz, 1H), 4.73 (dd, J=5.4, 4.5 Hz, 1H), 4.66 (t, J=5.0 Hz, 1H), 4.60 (dd, J=5.4, 4.5 Hz, 1H), 3.76 (s, 3H).

2. Synthesis of C18-2

Compound C18-1 (1.50 g, 4.46 mmol) and compound C1-3 (1.45 g, 4.91 mmol) were dissolved in a mixed solvent of 1,4-dioxane (50 mL) and water(10 mL), and palladium acetate (100 mg, 0.45 mmol), DPPF (495 mg, 0.89 mmol) and potassium carbonate (924 mg, 6.70 mmol) were added sequentially. The reaction solution was stirred at 90° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 1.91 g of compound C18-2. MS [M+H] 471. $^1$H NMR (400 MHz, Chloroform-d) δ 7.92 (s, 1H), 7.37 (d, J=8.6 Hz, 2H), 7.30-7.25 (m, 1H), 6.85 (d, J=8.6 Hz, 2H), 5.49 (s, 2H), 4.87 (t. J=5.2 Hz, 1H), 4.75 (t, J=5.1 Hz, 1H), 4.71-4.66 (m, 1H), 4.62 (dd, J=6.1, 4.8 Hz, 1H), 3.75 (d, J=4.4 Hz, 6H), 3.27 (s, 3H), 2.88-2.49 (m, 4H), 2.30-2.01 (m, 3H).

2. Synthesis of C18-3

Compound C18-2 (1.91 g, 4.06 mmol) was dissolved in a mixed solvent of ethyl acetate (25 mL) and methanol (25 mL), then wet palladium carbon (191 mg) was added, stirred overnight at room temperature under hydrogen atmosphere. After the reaction was completed, the reaction solution was filtered through diatomite, washed with methanol, and the filtrate was concentrated under reduced pressure to obtain 1.37 g of compound C18-3, MS [M+H] 353. $^1$H NMR (400 MHz, Chloroform-d) δ 11.99 (s, 1H), 8.11 (s, 1H), 4.95-4.90 (m, 1H), 4.84-4.77 (m, 1H), 4.71-4.65 (m, 1H), 4.65-4.58 (m, 1H), 3.79 (s, 3H), 3.29 (s, 3H), 2.92-2.71 (m, 1H), 2.36-2.05 (m, 3H), 2.04-1.80 (m, 5H).

3. Synthesis of C18-4

Compound C18-3 (1.37 g, 3.89 mmol) was dissolved in phosphorus oxychloride (30 mL), stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified by column chromatography to obtain 1.03 g of compound C18-4, MS [M+H] 371. $^1$H NMR (400 MHz, Chloroform-d)

δ 8.13 (s, 1H), 4.99-4.95 (m, 1H), 4.88-4.73 (m, 3H), 3.79 (s, 3H), 3.31 (s, 3H), 3.14-2.97 (m, 1H), 2.42-2.09 (m, 3H), 2.04-1.61 (m, 5H).

4. Synthesis of C18-5

Compound C18-4 (1.03 g, 2.80 mmol) and compound C2-7 (299 mg, 3.08 mmol) were dissolved in DMSO (10 mL), then DIPEA (722 mg, 5.59 mmol) was added, and the temperature was raised to 100° C. and stirred overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 866 mg of compound C18-5. MS [M+H] 431. $^1$H NMR (400 MHz, Chloroform-d) δ 7.82 (s, 1H), 6.58 (s, 1H), 4.93 (q, J=4.8 Hz, 1H), 4.81 (q, J=4.8 Hz, 1H), 4.68 (dq, J=24.4, 5.5 Hz, 2H), 3.79 (s, 3H), 3.33 (s, 3H), 3.01-2.78 (m, 1H), 2.34 (s, 3H), 2.22-1.78 (m, 8H).

5. Synthesis of C18-6

Compound C18-5 (866 mg, 2.01 mmol) was dissolved in a mixed solvent of methanol (15 mL) and water (2.5 mL), then lithium hydroxide monohydrate (254 mg, 6.03 mmol) was added, stirred overnight at 60° C. After the reaction was completed, the reaction solution was cooled to room temperature, the solvent was evaporated under reduced pressure, and crude solid was slurried with DCM, filtered by suction filtration to obtain 797 mg crude product C18-6 (MS [M+H] 418), which was used directly in the next step without purification.

6. Synthesis of C18

Compound C18-6 (62 mg, crude) and compound C1-7 (36 mg, 0.15 mmol) were dissolved in DMF(4 mL), then DIPEA (151 mg, 1.17 mmol) was added, stirred at room temperature for 15 min, then HATU (84 mg, 0.22 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C18 with Ms [M+H] 606, and compound C18A with [M+H]606.

Nuclear magnetic of compound C18: $^1$H NMR (400 MHz, Chloroform-d) δ 8.42-8.30 (m, 2H), 7.92 (d, J=8.5 Hz, 1H), 7.77 (dd, J=8.6, 2.3 Hz, 1H), 7.59 (dd, J=4.4, 0.9 Hz, 1H), 6.85 (d, J=8.0 Hz, 1H), 6.45 (s, 1H), 5.18 (p, J=7.1 Hz, 1H), 4.94 (t, J=5.1 Hz, 1H), 4.82 (t, J=5.1 Hz, 1H), 4.70 (dt, J=24.1, 5.1 Hz, 2H), 3.29 (s, 3H), 2.87 (br, 1H), 2.36 (s, 3H), 1.99 (m, 8H), 1.58 (d, J=7.0 Hz, 3H).

Example 19

The compound synthesized in the present invention:

C19

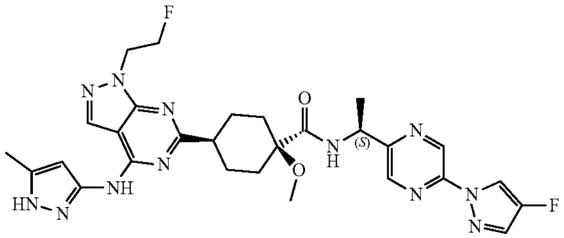

The synthetic route and experimental process were as follows:

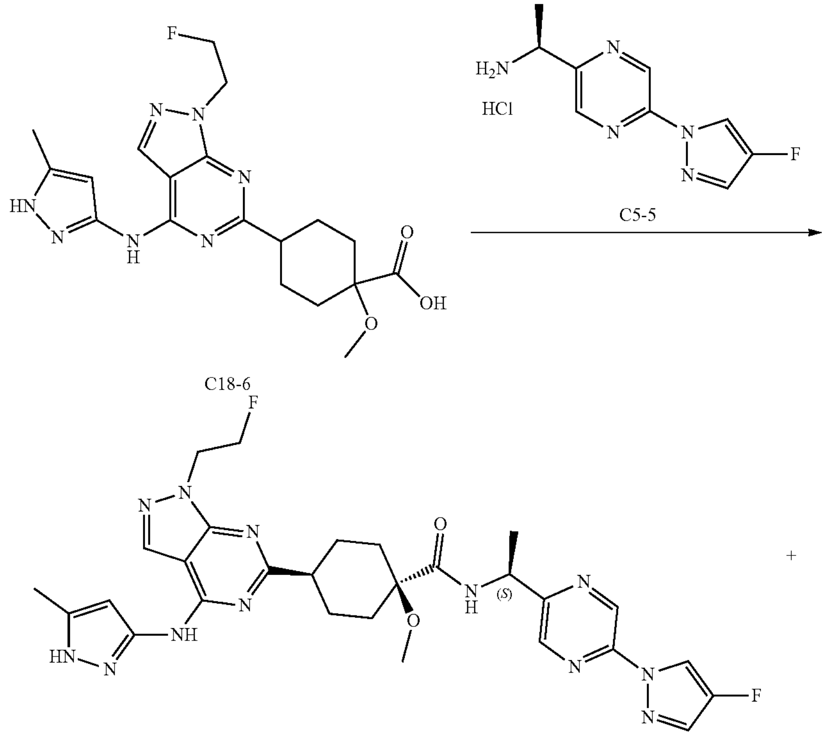

C5-5

C18-6

C19

-continued

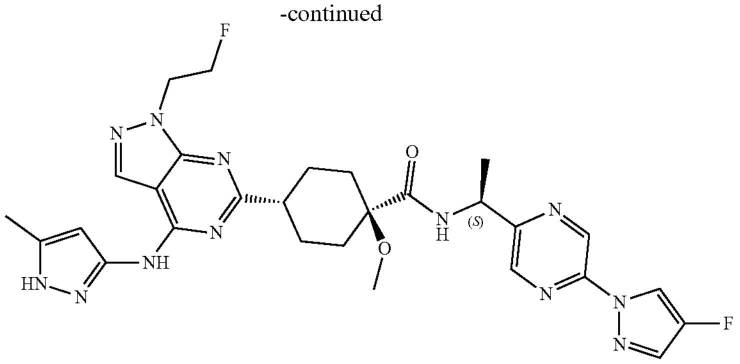

C19A

1. Synthesis of C19

Compound C18-6 (100 mg, crude) and compound C5-5 (70 mg, 0.24 mmol) were dissolved in DMF(5 mL), then DIPEA (250 mg, 1.92 mmol) was added, stirred at room temperature for 15 min, then HATU (140 mg, 0.36 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain compound C19, Ms [M+H] 607. $^1$H NMR (400 MHz, Chloroform-d) δ 9.23 (d, J=1.4 Hz, 1H), 8.57-8.21 (m, 2H), 7.97 (br, 2H), 7.66 (dd, J=4.3, 0.9 Hz, 1H), 6.51 (s, 1H), 5.40-5.22 (m, 1H), 4.92 (t, J=5.1 Hz, 1H), 4.80 (t, J=5.1 Hz, 1H), 4.72 (t, J=5.2 Hz, 1H), 4.66 (t, J=5.3 Hz, 1H), 3.32 (s, 3H), 2.85 (s, 1H), 2.38 (s, 3H), 2.11-1.90 (m, 8H), 1.56 (d, J=6.9 Hz, 3H).

Example 20

The compound synthesized in the resent invention:

C20

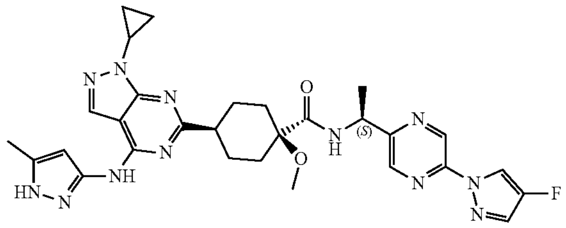

The synthetic route and experimental process were as follows:

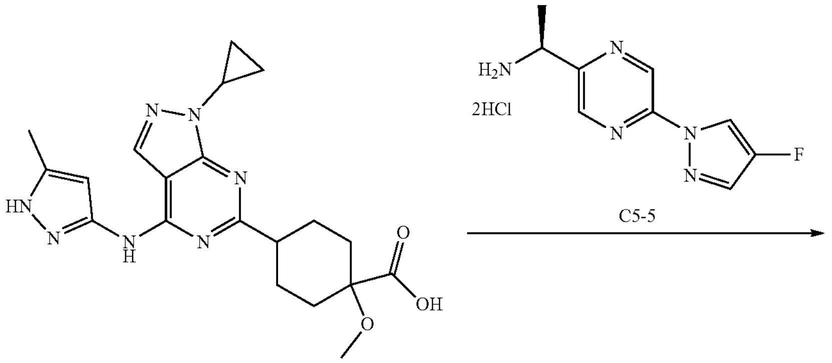

C14-6

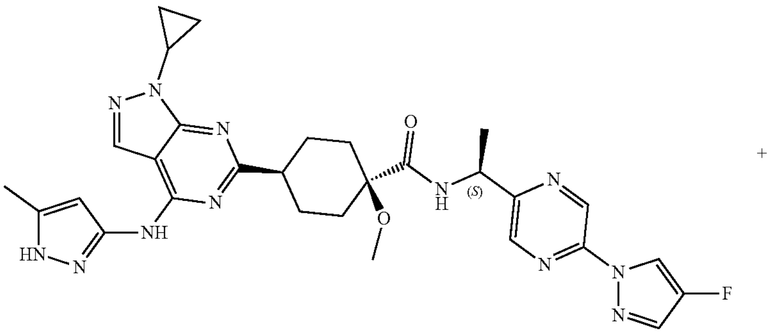

+

C20

-continued

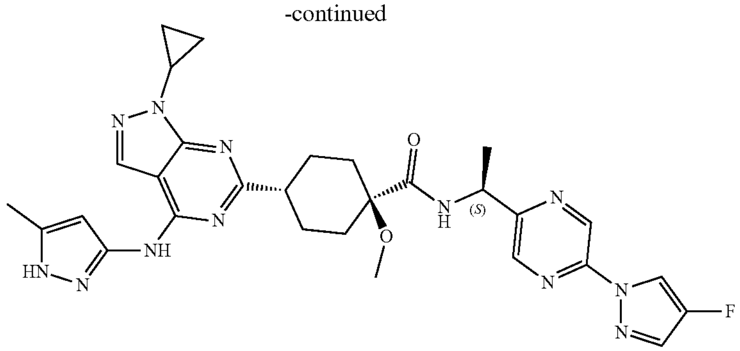

C20A

1. Synthesis of C20

Compound C14-6 (100 mg, 0.24 mmol) and compound C5-5 (70 mg, 0.24 mmol) were dissolved in DMF(5 mL), then DIPEA (250 mg, 1.95 mmol) was added, stirred at room temperature for 15 min, then HATU (140 mg, 0.36 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain 40 mg of compound C20 with Ms [M+H] 601, and compound C20A with Ms [M+H] 601.

Nuclear magnetic of compound C20: $^1$H NMR (400 MHz, Chloroform-d) δ 9.23 (d, J=1.4 Hz, 1H), 8.69 (s, 1H), 8.38 (s, 1H), 8.34 (d, J=4.6 Hz, 1H), 7.76 (s, 1H), 7.66 (d, J=4.3 Hz, 1H), 6.53 (s, 1H), 5.41-5.28 (m, 1H), 3.85-3.77 (m, 1H), 3.32 (s, 3H), 2.89 (d, J=11.0 Hz, 1H), 2.37 (s, 3H), 2.13-1.83 (m, 8H), 1.56 (d, J=6.9 Hz, 3H), 1.30-1.22 (m, 2H), 1.15-1.00 (m, 2H), 0.94-0.80 (m, 1H).

Example 21

The compound synthesized in the resent invention:

C21

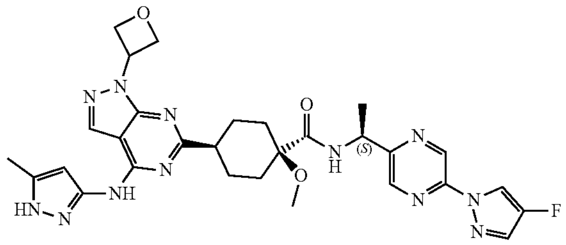

The synthetic route and experimental process were as follows:

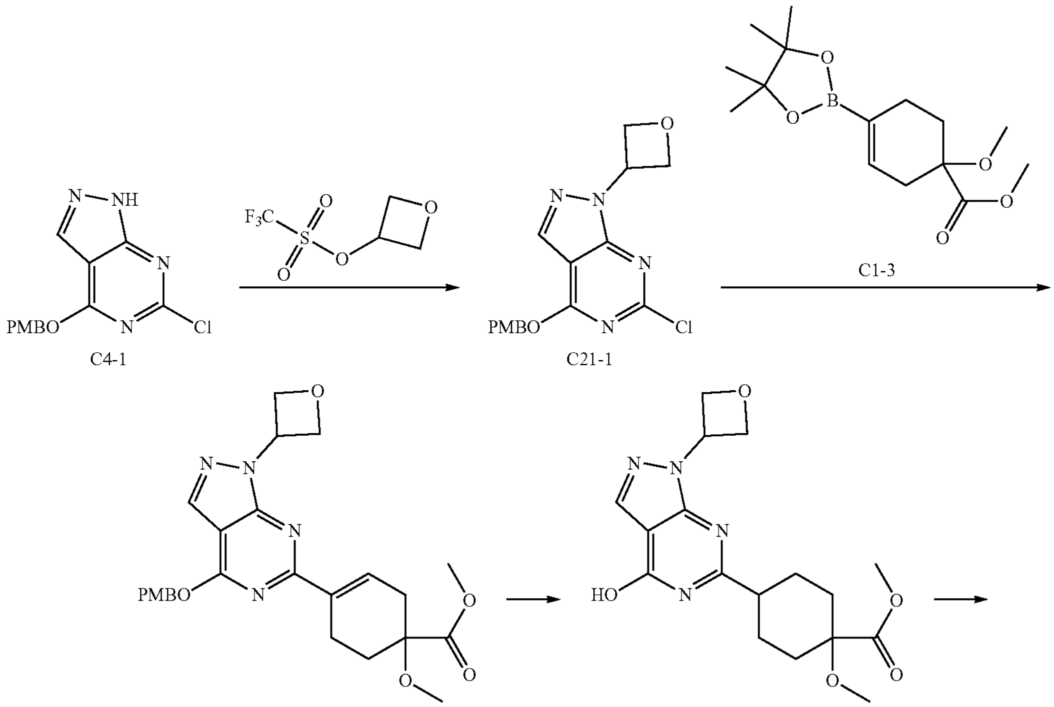

C4-1

C21-1

C1-3

C21-2

C21-3

-continued

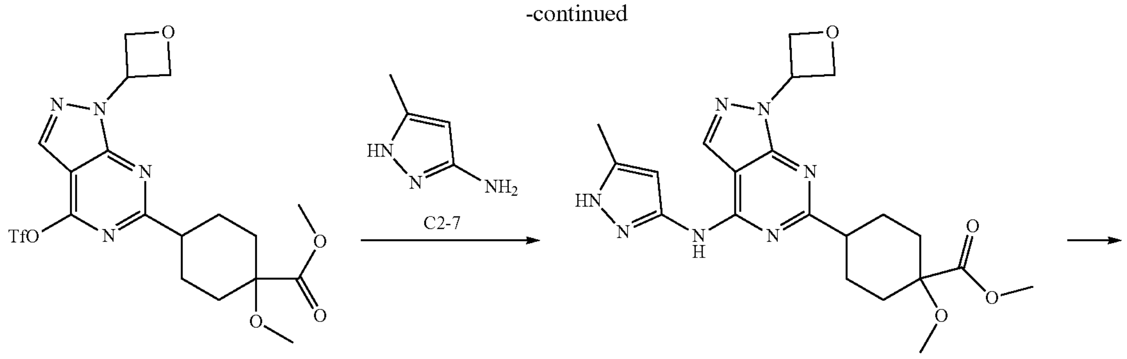

C21-4

C21-5

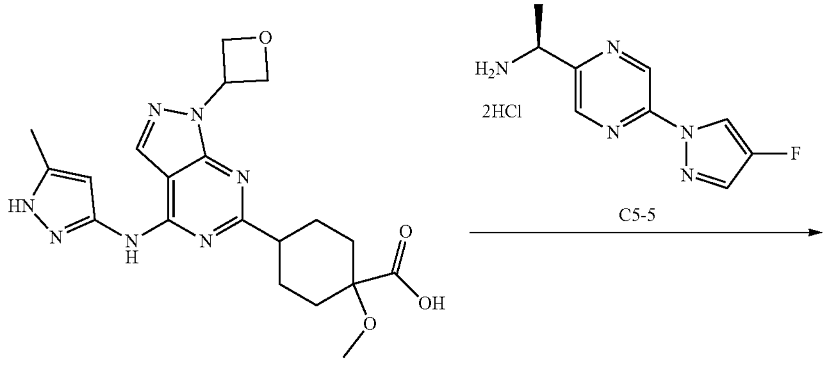

C21-6

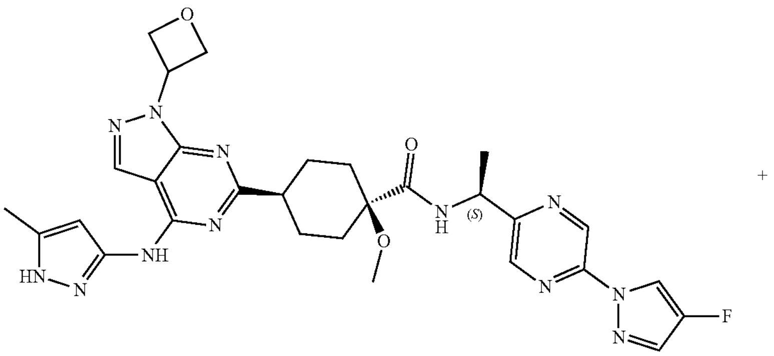

C21

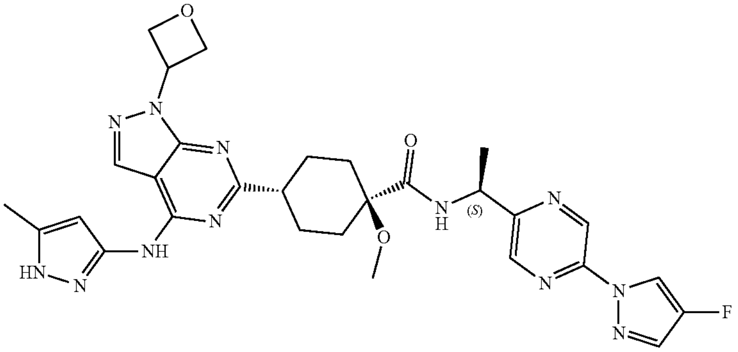

C21A

1. Synthesis of C21-1

Compound C4-1 (1.50 g, 5.17 mmol) was dissolved in 30 mL of anhydrous DMF, cesium carbonate (2.53 g, 7.76 mmol) and 1,1,1-trifluoro-3-oxetanyl Methanesulfonic acid ester (1.28 g, 6.21 mmol) were added sequentially, stirred overnight in an oil bath at 25° C. DMF was evaporated under reduced pressure. The reaction was quenched by adding saturated salt water, then extracted with ethyl acetate, the organic phase was separated and washed with saturated salt water, dried over anhydrous sodium sulfate, and concentrated under reduced pressure to obtain the crude product which was purified by column chromatography to obtain 844 mg of compound C21-1, MS [M+H] 347. $^1$H NMR (400 MHz, Chloroform-d) δ 8.11 (d, J=0.6 Hz, 1H), 7.45 (d, J=8.7 Hz, 2H), 7.06-6.86 (m, 2H), 6.13-5.98 (m, 1H), 5.55 (s, 2H), 5.25-5.19 (m, 2H), 5.10-5.05 (m, 2H), 3.83 (s, 3H).

2. Synthesis of C21-2

Compound C21-1 (300 mg, 0.86 mmol) and compound C1-3 (283 mg, 0.95 mmol) were dissolved in a mixed solvent of 1,4-dioxane (15 mL) and water(3 mL), and palladium acetate (20 mg, 0.09 mmol), DPPF (96 mg, 0.17 mmol) and potassium carbonate (178 mg, 1.29 mmol) were added sequentially. The reaction solution was stirred at 90° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 275 mg of compound C21-2, MS [M+H] 481. $^1$H NMR (400 MHz, Chloroform-d) δ 8.05 (s, 1H), 7.44 (d, J=8.7 Hz, 2H), 7.37-7.33 (m, 1H), 6.93 (d, J=8.7 Hz, 2H), 6.08 (tt, J=7.9, 6.6 Hz, 1H), 5.56 (s, 2H), 5.30 (dd, J=6.6, 1.3 Hz, 2H), 5.09 (dd, J=7.8, 6.6 Hz, 2H), 3.82 (d, J=4.1 Hz, 6H), 3.34 (s, 3H), 2.90-2.57 (m, 4H), 2.33-2.07 (m, 2H).

3. Synthesis of C21-3

Compound C21-2 (230 mg, 0.48 mmol) was dissolved in a mixed solvent of ethyl acetate (7 mL) and methanol (7 mL), then wet palladium carbon (23 mg) was added, stirred overnight at room temperature under hydrogen atmosphere. After the reaction was completed, the reaction solution was filtered through diatomite, washed with methanol, and the filtrate was concentrated under reduced pressure to obtain 169 mg of compound C21-3, MS [M+H] 363. $^1$H NMR (400 MHz, Chloroform-d) δ 11.77 (d, J=39.4 Hz, 1H), 8.28-7.91 (m, 1H), 6.12-5.70 (m, 1H), 5.28-5.13 (m, 2H), 5.10-4.93 (m, 2H), 3.75 (d, J=7.5 Hz, 3H), 3.24 (d, J=12.0 Hz, 3H), 2.86-2.65 (m, 1H), 2.47-1.53 (m, 8H).

4. Synthesis of C21-4

Compound C21-3 (100 mg, 0.28 mmol) and TEA (0.12 mL, 0.88 mol) were dissolved in DCM (5 mL), and $Tf_2O$ (0.14 mL, 0.88 mol) was added dropwise at −78° C. under nitrogen protection and stirred for 0.5 h. After the reaction was completed, the reaction was quenched by the addition of saturated aqueous sodium bicarbonate, followed by extraction with ethyl acetate, and the combined organic phases were washed with saturated salt water, dried over anhydrous sodium sulfate, concentrated under reduced pressure and spin-dried to obtain 132 mg of crude compound C21-4, MS [M+H] 495.

5. Synthesis of C21-5

Compound C21-4 (172 mg, 0.35 mmol) and compound C2-7 (38 mg, 0.38 mmol) were dissolved in DMSO (5 mL), then DIPEA (90 mg, 70 mmol) was added, and the temperature was raised to 100° C. and stirred overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 73 mg of compound C21-5. MS [M+H] 442.

6. Synthesis of C21-6

Compound C21-5 (51 mg, 0.07 mmol) was dissolved in a mixed solvent of methanol (3 mL) and water (1 mL), then lithium hydroxide monohydrate (9 mg, 0.21 mmol) was added, stirred overnight at 60° C. After the reaction was completed, the reaction solution was cooled to room temperature, the solvent was evaporated under reduced pressure, and crude solid was slurried with DCM, filtered by suction filtration to obtain 78 mg of crude product C21-6 (MS [M+H] 428), which was used directly in the next step without purification.

7. Synthesis of C21

Compound C21-6 (168 mg, 0.39 mmol) and compound C5-5 (96 mg, 0.39 mmol) were dissolved in DMF(5 mL), then DIPEA (406 mg, 3.15 mmol) was added, stirred at room temperature for 15 min, then HATU (225 mg, 0.59 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain 19 mg of compound C21 with Ms [M+H] 617, and compound C21A with MS [M+H] 617.

Nuclear magnetic of compound C21: $^1$H NMR (400 MHz, Chloroform-d) δ 9.23 (d, J=1.4 Hz, 1H), 8.36 (d, J=1.5 Hz, 1H), 8.34 (dd, J=4.6, 0.8 Hz, 1H), 7.84 (s, 1H), 7.66 (dd, J=4.3, 0.9 Hz, 1H), 7.57-7.48 (m, 1H), 6.09 (p, J=7.2 Hz, 1H), 5.37-5.28 (m, 1H), 5.25 (td, J=6.5, 2.4 Hz, 2H), 5.08 (t, J=7.2 Hz, 2H), 3.31 (s, 3H), 2.83 (s, 1H), 2.39 (s, 3H), 2.09-1.89 (m, 8H).

Example 22

The compound synthesized in the present invention:

C22

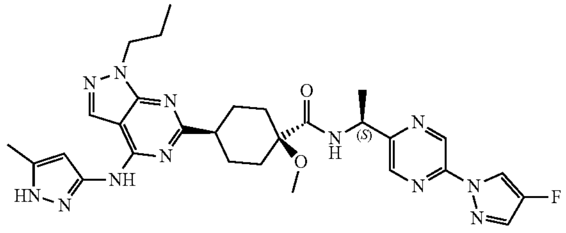

The synthetic route and experimental process were as follows:
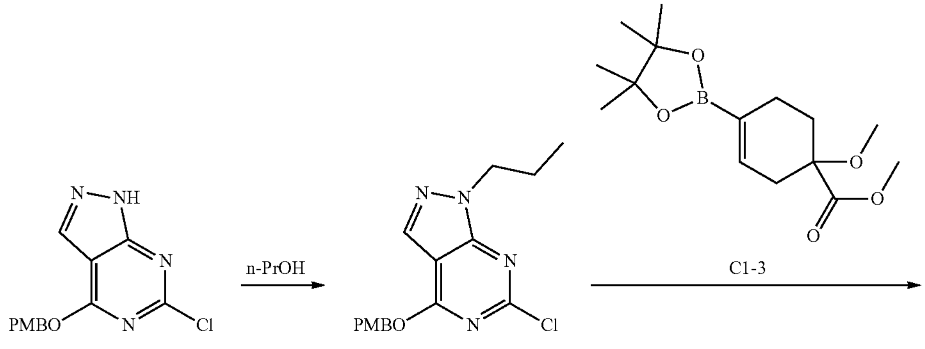
C4-1 C22-1
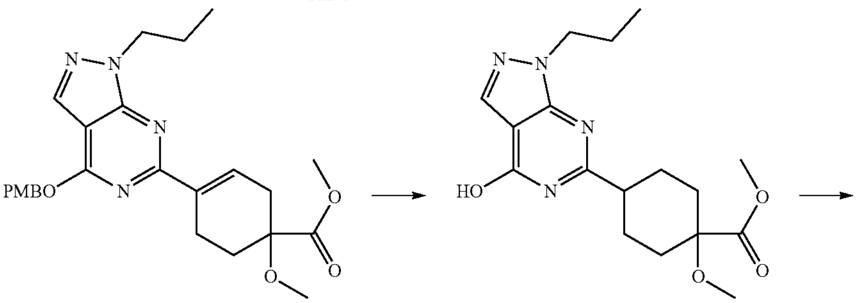
C22-2 C22-3
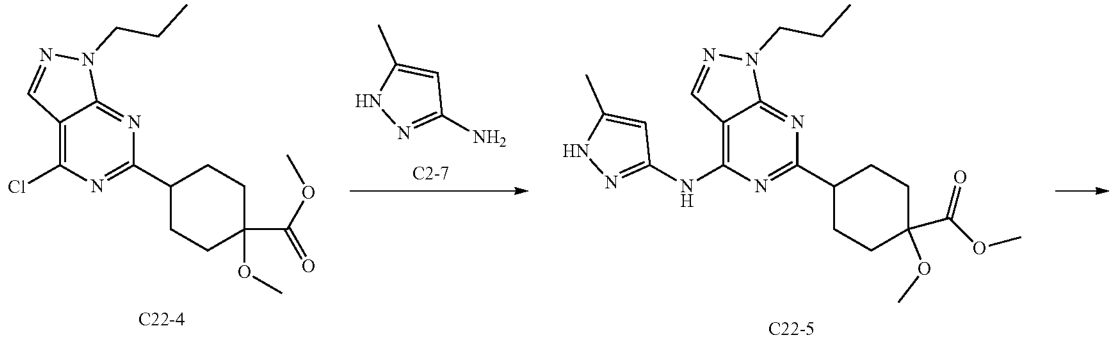
C22-4 C22-5
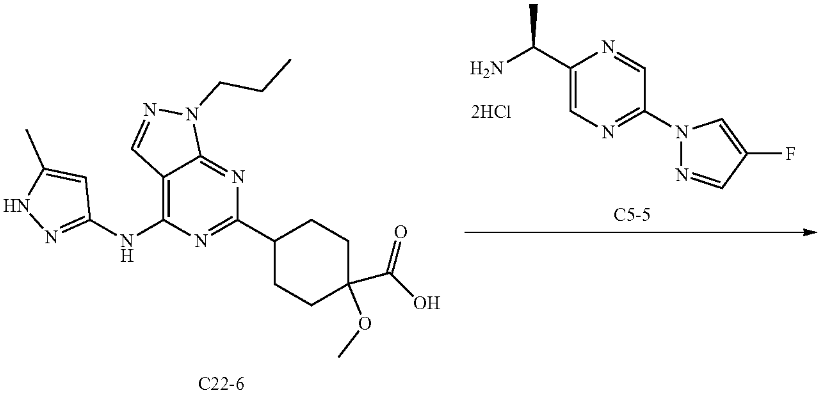
C22-6

-continued

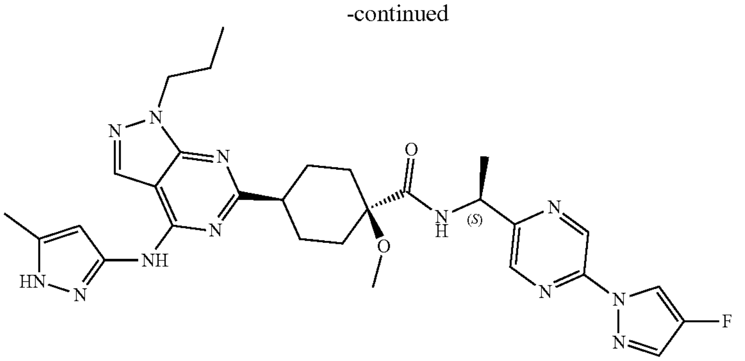

+

C22

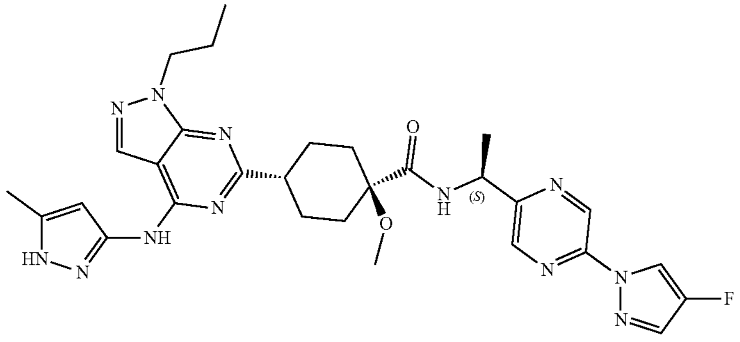

C22A

1. Synthesis of C22-1

Compound C4-1 (1.60 g, 5.52 mmol) was dissolved in anhydrous THF (50 mL), $PPh_3$ (2.31 g, 8.83 mmol) and n-propanol (829 mg, 13.80 mmol) were added sequentially, and DIAD (2.23 mg, 11.03 mmol) was added dropwise after cooling down to 0° C. in an ice bath under nitrogen protection, and warmed up naturally to room temperature, and continued to stir for 3 hours. After the reaction was completed, it was quenched by adding saturated salt water, then extracted with ethyl acetate, the organic phase was separated and washed with saturated salt water, dried over anhydrous sodium sulfate, concentrated under reduced pressure to obtain the crude product which was purified by column chromatography to obtain 1.82 g of compound C22-1, MS [M+H] 333. $^1$H NMR (400 MHz, Chloroform-d) δ 7.99 (s, 1H), 7.46 (d, J=8.7 Hz, 2H), 6.94 (d, J=8.7 Hz, 2H), 5.54 (s, 2H), 4.45-4.28 (m, 2H), 3.83 (s, 3H), 1.94 (q, J=7.3 Hz, 2H), 0.91 (t, J=7.4 Hz, 3H).

2. Synthesis of C22-2

Compound C22-1 (1.82 g, 5.48 mmol) and compound C1-3 (1.78 g, 6.03 mmol) were dissolved in a mixed solvent of 1,4-dioxane (60 mL) and water(12 mL), and palladium acetate (123 mg, 0.55 mmol), DPPF (607 mg, 1.10 mmol) and potassium carbonate (1.14 g, 8.22 mmol) were added sequentially. The reaction solution was stirred at 90° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 1.75 g of compound C22-2, MS [M+H] 467. $^1$H NMR (400 MHz, Chloroform-d) δ 7.94 (s, 1H), 7.44 (d, J=8.7 Hz, 2H), 7.35-7.32 (m, 1H), 6.92 (d, J=8.7 Hz, 2H), 5.56 (s, 2H), 4.38 (dd, J=7.4, 6.7 Hz, 2H), 3.82 (d, J=2.5 Hz, 6H), 3.34 (s, 3H), 2.94-2.58 (m, 4H), 2.35-2.07 (m, 2H), 1.95 (q, J=7.2 Hz, 2H), 0.90 (t, J=7.4 Hz, 3H).

3. Synthesis of C22-3

Compound C22-2 (1.75 g, 3.76 mmol) was dissolved in a mixed solvent of ethyl acetate (15 mL) and methanol (15 mL), then wet palladium carbon (175 mg) was added, stirred overnight at room temperature under hydrogen atmosphere. After the reaction was completed, the reaction solution was filtered through diatomite, washed with methanol, and the filtrate was concentrated under reduced pressure to obtain 1.41 g of compound C22-3, MS [M+H] 349. $^1$H NMR (400 MHz, Chloroform-d) δ 11.72 (s, 1H), 8.08 (s, 1H), 4.32 (dt, J=7.1, 6.2 Hz, 2H), 3.79 (d, J=6.9 Hz, 3H), 3.31 (d, J=12.3 Hz, 3H), 2.91-2.72 (m, 1H), 2.25-2.08 (m, 2H), 2.02-1.67 (m, 8H), 1.01-0.88 (m, 3H).

3. Synthesis of C22-4

Compound C22-3 (1.41 g, 4.05 mmol) was dissolved in phosphorus oxychloride (30 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified by column chromatography to obtain 1.13 mg of compound C22-4, MS [M+H] 367. $^1$H NMR (400 MHz, Chloroform-d) δ 8.08 (s, 1H), 4.57-4.28 (m, 2H), 3.79

(d, J=2.3 Hz, 3H), 3.30 (d, J=8.7 Hz, 3H), 3.14-2.92 (m, 1H), 2.37-2.12 (m, 2H), 2.06-1.70 (m, 8H), 1.08-0.87 (m, 3H).

4. Synthesis of C22-5

Compound C22-4 (1.13 g, 3.07 mmol) and C2-7 (328 mg, 3.38 mmol) were dissolved in DMSO (15 mL), then DIPEA (793 mg, 6.14 mmol) was added, and the temperature was raised to 100° C. and stirred overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 992 mg of compound C22-5, MS [M+H] 428.

$^1$H NMR (400 MHz, Chloroform-d) δ 7.78 (s, 1H), 6.57 (s, 1H), 4.49-4.25 (m, 2H), 3.80 (d, J=4.4 Hz, 3H), 3.32 (d, J=16.3 Hz, 3H), 3.02-2.81 (m, 1H), 2.36 (s, 3H), 2.21-1.75 (m, 10H), 0.94-0.89 (m, 3H).

5. Synthesis of C22-6

Compound C22-5 (992 mg, 2.32 mmol) was dissolved in a mixed solvent of 20 mL methanol and 3 mL water, then lithium hydroxide monohydrate (293 mg, 6.96 mmol) was added, stirred overnight at 60° C. After the reaction was completed, the reaction solution was cooled to room temperature, the solvent was evaporated under reduced pressure, and crude solid was slurried with DCM, filtered by suction filtration to obtain 1.21 g of crude product C22-6 (MS [M+H] 414), which was used directly in the next step without purification.

6. Synthesis of C22

Compound C22-6 (280 mg, crude) and compound C5-5 (165 mg, 0.68 mmol) were dissolved in 9 mL DMF, then DIPEA (700 mg, 5.42 mmol) was added, stirred at room temperature for 15 min, then HATU (387 mg, 1.02 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain 112 mg of compound C22 with Ms [M+H] 603, and compound C22A with MS [M+H] 603.

Nuclear magnetic of compound C22: $^1$H NMR (400 MHz, Chloroform-d) δ 9.23 (d, J=1.4 Hz, 1H), 8.37 (d, J=1.5 Hz, 1H), 8.34 (dd, J=4.6, 0.9 Hz, 1H), 7.78 (s, 1H), 7.66 (dd, J=4.2, 0.9 Hz, 2H), 5.37-5.26 (m, 1H), 4.34 (t, J=7.2 Hz, 2H), 3.32 (s, 3H), 2.86 (s, 1H), 2.38 (s, 3H), 2.12-1.85 (m, 10H), 1.56 (d, J=6.9 Hz, 3H), 0.91 (t, J=7.4 Hz, 3H).

Example 23

The compound synthesized in the present invention:

C23

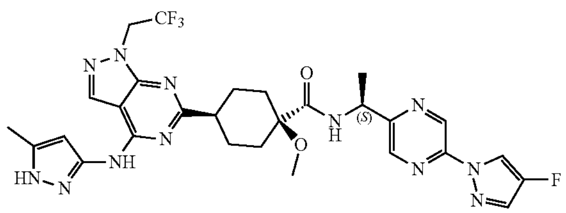

The synthetic route and experimental process were as follows:

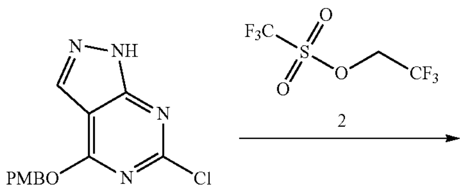

C4-1

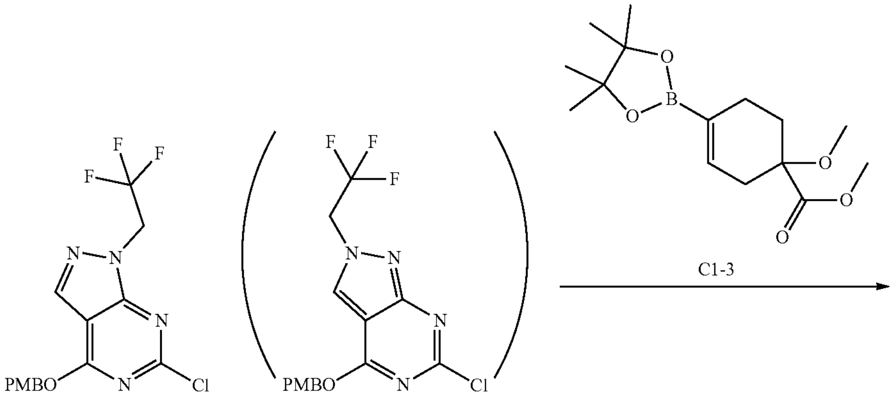

C23-1 C23-2

-continued
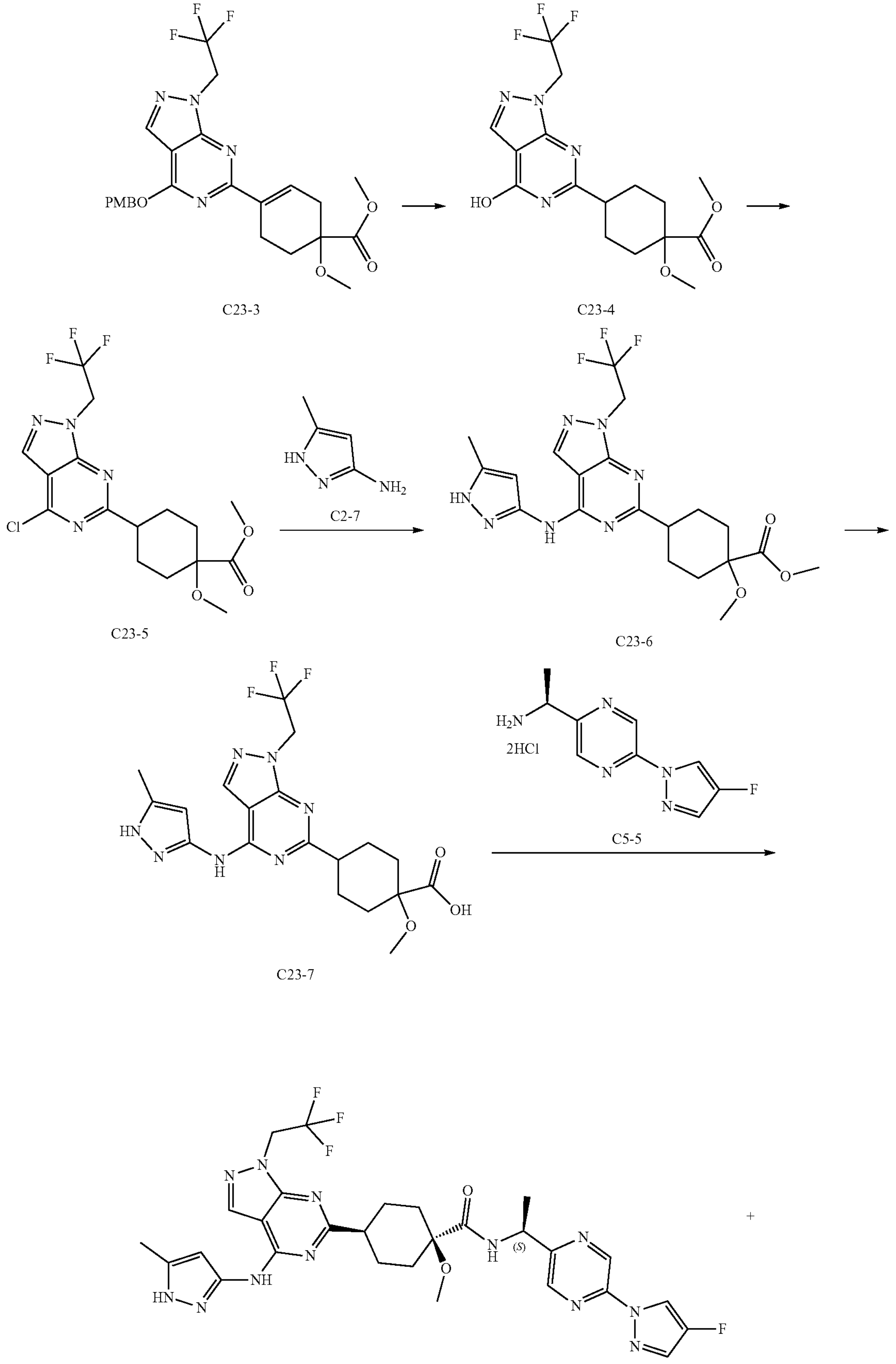
C23-3
C23-4
C23-5
C23-6
C23-7
C23

-continued

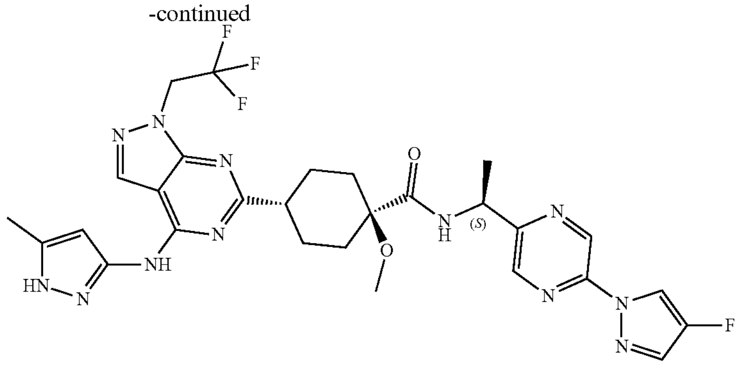

C23A

The synthetic route and experimental process were as follows:

1. Synthesis of C23-1

Compound C4-1 (1.50 g, 5.17 mmol) was dissolved in anhydrous DMF (30 mL) and cesium carbonate (2.53 g, 7.76 mmol) and 2,2,2-trifluoroethyl trifluoromethanesulfonate (1.44 g, 6.21 mmol) were added sequentially, stirred in an oil bath at 25° C. overnight, DMF was evaporated under reduced pressure, and the reaction was quenched by adding saturated salt water. Then extracted with ethyl acetate, the organic phase was separated and washed with saturated salt water, dried over anhydrous sodium sulfate and concentrated under reduced pressure to obtain the crude product, which was purified by column chromatography to obtain 917 mg of compound C23-1 and 831 mg of C23-2, MS [M+H] 373.

C23-1: $^1$H NMR (400 MHz, Chloroform-d) δ 8.09 (s, 1H), 7.46 (d, J=8.7 Hz, 2H), 6.94 (d, J=8.7 Hz, 2H), 5.56 (s, 2H), 4.98 (q, J=8.2 Hz, 2H), 3.83 (s, 3H).

C23-2: $^1$H NMR (4 (0) MHz, Chloroform-d) δ 8.13 (s, 1H), 7.45 (d, J=8.7 Hz, 2H), 6.94 (d, J=8.6 Hz, 2H), 5.55 (s, 2H), 4.96 (q, J=8.1 Hz, 2H), 3.83 (s, 3H).

2. Synthesis of C23-3

Compound C23-1 (500 mg, 1.30 mmol) and compound C1-3 (440 mg, 1.50 mmol) were dissolved in a mixed solvent of 1,4-dioxane (20 mL) and water(4 mL), and palladium acetate (30 mg, 0.13 mmol), DPPF (150 mg, 0.26 mmol) and potassium carbonate (280 mg, 2.02 mmol) were added sequentially. The reaction solution was stirred at 90° C. under nitrogen protection overnight. After the reaction was completed, the reaction was cooled to room temperature, concentrated under reduced pressure, and extracted with ethyl acetate. The combined organic phase was washed with saturated salt water, dried over anhydrous sodium sulfate, concentrated under reduced pressure and purified by column chromatography to obtain 495 mg of compound C23-3, MS [M+H] 507. $^1$H NMR (400 MHz, Chloroform-d) δ 8.04 (s, 1H), 7.44 (d, J=8.7 Hz, 2H), 7.40-7.37 (m, 1H), 6.93 (d, J=8.7 Hz, 2H), 5.57 (s, 2H), 5.0 (q, J=8.3 Hz, 2H), 3.82 (d, J=3.2 Hz, 6H), 3.34 (s, 3H), 2.95-2.49 (m, 5H), 2.39-2.23 (m, 2H), 2.19-2.10 (m, 1H).

3. Synthesis of C23-4

Compound C23-3 (445 mg, 0.88 mmol) was dissolved in a mixed solvent of ethyl acetate (10 mL) and methanol (10 mL), then wet palladium carbon (45 mg) was added, stirred overnight at room temperature under hydrogen atmosphere. After the reaction was completed, the reaction solution was filtered through diatomite, washed with methanol, and the filtrate was concentrated under reduced pressure to obtain 296 mg of compound C23-4, MS [M+H] 389. $^1$H NMR (400 MHz, Chloroform-d) δ 12.03 (d, J=41.6 Hz, 1H), 8.17 (s, 1H), 4.96 (q, J=8.4 Hz, 2H), 3.81 (d, J=1.7 Hz, 3H), 3.31 (d, J=11.1 Hz, 3H), 2.95-2.76 (m, 1H), 2.51-2.43 (m, 1H), 2.16-1.65 (m, 8H).

4. Synthesis of C23-5

Compound C23-4 (285 mg, 0.73 mmol) was dissolved in phosphorus oxychloride (6 mL) and stirred at 100° C. for 3 h under nitrogen protection. After the reaction was completed, the solvent was evaporated under reduced pressure, and crushed ice was added. The mixture was adjusted to neutral with saturated sodium bicarbonate solution, extracted with ethyl acetate, and the combined organic phases were washed with saturated salt water, dried over anhydrous sodium sulfate, concentrated under reduced pressure and purified by column chromatography to obtain 208 mg of compound C23-5, MS [M+H] 407. $^1$H NMR (400 MHz, Chloroform-d) δ 8.18 (s, 1H), 5.07 (q, J=8.1 Hz, 2H), 3.79 (s, 3H), 3.30 (d, J=7.6 Hz, 3H), 3.15-2.97 (m, 1H), 2.26-1.64 (m, 8H).

5. Synthesis of C23-6

Compound C23-5 (208 mg, 0.51 mmol) and compound C2-7 (55 mg, 0.56 mmol) were dissolved in DMSO (5 mL), then DIPEA (133 mg, 1.02 mmol) was added, and the reaction solution was stirred at 100° C. overnight under nitrogen protection. After the reaction was completed, the reaction was cooled to room temperature, and diluted with ethyl acetate. The organic phase was washed with saturated salt water, dried over anhydrous sodium sulfate, concentrated under reduced pressure and purified by column chromatography to obtain 226 mg of compound C23-6, MS [M+H] 468. $^1$H NMR (400 MHz, Chloroform-d) δ 7.87 (s, 1H), 6.54 (s, 1H), 4.97 (q, J=8.0 Hz, 2H), 3.79 (s, 3H), 3.32 (d, J=14.1 Hz, 3H), 3.01-2.79 (m, 1H), 2.37 (d, J=5.0 Hz, 3H), 2.21-1.73 (m, 8H).

6. Synthesis of C23-7

Compound C23-6 (226 mg, 0.48 mmol) was dissolved in a mixed solvent of methanol (6 mL) and water (1 mL), then lithium hydroxide monohydrate (61 mg, 1.45 mmol) was added, stirred at 60° C. overnight. After the reaction was completed, the reaction solution was cooled to room temperature, the solvent was evaporated under reduced pressure, and crude solid was slurried with DCM, filtered by suction filtration to obtain 197 mg of crude product C23-7 (MS [M+H] 454), which was used directly in the next step without purification.

7. Synthesis of C23

Compound C23-7 (187 mg, crude) and compound C5-5 (116 mg, 0.41 mmol) were dissolved in DMF(8 mL), then DIPEA (426 mg, 3.30 mmol) was added, stirred at room temperature for 15 min, then HATU (236 mg, 0.62 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain 84 mg of compound C23 with MS [M+H] 643, and compound C23A with MS [M+H] 643.

Nuclear magnetic of compound C23. $^{1}H$ NMR (400 MHz, Chloroform-d) δ 9.23 (d, J=1.5 Hz, 1H), 8.37 (d, J=1.4 Hz, 1H), 8.34 (dd, J=4.6, 0.8 Hz, 1H), 8.19 (s, 1H), 7.83 (s, 1H), 7.66 (dd, J=4.3, 0.9 Hz, 1H), 6.51 (s, 1H), 5.37-5.27 (m, 1H), 4.98 (q, J=8.3 Hz, 2H), 3.32 (s, 3H), 2.85 (s, 1H), 2.39 (s, 3H), 2.09-1.89 (m, 8H), 1.56 (d, J=6.9 Hz, 3H).

Example 24

The compound synthesized in the present invention:

C27

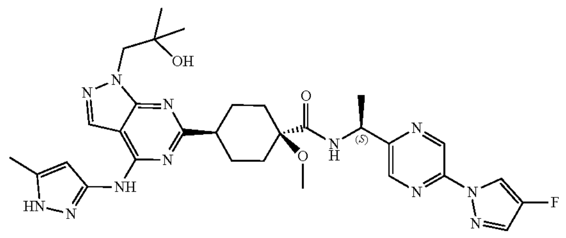

The synthetic route and experimental process were as follows:

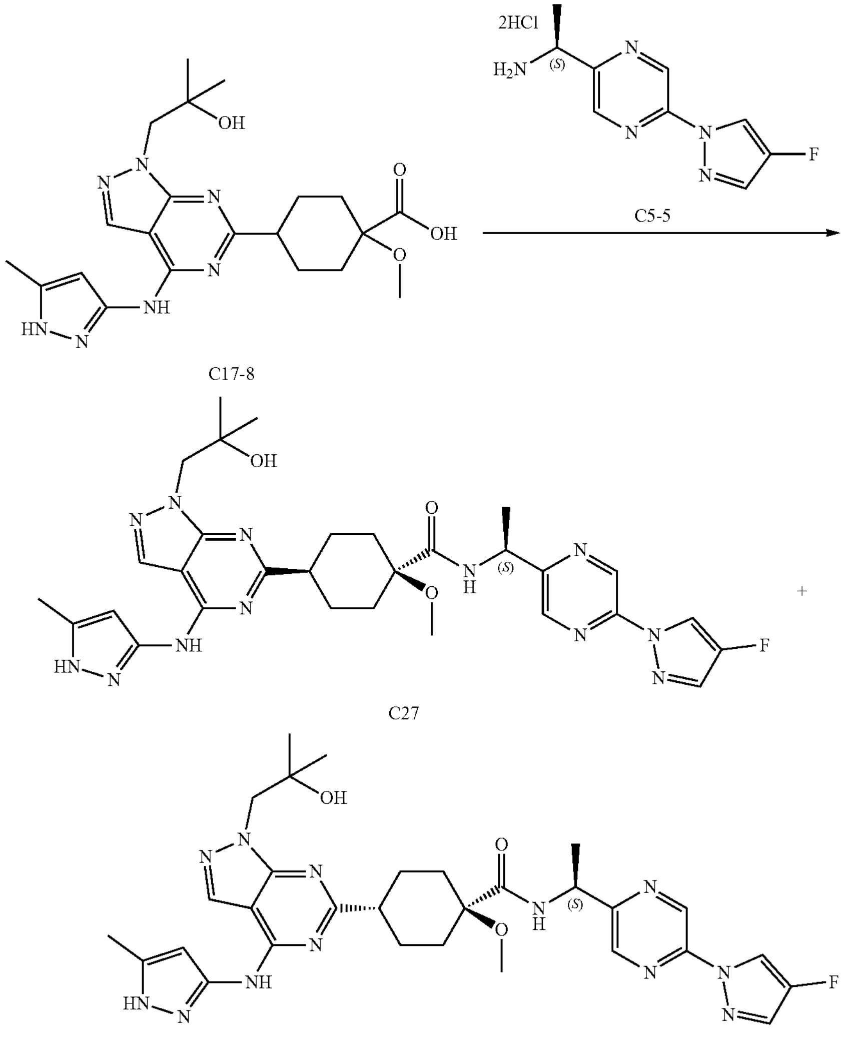

1. Synthesis of C27

Compound C17-8 (50 mg, crude) and compound C5-5 (32 mg, 0.11 mmol) were dissolved in 2 mL DMF, then DIPEA (117 mg, 0.91 mmol) was added, stirred at room temperature for 15 min, then HATU (64 mg, 0.168 mmol) was added, and stirred at room temperature for 1 h. The reaction solution was diluted with ethyl acetate, and the organic phase was washed with saturated brine, dried over anhydrous sodium sulfate, concentrated, and purified by HPLC to obtain compound C27. Ms [M+H] 633.

Control Example 1

The compound synthesized in the present invention:

Control Example 1

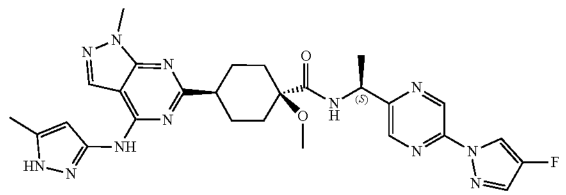

The synthetic route and experimental process were as follows:

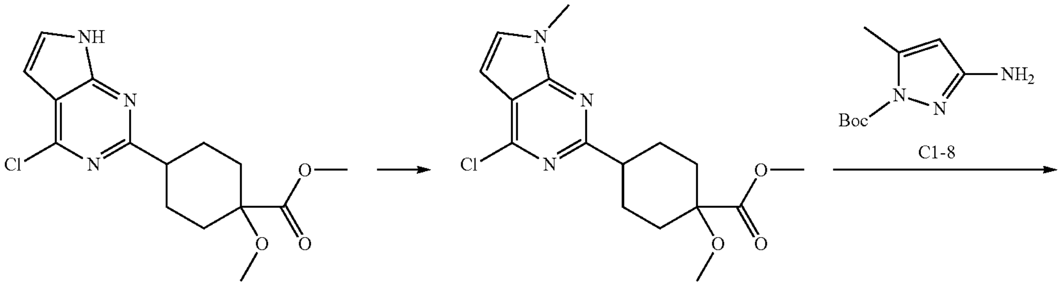

C24-1

C24-2

C1-8

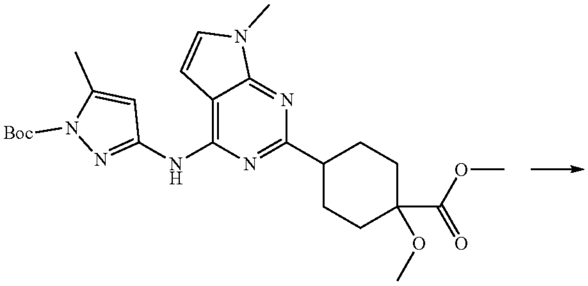

C24-3

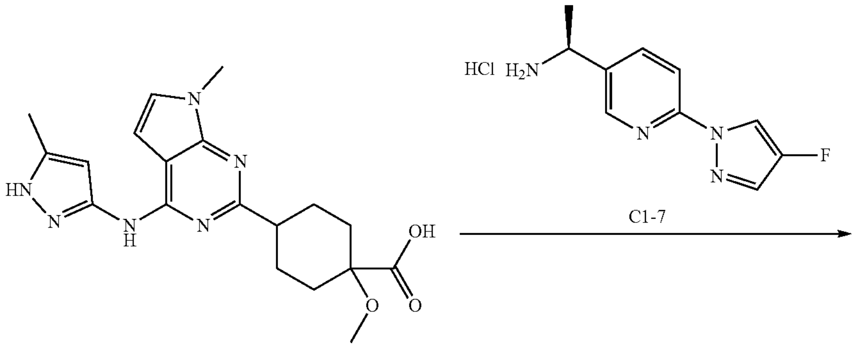

C24-4

C1-7

-continued

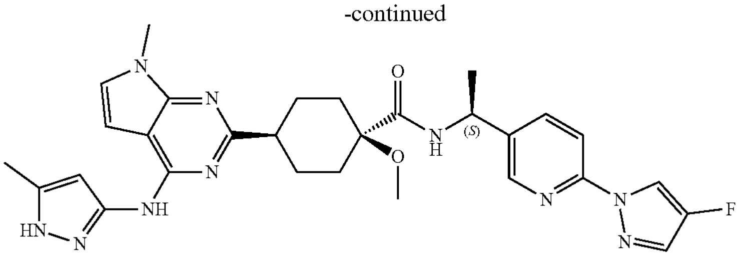

Control Example 1

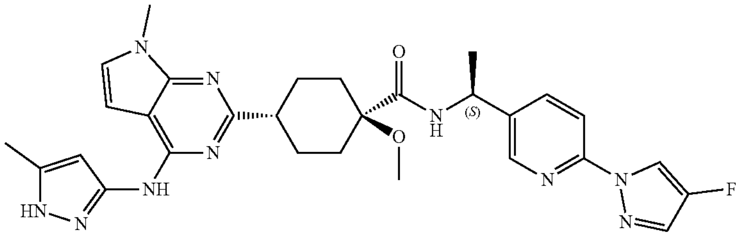

1. Synthesis of C24-2

Compound C24-1 (800 mg, 2.47 mmol), and $Cs_2CO_3$ (1208 mg, 3.71 mmol) were dissolved in DMF (10 mL), iodomethane (697 mg, 4.94 mmol) was added, stirred for 2 h at room temperature, water was added, extracted with EA, washed with saturated saline, dried over anhydrous sodium sulfate, and purified by column chromatography to obtain 832 mg of compound C24-1.

$^1$H NMR (400 MHz, $CDCl_3$) δ 7.06-7.05 (dd, 1H, J=3.47 Hz, 0.89 Hz), 6.47-6.45 (dd, 1H, J=3.47 Hz, 1.62 Hz), 3.79-3.77 (d, 3H, J=7.90 Hz), 3.72-3.71 (d, 3H, J=5.20 Hz), 3.24-3.21 (d, 3H, J=9.21 Hz), 3.00-2.87 (m, 1H), 2.37-2.32 (m, 1H), 2.13-1.75 (m, 6H), 1.63-1.56 (m, 1H).

2. Synthesis of C24-3

Compound C24-2 (832 mg, 2.47 mmol), compound C1-8 (584 mg, 2.96 mmol), $Pd_2(dba)_3$ (226 mg, 0.25 mmol), t-Buxphos (210 mg, 0.5 mmol) and KOAc (474 mg, 4.94 mmol) were dissolved in dry dioxane (25 mL), warmed to 6) ° C. and stirred overnight under nitrogen protection, water was added, extracted with ethyl acetate, washed with saturated saline, dried over anhydrous sodium sulfate and purified by column chromatography to obtain 671 mg of compound C24-3. $^1$H NMR (400 MHz, $CDCl_3$) δ 7.81 (br, 1H), 7.24-7.17 (d, 1H, J=31.17 Hz), 6.94-6.93 (d, 1H, J=3.74 Hz), 6.38 (s, 1H), 3.81-3.79 (m, 6H), 3.35-3.30 (d, 3H, J=20.88 Hz), 2.91-2.88 (m, 1H), 2.62-2.57 (d, 3H, J=20.57 Hz), 2.45-2.42 (m, 1H), 2.20-1.82 (m, 7H), 1.65 (s, 9H).

3. Synthesis of C24-4

Compound C24-3 (200 mg, 0.4 mmol) was dissolved in MeOH (10 mL) and $H_2O$ (2 mL), LiOH (67 mg, 1.6 mmol) was added, stirred overnight at 60° C., spin-dried and then slurried with DCM at reflux, filtered and spin dried to obtain 232 mg of compound C24-4. [M+H]: 385.3.

4. Synthesis of Control Example 1

Compound C24-4 (350 mg, crude) and compound C1-7 (254 mg, 0.9 mmol) were dissolved in 15 mL DMF, then DIPEA (1.27 mL, 7.3 mmol) was added, stirred at room temperature for 5 min, then HATU (519 mg, 1.4 mmol) was added, and stirred at room temperature for 1 h. The reaction solution was diluted with ethyl acetate, the organic phase was washed with saturated salt water, dried over anhydrous sodium sulfate, concentrated, and purified by Prep-HPLC to obtain 104 mg of Control Example 1. $^1$H NMR (400 MHz, DMSO-d6) δ 11.95 (br, 1H), 9.77 (br, 1H), 8.70-8.69 (dd, 1H, J=4.66 Hz, 0.80 Hz), 8.54-8.52 (d, 1H, J=8.78 Hz), 8.45-8.44 (d, 1H, J=1.86 Hz), 8.02-7.99 (dd, H, J=8.78 Hz, 2.39 Hz), 7.93-7.92 (dd, H, J=4.52 Hz, 0.80 Hz), 7.89-7.87 (d, 1H, J=8.51 Hz), 7.10-7.09 (d, 1H, J=2.93 Hz), 6.78 (br, 2H), 5.11-5.05 (m, 1H), 3.69 (s, 3H), 3.19 (s, 3H), 2.69-2.67 (m, 1H), 2.25 (s, 3H), 2.06-1.64 (m, 8H), 1.50-1.47 (d, 3H, J=6.92 Hz).

Control Example 2

The compound synthesized in the present invention:

Control Example 2

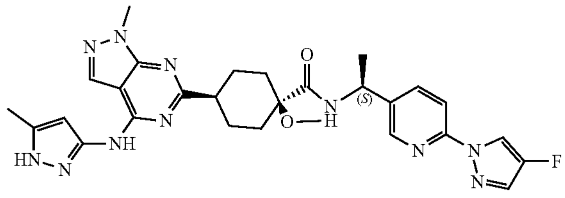

The synthetic route and experimental process were as follows:
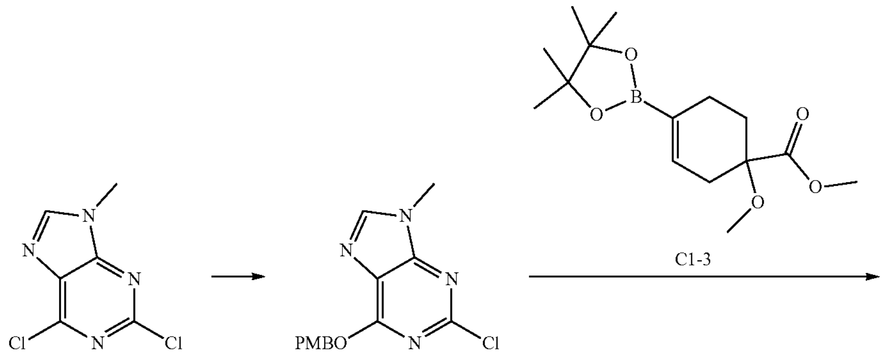
C25-1 C25-2
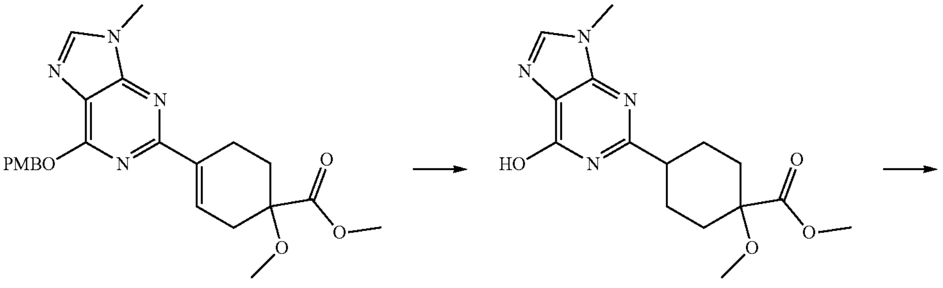
C25-3 C25-4
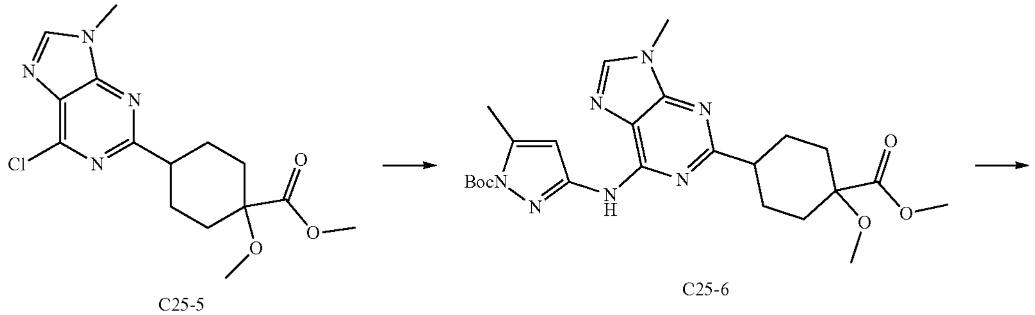
C25-5 C25-6
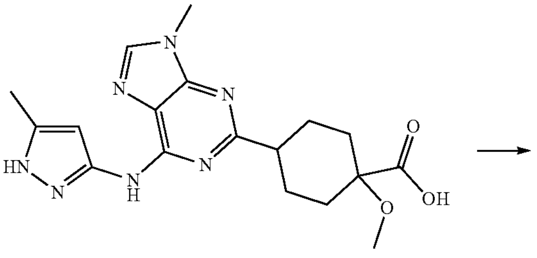
C25-7
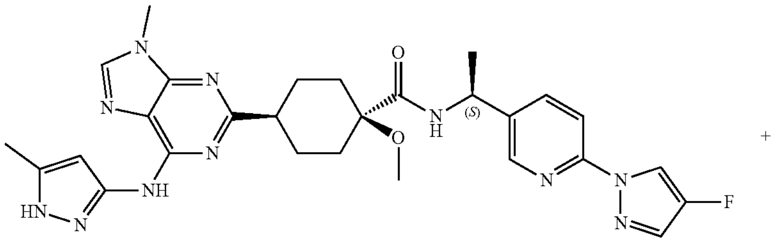
Control Example 2

-continued

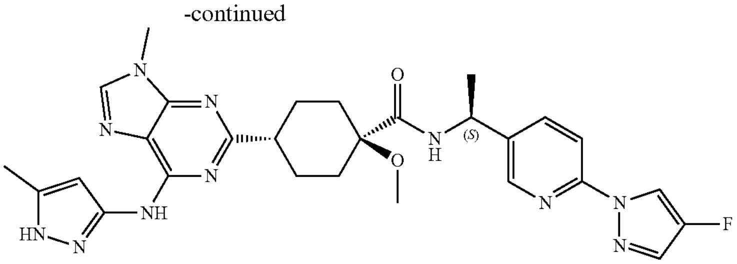

The experimental procedure refers to the synthesis of Control Example 1 to obtain Control Example 2.

Nuclear magnetic analysis data of Control Example 2: $^1$H NMR (400 MHz, CDCl3) 8.40-8.39 (m, 2H), 7.92 (d, 1H), 7.83 (s, 1H), 7.78 (dd, 1H), 7.58 (d, 1H), 6.85 (d, 1H), 6.77 (br, 1H), 5.22-5.15 (m, 1H), 3.86 (s, 3H), 3.33 (s, 3H), 2.93-2.88 (m, 1H), 2.40 (s, 3H), 2.05-1.97 (m, 8H), 1.58 (d, 3H).

Wherein, Control Examples 1 and 2 are the compounds reported in WO2020175968A1.

Control Example 3

The compound synthesized in the present invention:

Control Example 3

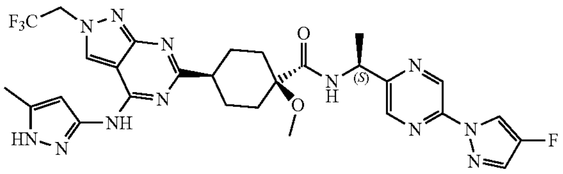

The synthetic route and experimental process were as follows:

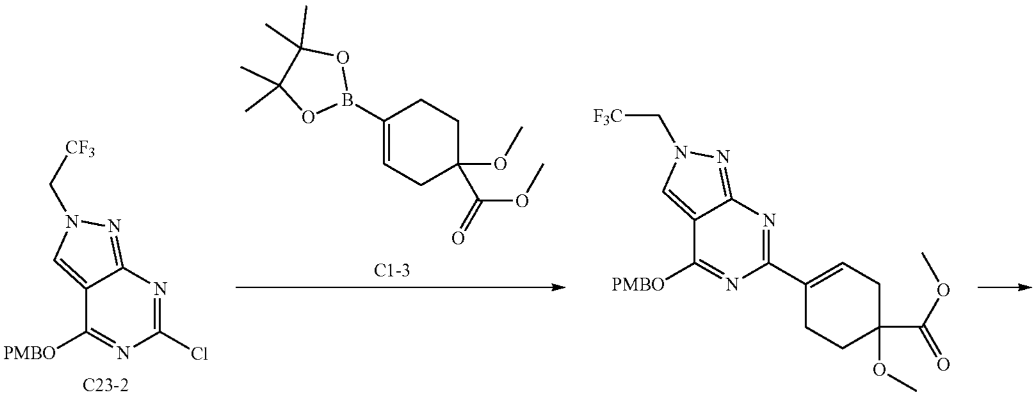

C23-2

C26-1

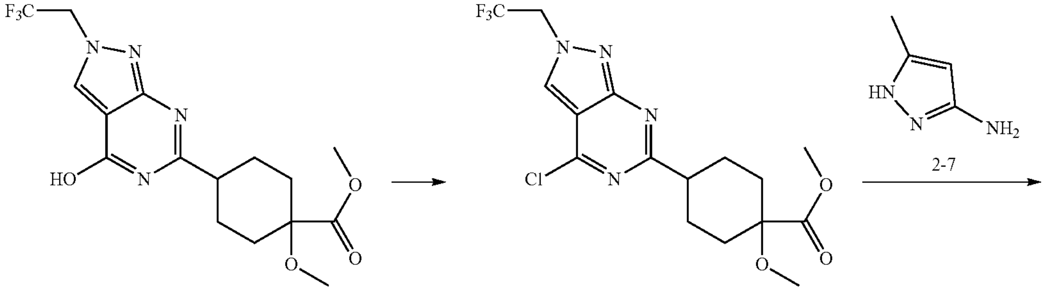

C26-2

C26-3

-continued

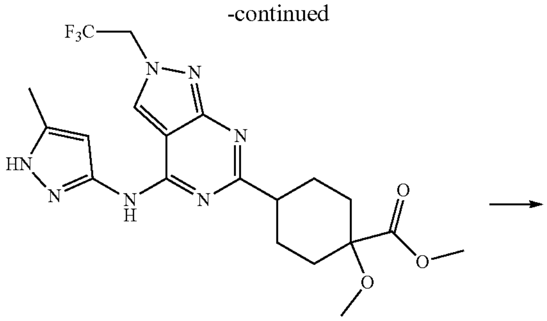

C26-4

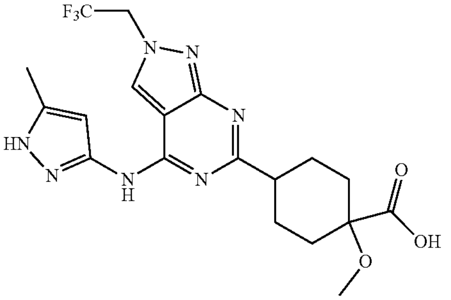

C26-5

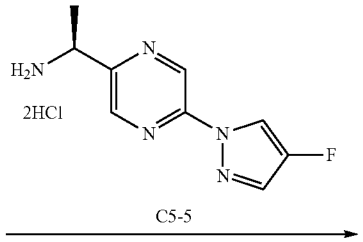

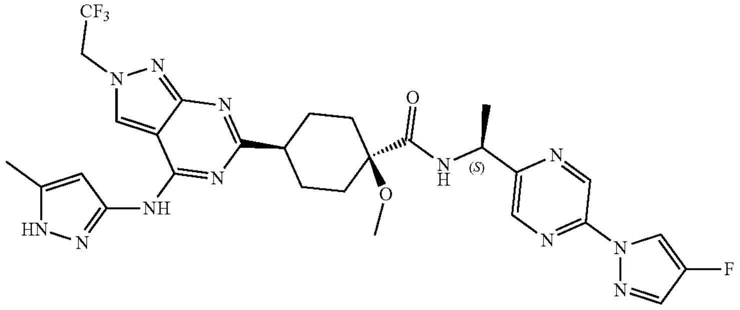

Control Example 3

The experimental procedure refers to the synthesis of C23 to obtain Control Example 3.

Nuclear magnetic analysis data of Control Example 3: $^{1}H$ NMR (400 MHz, Chloroform-d) δ 12.60 (s, 1H), 9.25-9.15 (m, 2H), 8.34 (t, J=3.0 Hz, 2H), 8.16 (s, 1H), 7.66 (d, J=4.1 Hz, 1H), 7.43 (d, J=8.2 Hz, 1H), 6.03 (s, 1H), 5.40-5.24 (m, 2H), 4.80 (q, J=8.1 Hz, 2H), 3.25 (s, 3H), 2.59 (s, 1H), 2.35 (s, 3H), 2.11-1.84 (m, 8H), 1.55 (d, J=6.9 Hz, 3H).

Test Example 1 Experiment of Cell Anti-Proliferation

I. Experimental Materials

RPMI-1640 was purchased from BI.

Fetal bovine serum was purchased from BI.

CellTiter-Glo® was purchased from Promega.

Dimethyl Sulfoxide (DMSO) was purchased from TCI.

BaF3 cells were purchased from RIKEN BRC CELL BANK.

Ba/F3-KIF5B-RET, Ba/F3-KIF5B-RET-V804L and Ba/F3-KIF5B-RET-V804M cells were constructed by PreceDo Pharmaceuticals Co., Ltd.

Ba/F3-KIF5B-RET, Ba/F3-KIF5B-RET-V804L and Ba/F3-KIF5B-RET-V804M medium: RPMI-1640+10% FBS+1% P/S.

Board reading instrument: Molecular Devices

II. Experimental Method

1. Dilution of Compounds

A 1000×solution of the compound was prepared with DMSO, the compound was diluted to 20 times to obtain the final concentration with a growth medium, and 2 μl 1000× cpd was added to 98 μl growth medium.

2. Cell Plating

Cells were centrifuged and resuspended with growth medium and cell counting was performed using a cell counter. The cell suspension was diluted with growth medium to the desired concentration. 95 uL of the diluted cell suspension was taken out to a 96-well plate. 5 μL of 20×compound solution was added to the 96-well plate to a final DMSO concentration of 0.1% per well. The 96-well plate was incubated for 72 h at 37° C. with 5% $CO_2$.

3. Detection

The 96-well plate was equilibrated to room temperature before the assay, 50 μl of CellTiter-Glo® Reagent was added to each well, the cells were fully lysed by shaking for 2 minutes on a shaker, incubated for 10 minutes at room temperature, and Paradigm was used to detect and record the fluorescence readings.

III. Data Analysis

Cell viability was analyzed using Graphpad 7.0 software according to the formula Cell viability (CV %)=(RLU compound−RLU blank)/(RLU control−RLU blank)*100%, and the corresponding IC50 data were calculated, in Table 1, the following names are used: <10.00 nM=A; 10.01-50.0 nM=B; >50 nM=C.

TABLE 1

| Compound | Ba/F3-KIF5B-RET (nM) | Ba/F3-KIF5B-RET-V804M (nM) | Ba/F3-KIF5B-RET-V804L (nM) |
|---|---|---|---|
| C1 | A | A | A |
| C2 | C | C | B |
| C3 | A | A | A |
| C4 | A | A | A |
| C5 | A | A | A |
| C6 | A | A | A |
| C7 | A | A | A |
| C8 | A | A | A |
| C9 | A | A | A |
| C10 | A | B | A |
| C11 | B | B | B |
| C12 | A | B | A |
| C13 | A | B | A |
| C14 | A | B | A |
| C15 | A | B | A |
| C16 | A | B | A |
| C18 | A | A | A |
| C20 | A | A | A |
| C21 | B | B | B |
| C22 | B | B | B |
| C23 | A | B | A |
| Control Example 1 | A | A | A |
| Control Example 2 | C | C | C |
| Control Example 3 | B | C | B |

As can be seen from Table 1, the compounds of the present invention have excellent RET inhibitory activity, especially Ba/F3-KIF5B-RET-V804M and Ba/F3-KIF5B-RET-V804L, and the parent nucleus structure and the position of the substituent have a significant effect on the activity of the compounds of the present invention, where the compound activity of the parent nucleus structure of pyrimidinopyrazole is superior to that of pyrimidinopyrrole and that of pyrimidinoimidazole. In addition, due to the different positions of the substituent, for example, the Control Example 3 and the compound C23 of the present invention show a large difference, and the inhibition effect of compound C23 is superior to that of Control Example 3.

Test Example 2 In Vivo Efficacy Study

Experimental Design

Cell culture: Ba/F3-KIF5B-RET cell line was cultured with 1640 medium (Biological Industries)+10%/f fetal bovine serum (BI)+1% double antibody (Penicillin Streptomycin solution, Corning, USA) at 37° C. with 5% $CO_2$. Two passages were performed for one week. When the cell saturation was 80%-90% and the number reached the required level, the cells were collected, counted and inoculated.

Animals: BALB/c nude mice, female, 6-8 weeks of age, weighing 18-22 g. A total of 18 mice were required, provided by Beijing Vital River Laboratory Animal Technology Co., Ltd.

Tumor inoculation: 0.2 ml (2×106) Ba/F3-KIF5B-RET cells (plus stromal gel, volume ratio 1:1) were inoculated subcutaneously on the right posterior dorsum of each mouse, and group dosing was started when the average tumor volume reached about 150-200 $mm^3$.

Animal Grouping and Dosing Regimen

The experimental groups and dosing regimen are shown in Table 2

TABLE 2

| Group Number | Animal | Dosing Group and Dosage (mg/kg) | | Dosing volume Parameter (μl/g) | | Dosing |
|---|---|---|---|---|---|---|
| 1 | 3 | Vehicle | — | 10 | P.O. | BID × 3 weeks |
| 2 | 3 | Control Example 1 | 10 | 10 | P.O. | BID × 3 weeks |
| 3 | 3 | C1 | 10 | 10 | P.O. | BID × 3 weeks |

Animal feeding: After arrival, the animals should be kept in quarantine in the experimental environment for 7 days before starting the experiment.

Experimental index: Tumor volume and body weight were measured twice a week. Tumor volume was measured by vernier calipers with the formula TV=0.5 a×b2, where a is the long diameter of the tumor and b is the short diameter of the tumor.

The tumor inhibition efficacy of the compounds was evaluated by TGI (%) or relative tumor proliferation rate T/C (%). TGI (%), reflects the tumor growth inhibition rate. Calculation of TGI (%): TGI (%)=[(1−(mean tumor volume at the end of dosing in a treatment group−mean tumor volume at the beginning of dosing in that treatment group))/(mean tumor volume at the end of treatment in the solvent control group−mean tumor volume at the beginning of treatment in the solvent control group)]×100%.

Relative tumor proliferation rate T/C (%): The formula was calculated as follows: T/C %=TRTV/CRTV×100% (TRTV: RTV of the treatment group; CRTV: RTV of the negative control group). The relative tumor volume (RTV) was calculated based on the results of tumor measurements with the formula RTV=Vt/V0, where V0 is the mean tumor volume measured at the time of group dosing (i.e., D0) and Vt is the mean tumor volume at a particular measurement, and TRTV and CRTV were data on the same day.

Tumor weight was measured at the end of the experiment and the $T/C_{weight}$ percentage was calculated, with $T_{weight}$ and $C_{weight}$ indicating the tumor weight of the dosing group and the vehicle control group, respectively.

The experimental results are shown in Table 3.

TABLE 3

| Tested | Tumor Volume($mm^3$) | | | | | | | |
|---|---|---|---|---|---|---|---|---|
| Compound | 0 day | 2 days | 5 days | 9 days | 12 days | 16 days | 19 days | 22 days |
| Blank control | 170.95 | 194.58 | 238.73 | 308.88 | 452.44 | 857.96 | 1204.47 | 1367.09 |
| Control Example 1 | 169.95 | 157.73 | 144.57 | 185.92 | 204.18 | 272.83 | 277.52 | 292.41 |
| C1 | 168.34 | 162.57 | 139.55 | 189.12 | 222.35 | 203.41 | 199.75 | 199.64 |

As can be seen from Table 3: compared with Control Example 1, the compounds of the present invention have excellent tumor inhibitory activity and have clinical application and good prospects for drug.

The above description is only examples of the present invention, and does not limit the patent scope of the present invention. Any equivalent modifications made by using the contents of the present specification or directly or indirectly applied to other related technical fields are included in the scope of the present invention.

The invention claimed is:

1. A compound of Formula I, or a pharmaceutically acceptable salt, stereoisomer, or solvate thereof,

I

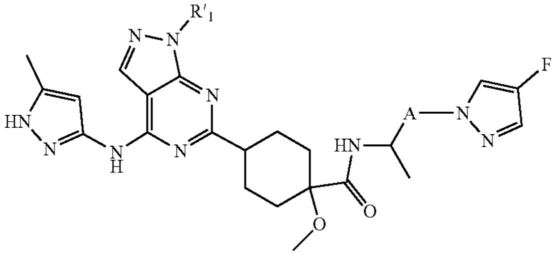

wherein, $R'_1$ comprises hydrogen, a C1-C6 alkyl, a C1-C6 deuterated alkyl, a C1-C6 alkoxy, a C1-C6 alkylamino, a C3-C6 cycloalkyl, a C1-C6 heteroalkyl, or a 3-6 membered heterocyclyl, wherein the alkyl, the deuterated alkyl, the alkoxy, the alkylamino, the cycloalkyl, the heteroalkyl and the heterocyclyl are optionally substituted with 0 to 5 $R^a$;

Ring A comprises a 3-7 membered saturated ring, an unsaturated ring, an aromatic ring, a heteroaromatic ring, a spiro ring or a bridge ring, wherein the ring optionally comprises 0-3 heteroatoms selected from the group consisting of N, O and S; any hydrogen atom on A is optionally substituted by one or more substituents selected from the group consisting of deuterium, hydroxyl, a halogen, cyano, an ester, an amido, a ketocarbonyl, an amino, a C1-C6 alkyl, a C1-C6 haloalkyl, a C1-C6 thioalkyl, a C1-C6 alkoxy, a C1-C6 heteroalkyl, a C1-C6 alkylamino, a C3-C6 cycloalkyl, a C3-C8 cycloalkylamino, an aryl and a heteroaryl;

$R^a$ comprises a C1-C6 alkyl, a halogen, hydroxyl, an amino, a C1-C6 heteroalkyl, a C1-C6 alkoxy, a C1-C6 alkylamino, a cycloalkyl, a heterocycloalkyl or cyano.

2. The compound, or the pharmaceutically acceptable salt, stereoisomer, or solvate thereof of claim 1, wherein A ring is selected from substituted or unsubstituted 5-6 membered heteroaryl; wherein any hydrogen atom on A is independently substituted by a substituent selected from C1-C6 alkyl, halogen, hydroxyl, amino, C1-C6 heteroalkyl, C1-C6 alkoxy, C1-C6 alkylamino, cycloalkyl, heterocycloalkyl or cyano.

3. The compound, or the pharmaceutically acceptable salt, stereoisomer, or solvate thereof of claim 1, wherein the compound has a structure represented by Formula II-1 or Formula III-1

II-1

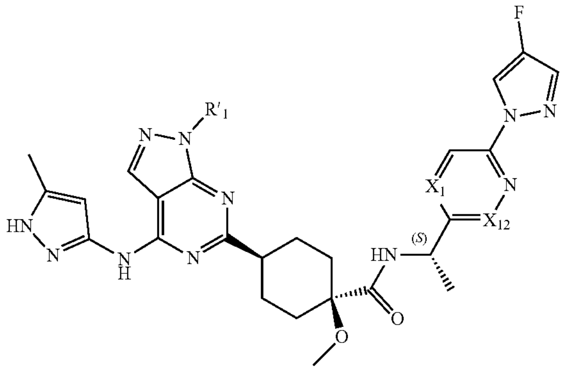

III-1

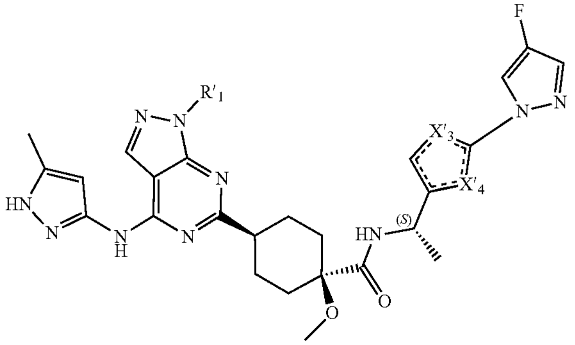

wherein, ⎓ represents a single bond or a double bond;

$X'_1$ and $X'_2$ are each independently being N or $CR_5$;

$X'_3$ and $X'_4$ are each independently being N or S;

$R_5$ is each independently selected from the group consisting of hydrogen, a C1-C6 alkyl, a C2-C6 alkenyl, a C2-C6 alkynyl, a C1-C6 alkoxy, a C1-C6 alkylamino, a halogen, a C1-C6 heteroalkyl, a cycloalkyl, nitro, cyano, or an amino; wherein each of the alkyl, alkenyl, alkynyl, alkoxy, alkylamino, heteroalkyl and cycloalkyl is independently substituted by 0 to 5 $R^a$; and wherein $R^a$ is selected from the group consisting of a C1-C6 alkyl, a halogen, hydroxyl, an amino, a C1-C6 heteroalkyl, a C1-C6 alkoxy, a C1-C6 alkylamino, a cycloalkyl, a heterocycloalkyl or cyano.

4. The compound, or the pharmaceutically acceptable salt, stereoisomer or solvate thereof of claim 1, wherein Ring A is selected from the group consisting of

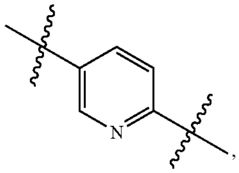
,
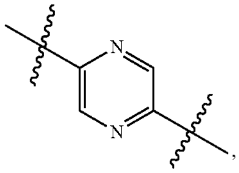
,
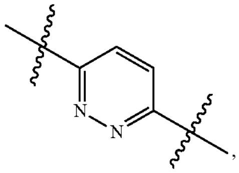
,
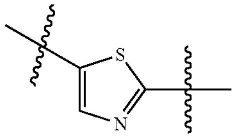
and
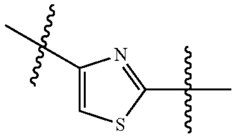

and is optionally substituted by one or more groups selected from the group consisting of a C1-C6 alkyl, a halogen, hydroxyl, an amino, a C1-C6 heteroalkyl, a C1-C6 alkoxy, a C1-C6 alkylamino, a cycloalkyl, a heterocycloalkyl or cyano.

5. The compound, or the pharmaceutically acceptable salt, stereoisomer or solvate thereof of claim 1, wherein Ring A is selected from the group consisting of

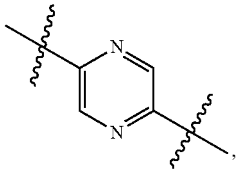
,
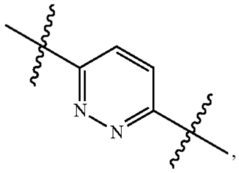
,
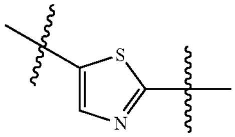
and

-continued

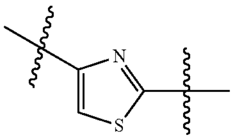

and is optionally;

substituted by one or more groups selected from the group consisting of a C1-C6 alkyl, a halogen, hydroxyl, an amino, a C1-C6 heteroalkyl, a C1-C6 alkoxy, a C1-C6 alkylamino, a cycloalkyl, a heterocycloalkyl and cyano.

6. A compound of claim 1 selected from the group consisting of:

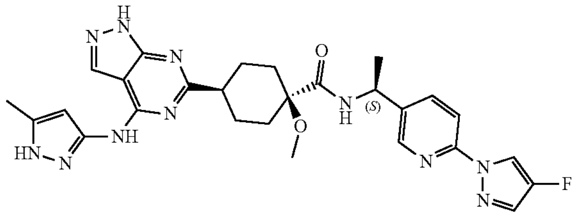

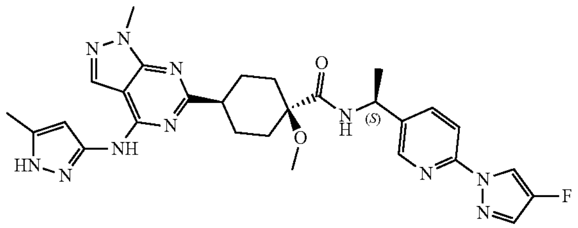

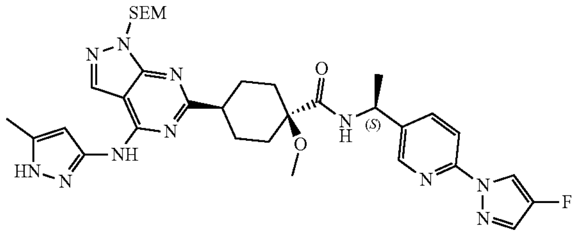

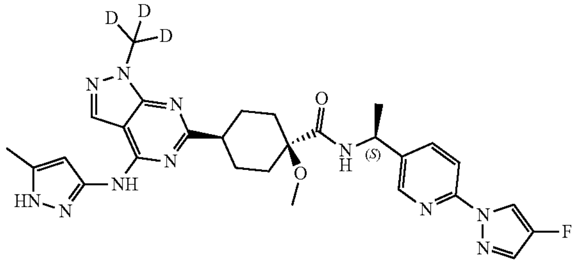

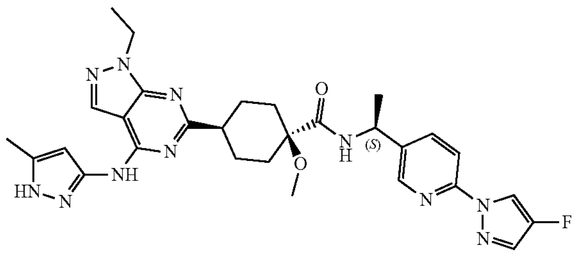

-continued
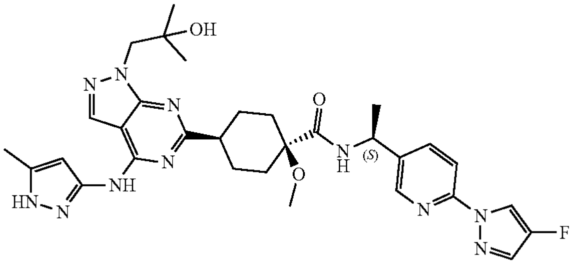
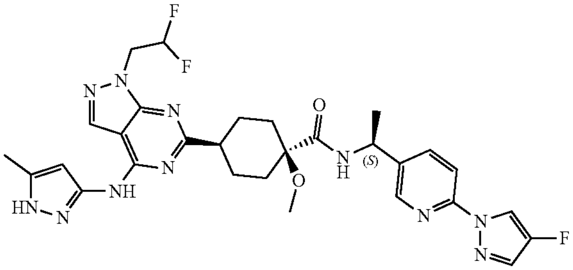
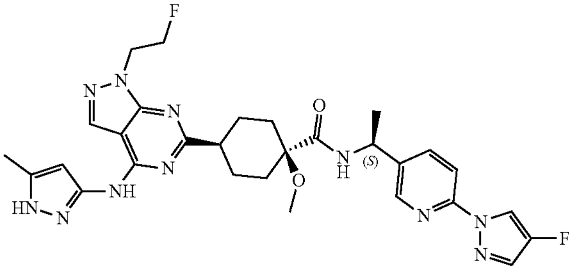
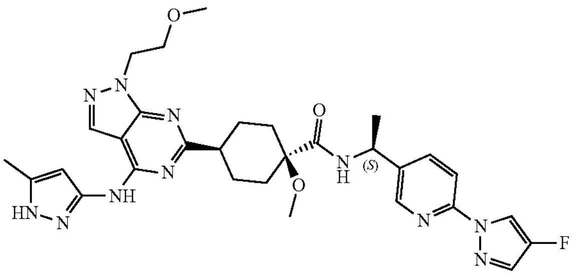
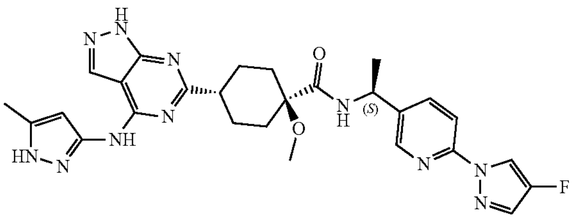
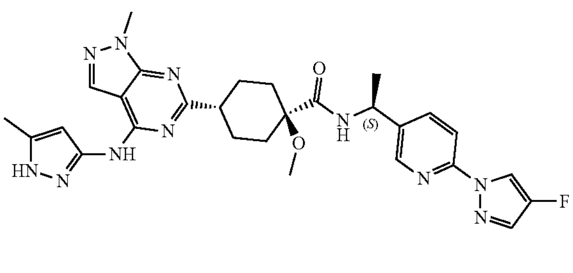
-continued
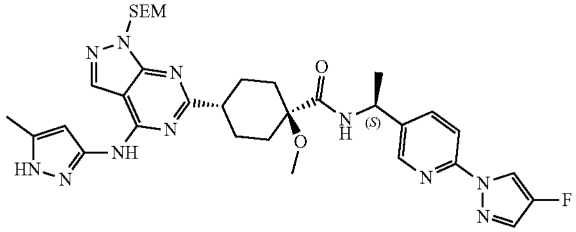
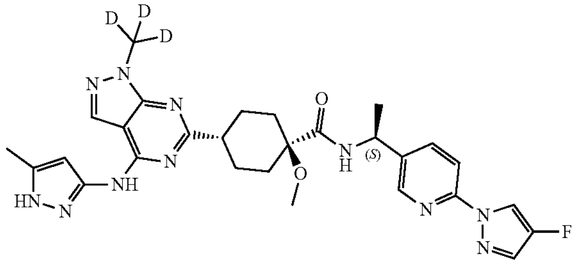
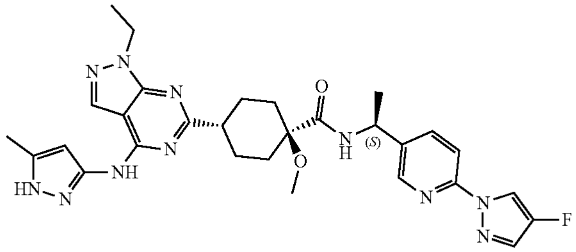
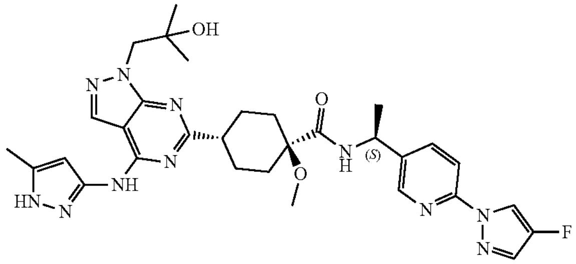
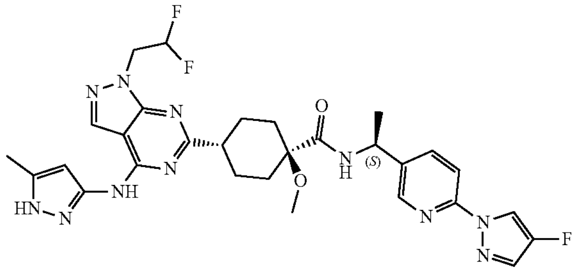
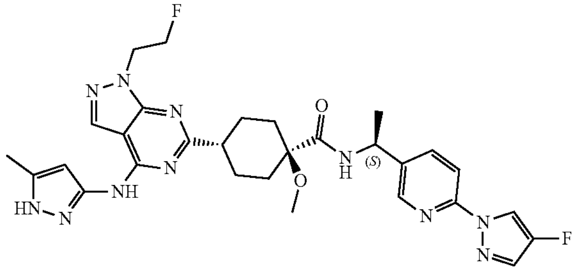

-continued
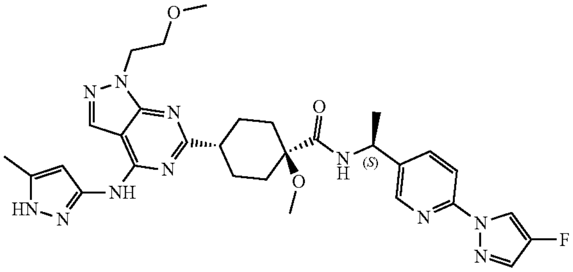
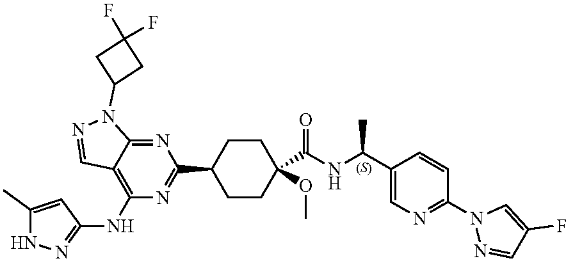
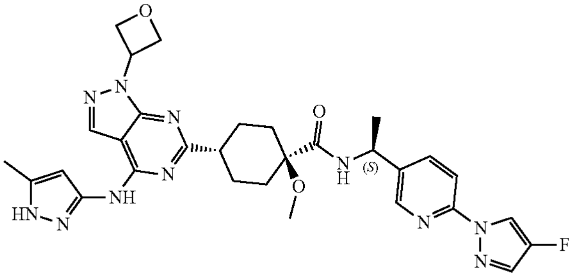
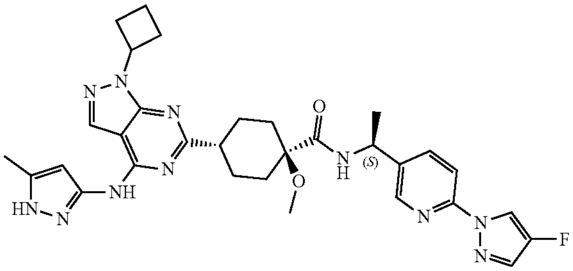
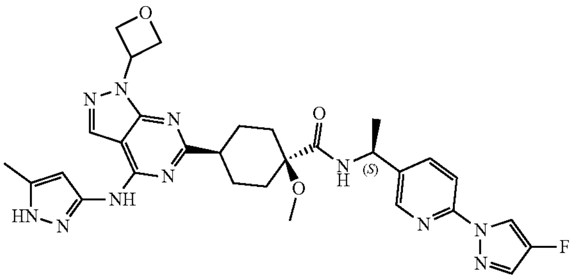
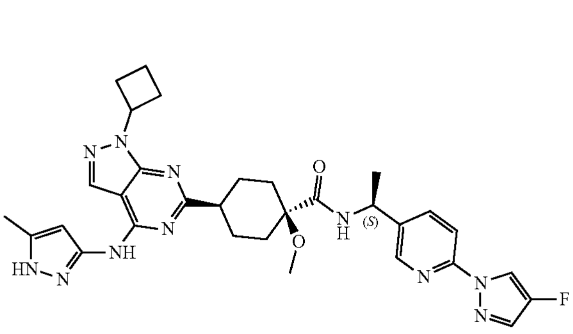
-continued
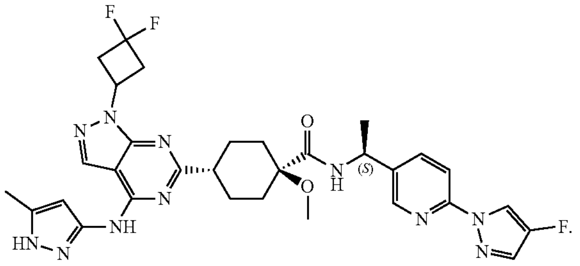
7. A compound of claim 1 selected from the group consisting of:
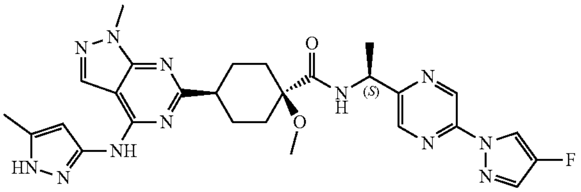
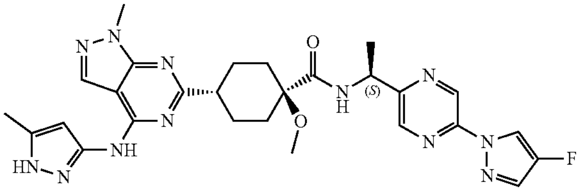
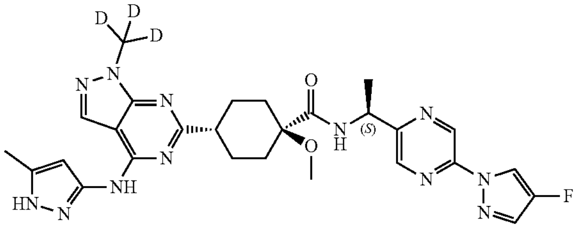
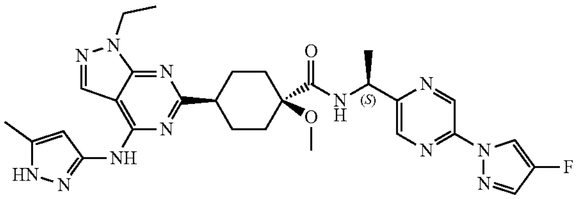
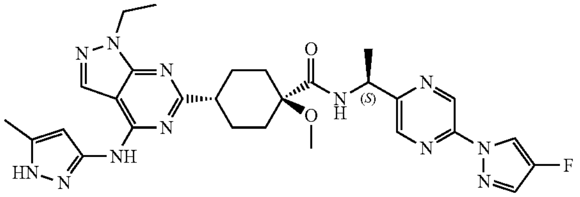
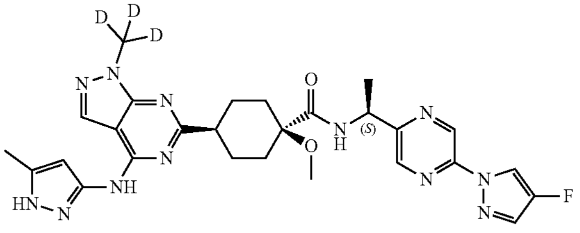

-continued
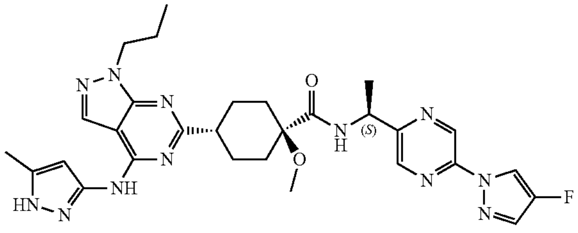
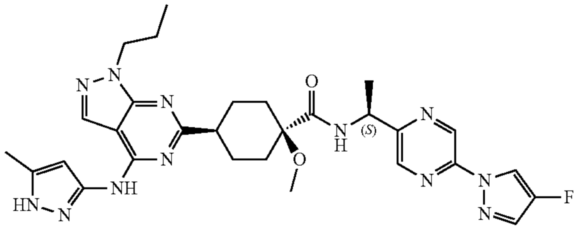
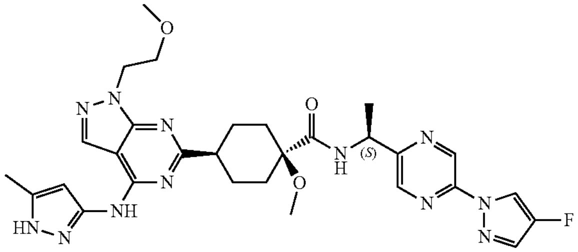
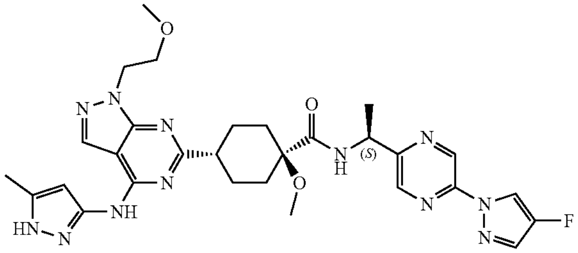
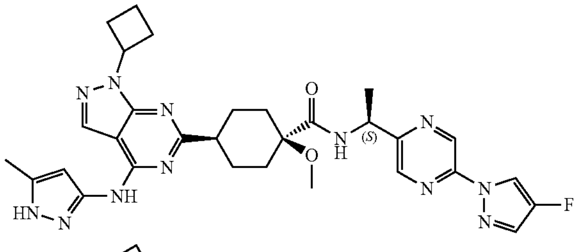
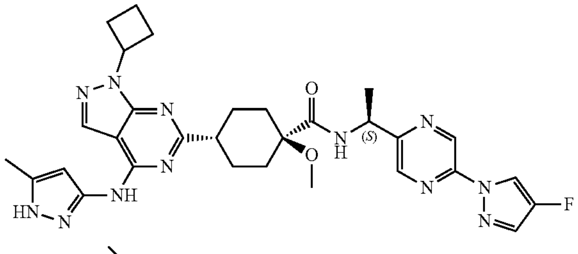
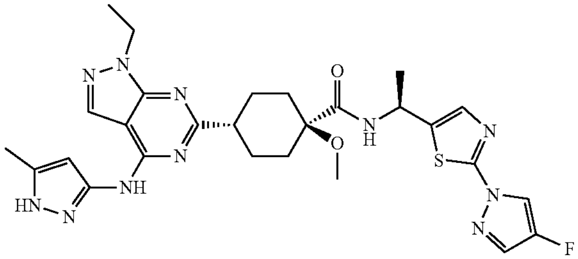
-continued
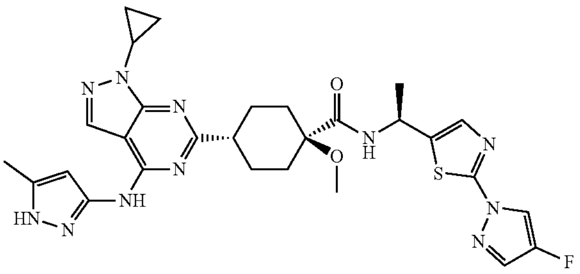
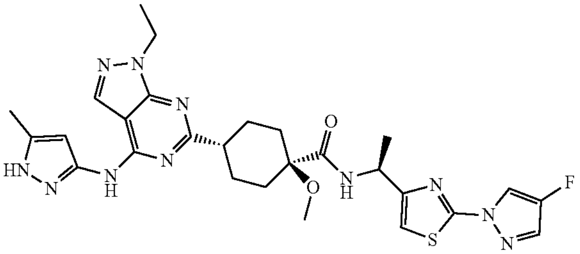
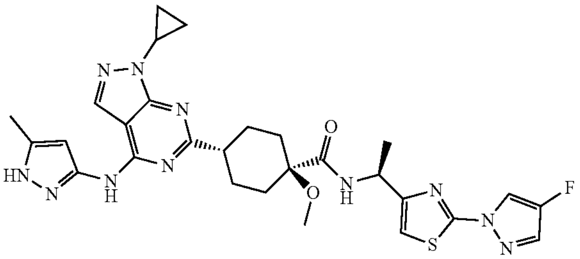
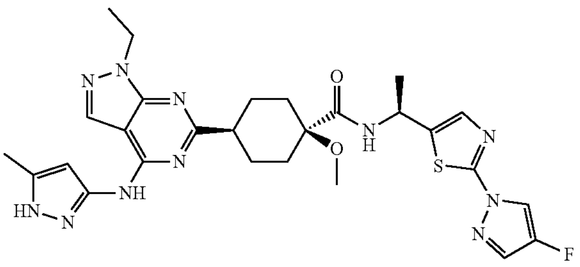
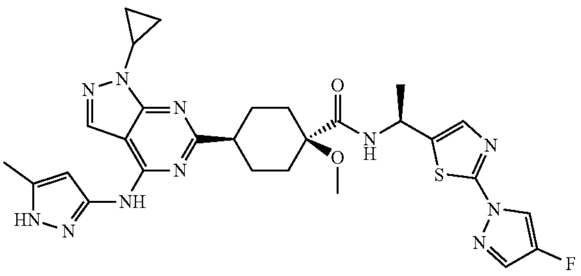
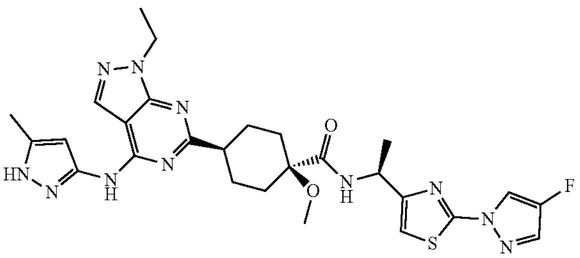

-continued
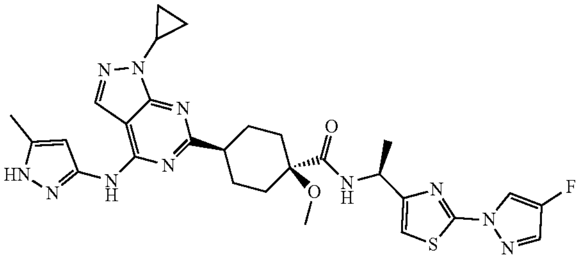
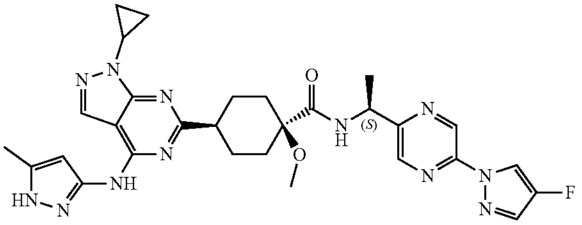
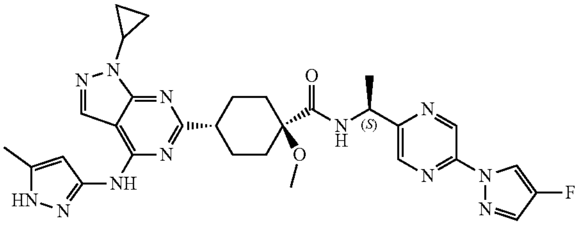
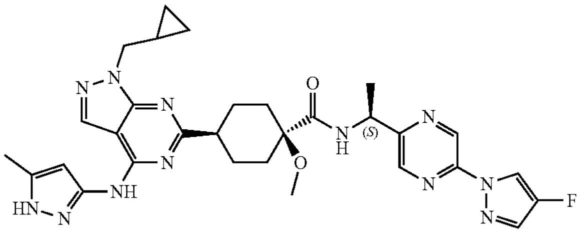
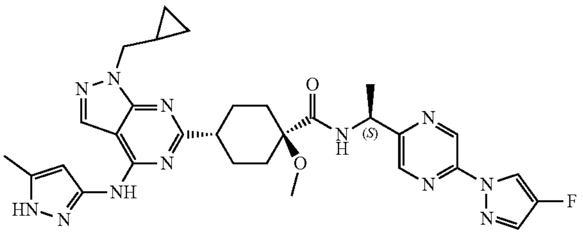
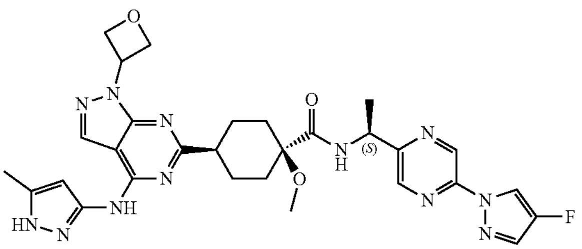
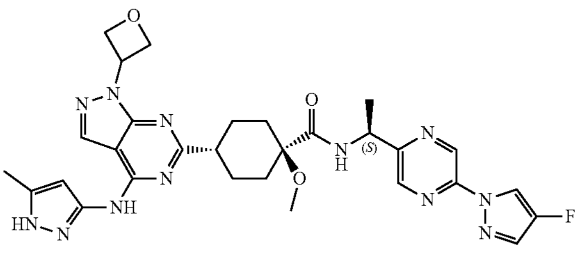
-continued
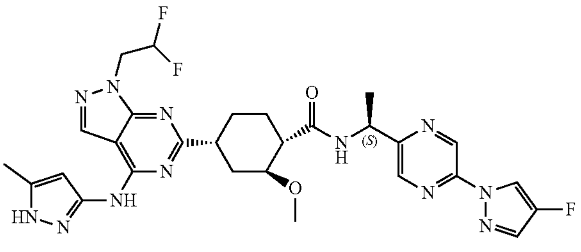
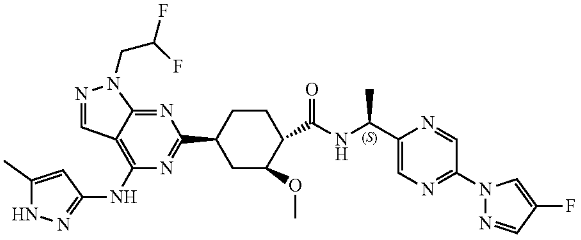
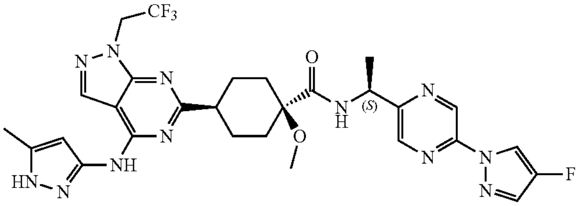
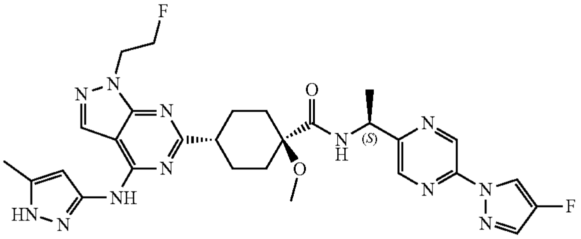
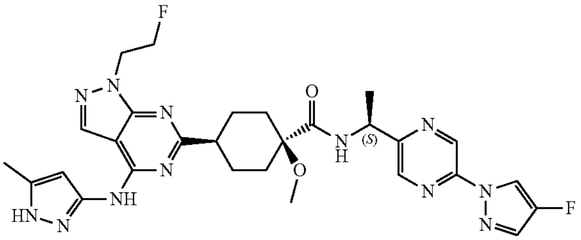
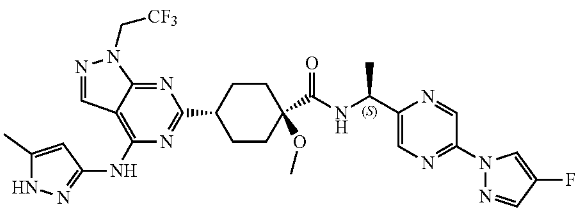
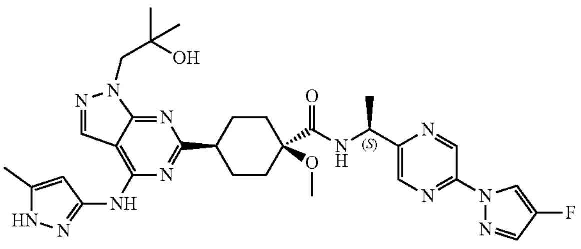

-continued

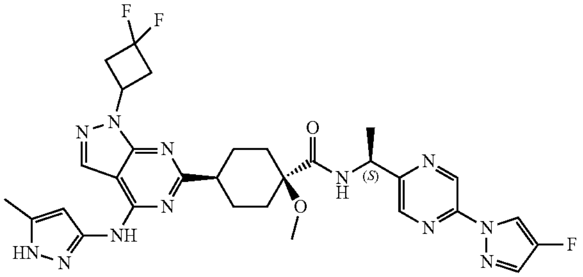

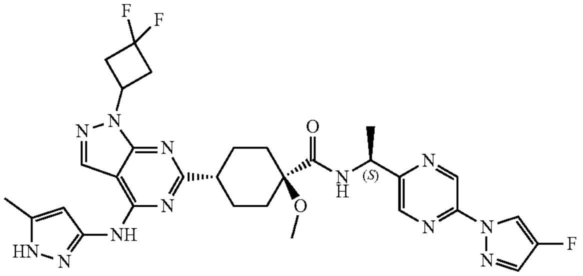

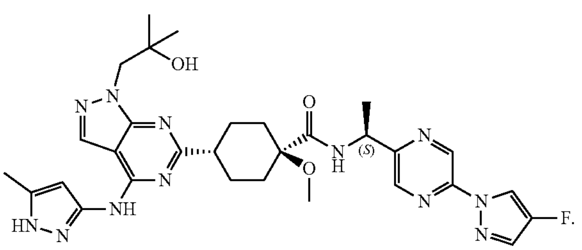

8. The compound, or the pharmaceutically acceptable salt, stereoisomer, or solvate thereof of claim 1, wherein the pharmaceutically acceptable salt is an inorganic acid salt or an organic acid salt, wherein the inorganic acid salt comprises a salt of hydrochloride, hydrobromide, hydroiodide, sulfate, bisulfate, nitrate, phosphate or acid phosphate; or wherein the organic acid salt comprises a salt of formate, acetate, trifluoroacetate, propionate, pyruvate, glycolate, oxalate, malonate, fumarate, maleate, lactate, malate, citrate, tartrate, methanesulfonate, ethanesulfonate, benzenesulfonate, salicylate, picrate, glutamate, ascorbate, camphorate, or camphor sulfonate.

9. A pharmaceutical composition comprising a therapeutically effective amount of the compound, or the pharmaceutically acceptable salt, stereoisomer or solvate thereof of claim 1, and a pharmaceutically acceptable carrier.

10. A method for preparing the compound of Formula I of claim 1 comprising a step of reacting

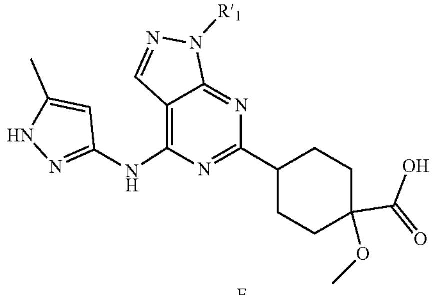

with

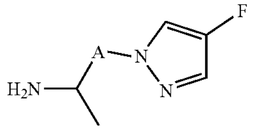

in an inert solvent and in the presence of a condensing agent to obtain the compound of claim 1 shown in the below Scheme.

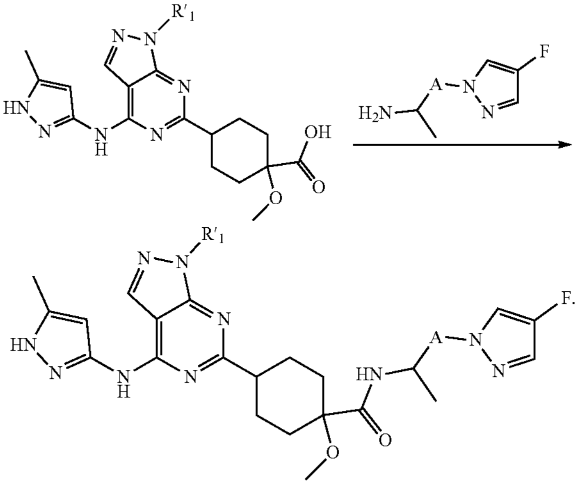

I

11. The method of claim 10, wherein the condensing agent comprises 4-Dimethylaminopyridine (DMAP), Hexafluorophosphate Azabenzotriazole Tetramethyl Uranium (HATU), or Benzotriazol-1-yloxy) tripyrrolidinophosphonium hexafluorophosphate (PyBOP).

12. A method of modulating RET kinase activity or treating a RET-related disease comprising administrating to a subject in need thereof an effective amount of the compound, or the pharmaceutically acceptable salt, stereoisomer or solvate thereof of claim 1, wherein the RET-related disease is thyroid cancer, or lung cancer.

13. The method of claim 12, wherein the cancer comprises medullary thyroid carcinoma or non-small cell lung cancer.

* * * * *